(12) United States Patent
Franano et al.

(10) Patent No.: US 10,301,612 B2
(45) Date of Patent: May 28, 2019

(54) RECOMBINANT ELASTASE PROTEINS AND METHODS OF MANUFACTURING AND USE THEREOF

(71) Applicant: Proteon Therapeutics, Inc., Waltham, MA (US)

(72) Inventors: F. Nicholas Franano, Kansas City, MO (US); Kimberly Bland, Kansas City, MO (US); Marco D. Wong, Overland Park, KS (US); Bee C. Ding, Overland Park, KS (US)

(73) Assignee: PROTEON THERAPEUTICS, INC., Waltham, MA (US)

( * ) Notice: Subject to any disclaimer, the term of this patent is extended or adjusted under 35 U.S.C. 154(b) by 0 days.

(21) Appl. No.: 15/880,029

(22) Filed: Jan. 25, 2018

(65) Prior Publication Data

US 2018/0155703 A1 Jun. 7, 2018

Related U.S. Application Data

(63) Continuation of application No. 12/823,098, filed on Jun. 24, 2010, now abandoned.

(51) Int. Cl.
| | | |
|---|---|---|
| *C12N 9/64* | (2006.01) | |
| *C12N 9/50* | (2006.01) | |
| *C12N 15/81* | (2006.01) | |
| *C07K 1/14* | (2006.01) | |
| *C12P 21/02* | (2006.01) | |
| *A61K 9/19* | (2006.01) | |
| *A61K 38/48* | (2006.01) | |
| *A61K 38/00* | (2006.01) | |

(52) U.S. Cl.
CPC .............. *C12N 9/6448* (2013.01); *A61K 9/19* (2013.01); *A61K 38/486* (2013.01); *C07K 1/14* (2013.01); *C12N 9/50* (2013.01); *C12N 15/815* (2013.01); *C12P 21/02* (2013.01); *C12Y 304/21036* (2013.01); *A61K 38/00* (2013.01); *C07K 2319/00* (2013.01); *C07K 2319/02* (2013.01); *C07K 2319/50* (2013.01); *C12Y 304/21037* (2013.01)

(58) Field of Classification Search
None
See application file for complete search history.

(56) References Cited

U.S. PATENT DOCUMENTS

| | | |
|---|---|---|
| 4,968,614 A | 11/1990 | Takiguchi et al. |
| 5,162,205 A | 11/1992 | Takiguchi et al. |
| 5,212,068 A | 5/1993 | Takiguchi et al. |
| 5,395,922 A | 3/1995 | Bjorn et al. |
| 5,427,927 A | 6/1995 | Meyer et al. |
| 5,503,333 A | 4/1996 | Laventure |
| 5,543,302 A | 8/1996 | Boguslawski et al. |
| 5,811,252 A | 9/1998 | Verheijen |
| 5,955,072 A | 9/1999 | Takahashi et al. |
| 7,063,838 B1 | 6/2006 | Franano |
| 7,351,549 B2 | 4/2008 | Mattanovich et al. |
| 7,745,391 B2 | 6/2010 | Mintz et al. |
| 8,211,428 B2 | 7/2012 | Madison |
| 8,501,449 B2 | 8/2013 | Franano et al. |
| 8,574,857 B2 | 11/2013 | Vandeghinste et al. |
| 9,057,060 B2 * | 6/2015 | Franano ............... C12N 9/6448 |
| 2001/0024789 A1 | 9/2001 | Kurz et al. |
| 2001/0049833 A1 | 12/2001 | Greenland et al. |
| 2003/0166162 A1 | 9/2003 | Rooijen et al. |
| 2003/0207402 A1 | 11/2003 | Kopetzki et al. |
| 2006/0193824 A1 | 8/2006 | Rubin et al. |
| 2009/0162343 A1 * | 6/2009 | Franano ............... C12N 9/6448 424/94.64 |
| 2009/0253183 A1 | 10/2009 | Han |
| 2011/0081705 A1 * | 4/2011 | Franano ............... C12N 9/6448 435/218 |
| 2013/0336956 A1 | 12/2013 | Franano et al. |
| 2015/0166974 A1 | 6/2015 | Franano et al. |
| 2016/0243205 A1 * | 8/2016 | Franano ............... C12N 9/6448 |
| 2016/0319267 A1 | 11/2016 | Franano et al. |

FOREIGN PATENT DOCUMENTS

| | | |
|---|---|---|
| EP | 0 244 189 | 11/1987 |
| WO | 1991/09118 | 6/1991 |
| WO | 2000/61728 | 10/2000 |

(Continued)

OTHER PUBLICATIONS

Bode, W. et al. 1989, "Perspectives in Biochemistry: Human Leukocyte and Porcine Pancreatic Elastase: X-ray Crystal Structures, Mechanism, Substrate Specificity, and Mechanism-Based Inhibitors," Biochemistry, 28(5): 1951-1963.

Chang et al., 1993, "Stabilization of lyophilized porcine pancreatic elastase", Pharmaceutical Research, 10(10):1478-1483.

Dall'Acqua, et al., 1999, "Elastase substrate specificity tailored through substrate-assisted catalysis and phage display," Protein Engineering, 12(11):981-987.

Katona, G. et al. 2002, "X-ray Structure ofa Serine Protease Acyl-Enzyme Complex at 0.95-A Resolution," The Journal of Biological Chemistry, 277(24):21962-21970.

(Continued)

*Primary Examiner* — Hope Robinson
(74) *Attorney, Agent, or Firm* — Biospark Intellectual Property Law

(57) ABSTRACT

The present invention relates to methods for the manufacture, purification, formulation, and use of biologically active recombinant elastase proteins. Described are recombinant methods for producing therapeutically useful elastase proteins, as are pharmaceutical compositions comprising said elastase proteins. Novel recombinant elastase proteins and protein preparations are also disclosed. Methods are described for treating and preventing diseases of biological conduits using pharmaceutical compositions containing the elastase proteins of the invention.

18 Claims, 24 Drawing Sheets

Specification includes a Sequence Listing.

(56) References Cited

FOREIGN PATENT DOCUMENTS

| WO | 2000/68363 | 11/2000 |
| WO | 2004/073504 | 9/2004 |
| WO | 2006/036804 | 4/2006 |
| WO | 2009/079220 | 6/2009 |

OTHER PUBLICATIONS

McIver et al., 1991, "Substitution of active-site His-223 in pseudomonas aeruginosa elastase and expression of the mutated lasB alleles in *Escherichia coli* show evidence for autoproteolytic processing of proelastase", Journal of Bacteriology, 173:(24):7781-7789 (1991).
Proteon Therapeutics 1. Press Release. "QSV Biologicals, Ltd., and Proteon Therapeutics, Inc., Enter into a Contract for Process Development and Manufacture of PRT-201." Jun. 21, 2006.
Proteon Therpeutics 2. Media Release. "Proteon Therapeutics Presents New Data on PRT-201 at the Annual Meeting of the American Society of Nephrology in Philadelphia." Nov. 6, 2008.
Shirasu et al., 1986, "Isolation and Expression in *Escherichia coli* of a cDNA Clone Encoding Porcine Pancreatic Elastase", J. Biochem. 99: 1707-1712.
Shirasu et al., 1987, "Molecular Cloning and Expression in *Escherichia coli* of a cDNA Encoding Human Pancreatic Elastase 2", J. Biochem. 102:1555-1563.
Szepessy et al., 2006, "Inactivity of Recombinant ELA2B Provides a New Example of Evolutionary Elastase Silencing in Humans", Pancreatology 6(1-2):117-122.
Talas, U. et al., 2000, "Human Elastase 1: Evidence for Expression in the Skin and the Identification of a Frequent Frameshift Polymorphism," The Journal of Investigative Dermatology,114(1):165-170.
Yuan, L. et al. 2005, "Laboratory-Directed Protein Evolution," Microbiology and Molecular Biology Reviews, 69(3):373-392.
International Search Report and Written Opinion dated Jun. 6, 2009 corresponding to International Patent Application No. PCT/US08/085559.
Branden et al., 1991, Introduction to Protein Structure, Garland Publishing Inc., New York, p. 247.
Braun et al., 1996, "Role of the propeptide in folding and secretion of elastase of Pseudomonas aeruginosa," Mol Microbial. 19(2):297-306.
GenBank databases, NCBI Accession No. AAH69454.I, Jul. 15, 2006 URL:http://www.ncbi.nlm.nih.gov/protein/ AAH69454.1.
GenBank databases, NCBI Accession No. AAV88109.1, Dec. 13, 2004 URL:http://www.ncbi.nlm.nih.gov/protein/ AAV88109.1.
Mciver, et al., 1993, "Pseudomonas aeruginosa lasB1 mutants produce an elastase, substituted at active-site His-223, that is defective in activity, processing, and secretion," J Bacterial. 17S(13):4008-15.
Ninth New Collegiate Dictionary (Merriam-Webster Inc., 1987)—pp. 213-214.
Q9UN11, 2006, UnitProtKB.
Sorensen, 1994, "pH dependent processing of yeast procarboxypeptidase Y by proteinase A in vivo and in vitro," Eur. J. Biochem. 220: 19-27.

\* cited by examiner

```
EcoRI                              XmaI
gaattcagt ACT CAG GAC CTT CCG GAA ACC AAT GCC CGG GTA GTC GGA GGG ACT GAG GCC GGG
          THR GLN ASP LEU PRO GLU THR ASN ALA ARG VAL VAL GLY GLY THR GLU ALA GLY
              Propeptide                              Mature Enzyme AGG AAC TCC TGG CCC TCT CAG ATT TCC CTC CAG TAC CGG TCT GGA GGT TCC TGG TAT CAC
ARG ASN SER TRP PRO SER GLN ILE SER LEU GLN TYR ARG SER GLY GLY SER TRP TYR HIS ACC TGT GGA GGG ACC CTT ATC AGA CAG AAC TGG GTG ATG ACA GCT GCA CAC TGC GTG GAT
THR CYS GLY GLY THR LEU ILE ARG GLN ASN TRP VAL MET THR ALA ALA HIS CYS VAL ASP TAC CAG AAG ACT TTC CGC GTG GTG GCT GGA GAC CAT AAC CTG AGC CAG AAT GAT GGC ACT
TYR GLN LYS THR PHE ARG VAL VAL ALA GLY ASP HIS ASN LEU SER GLN ASN ASP GLY THR GAG CAG TAC GTG AGT GTG CAG AAG ATC GTG GTG CAT CCA TAC TGG AAC AGC GAT AAC GTG
GLU GLN TYR VAL SER VAL GLN LYS ILE VAL VAL HIS PRO TYR TRP ASN SER ASP ASN VAL GCT GCA GGC TAT GAC ATC GCC CTG CTG CGC CTG GCC CAG AGC GTT ACC CTC AAT AGC TAT
ALA ALA GLY TYR ASP ILE ALA LEU LEU ARG LEU ALA GLN SER VAL THR LEU ASN SER TYR GTC CAG CTG GGT GTT CTG CCC CAG GAG GGA GCC ATC CTG GCT AAC AAC AGT CCC TGC TAC
VAL GLN LEU GLY VAL LEU PRO GLN GLU GLY ALA ILE LEU ALA ASN ASN SER PRO CYS TYR ATC ACA GGC TGG GGC AAG ACC AAG ACC AAT GGG CAG CTG GCC CAG ACC TTG CAG CAG GCT
ILE THR GLY TRP GLY LYS THR LYS THR ASN GLY GLN LEU ALA GLN THR LEU GLN GLN ALA TAC CTG CCC TCT GTG GAC TAT GCC ATC TGC TCC AGC TCC TCC TAC TGG GGC TCC ACT GTG
TYR LEU PRO SER VAL ASP TYR ALA ILE CYS SER SER SER SER TYR TRP GLY SER THR VAL AAG AAC ACT ATG GTG TGT GCT GGT GGA GAT GGA GTT CGC TCT GGA TGT CAG GGT GAC TCT
LYS ASN THR MET VAL CYS ALA GLY GLY ASP GLY VAL ARG SER GLY CYS GLN GLY ASP SER GGG GGC CCC CTC CAT TGC TTG GTG AAT GGC AAG TAT TCT CTT CAT GGA GTG ACC AGC TTT
GLY GLY PRO LEU HIS CYS LEU VAL ASN GLY LYS TYR SER LEU HIS GLY VAL THR SER PHE GTG TCC AGC CGG GGC TGT AAT GTC TCT AGA AAG CCT ACA GTC TTC ACA CGG GTC TCT GCT
VAL SER SER ARG GLY CYS ASN VAL SER ARG LYS PRO THR VAL PHE THR ARG VAL SER ALA HINDIII  BAMHI   SALI
TAC ATC TCC TGG ATA AAT AAT GTC ATC GCC TCC AAC TGA.TAA gct tgg atc cgt cga c
TYR ILE SER TRP ILE ASN ASN VAL ILE ALA SER ASN OPA OCH
```

Figure 1A

```
                                                         XhoI
- ACT ATT GCC AGC ATT GCT GCT AAA GAA GAA GGG GTA TCT CTC GAG AAA AGA
- THR ILE ALA SER ILE ALA ALA LYS GLU GLU GLY VAL SER LEU GLU LYS ARG
- Yeast alpha-factor propeptide          Kex2 signal cleavage↓

GAG GCT GAA GCT ACT CAG GAC CTT CCG GAA ACC AAT GCC CGG GTA GTC GGG GGG -
GLU ALA GLU ALA THR GLN ASP LEU PRO GLU THR ASN ALA ARG VAL VAL GLY GLY -
    ↑ STE13 ↓    Activation peptide                Mature Enzyme
     signal
     cleavage
```

Figure 1B

| Propeptide Sequence | SDS-PAGE Analysis | Shaker Flask Yield | Shaker Flask Stability | Conversion Rate | % N-Terminal Variants |
|---|---|---|---|---|---|
| 24 | | High | High | Fast<br>Figure 5B | 20% |
| 42 | | Low | Low | Intermediate<br>Figure 5C | 25% |
| 48 | | Intermediate | Low | Fast<br>Figure 5D | 15% |
| 49 | | High | High | Slow<br>Figure 5E | 35% |
| 55 | | Intermediate-High | Intermediate | Intermediate<br>Figure 5F | 15% |

Figure 5A

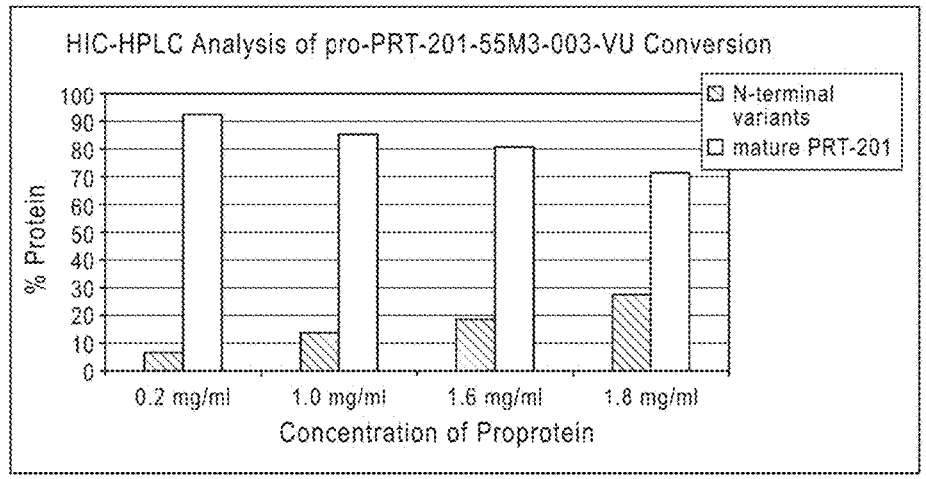

Figure 13

```
SacII
ccgcggacccaggactttccagaaaccaacgccgggtagttggagggaccgaggctcagaggaattctt
ggccatctcagatttccctccagtaccggtctggaagttcgtgggctcacacctgtggagggaccctcat
caggcagaactgggtgatgacagccgctcactgcgtggacagagagttgacttccgtgtggtggttgga
gagcacaacctgaaccagaacgatggcaccgagcagtacgtgggggtgcagaagatcgtggtgcatccct
actggaacaccgacgacgtggctgcaggctatgacatcgccctgctgcgcctggcccagagtgtaaccct
caacagctacgtccagctgggtgttctgccaagggctgggaccatcctggctaacaacagtccctgctac
atcacagggtggggcctgaccaggaccaatgggcagctggcccagaccctgcagcaggcttacctgccca
ccgtggactacgccatctgctccagctcctcgtactgggggctccaccgtgaagaacagcatggtgtgcgc
cggaggggacggagttcgctctggatgtcagggtgattctggggggccccttcattgcttggtgaatggt
cagtatgctgtccacggtgtaaccagcttcgtgtcccgcctgggctgtaatgtcaccaggaagccacag
tcttcaccagggtctctgcttacatctcttggataaataacgtcattgccagcaactgataatctaga
                                                           Stop Stop XbaI
```

Figure 14

```
TQDFPETNAR  VVGGTEAQRN  SWPSQISLQY  RSGSSWAHTC  GGTLIRQNWV
MTAAHCVDRE  LTFRVVVGEH  NLNQNDGTEQ  YVGVQKIVVH  PYWNTDDVAA
GYDIALLRLA  QSVTLNSYVQ  LGVLPRAGTI  LANNSPCYIT  GWGLTRTNGQ
LAQTLQQAYL  PTVDYAICSS  SSYWGSTVKN  SMVCAGGDGV  RSGCQGDSGG
PLHCLVNGQY  AVHGVTSFVS  RLGCNVTRKP  TVFTRVSAYI  SWINNVIASN
```

Figure 15

SEQUENCE LISTING

```
<160> NUMBER OF SEQ ID NOS: 131

<210> SEQ ID NO 1
<211> LENGTH: 240
<212> TYPE: PRT
<213> ORGANISM: Homo sapiens
<220> FEATURE:
<221> NAME/KEY: MOD_RES
<222> LOCATION: (202)..(202)
<223> OTHER INFORMATION: Val or Leu

<400> SEQUENCE: 1

Val Val Gly Gly Thr Glu Ala Gly Arg Asn Ser Trp Pro Ser Gln Ile
1               5                   10                  15

Ser Leu Gln Tyr Arg Ser Gly Gly Ser Arg Tyr His Thr Cys Gly Gly
            20                  25                  30

Thr Leu Ile Arg Gln Asn Trp Val Met Thr Ala Ala His Cys Val Asp
        35                  40                  45

Tyr Gln Lys Thr Phe Arg Val Val Ala Gly Asp His Asn Leu Ser Gln
    50                  55                  60

Asn Asp Gly Thr Glu Gln Tyr Val Ser Val Gln Lys Ile Val Val His
65                  70                  75                  80

Pro Tyr Trp Asn Ser Asp Asn Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Gln Glu Gly Ala Ile Leu Ala Asn Asn Ser Pro Cys Tyr
        115                 120                 125

Ile Thr Gly Trp Gly Lys Thr Lys Thr Asn Gly Gln Leu Ala Gln Thr
    130                 135                 140

Leu Gln Gln Ala Tyr Leu Pro Ser Val Asp Tyr Ala Ile Cys Ser Ser
145                 150                 155                 160

Ser Ser Tyr Trp Gly Ser Thr Val Lys Asn Thr Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Lys Tyr Ser Xaa His Gly Val Thr Ser Phe
        195                 200                 205

Val Ser Ser Arg Gly Cys Asn Val Ser Arg Lys Pro Thr Val Phe Thr
```

Gln Val Ser Ala Tyr Ile Ser Trp Ile Asn Asn Val Ile Ala Ser Asn
225                 230                 235                 240

<210> SEQ ID NO 2
<211> LENGTH: 239
<212> TYPE: PRT
<213> ORGANISM: Homo sapiens
<220> FEATURE:
<221> NAME/KEY: MOD_RES
<222> LOCATION: (201)..(201)
<223> OTHER INFORMATION: Val or Leu

<400> SEQUENCE: 2

Val Gly Gly Thr Glu Ala Gly Arg Asn Ser Trp Pro Ser Gln Ile Ser
1               5                   10                  15

Leu Gln Tyr Arg Ser Gly Gly Ser Arg Tyr His Thr Cys Gly Gly Thr
            20                  25                  30

Leu Ile Arg Gln Asn Trp Val Met Thr Ala Ala His Cys Val Asp Tyr
        35                  40                  45

Gln Lys Thr Phe Arg Val Val Ala Gly Asp His Asn Leu Ser Gln Asn
    50                  55                  60

Asp Gly Thr Glu Gln Tyr Val Ser Val Gln Lys Ile Val Val His Pro
65                  70                  75                  80

Tyr Trp Asn Ser Asp Asn Val Ala Ala Gly Tyr Asp Ile Ala Leu Leu
                85                  90                  95

Arg Leu Ala Gln Ser Val Thr Leu Asn Ser Tyr Val Gln Leu Gly Val
            100                 105                 110

Leu Pro Gln Glu Gly Ala Ile Leu Ala Asn Asn Ser Pro Cys Tyr Ile
        115                 120                 125

Thr Gly Trp Gly Lys Thr Lys Thr Asn Gly Gln Leu Ala Gln Thr Leu
    130                 135                 140

Gln Gln Ala Tyr Leu Pro Ser Val Asp Tyr Ala Ile Cys Ser Ser Ser
145                 150                 155                 160

Ser Tyr Trp Gly Ser Thr Val Lys Asn Thr Met Val Cys Ala Gly Gly
                165                 170                 175

Asp Gly Val Arg Ser Gly Cys Gln Gly Asp Ser Gly Gly Pro Leu His
            180                 185                 190

Cys Leu Val Asn Gly Lys Tyr Ser Xaa His Gly Val Thr Ser Phe Val
        195                 200                 205

Ser Ser Arg Gly Cys Asn Val Ser Arg Lys Pro Thr Val Phe Thr Gln
    210                 215                 220

Val Ser Ala Tyr Ile Ser Trp Ile Asn Asn Val Ile Ala Ser Asn
225                 230                 235

<210> SEQ ID NO 3
<211> LENGTH: 238
<212> TYPE: PRT
<213> ORGANISM: Homo sapiens
<220> FEATURE:
<221> NAME/KEY: MOD_RES
<222> LOCATION: (200)..(200)
<223> OTHER INFORMATION: Val or Leu

<400> SEQUENCE: 3

Gly Gly Thr Glu Ala Gly Arg Asn Ser Trp Pro Ser Gln Ile Ser Leu
1               5                   10                  15

Gln Tyr Arg Ser Gly Gly Ser Arg Tyr His Thr Cys Gly Gly Thr Leu
            20                  25                  30

```
Ile Arg Gln Asn Trp Val Met Thr Ala Ala His Cys Val Asp Tyr Gln
        35                  40                  45

Lys Thr Phe Arg Val Val Ala Gly Asp His Asn Leu Ser Gln Asn Asp
 50                  55                  60

Gly Thr Glu Gln Tyr Val Ser Val Gln Lys Ile Val Val His Pro Tyr
 65                  70                  75                  80

Trp Asn Ser Asp Asn Val Ala Ala Gly Tyr Asp Ile Ala Leu Leu Arg
                 85                  90                  95

Leu Ala Gln Ser Val Thr Leu Asn Ser Tyr Val Gln Leu Gly Val Leu
                100                 105                 110

Pro Gln Glu Gly Ala Ile Leu Ala Asn Asn Ser Pro Cys Tyr Ile Thr
                115                 120                 125

Gly Trp Gly Lys Thr Lys Thr Asn Gly Gln Leu Ala Gln Thr Leu Gln
        130                 135                 140

Gln Ala Tyr Leu Pro Ser Val Asp Tyr Ala Ile Cys Ser Ser Ser Ser
145                 150                 155                 160

Tyr Trp Gly Ser Thr Val Lys Asn Thr Met Val Cys Ala Gly Gly Asp
                165                 170                 175

Gly Val Arg Ser Gly Cys Gln Gly Asp Ser Gly Gly Pro Leu His Cys
                180                 185                 190

Leu Val Asn Gly Lys Tyr Ser Xaa His Gly Val Thr Ser Phe Val Ser
                195                 200                 205

Ser Arg Gly Cys Asn Val Ser Arg Lys Pro Thr Val Phe Thr Gln Val
        210                 215                 220

Ser Ala Tyr Ile Ser Trp Ile Asn Asn Val Ile Ala Ser Asn
225                 230                 235

<210> SEQ ID NO 4
<211> LENGTH: 240
<212> TYPE: PRT
<213> ORGANISM: Homo sapiens
<220> FEATURE:
<221> NAME/KEY: MOD_RES
<222> LOCATION: (202)..(202)
<223> OTHER INFORMATION: Val or Leu

<400> SEQUENCE: 4

Ala Val Gly Gly Thr Glu Ala Gly Arg Asn Ser Trp Pro Ser Gln Ile
 1               5                  10                  15

Ser Leu Gln Tyr Arg Ser Gly Gly Ser Arg Tyr His Thr Cys Gly Gly
                20                  25                  30

Thr Leu Ile Arg Gln Asn Trp Val Met Thr Ala Ala His Cys Val Asp
        35                  40                  45

Tyr Gln Lys Thr Phe Arg Val Val Ala Gly Asp His Asn Leu Ser Gln
 50                  55                  60

Asn Asp Gly Thr Glu Gln Tyr Val Ser Val Gln Lys Ile Val Val His
65                  70                  75                  80

Pro Tyr Trp Asn Ser Asp Asn Val Ala Ala Gly Tyr Asp Ile Ala Leu
                 85                  90                  95

Leu Arg Leu Ala Gln Ser Val Thr Leu Asn Ser Tyr Val Gln Leu Gly
                100                 105                 110

Val Leu Pro Gln Glu Gly Ala Ile Leu Ala Asn Asn Ser Pro Cys Tyr
                115                 120                 125

Ile Thr Gly Trp Gly Lys Thr Lys Thr Asn Gly Gln Leu Ala Gln Thr
        130                 135                 140
```

```
Leu Gln Gln Ala Tyr Leu Pro Ser Val Asp Tyr Ala Ile Cys Ser Ser
145                 150                 155                 160

Ser Ser Tyr Trp Gly Ser Thr Val Lys Asn Thr Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Lys Tyr Ser Xaa His Gly Val Thr Ser Phe
        195                 200                 205

Val Ser Ser Arg Gly Cys Asn Val Ser Arg Lys Pro Thr Val Phe Thr
        210                 215                 220

Gln Val Ser Ala Tyr Ile Ser Trp Ile Asn Asn Val Ile Ala Ser Asn
225                 230                 235                 240

<210> SEQ ID NO 5
<211> LENGTH: 186
<212> TYPE: PRT
<213> ORGANISM: Homo sapiens

<400> SEQUENCE: 5

Val Val Gly Gly Thr Glu Ala Gly Arg Asn Ser Trp Pro Ser Gln Ile
1               5                   10                  15

Ser Leu Gln Tyr Arg Ser Gly Gly Ser Arg Tyr His Thr Cys Gly Gly
            20                  25                  30

Thr Leu Ile Arg Gln Asn Trp Val Met Thr Ala Ala His Cys Val Asp
        35                  40                  45

Tyr Gln Lys Thr Phe Arg Val Val Ala Gly Asp His Asn Leu Ser Gln
    50                  55                  60

Asn Asp Gly Thr Glu Gln Tyr Val Ser Val Gln Lys Ile Val Val His
65                  70                  75                  80

Pro Tyr Trp Asn Ser Asp Asn Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Gln Glu Gly Ala Ile Leu Ala Asn Asn Ser Pro Cys Tyr
        115                 120                 125

Ile Thr Gly Trp Gly Lys Thr Lys Thr Asn Gly Gln Leu Ala Gln Thr
    130                 135                 140

Leu Gln Gln Ala Tyr Leu Pro Ser Val Asp Tyr Ala Ile Cys Ser Ser
145                 150                 155                 160

Ser Ser Tyr Trp Gly Ser Thr Val Lys Asn Thr Met Val Cys Ala Gly
                165                 170                 175

Gly Asp Gly Ser Ser Leu Trp Met Pro Gly
            180                 185

<210> SEQ ID NO 6
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (212)..(212)
<223> OTHER INFORMATION: Val or Leu

<400> SEQUENCE: 6

Thr Gln Asp Leu Pro Glu Thr Asn Ala Ala Val Val Gly Gly Thr Glu
1               5                   10                  15
```

Ala Gly Arg Asn Ser Trp Pro Ser Gln Ile Ser Leu Gln Tyr Arg Ser
            20                  25                  30

Gly Gly Ser Arg Tyr His Thr Cys Gly Gly Thr Leu Ile Arg Gln Asn
        35                  40                  45

Trp Val Met Thr Ala Ala His Cys Val Asp Tyr Gln Lys Thr Phe Arg
 50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Ser Arg Gly Cys
    210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 7
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (212)..(212)
<223> OTHER INFORMATION: Val or Leu

<400> SEQUENCE: 7

Thr Gln Asp Leu Pro Glu Thr Asn Ala Ala Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Arg Tyr His Thr Cys Gly Gly Thr Leu Ile Arg Gln Asn
        35                  40                  45

Trp Val Met Thr Ala Ala His Cys Val Asp Tyr Gln Lys Thr Phe Arg
 50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

```
Asn Val Ala Ala Gly Tyr Asp Ile Ala Leu Leu Arg Leu Ala Gln Ser
                100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
        180                 185                 190

Gly Cys Gln Gly Asp Ser Gly Gly Pro Leu His Cys Leu Val Asn Gly
    195                 200                 205

Lys Tyr Ser Xaa His Gly Val Thr Ser Phe Val Ser Ser Arg Gly Cys
        210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 8
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (212)..(212)
<223> OTHER INFORMATION: Val or Leu

<400> SEQUENCE: 8

Thr Gln Asp Leu Pro Glu Thr Ala Ala Val Val Gly Gly Thr Glu
1               5                   10                  15

Ala Gly Arg Asn Ser Trp Pro Ser Gln Ile Ser Leu Gln Tyr Arg Ser
                20                  25                  30

Gly Gly Ser Arg Tyr His Thr Cys Gly Gly Thr Leu Ile Arg Gln Asn
        35                  40                  45

Trp Val Met Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
                100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
```

```
                      180                 185                 190
Gly Cys Gln Gly Asp Ser Gly Gly Pro Leu His Cys Leu Val Asn Gly
            195                 200                 205

Lys Tyr Ser Xaa His Gly Val Thr Ser Phe Val Ser Ser Arg Gly Cys
210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
            245                 250

<210> SEQ ID NO 9
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (212)..(212)
<223> OTHER INFORMATION: Val or Leu

<400> SEQUENCE: 9

Thr Gln Asp Leu Pro Glu Thr Asn Asn Ala Pro Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Arg Tyr His Thr Cys Gly Gly Thr Leu Ile Arg Gln Asn
        35                  40                  45

Trp Val Met Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Ser Arg Gly Cys
    210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 10
```

-continued

```
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (212)..(212)
<223> OTHER INFORMATION: Val or Leu

<400> SEQUENCE: 10

Thr Gln Asp Leu Pro Glu Thr Asn Ala Arg Val Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Arg Tyr His Thr Cys Gly Gly Thr Leu Ile Arg Gln Asn
        35                  40                  45

Trp Val Met Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Ser Arg Gly Cys
    210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Leu, Ile, Met, Lys, Asp, or Val
<220> FEATURE:
<221> NAME/KEY: MOD_RES
<222> LOCATION: (2)..(2)
<223> OTHER INFORMATION: Pro, Ala, Leu, Ile, Gly, Val, or Thr
<220> FEATURE:
<221> NAME/KEY: MOD_RES
```

```
<222> LOCATION: (3)..(3)
<223> OTHER INFORMATION: Ala, Leu, Val, Ile, or Ser
<220> FEATURE:
<223> OTHER INFORMATION: see specification as filed for detailed
      description of substitutions and preferred embodiments

<400> SEQUENCE: 11

Xaa Xaa Xaa
1

<210> SEQ ID NO 12
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Leu, Ile, Met, Lys, or Val
<220> FEATURE:
<221> NAME/KEY: MOD_RES
<222> LOCATION: (3)..(3)
<223> OTHER INFORMATION: Ala, Leu, Val, Ile, or Ser
<220> FEATURE:
<223> OTHER INFORMATION: see specification as filed for detailed
      description of substitutions and preferred embodiments

<400> SEQUENCE: 12

Xaa Pro Xaa
1

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Ala
<220> FEATURE:
<221> NAME/KEY: MOD_RES
<222> LOCATION: (2)..(2)
<223> OTHER INFORMATION: Pro or Ala
<220> FEATURE:
<221> NAME/KEY: MOD_RES
<222> LOCATION: (3)..(3)
<223> OTHER INFORMATION: Ala, Leu, or Val

<400> SEQUENCE: 13

Xaa Xaa Xaa
1

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ala
1

<210> SEQ ID NO 15
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asn Ala Ala
1

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Ala Pro
1

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Ala Arg
1

<210> SEQ ID NO 18
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Pro Ala
1

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Pro
1

<210> SEQ ID NO 20
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Pro Ala
```

```
<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Pro Ala
1

<210> SEQ ID NO 22
<211> LENGTH: 10
<212> TYPE: PRT
<213> ORGANISM: Homo sapiens

<400> SEQUENCE: 22

Thr Gln Asp Leu Pro Glu Thr Asn Ala Arg
1               5                   10

<210> SEQ ID NO 23
<211> LENGTH: 10
<212> TYPE: PRT
<213> ORGANISM: Homo sapiens

<400> SEQUENCE: 23

Thr Gln Asp Leu Pro Glu Thr Asn Ala Ala
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Thr Asn Ala Arg Val Val Gly
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Ala Ala Ala Val Val Gly Gly
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Asn Ala Ala Ala Val Gly Gly
1               5
```

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Asn Ala Ala Val Val Gly Gly
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Asn Ala Pro Val Val Gly Gly
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Gly Ala Gly Ile Val Gly Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Val Pro Gly Val Val Gly Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Ala Pro Gly Val Val Gly Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Asn Pro Gly Val Val Gly Gly
1               5

<210> SEQ ID NO 33
<211> LENGTH: 753
<212> TYPE: DNA
<213> ORGANISM: Homo sapiens

<400> SEQUENCE: 33

| acccaggacc ttccggaaac caatgcccgc gtagtcggag ggactgaggc cgggaggaat | 60 |
| tcctggccct ctcagatttc cctccagtac cggtctggag gttcccggta tcacacctgt | 120 |
| ggagggaccc ttatcagaca gaactgggtg atgacagctg ctcactgcgt ggattaccag | 180 |
| aagactttcc gcgtggtggc tggagaccat aacctgagcc agaatgatgg cactgagcag | 240 |
| tacgtgagtg tgcagaagat cgtggtgcat ccatactgga acagcgataa cgtggctgcc | 300 |
| ggctatgaca tcgccctgct cgcctggcc cagagcgtta ccctcaatag ctatgtccag | 360 |
| ctgggtgttc tgcccagga gggagccatc ctggctaaca acagtccctg ctacatcaca | 420 |
| ggctggggca agaccaagac caatgggcag ctggcccaga ccctgcagca ggcttacctg | 480 |
| ccctctgtgg actacgccat ctgctccagc tcctcctact ggggctccac tgtgaagaac | 540 |
| accatggtgt gtgctggtgg agatggagtt cgctctggat gccagggtga ctctgggggc | 600 |
| cccctccatt gcttggtgaa tggcaagtat tctgtccatg gagtgaccag ctttgtgtcc | 660 |
| agccggggct gtaatgtctc caggaagcct acagtcttca cccaggtctc tgcttacatc | 720 |
| tcctggataa ataatgtcat cgcctccaac tga | 753 |

<210> SEQ ID NO 34
<211> LENGTH: 24
<212> TYPE: PRT
<213> ORGANISM: Unknown
<220> FEATURE:
<223> OTHER INFORMATION: Description of Unknown: Yeast alpha factor
      signal peptide

<400> SEQUENCE: 34

Met Arg Phe Pro Ser Ile Phe Thr Ala Val Leu Phe Ala Ala Ser Ser
1               5                   10                  15

Ala Leu Ala Ala Pro Val Asn Thr
            20

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggctcgagaa aagagaggct gaagctactc aggaccttcc ggaaaccaat gcccgg      56

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 36
gggccgcggc ttatcagttg gaggcgatga cat                                  33

<210> SEQ ID NO 37
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (204)..(204)
<223> OTHER INFORMATION: Val or Leu

<400> SEQUENCE: 37
```

Ala Ala Val Val Gly Gly Thr Glu Ala Gly Arg Asn Ser Trp Pro Ser
1               5                   10                  15

Gln Ile Ser Leu Gln Tyr Arg Ser Gly Gly Ser Arg Tyr His Thr Cys
            20                  25                  30

Gly Gly Thr Leu Ile Arg Gln Asn Trp Val Met Thr Ala Ala His Cys
        35                  40                  45

Val Asp Tyr Gln Lys Thr Phe Arg Val Val Ala Gly Asp His Asn Leu
    50                  55                  60

Ser Gln Asn Asp Gly Thr Glu Gln Tyr Val Ser Val Gln Lys Ile Val
65                  70                  75                  80

Val His Pro Tyr Trp Asn Ser Asp Asn Val Ala Ala Gly Tyr Asp Ile
                85                  90                  95

Ala Leu Leu Arg Leu Ala Gln Ser Val Thr Leu Asn Ser Tyr Val Gln
            100                 105                 110

Leu Gly Val Leu Pro Gln Glu Gly Ala Ile Leu Ala Asn Asn Ser Pro
        115                 120                 125

Cys Tyr Ile Thr Gly Trp Gly Lys Thr Lys Thr Asn Gly Gln Leu Ala
    130                 135                 140

Gln Thr Leu Gln Gln Ala Tyr Leu Pro Ser Val Asp Tyr Ala Ile Cys
145                 150                 155                 160

Ser Ser Ser Ser Tyr Trp Gly Ser Thr Val Lys Asn Thr Met Val Cys
                165                 170                 175

Ala Gly Gly Asp Gly Val Arg Ser Gly Cys Gln Gly Asp Ser Gly Gly
            180                 185                 190

Pro Leu His Cys Leu Val Asn Gly Lys Tyr Ser Xaa His Gly Val Thr
        195                 200                 205

Ser Phe Val Ser Ser Arg Gly Cys Asn Val Ser Arg Lys Pro Thr Val
    210                 215                 220

Phe Thr Gln Val Ser Ala Tyr Ile Ser Trp Ile Asn Asn Val Ile Ala
225                 230                 235                 240

Ser Asn

```
<210> SEQ ID NO 38
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (203)..(203)
<223> OTHER INFORMATION: Val or Leu
```

<400> SEQUENCE: 38

```
Ala Val Val Gly Gly Thr Glu Ala Gly Arg Asn Ser Trp Pro Ser Gln
1               5                   10                  15

Ile Ser Leu Gln Tyr Arg Ser Gly Gly Ser Arg Tyr His Thr Cys Gly
            20                  25                  30

Gly Thr Leu Ile Arg Gln Asn Trp Val Met Thr Ala Ala His Cys Val
        35                  40                  45

Asp Tyr Gln Lys Thr Phe Arg Val Val Ala Gly Asp His Asn Leu Ser
    50                  55                  60

Gln Asn Asp Gly Thr Glu Gln Tyr Val Ser Val Gln Lys Ile Val Val
65                  70                  75                  80

His Pro Tyr Trp Asn Ser Asp Asn Val Ala Ala Gly Tyr Asp Ile Ala
                85                  90                  95

Leu Leu Arg Leu Ala Gln Ser Val Thr Leu Asn Ser Tyr Val Gln Leu
            100                 105                 110

Gly Val Leu Pro Gln Glu Gly Ala Ile Leu Ala Asn Asn Ser Pro Cys
        115                 120                 125

Tyr Ile Thr Gly Trp Gly Lys Thr Lys Thr Asn Gly Gln Leu Ala Gln
    130                 135                 140

Thr Leu Gln Gln Ala Tyr Leu Pro Ser Val Asp Tyr Ala Ile Cys Ser
145                 150                 155                 160

Ser Ser Ser Tyr Trp Gly Ser Thr Val Lys Asn Thr Met Val Cys Ala
                165                 170                 175

Gly Gly Asp Gly Val Arg Ser Gly Cys Gln Gly Asp Ser Gly Gly Pro
            180                 185                 190

Leu His Cys Leu Val Asn Gly Lys Tyr Ser Xaa His Gly Val Thr Ser
        195                 200                 205

Phe Val Ser Ser Arg Gly Cys Asn Val Ser Arg Lys Pro Thr Val Phe
    210                 215                 220

Thr Gln Val Ser Ala Tyr Ile Ser Trp Ile Asn Asn Val Ile Ala Ser
225                 230                 235                 240

Asn

<210> SEQ ID NO 39
<211> LENGTH: 240
<212> TYPE: PRT
<213> ORGANISM: Sus scrofa

<400> SEQUENCE: 39

Val Val Gly Gly Thr Glu Ala Gln Arg Asn Ser Trp Pro Ser Gln Ile
1               5                   10                  15

Ser Leu Gln Tyr Arg Ser Gly Ser Ser Trp Ala His Thr Cys Gly Gly
            20                  25                  30

Thr Leu Ile Arg Gln Asn Trp Val Met Thr Ala Ala His Cys Val Asp
        35                  40                  45

Arg Glu Leu Thr Phe Arg Val Val Val Gly Glu His Asn Leu Asn Gln
    50                  55                  60

Asn Asp Gly Thr Glu Gln Tyr Val Gly Val Gln Lys Ile Val Val His
65                  70                  75                  80

Pro Tyr Trp Asn Thr Asp Asp Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Arg Ala Gly Thr Ile Leu Ala Asn Asn Ser Pro Cys Tyr
```

```
                115                 120                 125
Ile Thr Gly Trp Gly Leu Thr Arg Thr Asn Gly Gln Leu Ala Gln Thr
            130                 135                 140

Leu Gln Gln Ala Tyr Leu Pro Thr Val Asp Tyr Ala Ile Cys Ser Ser
145                 150                 155                 160

Ser Ser Tyr Trp Gly Ser Thr Val Lys Asn Ser Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Gln Tyr Ala Val His Gly Val Thr Ser Phe
            195                 200                 205

Val Ser Arg Leu Gly Cys Asn Val Thr Arg Lys Pro Thr Val Phe Thr
210                 215                 220

Arg Val Ser Ala Tyr Ile Ser Trp Ile Asn Asn Val Ile Ala Ser Asn
225                 230                 235                 240

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Thr Ala Ala Ala Val Val Gly
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Thr Asn Ala Ala Ala Val Gly
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Thr Asn Ala Ala Val Val Gly
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Thr Asn Ala Pro Val Val Gly
1               5
```

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Thr Gly Ala Gly Ile Val Gly
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Glu Thr Val Pro Gly Val Val Gly
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Glu Thr Ala Pro Gly Val Val Gly
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Thr Asn Pro Gly Val Val Gly
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Thr Asn Pro Ala Val Val Gly
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 49

Glu Thr Asn His Ala Val Val Gly
1               5

<210> SEQ ID NO 50
<211> LENGTH: 90
<212> TYPE: PRT
<213> ORGANISM: Unknown
<220> FEATURE:
<223> OTHER INFORMATION: Description of Unknown: Yeast alpha-mating
      factor signal peptide, propeptide, and spacer sequence 1

<400> SEQUENCE: 50

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Asn Gly Leu
    50                  55                  60

Leu Phe Ile Asn Thr Thr Ile Ala Ser Ile Ala Ala Lys Glu Glu Gly
65                  70                  75                  80

Val Ser Leu Asp Lys Arg Glu Ala Glu Ala
                85                  90

<210> SEQ ID NO 51
<211> LENGTH: 84
<212> TYPE: PRT
<213> ORGANISM: Unknown
<220> FEATURE:
<223> OTHER INFORMATION: Description of Unknown: Yeast alpha-mating
      factor signal peptide and propeptide sequence 2

<400> SEQUENCE: 51

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Asn Gly Leu
    50                  55                  60

Leu Phe Ile Asn Thr Thr Ile Ala Ser Ile Ala Ala Lys Glu Glu Gly
65                  70                  75                  80

Val Ser Leu Asp

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Thr Lys Pro Ala Val Val Gly
1               5

<210> SEQ ID NO 53
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Thr His Pro Ala Val Val Gly
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu His Asn Pro Ala Val Val Gly
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

His Thr Asn Pro Ala Val Val Gly
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Pro Thr His Pro Ala Val Val Gly
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Thr Asn Pro Ala Val Val Gly
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His Thr His Pro Ala Val Val Gly
```

```
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Glu Thr Phe Pro Ala Val Val Gly
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

His Thr Phe Pro Ala Val Val Gly
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Thr Phe Pro Ala Val Val Gly
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His Thr Gly Pro Ala Val Val Gly
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

His Thr Lys Pro Ala Val Val Gly
1               5

<210> SEQ ID NO 64
<211> LENGTH: 250
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<221> NAME/KEY: MOD_RES
<222> LOCATION: (212)..(212)
<223> OTHER INFORMATION: Val or Leu

<400> SEQUENCE: 64

Thr Gln Asp Leu Pro Glu Thr Asn Pro Ala Val Val Gly Gly Thr Glu
1               5                  10                  15

Ala Gly Arg Asn Ser Trp Pro Ser Gln Ile Ser Leu Gln Tyr Arg Ser
            20                  25                  30

Gly Gly Ser Arg Tyr His Thr Cys Gly Gly Thr Leu Ile Arg Gln Asn
        35                  40                  45

Trp Val Met Thr Ala Ala His Cys Val Asp Tyr Gln Lys Thr Phe Arg
50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Ser Arg Gly Cys
    210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 65
<211> LENGTH: 250
<212> TYPE: PRT
<213> ORGANISM: Artificial Sequence
<220> FEATURE:
<223> OTHER INFORMATION: Description of Artificial Sequence: Synthetic
        polypeptide
<220> FEATURE:
<221> NAME/KEY: MOD_RES
<222> LOCATION: (212)..(212)
<223> OTHER INFORMATION: Val or Leu

<400> SEQUENCE: 65

Thr Gln Asp Leu Pro Glu Thr Asn His Ala Val Val Gly Gly Thr Glu
1               5                  10                  15

Ala Gly Arg Asn Ser Trp Pro Ser Gln Ile Ser Leu Gln Tyr Arg Ser
            20                  25                  30

Gly Gly Ser Arg Tyr His Thr Cys Gly Gly Thr Leu Ile Arg Gln Asn
        35                  40                  45
```

Trp Val Met Thr Ala Ala His Cys Val Asp Tyr Gln Lys Thr Phe Arg
            50                  55                  60

Val Val Ala Gly Asp His Asn Leu Ser Gln Asn Asp Gly Thr Glu Gln
 65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
               100                 105                 110

Val Thr Leu Asn Ser Tyr Val Gln Leu Gly Val Leu Pro Gln Glu Gly
               115                 120                 125

Ala Ile Leu Ala Asn Asn Ser Pro Cys Tyr Ile Thr Gly Trp Gly Lys
           130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
                180                 185                 190

Gly Cys Gln Gly Asp Ser Gly Gly Pro Leu His Cys Leu Val Asn Gly
                195                 200                 205

Lys Tyr Ser Xaa His Gly Val Thr Ser Phe Val Ser Ser Arg Gly Cys
            210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 66
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (212)..(212)
<223> OTHER INFORMATION: Val or Leu

<400> SEQUENCE: 66

Thr Gln Asp Leu Pro Glu Thr Lys Pro Ala Val Val Gly Gly Thr Glu
 1               5                  10                  15

Ala Gly Arg Asn Ser Trp Pro Ser Gln Ile Ser Leu Gln Tyr Arg Ser
                20                  25                  30

Gly Gly Ser Arg Tyr His Thr Cys Gly Gly Thr Leu Ile Arg Gln Asn
            35                  40                  45

Trp Val Met Thr Ala Ala His Cys Val Asp Tyr Gln Lys Thr Phe Arg
            50                  55                  60

Val Val Ala Gly Asp His Asn Leu Ser Gln Asn Asp Gly Thr Glu Gln
 65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
               100                 105                 110

Val Thr Leu Asn Ser Tyr Val Gln Leu Gly Val Leu Pro Gln Glu Gly
               115                 120                 125

```
Ala Ile Leu Ala Asn Asn Ser Pro Cys Tyr Ile Thr Gly Trp Gly Lys
        130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Ser Arg Gly Cys
        210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 67
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (212)..(212)
<223> OTHER INFORMATION: Val or Leu

<400> SEQUENCE: 67

Thr Gln Asp Leu Pro Glu Thr His Pro Ala Val Val Gly Gly Thr Glu
1               5                   10                  15

Ala Gly Arg Asn Ser Trp Pro Ser Gln Ile Ser Leu Gln Tyr Arg Ser
                20                  25                  30

Gly Gly Ser Arg Tyr His Thr Cys Gly Gly Thr Leu Ile Arg Gln Asn
            35                  40                  45

Trp Val Met Thr Ala Ala His Cys Val Asp Tyr Gln Lys Thr Phe Arg
50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
        130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Ser Arg Gly Cys
```

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 68
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (212)..(212)
<223> OTHER INFORMATION: Val or Leu

<400> SEQUENCE: 68

Thr Gln Asp Leu Pro Glu His Asn Pro Ala Val Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Arg Tyr His Thr Cys Gly Gly Thr Leu Ile Arg Gln Asn
        35                  40                  45

Trp Val Met Thr Ala Ala His Cys Val Asp Tyr Gln Lys Thr Phe Arg
50                  55                  60

Val Val Ala Gly Asp His Asn Leu Ser Gln Asn Asp Gly Thr Glu Gln
65                  70                  75                  80

Tyr Val Ser Val Gln Lys Ile Val His Pro Tyr Trp Asn Ser Asp
                85                  90                  95

Asn Val Ala Ala Gly Tyr Asp Ile Ala Leu Leu Arg Leu Ala Gln Ser
                100                 105                 110

Val Thr Leu Asn Ser Tyr Val Gln Leu Gly Val Leu Pro Gln Glu Gly
            115                 120                 125

Ala Ile Leu Ala Asn Asn Ser Pro Cys Tyr Ile Thr Gly Trp Gly Lys
        130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Ser Arg Gly Cys
    210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 69
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<221> NAME/KEY: MOD_RES
<222> LOCATION: (212)..(212)
<223> OTHER INFORMATION: Val or Leu

<400> SEQUENCE: 69

Thr Gln Asp Leu Pro His Thr Asn Pro Ala Val Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Arg Tyr His Thr Cys Gly Gly Thr Leu Ile Arg Gln Asn
        35                  40                  45

Trp Val Met Thr Ala Ala His Cys Val Asp Tyr Gln Lys Thr Phe Arg
50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Ser Arg Gly Cys
210                 215                 220

Asn Val Ser Arg Lys Pro Thr Val Phe Thr Gln Val Ser Ala Tyr Ile
225                 230                 235                 240

Ser Trp Ile Asn Asn Val Ile Ala Ser Asn
                245                 250

<210> SEQ ID NO 70
<211> LENGTH: 242
<212> TYPE: PRT
<213> ORGANISM: Homo sapiens
<220> FEATURE:
<221> NAME/KEY: MOD_RES
<222> LOCATION: (204)..(204)
<223> OTHER INFORMATION: Val or Leu

<400> SEQUENCE: 70

Ala Arg Val Val Gly Gly Thr Glu Ala Gly Arg Asn Ser Trp Pro Ser
1               5                   10                  15

Gln Ile Ser Leu Gln Tyr Arg Ser Gly Gly Ser Arg Tyr His Thr Cys
            20                  25                  30

Gly Gly Thr Leu Ile Arg Gln Asn Trp Val Met Thr Ala Ala His Cys
        35                  40                  45

Val Asp Tyr Gln Lys Thr Phe Arg Val Val Ala Gly Asp His Asn Leu
50                  55                  60

```
Ser Gln Asn Asp Gly Thr Glu Gln Tyr Val Ser Val Gln Lys Ile Val
 65                  70                  75                  80

Val His Pro Tyr Trp Asn Ser Asp Asn Val Ala Ala Gly Tyr Asp Ile
                 85                  90                  95

Ala Leu Leu Arg Leu Ala Gln Ser Val Thr Leu Asn Ser Tyr Val Gln
            100                 105                 110

Leu Gly Val Leu Pro Gln Glu Gly Ala Ile Leu Ala Asn Asn Ser Pro
            115                 120                 125

Cys Tyr Ile Thr Gly Trp Gly Lys Thr Lys Thr Asn Gly Gln Leu Ala
130                 135                 140

Gln Thr Leu Gln Gln Ala Tyr Leu Pro Ser Val Asp Tyr Ala Ile Cys
145                 150                 155                 160

Ser Ser Ser Ser Tyr Trp Gly Ser Thr Val Lys Asn Thr Met Val Cys
                165                 170                 175

Ala Gly Gly Asp Gly Val Arg Ser Gly Cys Gln Gly Asp Ser Gly Gly
                180                 185                 190

Pro Leu His Cys Leu Val Asn Gly Lys Tyr Ser Xaa His Gly Val Thr
            195                 200                 205

Ser Phe Val Ser Ser Arg Gly Cys Asn Val Ser Arg Lys Pro Thr Val
210                 215                 220

Phe Thr Gln Val Ser Ala Tyr Ile Ser Trp Ile Asn Asn Val Ile Ala
225                 230                 235                 240

Ser Asn

<210> SEQ ID NO 71
<211> LENGTH: 241
<212> TYPE: PRT
<213> ORGANISM: Homo sapiens
<220> FEATURE:
<221> NAME/KEY: MOD_RES
<222> LOCATION: (203)..(203)
<223> OTHER INFORMATION: Val or Leu

<400> SEQUENCE: 71

Arg Val Val Gly Gly Thr Glu Ala Gly Arg Asn Ser Trp Pro Ser Gln
  1               5                  10                  15

Ile Ser Leu Gln Tyr Arg Ser Gly Gly Ser Arg Tyr His Thr Cys Gly
                 20                  25                  30

Gly Thr Leu Ile Arg Gln Asn Trp Val Met Thr Ala Ala His Cys Val
             35                  40                  45

Asp Tyr Gln Lys Thr Phe Arg Val Val Ala Gly Asp His Asn Leu Ser
         50                  55                  60

Gln Asn Asp Gly Thr Glu Gln Tyr Val Ser Val Gln Lys Ile Val Val
 65                  70                  75                  80

His Pro Tyr Trp Asn Ser Asp Asn Val Ala Ala Gly Tyr Asp Ile Ala
                 85                  90                  95

Leu Leu Arg Leu Ala Gln Ser Val Thr Leu Asn Ser Tyr Val Gln Leu
            100                 105                 110

Gly Val Leu Pro Gln Glu Gly Ala Ile Leu Ala Asn Asn Ser Pro Cys
            115                 120                 125

Tyr Ile Thr Gly Trp Gly Lys Thr Lys Thr Asn Gly Gln Leu Ala Gln
130                 135                 140

Thr Leu Gln Gln Ala Tyr Leu Pro Ser Val Asp Tyr Ala Ile Cys Ser
145                 150                 155                 160

Ser Ser Ser Tyr Trp Gly Ser Thr Val Lys Asn Thr Met Val Cys Ala
                165                 170                 175
```

-continued

```
Gly Gly Asp Gly Val Arg Ser Gly Cys Gln Gly Asp Ser Gly Gly Pro
            180                 185                 190

Leu His Cys Leu Val Asn Gly Lys Tyr Ser Xaa His Gly Val Thr Ser
        195                 200                 205

Phe Val Ser Ser Arg Gly Cys Asn Val Ser Arg Lys Pro Thr Val Phe
    210                 215                 220

Thr Gln Val Ser Ala Tyr Ile Ser Trp Ile Asn Asn Val Ile Ala Ser
225                 230                 235                 240

Asn

<210> SEQ ID NO 72
<211> LENGTH: 10
<212> TYPE: PRT
<213> ORGANISM: Homo sapiens

<400> SEQUENCE: 72

Thr Gln Asp Leu Pro Glu Thr Asn Pro Ala
1               5                   10

<210> SEQ ID NO 73
<211> LENGTH: 10
<212> TYPE: PRT
<213> ORGANISM: Homo sapiens

<400> SEQUENCE: 73

Thr Gln Asp Leu Pro His Thr Asn Pro Ala
1               5                   10

<210> SEQ ID NO 74
<211> LENGTH: 8
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Glu, His, Pro, Gly, Asp, Lys, or Ala
<220> FEATURE:
<221> NAME/KEY: MOD_RES
<222> LOCATION: (2)..(2)
<223> OTHER INFORMATION: Thr, Ala, Pro or His
<220> FEATURE:
<221> NAME/KEY: MOD_RES
<222> LOCATION: (3)..(3)
<223> OTHER INFORMATION: Ala, Leu, Ile, Met, Lys, Asp, or Val
<220> FEATURE:
<221> NAME/KEY: MOD_RES
<222> LOCATION: (4)..(4)
<223> OTHER INFORMATION: Pro, Ala, Leu, Ile, Gly, Val, or Thr
<220> FEATURE:
<221> NAME/KEY: MOD_RES
<222> LOCATION: (5)..(6)
<223> OTHER INFORMATION: Ala, Leu, Val, Ile, or Ser
<220> FEATURE:
<221> NAME/KEY: MOD_RES
<222> LOCATION: (7)..(7)
<223> OTHER INFORMATION: Gly, Ala, or Val
<220> FEATURE:
<221> NAME/KEY: MOD_RES
<222> LOCATION: (8)..(8)
<223> OTHER INFORMATION: Val, Thr, Phe, Tyr, or Trp

<400> SEQUENCE: 74

Xaa Xaa Xaa Xaa Xaa Xaa Xaa Xaa
1               5

<210> SEQ ID NO 75
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
atctacgtag tcggagggac tgaggcc                                         27

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gtcgacaagc ttatcagttg gaggcgat                                        28

<210> SEQ ID NO 77
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77
```

Val Val Gly Gly Thr Glu Ala Gly Arg Asn Ser Trp Pro Ser Gln Ile
1               5                   10                  15

Ser Leu Gln Tyr Arg Ser Gly Ser Arg Tyr His Thr Cys Gly Gly
            20                  25                  30

Thr Leu Ile Arg Gln Asn Trp Val Met Thr Ala Ala His Cys Val Asp
        35                  40                  45

Tyr Gln Lys Thr Phe Arg Val Val Ala Gly Asp His Asn Leu Ser Gln
    50                  55                  60

Asn Asp Gly Thr Glu Gln Tyr Val Ser Val Gln Lys Ile Val Val His
65                  70                  75                  80

Pro Tyr Trp Asn Ser Asp Asn Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Gln Glu Gly Ala Ile Leu Ala Asn Asn Ser Pro Cys Tyr
        115                 120                 125

Ile Thr Gly Trp Gly Lys Thr Lys Thr Asn Gly Gln Leu Ala Gln Thr
130                 135                 140

Leu Gln Gln Ala Tyr Leu Pro Ser Val Asp Tyr Ala Ile Cys Ser Ser
145                 150                 155                 160

Ser Ser Tyr Trp Gly Ser Thr Val Lys Asn Thr Met Val Cys Ala Gly
                165                 170                 175

Gly Asp Gly Val Arg Ser Gly Cys Gln Gly Asp Ser Gly Gly Pro Pro
            180                 185                 190

Pro Leu Leu Gly Glu Trp Gln Val Phe Ser Pro Trp Ser Asp Gln Leu
        195                 200                 205

Cys Val Gln Pro Gly Leu
    210

```
<210> SEQ ID NO 78
<211> LENGTH: 240
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
<223> OTHER INFORMATION: Trp or Arg
<220> FEATURE:
<221> NAME/KEY: MOD_RES
<222> LOCATION: (41)..(41)
<223> OTHER INFORMATION: Met or Val
<220> FEATURE:
<221> NAME/KEY: MOD_RES
<222> LOCATION: (202)..(202)
<223> OTHER INFORMATION: Val or Leu
<220> FEATURE:
<221> NAME/KEY: MOD_RES
<222> LOCATION: (225)..(225)
<223> OTHER INFORMATION: Gln or Arg

<400> SEQUENCE: 78

Val Val Gly Gly Thr Glu Ala Gly Arg Asn Ser Trp Pro Ser Gln Ile
1               5                   10                  15

Ser Leu Gln Tyr Arg Ser Gly Gly Ser Xaa Tyr His Thr Cys Gly Gly
            20                  25                  30

Thr Leu Ile Arg Gln Asn Trp Val Xaa Thr Ala Ala His Cys Val Asp
        35                  40                  45

Tyr Gln Lys Thr Phe Arg Val Val Ala Gly Asp His Asn Leu Ser Gln
    50                  55                  60

Asn Asp Gly Thr Glu Gln Tyr Val Ser Val Gln Lys Ile Val Val His
65                  70                  75                  80

Pro Tyr Trp Asn Ser Asp Asn Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Gln Glu Gly Ala Ile Leu Ala Asn Asn Ser Pro Cys Tyr
        115                 120                 125

Ile Thr Gly Trp Gly Lys Thr Lys Thr Asn Gly Gln Leu Ala Gln Thr
    130                 135                 140

Leu Gln Gln Ala Tyr Leu Pro Ser Val Asp Tyr Ala Ile Cys Ser Ser
145                 150                 155                 160

Ser Ser Tyr Trp Gly Ser Thr Val Lys Asn Thr Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Lys Tyr Ser Xaa His Gly Val Thr Ser Phe
        195                 200                 205

Val Ser Ser Arg Gly Cys Asn Val Ser Arg Lys Pro Thr Val Phe Thr
    210                 215                 220

Xaa Val Ser Ala Tyr Ile Ser Trp Ile Asn Asn Val Ile Ala Ser Asn
225                 230                 235                 240

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (2)..(2)
<223> OTHER INFORMATION: Gln or His

<400> SEQUENCE: 79

Thr Xaa Asp Leu Pro Glu Thr Asn Ala Arg
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu or His
<220> FEATURE:
<221> NAME/KEY: MOD_RES
<222> LOCATION: (6)..(6)
<223> OTHER INFORMATION: Glu, His, Pro, Gly, Asp, Lys, or Ala
<220> FEATURE:
<221> NAME/KEY: MOD_RES
<222> LOCATION: (7)..(7)
<223> OTHER INFORMATION: Thr, Ala, Pro or His
<220> FEATURE:
<221> NAME/KEY: MOD_RES
<222> LOCATION: (8)..(8)
<223> OTHER INFORMATION: Ala, Leu, Ile, Met, Lys, Asp, or Val
<220> FEATURE:
<221> NAME/KEY: MOD_RES
<222> LOCATION: (9)..(9)
<223> OTHER INFORMATION: Pro, Ala, Leu, Ile, Gly, Val, or Thr
<220> FEATURE:
<221> NAME/KEY: MOD_RES
<222> LOCATION: (10)..(10)
<223> OTHER INFORMATION: Ala, Leu, Val, Ile, or Ser

<400> SEQUENCE: 80

Thr Xaa Asp Leu Pro Xaa Xaa Xaa Xaa Xaa
1               5                   10

<210> SEQ ID NO 81
<211> LENGTH: 756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
actcaggacc ttccggaaac caatgcccgg gtagtcggag ggactgaggc cgggaggaac    60
tcctggccct ctcagatttc cctccagtac cggtctggag gttcctggta tcacacctgt   120
ggagggaccc ttatcagaca gaactgggtg atgacagctg cacactgcgt ggattaccag   180
aagactttcc gcgtggtggc tggagaccat aacctgagcc agaatgatgg cactgagcag   240
tacgtgagtg tgcagaagat cgtggtgcat ccatactgga acagcgataa cgtggctgca   300
ggctatgaca tcgccctgct gcgcctggcc cagagcgtta ccctcaatag ctatgtccag   360
ctgggtgttc tgccccagga gggagccatc ctggctaaca acagtccctg ctacatcaca   420 ggctgggca agaccaagac caatgggcag ctggcccaga ccttgcagca ggcttacctg   480
ccctctgtgg actatgccat ctgctccagc tcctcctact ggggctccac tgtgaagaac   540
actatggtgt gtgctggtgg agatggagtt cgctctggat gtcagggtga ctctgggggc   600
cccctccatt gcttggtgaa tggcaagtat tctcttcatg gagtgaccag ctttgtgtcc   660

```
agccggggct gtaatgtctc tagaaagcct acagtcttca cacgggtctc tgcttacatc    720
tcctggataa ataatgtcat cgcctccaac tgataa                              756
```

<210> SEQ ID NO 82
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Thr Gln Asp Leu Pro Glu Thr Asn Ala Arg Val Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Trp Tyr His Thr Cys Gly Gly Thr Leu Ile Arg Gln Asn
        35                  40                  45

Trp Val Met Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Leu His Gly Val Thr Ser Phe Val Ser Ser Arg Gly Cys
    210                 215                 220

Asn Val Ser Arg Lys Pro Thr Val Phe Thr Arg Val Ser Ala Tyr Ile
225                 230                 235                 240

Ser Trp Ile Asn Asn Val Ile Ala Ser Asn
                245                 250
```

<210> SEQ ID NO 83
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg

```
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 83

Thr Xaa Asp Leu Pro Glu Thr Asn Ala Arg Val Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Xaa Tyr His Thr Cys Gly Gly Thr Leu Ile Arg Gln Asn
        35                  40                  45

Trp Val Xaa Thr Ala Ala His Cys Val Asp Tyr Gln Lys Thr Phe Arg
50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Ser Arg Gly Cys
    210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 84
<211> LENGTH: 240
<212> TYPE: PRT
<213> ORGANISM: Homo sapiens
<220> FEATURE:
<221> NAME/KEY: MOD_RES
<222> LOCATION: (26)..(26)
<223> OTHER INFORMATION: Trp or Arg
<220> FEATURE:
<221> NAME/KEY: MOD_RES
<222> LOCATION: (41)..(41)
<223> OTHER INFORMATION: Met or Val
<220> FEATURE:
<221> NAME/KEY: MOD_RES
<222> LOCATION: (202)..(202)
```

```
<223> OTHER INFORMATION: Val or Leu
<220> FEATURE:
<221> NAME/KEY: MOD_RES
<222> LOCATION: (225)..(225)
<223> OTHER INFORMATION: Gln or Arg

<400> SEQUENCE: 84

Val Val Gly Gly Thr Glu Ala Gly Arg Asn Ser Trp Pro Ser Gln Ile
1               5                   10                  15

Ser Leu Gln Tyr Arg Ser Gly Gly Ser Xaa Tyr His Thr Cys Gly Gly
            20                  25                  30

Thr Leu Ile Arg Gln Asn Trp Val Xaa Thr Ala Ala His Cys Val Asp
        35                  40                  45

Tyr Gln Lys Thr Phe Arg Val Val Ala Gly Asp His Asn Leu Ser Gln
    50                  55                  60

Asn Asp Gly Thr Glu Gln Tyr Val Ser Val Gln Lys Ile Val Val His
65                  70                  75                  80

Pro Tyr Trp Asn Ser Asp Asn Val Ala Ala Gly Tyr Asp Ile Ala Leu
                85                  90                  95

Leu Arg Leu Ala Gln Ser Val Thr Leu Asn Ser Tyr Val Gln Leu Gly
            100                 105                 110

Val Leu Pro Gln Glu Gly Ala Ile Leu Ala Asn Asn Ser Pro Cys Tyr
        115                 120                 125

Ile Thr Gly Trp Gly Lys Thr Lys Thr Asn Gly Gln Leu Ala Gln Thr
    130                 135                 140

Leu Gln Gln Ala Tyr Leu Pro Ser Val Asp Tyr Ala Ile Cys Ser Ser
145                 150                 155                 160

Ser Ser Tyr Trp Gly Ser Thr Val Lys Asn Thr Met Val Cys Ala Gly
                165                 170                 175

Gly Asp Gly Val Arg Ser Gly Cys Gln Gly Asp Ser Gly Gly Pro Leu
            180                 185                 190

His Cys Leu Val Asn Gly Lys Tyr Ser Xaa His Gly Val Thr Ser Phe
        195                 200                 205

Val Ser Ser Arg Gly Cys Asn Val Ser Arg Lys Pro Thr Val Phe Thr
    210                 215                 220

Xaa Val Ser Ala Tyr Ile Ser Trp Ile Asn Asn Val Ile Ala Ser Asn
225                 230                 235                 240

<210> SEQ ID NO 85
<211> LENGTH: 239
<212> TYPE: PRT
<213> ORGANISM: Homo sapiens
<220> FEATURE:
<221> NAME/KEY: MOD_RES
<222> LOCATION: (25)..(25)
<223> OTHER INFORMATION: Trp or Arg
<220> FEATURE:
<221> NAME/KEY: MOD_RES
<222> LOCATION: (40)..(40)
<223> OTHER INFORMATION: Met or Val
<220> FEATURE:
<221> NAME/KEY: MOD_RES
<222> LOCATION: (201)..(201)
<223> OTHER INFORMATION: Val or Leu
<220> FEATURE:
<221> NAME/KEY: MOD_RES
<222> LOCATION: (224)..(224)
<223> OTHER INFORMATION: Gln or Arg

<400> SEQUENCE: 85

Val Gly Gly Thr Glu Ala Gly Arg Asn Ser Trp Pro Ser Gln Ile Ser
1               5                   10                  15
```

```
Leu Gln Tyr Arg Ser Gly Gly Ser Xaa Tyr His Thr Cys Gly Gly Thr
                20                  25                  30

Leu Ile Arg Gln Asn Trp Val Xaa Thr Ala Ala His Cys Val Asp Tyr
            35                  40                  45

Gln Lys Thr Phe Arg Val Val Ala Gly Asp His Asn Leu Ser Gln Asn
 50                  55                  60

Asp Gly Thr Glu Gln Tyr Val Ser Val Gln Lys Ile Val His Pro
 65                  70                  75                  80

Tyr Trp Asn Ser Asp Asn Val Ala Ala Gly Tyr Asp Ile Ala Leu Leu
                85                  90                  95

Arg Leu Ala Gln Ser Val Thr Leu Asn Ser Tyr Val Gln Leu Gly Val
                100                 105                 110

Leu Pro Gln Glu Gly Ala Ile Leu Ala Asn Asn Ser Pro Cys Tyr Ile
            115                 120                 125

Thr Gly Trp Gly Lys Thr Lys Thr Asn Gly Gln Leu Ala Gln Thr Leu
130                 135                 140

Gln Gln Ala Tyr Leu Pro Ser Val Asp Tyr Ala Ile Cys Ser Ser Ser
145                 150                 155                 160

Ser Tyr Trp Gly Ser Thr Val Lys Asn Thr Met Val Cys Ala Gly Gly
                165                 170                 175

Asp Gly Val Arg Ser Gly Cys Gln Gly Asp Ser Gly Gly Pro Leu His
            180                 185                 190

Cys Leu Val Asn Gly Lys Tyr Ser Xaa His Gly Val Thr Ser Phe Val
            195                 200                 205

Ser Ser Arg Gly Cys Asn Val Ser Arg Lys Pro Thr Val Phe Thr Xaa
210                 215                 220

Val Ser Ala Tyr Ile Ser Trp Ile Asn Asn Val Ile Ala Ser Asn
225                 230                 235

<210> SEQ ID NO 86
<211> LENGTH: 238
<212> TYPE: PRT
<213> ORGANISM: Homo sapiens
<220> FEATURE:
<221> NAME/KEY: MOD_RES
<222> LOCATION: (24)..(24)
<223> OTHER INFORMATION: Trp or Arg
<220> FEATURE:
<221> NAME/KEY: MOD_RES
<222> LOCATION: (39)..(39)
<223> OTHER INFORMATION: Met or Val
<220> FEATURE:
<221> NAME/KEY: MOD_RES
<222> LOCATION: (200)..(200)
<223> OTHER INFORMATION: Val or Leu
<220> FEATURE:
<221> NAME/KEY: MOD_RES
<222> LOCATION: (223)..(223)
<223> OTHER INFORMATION: Gln or Arg

<400> SEQUENCE: 86

Gly Gly Thr Glu Ala Gly Arg Asn Ser Trp Pro Ser Gln Ile Ser Leu
 1               5                  10                  15

Gln Tyr Arg Ser Gly Gly Ser Xaa Tyr His Thr Cys Gly Gly Thr Leu
                20                  25                  30

Ile Arg Gln Asn Trp Val Xaa Thr Ala Ala His Cys Val Asp Tyr Gln
            35                  40                  45

Lys Thr Phe Arg Val Val Ala Gly Asp His Asn Leu Ser Gln Asn Asp
 50                  55                  60
```

```
Gly Thr Glu Gln Tyr Val Ser Val Gln Lys Ile Val Val His Pro Tyr
 65                  70                  75                  80

Trp Asn Ser Asp Asn Val Ala Ala Gly Tyr Asp Ile Ala Leu Leu Arg
                 85                  90                  95

Leu Ala Gln Ser Val Thr Leu Asn Ser Tyr Val Gln Leu Gly Val Leu
            100                 105                 110

Pro Gln Glu Gly Ala Ile Leu Ala Asn Asn Ser Pro Cys Tyr Ile Thr
        115                 120                 125

Gly Trp Gly Lys Thr Lys Thr Asn Gly Gln Leu Ala Gln Thr Leu Gln
130                 135                 140

Gln Ala Tyr Leu Pro Ser Val Asp Tyr Ala Ile Cys Ser Ser Ser Ser
145                 150                 155                 160

Tyr Trp Gly Ser Thr Val Lys Asn Thr Met Val Cys Ala Gly Gly Asp
                165                 170                 175

Gly Val Arg Ser Gly Cys Gln Gly Asp Ser Gly Gly Pro Leu His Cys
            180                 185                 190

Leu Val Asn Gly Lys Tyr Ser Xaa His Gly Val Thr Ser Phe Val Ser
        195                 200                 205

Ser Arg Gly Cys Asn Val Ser Arg Lys Pro Thr Val Phe Thr Xaa Val
    210                 215                 220

Ser Ala Tyr Ile Ser Trp Ile Asn Asn Val Ile Ala Ser Asn
225                 230                 235

<210> SEQ ID NO 87
<211> LENGTH: 240
<212> TYPE: PRT
<213> ORGANISM: Homo sapiens
<220> FEATURE:
<221> NAME/KEY: MOD_RES
<222> LOCATION: (26)..(26)
<223> OTHER INFORMATION: Trp or Arg
<220> FEATURE:
<221> NAME/KEY: MOD_RES
<222> LOCATION: (41)..(41)
<223> OTHER INFORMATION: Met or Val
<220> FEATURE:
<221> NAME/KEY: MOD_RES
<222> LOCATION: (202)..(202)
<223> OTHER INFORMATION: Val or Leu
<220> FEATURE:
<221> NAME/KEY: MOD_RES
<222> LOCATION: (225)..(225)
<223> OTHER INFORMATION: Gln or Arg

<400> SEQUENCE: 87

Ala Val Gly Gly Thr Glu Ala Gly Arg Asn Ser Trp Pro Ser Gln Ile
 1               5                  10                  15

Ser Leu Gln Tyr Arg Ser Gly Gly Ser Xaa Tyr His Thr Cys Gly Gly
            20                  25                  30

Thr Leu Ile Arg Gln Asn Trp Val Xaa Thr Ala Ala His Cys Val Asp
        35                  40                  45

Tyr Gln Lys Thr Phe Arg Val Val Ala Gly Asp His Asn Leu Ser Gln
    50                  55                  60

Asn Asp Gly Thr Glu Gln Tyr Val Ser Val Gln Lys Ile Val Val His
 65                  70                  75                  80

Pro Tyr Trp Asn Ser Asp Asn Val Ala Ala Gly Tyr Asp Ile Ala Leu
                 85                  90                  95

Leu Arg Leu Ala Gln Ser Val Thr Leu Asn Ser Tyr Val Gln Leu Gly
            100                 105                 110

Val Leu Pro Gln Glu Gly Ala Ile Leu Ala Asn Asn Ser Pro Cys Tyr
```

```
        115                 120                 125

Ile Thr Gly Trp Gly Lys Thr Lys Thr Asn Gly Gln Leu Ala Gln Thr
        130                 135                 140

Leu Gln Gln Ala Tyr Leu Pro Ser Val Asp Tyr Ala Ile Cys Ser Ser
145                 150                 155                 160

Ser Ser Tyr Trp Gly Ser Thr Val Lys Asn Thr Met Val Cys Ala Gly
                    165                 170                 175

Gly Asp Gly Val Arg Ser Gly Cys Gln Gly Asp Ser Gly Gly Pro Leu
                180                 185                 190

His Cys Leu Val Asn Gly Lys Tyr Ser Xaa His Gly Val Thr Ser Phe
                195                 200                 205

Val Ser Ser Arg Gly Cys Asn Val Ser Arg Lys Pro Thr Val Phe Thr
210                 215                 220

Xaa Val Ser Ala Tyr Ile Ser Trp Ile Asn Asn Val Ile Ala Ser Asn
225                 230                 235                 240
```

<210> SEQ ID NO 88
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 88

```
Thr Xaa Asp Leu Pro Glu Thr Asn Ala Ala Val Val Gly Gly Thr Glu
1               5                   10                  15

Ala Gly Arg Asn Ser Trp Pro Ser Gln Ile Ser Leu Gln Tyr Arg Ser
                20                  25                  30

Gly Gly Ser Xaa Tyr His Thr Cys Gly Gly Thr Leu Ile Arg Gln Asn
            35                  40                  45

Trp Val Xaa Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
                100                 105                 110

Val Thr Leu Asn Ser Tyr Val Gln Leu Gly Val Leu Pro Gln Glu Gly
            115                 120                 125

Ala Ile Leu Ala Asn Asn Ser Pro Cys Tyr Ile Thr Gly Trp Gly Lys
```

```
            130                 135                 140
Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
                180                 185                 190

Gly Cys Gln Gly Asp Ser Gly Gly Pro Leu His Cys Leu Val Asn Gly
            195                 200                 205

Lys Tyr Ser Xaa His Gly Val Thr Ser Phe Val Ser Ser Arg Gly Cys
        210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 89
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 89

Thr Xaa Asp Leu Pro Glu Thr Asn Ala Ala Val Gly Gly Thr Glu
1               5                   10                  15

Ala Gly Arg Asn Ser Trp Pro Ser Gln Ile Ser Leu Gln Tyr Arg Ser
                20                  25                  30

Gly Gly Ser Xaa Tyr His Thr Cys Gly Gly Thr Leu Ile Arg Gln Asn
            35                  40                  45

Trp Val Xaa Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
                100                 105                 110

Val Thr Leu Asn Ser Tyr Val Gln Leu Gly Val Leu Pro Gln Glu Gly
            115                 120                 125

Ala Ile Leu Ala Asn Asn Ser Pro Cys Tyr Ile Thr Gly Trp Gly Lys
```

```
            130                 135                 140
Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
                180                 185                 190

Gly Cys Gln Gly Asp Ser Gly Gly Pro Leu His Cys Leu Val Asn Gly
                195                 200                 205

Lys Tyr Ser Xaa His Gly Val Thr Ser Phe Val Ser Arg Gly Cys
            210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 90
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 90

Thr Xaa Asp Leu Pro Glu Thr Ala Ala Val Val Gly Gly Thr Glu
1               5                   10                  15

Ala Gly Arg Asn Ser Trp Pro Ser Gln Ile Ser Leu Gln Tyr Arg Ser
                20                  25                  30

Gly Gly Ser Xaa Tyr His Thr Cys Gly Gly Thr Leu Ile Arg Gln Asn
            35                  40                  45

Trp Val Xaa Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
                100                 105                 110

Val Thr Leu Asn Ser Tyr Val Gln Leu Gly Val Leu Pro Gln Glu Gly
            115                 120                 125

Ala Ile Leu Ala Asn Asn Ser Pro Cys Tyr Ile Thr Gly Trp Gly Lys
```

```
              130                 135                 140
Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
                180                 185                 190

Gly Cys Gln Gly Asp Ser Gly Gly Pro Leu His Cys Leu Val Asn Gly
            195                 200                 205

Lys Tyr Ser Xaa His Gly Val Thr Ser Phe Val Ser Ser Arg Gly Cys
            210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 91
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 91

Thr Xaa Asp Leu Pro Glu Thr Asn Asn Ala Pro Val Gly Gly Thr Glu
1               5                   10                  15

Ala Gly Arg Asn Ser Trp Pro Ser Gln Ile Ser Leu Gln Tyr Arg Ser
                20                  25                  30

Gly Gly Ser Xaa Tyr His Thr Cys Gly Gly Thr Leu Ile Arg Gln Asn
            35                  40                  45

Trp Val Xaa Thr Ala Ala His Cys Val Asp Tyr Gln Lys Thr Phe Arg
50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
                100                 105                 110

Val Thr Leu Asn Ser Tyr Val Gln Leu Gly Val Leu Pro Gln Glu Gly
            115                 120                 125

Ala Ile Leu Ala Asn Asn Ser Pro Cys Tyr Ile Thr Gly Trp Gly Lys
```

```
                130                 135                 140
Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
                180                 185                 190

Gly Cys Gln Gly Asp Ser Gly Gly Pro Leu His Cys Leu Val Asn Gly
                195                 200                 205

Lys Tyr Ser Xaa His Gly Val Thr Ser Phe Val Ser Arg Gly Cys
                210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 92
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 92

Thr Xaa Asp Leu Pro Glu Thr Asn Ala Arg Val Val Gly Gly Thr Glu
1               5                   10                  15

Ala Gly Arg Asn Ser Trp Pro Ser Gln Ile Ser Leu Gln Tyr Arg Ser
                20                  25                  30

Gly Gly Ser Xaa Tyr His Thr Cys Gly Gly Thr Leu Ile Arg Gln Asn
                35                  40                  45

Trp Val Xaa Thr Ala Ala His Cys Val Asp Tyr Gln Lys Thr Phe Arg
        50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
                100                 105                 110

Val Thr Leu Asn Ser Tyr Val Gln Leu Gly Val Leu Pro Gln Glu Gly
                115                 120                 125

Ala Ile Leu Ala Asn Asn Ser Pro Cys Tyr Ile Thr Gly Trp Gly Lys
```

```
                130             135             140
Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175

Thr Val Lys Asn Thr Met Val Cys Ala Gly Gly Asp Gly Val Arg Ser
                180                 185                 190

Gly Cys Gln Gly Asp Ser Gly Gly Pro Leu His Cys Leu Val Asn Gly
                195                 200                 205

Lys Tyr Ser Xaa His Gly Val Thr Ser Phe Val Ser Arg Gly Cys
                210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Leu, Ile, Met, Lys, Asp, or Val
<220> FEATURE:
<221> NAME/KEY: MOD_RES
<222> LOCATION: (3)..(3)
<223> OTHER INFORMATION: Ala, Leu, Val, Ile, or Ser

<400> SEQUENCE: 93

Xaa Pro Xaa
1

<210> SEQ ID NO 94
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Trp or Arg
<220> FEATURE:
<221> NAME/KEY: MOD_RES
<222> LOCATION: (43)..(43)
<223> OTHER INFORMATION: Met or Val
<220> FEATURE:
<221> NAME/KEY: MOD_RES
<222> LOCATION: (204)..(204)
<223> OTHER INFORMATION: Val or Leu
<220> FEATURE:
<221> NAME/KEY: MOD_RES
<222> LOCATION: (227)..(227)
<223> OTHER INFORMATION: Gln or Arg

<400> SEQUENCE: 94

Ala Ala Val Val Gly Gly Thr Glu Ala Gly Arg Asn Ser Trp Pro Ser
1               5                   10                  15

Gln Ile Ser Leu Gln Tyr Arg Ser Gly Gly Ser Xaa Tyr His Thr Cys
                20                  25                  30

Gly Gly Thr Leu Ile Arg Gln Asn Trp Val Xaa Thr Ala Ala His Cys
```

```
                     35                  40                  45
Val Asp Tyr Gln Lys Thr Phe Arg Val Val Ala Gly Asp His Asn Leu
 50                  55                  60

Ser Gln Asn Asp Gly Thr Glu Gln Tyr Val Ser Val Gln Lys Ile Val
 65                  70                  75                  80

Val His Pro Tyr Trp Asn Ser Asp Asn Val Ala Ala Gly Tyr Asp Ile
                     85                  90                  95

Ala Leu Leu Arg Leu Ala Gln Ser Val Thr Leu Asn Ser Tyr Val Gln
                100                 105                 110

Leu Gly Val Leu Pro Gln Glu Gly Ala Ile Leu Ala Asn Asn Ser Pro
                115                 120                 125

Cys Tyr Ile Thr Gly Trp Gly Lys Thr Lys Thr Asn Gly Gln Leu Ala
                130                 135                 140

Gln Thr Leu Gln Gln Ala Tyr Leu Pro Ser Val Asp Tyr Ala Ile Cys
145                 150                 155                 160

Ser Ser Ser Ser Tyr Trp Gly Ser Thr Val Lys Asn Thr Met Val Cys
                165                 170                 175

Ala Gly Gly Asp Gly Val Arg Ser Gly Cys Gln Gly Asp Ser Gly Gly
                180                 185                 190

Pro Leu His Cys Leu Val Asn Gly Lys Tyr Ser Xaa His Gly Val Thr
                195                 200                 205

Ser Phe Val Ser Ser Arg Gly Cys Asn Val Ser Arg Lys Pro Thr Val
                210                 215                 220

Phe Thr Xaa Val Ser Ala Tyr Ile Ser Trp Ile Asn Asn Val Ile Ala
225                 230                 235                 240

Ser Asn

<210> SEQ ID NO 95
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Trp or Arg
<220> FEATURE:
<221> NAME/KEY: MOD_RES
<222> LOCATION: (42)..(42)
<223> OTHER INFORMATION: Met or Val
<220> FEATURE:
<221> NAME/KEY: MOD_RES
<222> LOCATION: (203)..(203)
<223> OTHER INFORMATION: Val or Leu
<220> FEATURE:
<221> NAME/KEY: MOD_RES
<222> LOCATION: (226)..(226)
<223> OTHER INFORMATION: Gln or Arg

<400> SEQUENCE: 95

Ala Val Val Gly Gly Thr Glu Ala Gly Arg Asn Ser Trp Pro Ser Gln
 1                   5                  10                  15

Ile Ser Leu Gln Tyr Arg Ser Gly Gly Ser Xaa Tyr His Thr Cys Gly
                 20                  25                  30

Gly Thr Leu Ile Arg Gln Asn Trp Val Xaa Thr Ala Ala His Cys Val
                 35                  40                  45

Asp Tyr Gln Lys Thr Phe Arg Val Val Ala Gly Asp His Asn Leu Ser
 50                  55                  60
```

Gln Asn Asp Gly Thr Glu Gln Tyr Val Ser Val Gln Lys Ile Val Val
 65                  70                  75                  80

His Pro Tyr Trp Asn Ser Asp Asn Val Ala Ala Gly Tyr Asp Ile Ala
                 85                  90                  95

Leu Leu Arg Leu Ala Gln Ser Val Thr Leu Asn Ser Tyr Val Gln Leu
            100                 105                 110

Gly Val Leu Pro Gln Glu Gly Ala Ile Leu Ala Asn Asn Ser Pro Cys
        115                 120                 125

Tyr Ile Thr Gly Trp Gly Lys Thr Lys Thr Asn Gly Gln Leu Ala Gln
    130                 135                 140

Thr Leu Gln Gln Ala Tyr Leu Pro Ser Val Asp Tyr Ala Ile Cys Ser
145                 150                 155                 160

Ser Ser Ser Tyr Trp Gly Ser Thr Val Lys Asn Thr Met Val Cys Ala
                165                 170                 175

Gly Gly Asp Gly Val Arg Ser Gly Cys Gln Gly Asp Ser Gly Gly Pro
            180                 185                 190

Leu His Cys Leu Val Asn Gly Lys Tyr Ser Xaa His Gly Val Thr Ser
        195                 200                 205

Phe Val Ser Ser Arg Gly Cys Asn Val Ser Arg Lys Pro Thr Val Phe
    210                 215                 220

Thr Xaa Val Ser Ala Tyr Ile Ser Trp Ile Asn Asn Val Ile Ala Ser
225                 230                 235                 240

Asn

<210> SEQ ID NO 96
<211> LENGTH: 89
<212> TYPE: PRT
<213> ORGANISM: Unknown
<220> FEATURE:
<223> OTHER INFORMATION: Description of Unknown: Yeast alpha-mating
      factor signal peptide, propeptide, and spacer sequence 1

<400> SEQUENCE: 96

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala
                85

<210> SEQ ID NO 97
<211> LENGTH: 83
<212> TYPE: PRT
<213> ORGANISM: Unknown
<220> FEATURE:
<223> OTHER INFORMATION: Description of Unknown: Yeast alpha-mating
      factor signal peptide and propeptide sequence 2

<400> SEQUENCE: 97

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln

```
                    20                  25                  30

Ile Pro Ala Glu Ala Val Ile Gly Tyr Ser Asp Leu Glu Gly Asp Phe
             35                  40                  45

Asp Val Ala Val Leu Pro Phe Ser Asn Ser Thr Asn Asn Gly Leu Leu
         50                  55                  60

Phe Ile Asn Thr Thr Ile Ala Ser Ile Ala Ala Lys Glu Glu Gly Val
 65                  70                  75                  80

Ser Leu Glu

<210> SEQ ID NO 98
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 98

Thr Xaa Asp Leu Pro Glu Thr Asn Pro Ala Val Val Gly Gly Thr Glu
 1               5                  10                  15

Ala Gly Arg Asn Ser Trp Pro Ser Gln Ile Ser Leu Gln Tyr Arg Ser
             20                  25                  30

Gly Gly Ser Xaa Tyr His Thr Cys Gly Gly Thr Leu Ile Arg Gln Asn
         35                  40                  45

Trp Val Xaa Thr Ala Ala His Cys Val Asp Tyr Gln Lys Thr Phe Arg
     50                  55                  60

Val Val Ala Gly Asp His Asn Leu Ser Gln Asn Asp Gly Thr Glu Gln
 65                  70                  75                  80

Tyr Val Ser Val Gln Lys Ile Val Val His Pro Tyr Trp Asn Ser Asp
             85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Ser Tyr Trp Gly Ser
                165                 170                 175

Thr Val Lys Asn Thr Met Val Cys Ala Gly Gly Asp Gly Val Arg Ser
            180                 185                 190
```

```
Gly Cys Gln Gly Asp Ser Gly Gly Pro Leu His Cys Leu Val Asn Gly
            195                 200                 205

Lys Tyr Ser Xaa His Gly Val Thr Ser Phe Val Ser Ser Arg Gly Cys
        210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 99
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 99

Thr Xaa Asp Leu Pro Glu Thr Asn His Ala Val Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Xaa Tyr His Thr Cys Gly Gly Thr Leu Ile Arg Gln Asn
        35                  40                  45

Trp Val Xaa Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Tyr Trp Gly Ser
                165                 170                 175
```

-continued

```
Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Arg Gly Cys
    210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 100
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 100

Thr Xaa Asp Leu Pro Glu Thr Lys Pro Ala Val Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Xaa Tyr His Thr Cys Gly Gly Thr Leu Ile Arg Gln Asn
        35                  40                  45

Trp Val Xaa Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Ser Tyr Trp Gly Ser
                165                 170                 175
```

```
Thr Val Lys Asn Thr Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Arg Gly Cys
    210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 101
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 101

Thr Xaa Asp Leu Pro Glu Thr His Pro Ala Val Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Xaa Tyr His Thr Cys Gly Gly Thr Leu Ile Arg Gln Asn
        35                  40                  45

Trp Val Xaa Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160

Pro Ser Val Asp Tyr Ala Ile Cys Ser Ser Ser Ser Tyr Trp Gly Ser
                165                 170                 175
```

```
Thr Val Lys Asn Thr Met Val Cys Ala Gly Gly Asp Gly Val Arg Ser
            180                 185                 190

Gly Cys Gln Gly Asp Ser Gly Pro Leu His Cys Leu Val Asn Gly
        195                 200                 205

Lys Tyr Ser Xaa His Gly Val Thr Ser Phe Val Ser Arg Gly Cys
    210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
                245                 250

<210> SEQ ID NO 102
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 102

Thr Xaa Asp Leu Pro Glu His Asn Pro Ala Val Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Xaa Tyr His Thr Cys Gly Gly Thr Leu Ile Arg Gln Asn
        35                  40                  45

Trp Val Xaa Thr Ala Ala His Cys Val Asp Tyr Gln Lys Thr Phe Arg
    50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160
```

```
Pro Ser Val Asp Tyr Ala Ile Cys Ser Ser Ser Tyr Trp Gly Ser
            165                 170                 175

Thr Val Lys Asn Thr Met Val Cys Ala Gly Gly Asp Gly Val Arg Ser
        180                 185                 190

Gly Cys Gln Gly Asp Ser Gly Gly Pro Leu His Cys Leu Val Asn Gly
        195                 200                 205

Lys Tyr Ser Xaa His Gly Val Thr Ser Phe Val Ser Arg Gly Cys
        210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
            245                 250
```

```
<210> SEQ ID NO 103
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (36)..(36)
<223> OTHER INFORMATION: Trp or Arg
<220> FEATURE:
<221> NAME/KEY: MOD_RES
<222> LOCATION: (51)..(51)
<223> OTHER INFORMATION: Met or Val
<220> FEATURE:
<221> NAME/KEY: MOD_RES
<222> LOCATION: (212)..(212)
<223> OTHER INFORMATION: Val or Leu
<220> FEATURE:
<221> NAME/KEY: MOD_RES
<222> LOCATION: (235)..(235)
<223> OTHER INFORMATION: Gln or Arg

<400> SEQUENCE: 103

Thr Xaa Asp Leu Pro His Thr Asn Pro Ala Val Gly Gly Thr Glu
1               5                   10                  15

Ala Gly Arg Asn Ser Trp Pro Ser Gln Ile Ser Leu Gln Tyr Arg Ser
            20                  25                  30

Gly Gly Ser Xaa Tyr His Thr Cys Gly Gly Thr Leu Ile Arg Gln Asn
        35                  40                  45

Trp Val Xaa Thr Ala Ala His Cys Val Asp Tyr Gln Lys Thr Phe Arg
50                  55                  60

Val Val Ala Gly Asp His Asn Leu Ser Gln Asn Asp Gly Thr Glu Gln
65                  70                  75                  80

Tyr Val Ser Val Gln Lys Ile Val Val His Pro Tyr Trp Asn Ser Asp
                85                  90                  95

Asn Val Ala Ala Gly Tyr Asp Ile Ala Leu Leu Arg Leu Ala Gln Ser
            100                 105                 110

Val Thr Leu Asn Ser Tyr Val Gln Leu Gly Val Leu Pro Gln Glu Gly
        115                 120                 125

Ala Ile Leu Ala Asn Asn Ser Pro Cys Tyr Ile Thr Gly Trp Gly Lys
    130                 135                 140

Thr Lys Thr Asn Gly Gln Leu Ala Gln Thr Leu Gln Gln Ala Tyr Leu
145                 150                 155                 160
```

```
Pro Ser Val Asp Tyr Ala Ile Cys Ser Ser Ser Tyr Trp Gly Ser
            165                 170                 175

Thr Val Lys Asn Thr Met Val Cys Ala Gly Gly Asp Gly Val Arg Ser
            180                 185                 190

Gly Cys Gln Gly Asp Ser Gly Pro Leu His Cys Leu Val Asn Gly
            195                 200                 205

Lys Tyr Ser Xaa His Gly Val Thr Ser Phe Val Ser Ser Arg Gly Cys
            210                 215                 220

Asn Val Ser Arg Lys Pro Thr Val Phe Thr Xaa Val Ser Ala Tyr Ile
225                 230                 235                 240

Ser Trp Ile Asn Asn Val Ile Ala Ser Asn
            245                 250

<210> SEQ ID NO 104
<211> LENGTH: 242
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: Trp or Arg
<220> FEATURE:
<221> NAME/KEY: MOD_RES
<222> LOCATION: (43)..(43)
<223> OTHER INFORMATION: Met or Val
<220> FEATURE:
<221> NAME/KEY: MOD_RES
<222> LOCATION: (204)..(204)
<223> OTHER INFORMATION: Val or Leu
<220> FEATURE:
<221> NAME/KEY: MOD_RES
<222> LOCATION: (227)..(227)
<223> OTHER INFORMATION: Gln or Arg

<400> SEQUENCE: 104

Ala Arg Val Val Gly Gly Thr Glu Ala Gly Arg Asn Ser Trp Pro Ser
1               5                   10                  15

Gln Ile Ser Leu Gln Tyr Arg Ser Gly Gly Ser Xaa Tyr His Thr Cys
            20                  25                  30

Gly Gly Thr Leu Ile Arg Gln Asn Trp Val Xaa Thr Ala Ala His Cys
            35                  40                  45

Val Asp Tyr Gln Lys Thr Phe Arg Val Val Ala Gly Asp His Asn Leu
            50                  55                  60

Ser Gln Asn Asp Gly Thr Glu Gln Tyr Val Ser Val Gln Lys Ile Val
65                  70                  75                  80

Val His Pro Tyr Trp Asn Ser Asp Asn Val Ala Ala Gly Tyr Asp Ile
            85                  90                  95

Ala Leu Leu Arg Leu Ala Gln Ser Val Thr Leu Asn Ser Tyr Val Gln
            100                 105                 110

Leu Gly Val Leu Pro Gln Glu Gly Ala Ile Leu Ala Asn Asn Ser Pro
            115                 120                 125

Cys Tyr Ile Thr Gly Trp Gly Lys Thr Lys Thr Asn Gly Gln Leu Ala
            130                 135                 140

Gln Thr Leu Gln Gln Ala Tyr Leu Pro Ser Val Asp Tyr Ala Ile Cys
145                 150                 155                 160

Ser Ser Ser Ser Tyr Trp Gly Ser Thr Val Lys Asn Thr Met Val Cys
            165                 170                 175

Ala Gly Gly Asp Gly Val Arg Ser Gly Cys Gln Gly Asp Ser Gly Gly
            180                 185                 190
```

```
Pro Leu His Cys Leu Val Asn Gly Lys Tyr Ser Xaa His Gly Val Thr
            195                 200                 205

Ser Phe Val Ser Ser Arg Gly Cys Asn Val Ser Arg Lys Pro Thr Val
    210                 215                 220

Phe Thr Xaa Val Ser Ala Tyr Ile Ser Trp Ile Asn Asn Val Ile Ala
225                 230                 235                 240

Ser Asn

<210> SEQ ID NO 105
<211> LENGTH: 241
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: Trp or Arg
<220> FEATURE:
<221> NAME/KEY: MOD_RES
<222> LOCATION: (42)..(42)
<223> OTHER INFORMATION: Met or Val
<220> FEATURE:
<221> NAME/KEY: MOD_RES
<222> LOCATION: (203)..(203)
<223> OTHER INFORMATION: Val or Leu
<220> FEATURE:
<221> NAME/KEY: MOD_RES
<222> LOCATION: (226)..(226)
<223> OTHER INFORMATION: Gln or Arg

<400> SEQUENCE: 105

Arg Val Val Gly Gly Thr Glu Ala Gly Arg Asn Ser Trp Pro Ser Gln
1               5                   10                  15

Ile Ser Leu Gln Tyr Arg Ser Gly Gly Ser Xaa Tyr His Thr Cys Gly
                20                  25                  30

Gly Thr Leu Ile Arg Gln Asn Trp Val Xaa Thr Ala Ala His Cys Val
            35                  40                  45

Asp Tyr Gln Lys Thr Phe Arg Val Val Ala Gly Asp His Asn Leu Ser
        50                  55                  60

Gln Asn Asp Gly Thr Glu Gln Tyr Val Ser Val Gln Lys Ile Val Val
65                  70                  75                  80

His Pro Tyr Trp Asn Ser Asp Asn Val Ala Ala Gly Tyr Asp Ile Ala
                85                  90                  95

Leu Leu Arg Leu Ala Gln Ser Val Thr Leu Asn Ser Tyr Val Gln Leu
            100                 105                 110

Gly Val Leu Pro Gln Glu Gly Ala Ile Leu Ala Asn Asn Ser Pro Cys
        115                 120                 125

Tyr Ile Thr Gly Trp Gly Lys Thr Lys Thr Asn Gly Gln Leu Ala Gln
130                 135                 140

Thr Leu Gln Gln Ala Tyr Leu Pro Ser Val Asp Tyr Ala Ile Cys Ser
145                 150                 155                 160

Ser Ser Ser Tyr Trp Gly Ser Thr Val Lys Asn Thr Met Val Cys Ala
                165                 170                 175

Gly Gly Asp Gly Val Arg Ser Gly Cys Gln Gly Asp Ser Gly Gly Pro
            180                 185                 190

Leu His Cys Leu Val Asn Gly Lys Tyr Ser Xaa His Gly Val Thr Ser
        195                 200                 205

Phe Val Ser Ser Arg Gly Cys Asn Val Ser Arg Lys Pro Thr Val Phe
    210                 215                 220

Thr Xaa Val Ser Ala Tyr Ile Ser Trp Ile Asn Asn Val Ile Ala Ser
225                 230                 235                 240
```

Asn

<210> SEQ ID NO 106
<211> LENGTH: 236
<212> TYPE: PRT
<213> ORGANISM: Homo sapiens
<220> FEATURE:
<221> NAME/KEY: MOD_RES
<222> LOCATION: (22)..(22)
<223> OTHER INFORMATION: Trp or Arg
<220> FEATURE:
<221> NAME/KEY: MOD_RES
<222> LOCATION: (37)..(37)
<223> OTHER INFORMATION: Met or Val
<220> FEATURE:
<221> NAME/KEY: MOD_RES
<222> LOCATION: (198)..(198)
<223> OTHER INFORMATION: Val or Leu
<220> FEATURE:
<221> NAME/KEY: MOD_RES
<222> LOCATION: (221)..(221)
<223> OTHER INFORMATION: Gln or Arg

<400> SEQUENCE: 106

Thr Glu Ala Gly Arg Asn Ser Trp Pro Ser Gln Ile Ser Leu Gln Tyr
1               5                   10                  15

Arg Ser Gly Gly Ser Xaa Tyr His Thr Cys Gly Gly Thr Leu Ile Arg
            20                  25                  30

Gln Asn Trp Val Xaa Thr Ala Ala His Cys Val Asp Tyr Gln Lys Thr
        35                  40                  45

Phe Arg Val Val Ala Gly Asp His Asn Leu Ser Gln Asn Asp Gly Thr
50                  55                  60

Glu Gln Tyr Val Ser Val Gln Lys Ile Val His Pro Tyr Trp Asn
65                  70                  75                  80

Ser Asp Asn Val Ala Ala Gly Tyr Asp Ile Ala Leu Leu Arg Leu Ala
                85                  90                  95

Gln Ser Val Thr Leu Asn Ser Tyr Val Gln Leu Gly Val Leu Pro Gln
            100                 105                 110

Glu Gly Ala Ile Leu Ala Asn Asn Ser Pro Cys Tyr Ile Thr Gly Trp
        115                 120                 125

Gly Lys Thr Lys Thr Asn Gly Gln Leu Ala Gln Thr Leu Gln Gln Ala
130                 135                 140

Tyr Leu Pro Ser Val Asp Tyr Ala Ile Cys Ser Ser Ser Ser Tyr Trp
145                 150                 155                 160

Gly Ser Thr Val Lys Asn Thr Met Val Cys Ala Gly Gly Asp Gly Val
                165                 170                 175

Arg Ser Gly Cys Gln Gly Asp Ser Gly Gly Pro Leu His Cys Leu Val
            180                 185                 190

Asn Gly Lys Tyr Ser Xaa His Gly Val Thr Ser Phe Val Ser Ser Arg
        195                 200                 205

Gly Cys Asn Val Ser Arg Lys Pro Thr Val Phe Thr Xaa Val Ser Ala
210                 215                 220

Tyr Ile Ser Trp Ile Asn Asn Val Ile Ala Ser Asn
225                 230                 235

<210> SEQ ID NO 107
<211> LENGTH: 234
<212> TYPE: PRT
<213> ORGANISM: Homo sapiens
<220> FEATURE:
<221> NAME/KEY: MOD_RES

```
<222> LOCATION: (20)..(20)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (219)..(219)
<223> OTHER INFORMATION: Any amino acid

<400> SEQUENCE: 107

Ala Gly Arg Asn Ser Trp Pro Ser Gln Ile Ser Leu Gln Tyr Arg Ser
1               5                   10                  15

Gly Gly Ser Xaa Tyr His Thr Cys Gly Gly Thr Leu Ile Arg Gln Asn
            20                  25                  30

Trp Val Xaa Thr Ala Ala His Cys Val Asp Tyr Gln Lys Thr Phe Arg
        35                  40                  45

Val Val Ala Gly Asp His Asn Leu Ser Gln Asn Asp Gly Thr Glu Gln
50                  55                  60

Tyr Val Ser Val Gln Lys Ile Val His Pro Tyr Trp Asn Ser Asp
65                  70                  75                  80

Asn Val Ala Ala Gly Tyr Asp Ile Ala Leu Leu Arg Leu Ala Gln Ser
                85                  90                  95

Val Thr Leu Asn Ser Tyr Val Gln Leu Gly Val Leu Pro Gln Glu Gly
            100                 105                 110

Ala Ile Leu Ala Asn Asn Ser Pro Cys Tyr Ile Thr Gly Trp Gly Lys
        115                 120                 125

Thr Lys Thr Asn Gly Gln Leu Ala Gln Thr Leu Gln Gln Ala Tyr Leu
130                 135                 140

Pro Ser Val Asp Tyr Ala Ile Cys Ser Ser Ser Tyr Trp Gly Ser
145                 150                 155                 160

Thr Val Lys Asn Thr Met Val Cys Ala Gly Gly Asp Gly Val Arg Ser
                165                 170                 175

Gly Cys Gln Gly Asp Ser Gly Gly Pro Leu His Cys Leu Val Asn Gly
            180                 185                 190

Lys Tyr Ser Xaa His Gly Val Thr Ser Phe Val Ser Arg Gly Cys
        195                 200                 205

Asn Val Ser Arg Lys Pro Thr Val Phe Thr Xaa Val Ser Ala Tyr Ile
210                 215                 220

Ser Trp Ile Asn Asn Val Ile Ala Ser Asn
225                 230

<210> SEQ ID NO 108
<211> LENGTH: 231
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: Trp or Arg
<220> FEATURE:
<221> NAME/KEY: MOD_RES
<222> LOCATION: (32)..(32)
<223> OTHER INFORMATION: Met or Val
<220> FEATURE:
<221> NAME/KEY: MOD_RES
<222> LOCATION: (193)..(193)
<223> OTHER INFORMATION: Val or Leu
```

<220> FEATURE:
<221> NAME/KEY: MOD_RES
<222> LOCATION: (216)..(216)
<223> OTHER INFORMATION: Gln or Arg

<400> SEQUENCE: 108

Asn Ser Trp Pro Ser Gln Ile Ser Leu Gln Tyr Arg Ser Gly Gly Ser
1               5                   10                  15

Xaa Tyr His Thr Cys Gly Gly Thr Leu Ile Arg Gln Asn Trp Val Xaa
            20                  25                  30

Thr Ala Ala His Cys Val Asp Tyr Gln Lys Thr Phe Arg Val Val Ala
        35                  40                  45

Gly Asp His Asn Leu Ser Gln Asn Asp Gly Thr Glu Gln Tyr Val Ser
    50                  55                  60

Val Gln Lys Ile Val His Pro Tyr Trp Asn Ser Asp Asn Val Ala
65                  70                  75                  80

Ala Gly Tyr Asp Ile Ala Leu Leu Arg Leu Ala Gln Ser Val Thr Leu
                85                  90                  95

Asn Ser Tyr Val Gln Leu Gly Val Leu Pro Gln Glu Gly Ala Ile Leu
            100                 105                 110

Ala Asn Asn Ser Pro Cys Tyr Ile Thr Gly Trp Gly Lys Thr Lys Thr
        115                 120                 125

Asn Gly Gln Leu Ala Gln Thr Leu Gln Gln Ala Tyr Leu Pro Ser Val
130                 135                 140

Asp Tyr Ala Ile Cys Ser Ser Ser Tyr Trp Gly Ser Thr Val Lys
145                 150                 155                 160

Asn Thr Met Val Cys Ala Gly Gly Asp Gly Val Arg Ser Gly Cys Gln
                165                 170                 175

Gly Asp Ser Gly Gly Pro Leu His Cys Leu Val Asn Gly Lys Tyr Ser
            180                 185                 190

Xaa His Gly Val Thr Ser Phe Val Ser Ser Arg Gly Cys Asn Val Ser
        195                 200                 205

Arg Lys Pro Thr Val Phe Thr Xaa Val Ser Ala Tyr Ile Ser Trp Ile
    210                 215                 220

Asn Asn Val Ile Ala Ser Asn
225                 230

<210> SEQ ID NO 109
<211> LENGTH: 781
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
gaattcagta ctcaggacct tccggaaacc aatgcccggg tagtcggagg gactgaggcc      60
gggaggaact cctggccctc tcagatttcc ctccagtacc ggtctggagg ttcctggtat     120
cacacctgtg gagggaccct tatcagacag aactgggtga tgacagctgc acactgcgtg     180
gattaccaga agactttccg cgtggtggct ggagaccata acctgagcca gaatgatggc     240
actgagcagt acgtgagtgt gcagaagatc gtggtgcatc catactggaa cagcgataac     300
gtggctgcag gctatgacat cgccctgctg cgcctggccc agagcgttac cctcaatagc     360
tatgtccagc tgggtgttct gccccaggag ggagccatcc tggctaacaa cagtccctgc     420
tacatcacag gctggggcaa gaccaagacc aatgggcagc tggcccagac cttgcagcag     480

```
gcttacctgc cctctgtgga ctatgccatc tgctccagct cctcctactg gggctccact    540
gtgaagaaca ctatggtgtg tgctggtgga gatggagttc gctctggatg tcagggtgac    600
tctgggggcc ccctccattg cttggtgaat ggcaagtatt ctcttcatgg agtgaccagc    660
tttgtgtcca gccggggctg taatgtctct agaaagccta cagtcttcac acgggtctct    720
gcttacatct cctggataaa taatgtcatc gcctccaact gataagcttg gatccgtcga    780
c                                                                    781
```

```
<210> SEQ ID NO 110
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Met Lys Arg Ile Leu Ala Ile His Gln Ala Met Glu Gly Ala Pro Arg
1               5                   10                  15

Val Thr Leu Thr Ser Arg Ala Asn Ser Ile Ser Thr Ser Thr His His
            20                  25                  30

Ser Val Leu His Ser Gly Ala Pro Val Gly Gly Ala Gly Ala Asp Gly
        35                  40                  45

Ile Val His Arg Gly Gln Val Ser Leu Leu Gly Leu Gly Gln Leu
    50                  55                  60

Pro Ile Gly Leu Gly Leu Ala Pro Ala Cys Asp Val Ala Gly Thr Val
65                  70                  75                  80

Val Ser Gln Asp Gly Ser Leu Leu Gly Gln Asn Thr Gln Leu Asp Ile
                85                  90                  95

Ala Ile Glu Gly Asn Ala Leu Gly Gln Ala Gln Gly Asp Val Ile
            100                 105                 110

Ala Cys Ser His Val Ile Ala Val Pro Val Trp Met His His Asp Leu
        115                 120                 125

Leu His Thr His Val Leu Leu Ser Ala Ile Ile Leu Ala Gln Val Met
    130                 135                 140

Val Ser Ser His His Ala Glu Ser Leu Leu Val Ile His Ala Val Cys
145                 150                 155                 160

Ser Cys His His Pro Val Leu Ser Asp Lys Gly Pro Ser Thr Gly Val
                165                 170                 175

Ile Pro Gly Thr Ser Arg Pro Val Leu Glu Gly Asn Leu Arg Gly Pro
            180                 185                 190

Gly Val Pro Pro Gly Leu Ser Pro Ser Asp Tyr Pro Gly Ile Gly Phe
        195                 200                 205

Arg Lys Val Leu Ser
    210

<210> SEQ ID NO 111
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(105)

<400> SEQUENCE: 111
```

```
act att gcc agc att gct gct aaa gaa gaa ggg gta tct ctc gag aaa        48
Thr Ile Ala Ser Ile Ala Ala Lys Glu Glu Gly Val Ser Leu Glu Lys
1               5                   10                  15 aga gag gct gaa gct act cag gac ctt ccg gaa acc aat gcc cgg gta        96
Arg Glu Ala Glu Ala Thr Gln Asp Leu Pro Glu Thr Asn Ala Arg Val
            20                  25                  30 gtc ggg ggg                                                           105
Val Gly Gly
        35
```

<210> SEQ ID NO 112
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Thr Ile Ala Ser Ile Ala Ala Lys Glu Glu Gly Val Ser Leu Glu Lys
1               5                   10                  15

Arg Glu Ala Glu Ala Thr Gln Asp Leu Pro Glu Thr Asn Ala Arg Val
            20                  25                  30

Val Gly Gly
        35
```

<210> SEQ ID NO 113
<211> LENGTH: 768
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
ccgcggaccc aggactttcc agaaaccaac gcccgggtag ttggagggac cgaggctcag     60
aggaattctt ggccatctca gatttccctc cagtaccggt ctggaagttc gtgggctcac    120
acctgtggag ggaccctcat caggcagaac tgggtgatga cagccgctca ctgcgtggac    180
agagagttga ccttccgtgt ggtggttgga gagcacaacc tgaaccagaa cgatggcacc    240
gagcagtacg tgggggtgca gaagatcgtg gtgcatccct actggaacac cgacgacgtg    300
gctgcaggct atgacatcgc cctgctgcgc ctggcccaga gtgtaaccct caacagctac    360
gtccagctgg gtgttctgcc aagggctggg accatcctgg ctaacaacag tccctgctac    420
atcacagggt gggggctgac caggaccaat gggcagctgg cccagaccct gcagcaggct    480
tacctgccca ccgtggacta cgccatctgc tccagctcct cgtactgggg ctccaccgtg    540
aagaacagca tggtgtgcgc cggaggggac ggagttcgct ctggatgtca gggtgattct    600
gggggccccc ttcattgctt ggtgaatggt cagtatgctg tccacggtgt aaccagcttc    660
gtgtcccgcc tgggctgtaa tgtcaccagg aagcccacag tcttcaccag ggtctctgct    720
tacatctctt ggataaataa cgtcattgcc agcaactgat aatctaga                 768
```

<210> SEQ ID NO 114
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Thr Gln Asp Phe Pro Glu Thr Asn Ala Arg Val Val Gly Gly Thr Glu
1               5                   10                  15

Ala Gln Arg Asn Ser Trp Pro Ser Gln Ile Ser Leu Gln Tyr Arg Ser
            20                  25                  30

Gly Ser Ser Trp Ala His Thr Cys Gly Gly Thr Leu Ile Arg Gln Asn
        35                  40                  45

Trp Val Met Thr Ala Ala His Cys Val Asp Arg Glu Leu Thr Phe Arg
50                  55                  60

Val Val Val Gly Glu His Asn Leu Asn Gln Asn Asp Gly Thr Glu Gln
65                  70                  75                  80

Tyr Val Gly Val Gln Lys Ile Val Val His Pro Tyr Trp Asn Thr Asp
                85                  90                  95

Asp Val Ala Ala Gly Tyr Asp Ile Ala Leu Leu Arg Leu Ala Gln Ser
                100                 105                 110

Val Thr Leu Asn Ser Tyr Val Gln Leu Gly Val Leu Pro Arg Ala Gly
            115                 120                 125

Thr Ile Leu Ala Asn Asn Ser Pro Cys Tyr Ile Thr Gly Trp Gly Leu
        130                 135                 140

Thr Arg Thr Asn Gly Gln Leu Ala Gln Thr Leu Gln Gln Ala Tyr Leu
145                 150                 155                 160

Pro Thr Val Asp Tyr Ala Ile Cys Ser Ser Ser Tyr Trp Gly Ser
                165                 170                 175

Thr Val Lys Asn Ser Met Val Cys Ala Gly Gly Asp Gly Val Arg Ser
            180                 185                 190

Gly Cys Gln Gly Asp Ser Gly Gly Pro Leu His Cys Leu Val Asn Gly
        195                 200                 205

Gln Tyr Ala Val His Gly Val Thr Ser Phe Val Ser Arg Leu Gly Cys
        210                 215                 220

Asn Val Thr Arg Lys Pro Thr Val Phe Thr Arg Val Ser Ala Tyr Ile
225                 230                 235                 240

Ser Trp Ile Asn Asn Val Ile Ala Ser Asn
                245                 250

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Phe Pro Glu Thr Asn Ala Arg Val Val Gly
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Phe Pro Glu Thr Asn Ala Ala Val Val Gly
1               5                   10

<210> SEQ ID NO 117

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Leu Pro His Thr Asn Pro Ala Val Val Gly
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Phe Pro Glu Thr Asn His Ala Val Val Gly
1               5                   10

<210> SEQ ID NO 119
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any natural amino acid except Pro or Gly
<220> FEATURE:
<221> NAME/KEY: MOD_RES
<222> LOCATION: (2)..(2)
<223> OTHER INFORMATION: Pro, Ala, Leu, Ile, Gly, Val, His, or Thr
<220> FEATURE:
<221> NAME/KEY: MOD_RES
<222> LOCATION: (3)..(3)
<223> OTHER INFORMATION: Ala, Leu, Val, Ile, or Ser

<400> SEQUENCE: 119

Xaa Xaa Xaa
1

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any natural amino acid
<220> FEATURE:
<221> NAME/KEY: MOD_RES
<222> LOCATION: (2)..(2)
<223> OTHER INFORMATION: Any natural amino acid except Gly, Lys, Phe,
      Tyr, Trp, or Arg
<220> FEATURE:
<221> NAME/KEY: MOD_RES
<222> LOCATION: (3)..(3)
<223> OTHER INFORMATION: Any natural amino acid except Pro or Gly
<220> FEATURE:
<221> NAME/KEY: MOD_RES
<222> LOCATION: (4)..(4)
<223> OTHER INFORMATION: Pro, Ala, Leu, Ile, Gly, Val, His, or Thr
<220> FEATURE:
<221> NAME/KEY: MOD_RES
```

<222> LOCATION: (5)..(5)
<223> OTHER INFORMATION: Ala, Leu, Val, Ile, or Ser

<400> SEQUENCE: 120

Xaa Xaa Xaa Xaa Xaa
1               5

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (6)..(6)
<223> OTHER INFORMATION: Any natural amino acid
<220> FEATURE:
<221> NAME/KEY: MOD_RES
<222> LOCATION: (7)..(7)
<223> OTHER INFORMATION: Any natural amino acid except Gly, Lys, Phe,
      Tyr, Trp, or Arg
<220> FEATURE:
<221> NAME/KEY: MOD_RES
<222> LOCATION: (8)..(8)
<223> OTHER INFORMATION: Any natural amino acid except Pro or Gly
<220> FEATURE:
<221> NAME/KEY: MOD_RES
<222> LOCATION: (9)..(9)
<223> OTHER INFORMATION: Pro, Ala, Leu, Ile, Gly, Val, His, or Thr
<220> FEATURE:
<221> NAME/KEY: MOD_RES
<222> LOCATION: (10)..(10)
<223> OTHER INFORMATION: Ala, Leu, Val, Ile, or Ser

<400> SEQUENCE: 121

Thr Xaa Asp Leu Pro Xaa Xaa Xaa Xaa Xaa
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (6)..(6)
<223> OTHER INFORMATION: Any natural amino acid
<220> FEATURE:
<221> NAME/KEY: MOD_RES
<222> LOCATION: (7)..(7)
<223> OTHER INFORMATION: Any natural amino acid except Gly, Lys, Phe,
      Tyr, Trp, or Arg
<220> FEATURE:
<221> NAME/KEY: MOD_RES
<222> LOCATION: (8)..(8)
<223> OTHER INFORMATION: Any natural amino acid except Pro or Gly
<220> FEATURE:
<221> NAME/KEY: MOD_RES
<222> LOCATION: (9)..(9)
<223> OTHER INFORMATION: Pro, Ala, Leu, Ile, Gly, Val, His, or Thr
<220> FEATURE:
<221> NAME/KEY: MOD_RES
<222> LOCATION: (10)..(11)

```
<223> OTHER INFORMATION: Ala, Leu, Val, Ile, or Ser
<220> FEATURE:
<221> NAME/KEY: MOD_RES
<222> LOCATION: (12)..(12)
<223> OTHER INFORMATION: Gly, Ala, or Val
<220> FEATURE:
<221> NAME/KEY: MOD_RES
<222> LOCATION: (13)..(13)
<223> OTHER INFORMATION: Gly, Val, Thr, Phe, Tyr, or Trp

<400> SEQUENCE: 122

Thr Xaa Asp Leu Pro Xaa Xaa Xaa Xaa Xaa Xaa Xaa Xaa
1               5                   10

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, His, Pro, Gly, Asn, Lys, or Ala
<220> FEATURE:
<221> NAME/KEY: MOD_RES
<222> LOCATION: (2)..(2)
<223> OTHER INFORMATION: Thr, Ala, Pro, or His
<220> FEATURE:
<221> NAME/KEY: MOD_RES
<222> LOCATION: (3)..(3)
<223> OTHER INFORMATION: Ala, Leu, Ile, Met, Lys, Asn, or Val
<220> FEATURE:
<221> NAME/KEY: MOD_RES
<222> LOCATION: (4)..(4)
<223> OTHER INFORMATION: Pro, Ala, Leu, Ile, Gly, Val, or Thr
<220> FEATURE:
<221> NAME/KEY: MOD_RES
<222> LOCATION: (5)..(6)
<223> OTHER INFORMATION: Ala, Leu, Val, Ile, or Ser
<220> FEATURE:
<221> NAME/KEY: MOD_RES
<222> LOCATION: (7)..(7)
<223> OTHER INFORMATION: Gly, Ala, or Val
<220> FEATURE:
<221> NAME/KEY: MOD_RES
<222> LOCATION: (8)..(8)
<223> OTHER INFORMATION: Gly, Val, Thr, Phe, Tyr, or Trp

<400> SEQUENCE: 123

Xaa Xaa Xaa Xaa Xaa Xaa Xaa Xaa
1               5

<210> SEQ ID NO 124
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Leu, Ile, Met, Lys, Asn, His, or Val
<220> FEATURE:
<221> NAME/KEY: MOD_RES
<222> LOCATION: (2)..(2)
<223> OTHER INFORMATION: Pro, Ala, Leu, Ile, Gly, Val, or Thr
<220> FEATURE:
<221> NAME/KEY: MOD_RES
<222> LOCATION: (3)..(3)
<223> OTHER INFORMATION: Ala, Leu, Val, Ile, or Ser

<400> SEQUENCE: 124
```

Xaa Xaa Xaa
1

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, His, Pro, Gly, Asn, Lys, or Ala
<220> FEATURE:
<221> NAME/KEY: MOD_RES
<222> LOCATION: (2)..(2)
<223> OTHER INFORMATION: Thr, Ala, Pro, or His
<220> FEATURE:
<221> NAME/KEY: MOD_RES
<222> LOCATION: (3)..(3)
<223> OTHER INFORMATION: Ala, Leu, Ile, Met, Lys, Asn, Thr, or Val
<220> FEATURE:
<221> NAME/KEY: MOD_RES
<222> LOCATION: (4)..(4)
<223> OTHER INFORMATION: Pro, Ala, Leu, Ile, Gly, Val, Asn, or Thr
<220> FEATURE:
<221> NAME/KEY: MOD_RES
<222> LOCATION: (5)..(5)
<223> OTHER INFORMATION: Ala, Leu, Val, Ile, Asn, or Ser
<220> FEATURE:
<221> NAME/KEY: MOD_RES
<222> LOCATION: (6)..(6)
<223> OTHER INFORMATION: Ala, Leu, Val, Ile, or Ser
<220> FEATURE:
<221> NAME/KEY: MOD_RES
<222> LOCATION: (7)..(7)
<223> OTHER INFORMATION: Gly, Ala, or Val
<220> FEATURE:
<221> NAME/KEY: MOD_RES
<222> LOCATION: (8)..(8)
<223> OTHER INFORMATION: Gly, Val, Thr, Phe, Tyr, or Trp

<400> SEQUENCE: 125

Xaa Xaa Xaa Xaa Xaa Xaa Xaa Xaa
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any natural amino acid
<220> FEATURE:
<221> NAME/KEY: MOD_RES
<222> LOCATION: (2)..(2)
<223> OTHER INFORMATION: Any natural amino acid except Gly, Lys, Phe,
      Tyr, Trp, or Arg
<220> FEATURE:
<221> NAME/KEY: MOD_RES
<222> LOCATION: (3)..(3)
<223> OTHER INFORMATION: Any natural amino acid
<220> FEATURE:
<221> NAME/KEY: MOD_RES
<222> LOCATION: (4)..(4)
<223> OTHER INFORMATION: Pro, Ala, Leu, Ile, Gly, Val, His, Asn, or Thr
<220> FEATURE:
<221> NAME/KEY: MOD_RES
<222> LOCATION: (5)..(5)
<223> OTHER INFORMATION: Ala, Leu, Val, Ile, Asn, or Ser

```
<400> SEQUENCE: 126

Xaa Xaa Xaa Xaa Xaa
1               5

<210> SEQ ID NO 127
<211> LENGTH: 4
<212> TYPE: PRT
<213> ORGANISM: Homo sapiens

<400> SEQUENCE: 127

Val Val Gly Gly
1

<210> SEQ ID NO 128
<211> LENGTH: 6
<212> TYPE: PRT
<213> ORGANISM: Homo sapiens

<400> SEQUENCE: 128

Val Val Gly Gly Thr Glu
1               5

<210> SEQ ID NO 129
<211> LENGTH: 9
<212> TYPE: PRT
<213> ORGANISM: Homo sapiens

<400> SEQUENCE: 129

Val Val Gly Gly Thr Glu Ala Gly Arg
1               5

<210> SEQ ID NO 130
<211> LENGTH: 781
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(759)

<400> SEQUENCE: 130 gaattcagt act cag gac ctt ccg gaa acc aat gcc cgg gta gtc gga ggg       51
          Thr Gln Asp Leu Pro Glu Thr Asn Ala Arg Val Val Gly Gly
          1               5                  10 act gag gcc ggg agg aac tcc tgg ccc tct cag att tcc ctc cag tac         99
Thr Glu Ala Gly Arg Asn Ser Trp Pro Ser Gln Ile Ser Leu Gln Tyr
15                  20                  25                  30 cgg tct gga ggt tcc tgg tat cac acc tgt gga ggg acc ctt atc aga        147
Arg Ser Gly Gly Ser Trp Tyr His Thr Cys Gly Gly Thr Leu Ile Arg
                35                  40                  45 cag aac tgg gtg atg aca gct gca cac tgc gtg gat tac cag aag act        195
Gln Asn Trp Val Met Thr Ala Ala His Cys Val Asp Tyr Gln Lys Thr
            50                  55                  60 ttc cgc gtg gtg gct gga gac cat aac ctg agc cag aat gat ggc act        243
Phe Arg Val Val Ala Gly Asp His Asn Leu Ser Gln Asn Asp Gly Thr
        65                  70                  75 gag cag tac gtg agt gtg cag aag atc gtg gtg cat cca tac tgg aac        291
Glu Gln Tyr Val Ser Val Gln Lys Ile Val Val His Pro Tyr Trp Asn
    80                  85                  90 agc gat aac gtg gct gca ggc tat gac atc gcc ctg ctg cgc ctg gcc        339
```

```
                                          -continued
Ser Asp Asn Val Ala Ala Gly Tyr Asp Ile Ala Leu Leu Arg Leu Ala
 95             100                 105                 110 cag agc gtt acc ctc aat agc tat gtc cag ctg ggt gtt ctg ccc cag        387
Gln Ser Val Thr Leu Asn Ser Tyr Val Gln Leu Gly Val Leu Pro Gln
                115                 120                 125 gag gga gcc atc ctg gct aac aac agt ccc tgc tac atc aca ggc tgg        435
Glu Gly Ala Ile Leu Ala Asn Asn Ser Pro Cys Tyr Ile Thr Gly Trp
                130                 135                 140 ggc aag acc aag acc aat ggg cag ctg gcc cag acc ttg cag cag gct        483
Gly Lys Thr Lys Thr Asn Gly Gln Leu Ala Gln Thr Leu Gln Gln Ala
                145                 150                 155 tac ctg ccc tct gtg gac tat gcc atc tgc tcc agc tcc tac tgg            531
Tyr Leu Pro Ser Val Asp Tyr Ala Ile Cys Ser Ser Ser Tyr Trp
        160                 165                 170 ggc tcc act gtg aag aac act atg gtg tgt gct ggt gga gat gga gtt        579
Gly Ser Thr Val Lys Asn Thr Met Val Cys Ala Gly Gly Asp Gly Val
175                 180                 185                 190 cgc tct gga tgt cag ggt gac tct ggg ggc ccc ctc cat tgc ttg gtg        627
Arg Ser Gly Cys Gln Gly Asp Ser Gly Gly Pro Leu His Cys Leu Val
                195                 200                 205 aat ggc aag tat tct ctt cat gga gtg acc agc ttt gtg tcc agc cgg        675
Asn Gly Lys Tyr Ser Leu His Gly Val Thr Ser Phe Val Ser Ser Arg
                210                 215                 220 ggc tgt aat gtc tct aga aag cct aca gtc ttc aca cgg gtc tct gct        723
Gly Cys Asn Val Ser Arg Lys Pro Thr Val Phe Thr Arg Val Ser Ala
                225                 230                 235 tac atc tcc tgg ata aat aat gtc atc gcc tcc aac tgataagctt             769
Tyr Ile Ser Trp Ile Asn Asn Val Ile Ala Ser Asn
        240                 245                 250 ggatccgtcg ac                                                           781

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Thr Asn Ala Arg Val Val Gly Gly
1               5
```

RECOMBINANT ELASTASE PROTEINS AND METHODS OF MANUFACTURING AND USE THEREOF

This application is a continuation of U.S. application Ser. No. 12/823,098, filed Jun. 24, 2010, now abandoned, the contents of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Jan. 23, 2018, is named 180125_PRT-004C-C1_Sequence_Listing_ACK.txt and is 149,500 bytes in size.

FIELD OF THE INVENTION

The present invention relates to recombinant methods of manufacturing and formulating elastase proteins for use in treating and preventing diseases of biological conduits. The present invention further relates to novel recombinant elastase proteins and pharmaceutical compositions containing such proteins. Yet further, the present invention relates to the use of pharmaceutical compositions comprising recombinant elastase proteins for the treatment and prevention of diseases of biological conduits.

BACKGROUND OF THE INVENTION

Elastin is a protein capable of spontaneously recoiling after being stretched. Cross-linked elastin is the major structural component of elastic fibers, which confers tissue elasticity. A proteinase may be named an elastase if it possesses the ability to solubilize mature, cross-linked elastin (Bieth, J G "Elastases: catalytic and biological properties," at pp. 217-320 (Mecham Edition, Regulation of Matrix Accumulation, New York, Academic Press, 1986). Several published patent applications (WO 2001/21574; WO 2004/073504; and WO 2006/036804) indicate that elastase, alone and in combination with other agents, is beneficial in the treatment of diseases of biological conduits, including biological conduits which are experiencing, or susceptible to experiencing, obstruction and vasospasm. For elastase therapy of human subjects, the use of a human elastase is desirable to reduce the risk of immune reaction to a non-human elastase.

To this date, however, there is no known commercially viable means of producing biologically active elastase in sufficiently pure form and in sufficient quantities for clinical applications. Because elastases are powerful proteases that can hydrolyze numerous proteins other than elastin, the proteolytic activity of elastase poses potential obstacles for its recombinant production. For example, the activity of mature elastase can damage the host cell which is expressing it, degrade itself, or degrade agents used to assist in the production or characterization of the elastase.

Elastases are often expressed as preproproteins, containing a signal peptide, an activation peptide, and a mature, active portion. Cleavage of the signal sequence upon secretion yields a proprotein that can have little or no enzymatic activity, and whose amino acid sequence contains the amino acid sequence of an activation peptide and a mature protein. Generally, for recombinant expression, an inactive precursor may be expressed instead of the mature active enzyme to circumvent damage to the cell that expresses it. For example, U.S. Pat. No. 5,212,068 describes the cloning of human pancreatic elastase cDNAs (referred to therein as elastase "IIA," "IIIA" and "IIIB"). The various elastases were expressed as full-length cDNAs, including the native signal sequences, in mammalian COS-1 cells. In addition, engineered versions of the elastases, containing a B. subtilis signal sequence and a β-galactosidase signal sequence, were also expressed in B. subtilis and E. coli, respectively. U.S. Pat. No. 5,212,068 also suggests expressing elastases in S. cerevisiae. Generally, working examples of elastase expression in U.S. Pat. No. 5,212,068 show low activity of the recovered elastase or require an activation step involving treatment with trypsin, to generate the active elastase. In addition, the elastases were largely present in inclusion bodies when expressed in E. coli, and only small portions of the expressed elastase were soluble and active. None of the elastase preparations described in U.S. Pat. No. 5,212,068 was purified to pharmaceutical grade.

Thus, there is a need in the art for recombinant manufacturing methods that allow the generation of therapeutic amounts of biologically active pharmaceutical grade elastases, and preferably avoid a trypsin activation step that is costly for large-scale preparation and can result in trypsin contamination of the final product. Administration of an elastase containing trypsin to a patient could result in activation of the protease-activated receptors 1 and 2, which may reduce some of the beneficial effects of elastase treatment.

Citation or identification of any reference in Section 2 or in any other section of this application shall not be construed as an admission that such reference is available as prior art to the present invention.

SUMMARY OF THE INVENTION

The present invention provides novel, efficient methods of making recombinant elastase proteins and the use of the recombinant proteins in compositions, e.g., pharmaceutical compositions, elastase formulations or unit dosages, for the treatment and prevention of diseases of biological conduits.

The present invention is directed to auto-activated proelastase proteins, nucleic acids encoding auto-activated proelastase proteins, host cells comprising said nucleic acids, methods of making auto-activated proelastase proteins and the use of auto-activated proelastase proteins in the manufacture of mature, biologically active elastase proteins, for example for use in pharmaceutical formulations. The term "auto-activated" (or "autoactivated") is used herein interchangeably with the terms "auto-activating," "self-activating," and "self-activated" and is not intended to imply that an activation step has taken place. The term "activation" is used herein interchangeably with the term "conversion" and is not intended to imply that a protein resulting from "activation" necessarily possesses enzymatic activity.

As used hereinbelow, and unless indicated otherwise, the term "elastase" generally refers to mature elastase proteins with elastase activity as well as immature elastase proteins, including immature proelastase proteins (also referred to herein as elastase proproteins) and immature preproelastase proteins (also referred to herein as elastase preproproteins).

Preferred elastases of the invention are type I pancreatic elastases, e.g., human type I pancreatic elastase and porcine type I pancreatic elastase. Type I pancreatic elastases are sometimes referred to herein as "elastase-1," "elastase I," "elastase type 1," "type 1 elastase" or "ELA-1." Human type I pancreatic elastase is also referred to herein as hELA-1 or human ELA-1, and porcine type I pancreatic elastase is also referred to herein as pELA-1 or porcine ELA-1.

A mature elastase protein of the invention typically has an amino acid sequence encoded by a naturally occurring elastase gene or a variant of such sequence. Preferred sequence variants, including variants containing amino acid substitutions, are described herein. A proelastase protein is a largely inactive precursor of a mature elastase protein, and a preproelastase protein further contains a signal sequence for protein secretion. Pre and pro sequences of the elastase proteins of the invention are typically not native to the elastase genes encoding the mature elastase proteins of the invention. Thus, in a sense, the immature elastase proteins of the invention are "chimeric" proteins, with their mature portions encoded by a naturally-occurring elastase gene and their immature portions encoded by non-elastase gene sequences.

For ease of reference, the elastase proteins of the invention and their core sequence components are depicted in FIG. 2. As shown in FIG. 2, the amino acid residues within the proelastase sequence that are N-terminal to the cleavage bond (i.e., the bond that is cleaved to yield mature elastase protein) are designated herein as PX, . . . P5, P4, P3, P2, and P1, where P1 is immediately N-terminal to the cleavage bond, whereas amino acids residues located to the C-terminus to the cleavage bond (and to the N-terminus) of the mature elastase protein are designated P1', P2', P3', . . . PX', where P1' is immediately C-terminal to the cleavage bond and represents the N-terminal amino acid residue of the mature protein. FIG. 2 also shows the following components:

(1) SIGNAL SEQUENCE: A sequence that increases the proportion of expressed molecules that are secreted from the cell. An exemplary sequence is amino acids 1-22 of SEQ ID NOS:50 or 51.

(2) PROPEPTIDE+SPACER: An optional, preferably a non-elastase, propeptide sequence (such as yeast α-factor propropeptide) that can further optionally include one or more spacer sequences (a yeast α-factor propeptide sequences and Kex2 and STE13 spacer sequences are depicted in FIG. 1B). In a specific embodiment, the propeptide sequence does not include a spacer.

(3) ELASTASE PROPEPTIDE: Peptide that, when present on the N-terminal end of an elastase, renders the molecule inactive or less active as compared to the corresponding mature elastase protein. The elastase propeptide may be contiguous with the activation peptide or may contain additional amino acids relative to the activation peptide. Exemplary elastase propeptide sequences are amino acids 1-10 of SEQ ID NOS:64 and 69.

(4) ACTIVATION PEPTIDE: Used interchangeably herein with "activation sequence," an activation peptide is a component of, and can be contiguous with, the elastase propeptide. As shown in FIG. 2, the activation peptide contains amino acid residues P10 through P1. An exemplary activation peptide consensus sequence is SEQ ID NO:80 or SEQ ID NO:121; other examples of activation peptide sequences are SEQ ID NOS: 23, 72 and 73.

(5) RECOGNITION SEQUENCE: A recognition sequence is a component of the elastase propeptide. As shown in FIG. 2, the recognition sequence contains amino acid residues P3 through P1. Exemplary recognition sequence consensus sequences are SEQ ID NOS:11-13, 93, and 119, and an exemplary recognition sequence is SEQ ID NO:20.

(6) CLEAVAGE DOMAIN: A region in the proelastase protein that spans the cleavage bond. As shown in FIG. 2, the cleavage domain contains amino acid residues P5 through P3'. Exemplary cleavage domain consensus sequences are SEQ ID NOS:74, 135 and 125. Exemplary cleavage domain sequences are SEQ ID NOS:42, 43, 48, 49, 53, 53, 54 and 55.

(7) CLEAVAGE SITE: Another region in the proelastase protein that also spans the cleavage bond. As shown in FIG. 2, the cleavage site contains amino acid residues P4 through P4'. An exemplary cleavage site sequence is SEQ ID NO:27.

(8) PREPROELASTASE PROTEIN: A protein that can comprise all of the component parts. An exemplary preproelastase protein can comprise a peptides of SEQ ID NO:50, 51, 96, or 97 followed by an operably linked protein of SEQ ID NO:64 or SEQ ID NO:69.

(9) PROELASTASE PROTEIN: A protein that comprises mature elastase protein, an elastase propeptide, and the optional propeptide and spacer sequences. Exemplary proelastase sequences are SEQ ID NOS:64 and 69.

(10) MATURE ELASTASE PROTEIN: A protein that when properly processed displays elastase activity. Exemplary mature sequences are SEQ ID NO:1 (human) and SEQ ID NO:39 (porcine).

The elastase protein components can be considered modular building blocks of the elastase proteins, proelastase proteins and preproelastase proteins. For example, the present invention provides a proelastase protein comprising the sequence of an elastase propeptide and a mature elastase protein. The elastase propeptide can contain an activation peptide. The elastase propeptide can also contain an elastase recognition sequence. The present invention also provides a proelastase protein comprising a cleavage domain or cleavage site in the region spanning the junction between the elastase propeptide and the mature elastase protein. The proelastase proteins may further comprise a signal sequence for secretion. Such proteins are considered preproelastase proteins. The preproelastase proteins may further comprise a yeast alpha factor propeptide and optionally a spacer sequence between the signal sequence and the elastase propeptide. The elastase proteins of the invention may also contain components in addition to the core modular components illustrated in FIG. 2. For example, an elastase protein can contain an epitope tag or a histidine tag for purification. It should also be noted that the elastase proteins of the invention need not contain all the components depicted in FIG. 2, but generally contain at least one of the components (including, by way of example but not limitation, a mature elastase or a proelastase sequence) depicted in FIG. 2. Exemplary elastase proteins of the invention are set forth in embodiments 1-12, 28-39 and 68-69 in Section 8 below, including exemplary type I proelastase proteins set forth in embodiments 13-27 in Section 8 below.

In certain aspects, the proelastase proteins of the disclosure have an elastase recognition sequence P3-P2-P1, wherein the amino acid residue at the P3 position is selected from:
(a) any of the 26 natural amino acid residues except proline or glycine;
(b) alanine, leucine, isoleucine, methionine, lysine, asparagine, histidine, threonine, or valine; and
(c) alanine, leucine, isoleucine, methionine, lysine, asparagine, or valine; wherein the amino acid residue at the P2 position independently selected from:
(a) proline, alanine, leucine, isoleucine, glycine, valine, histidine asparagine, or threonine;
(b) proline, alanine, leucine, isoleucine, glycine, valine, asparagine, threonine;

(c) proline, alanine, leucine, isoleucine, glycine, valine, threonine; and
(d) proline;
and wherein the amino acid residue at the P1 position is independently selected from:
(a) alanine, leucine, valine, isoleucine or serine;
(b) alanine, leucine, valine, isoleucine, asparagine or serine; and
(c) alanine.

In other aspects, the proelastase proteins of the disclosure have a propeptide portion of an elastase cleavage domain P5-P4-P3-P2-P1, wherein the amino acid residue at the P5 position is selected from:
(a) any of the 26 natural amino acid residues;
(b) glutamate, histidine, proline, glycine, asparagine, lysine or alanine,
(c) histidine or glutamate; and
(d) histidine,
wherein the amino acid at the P4 position is independently selected from:
(a) any of the 26 natural amino acid residues except glycine, lysine, phenylalanine, tyrosine, tryptophan, or arginine; and
(b) threonine, alanine, proline, or histidine,
wherein the amino acid residue at the P3 position is independently selected from:
(a) any of the 26 natural amino acid residues except proline or glycine;
(b) alanine, leucine, isoleucine, methionine, lysine, asparagine, histidine, threonine, or valine; and
(c) alanine, leucine, isoleucine, methionine, lysine, asparagine, or valine;
wherein the amino acid residue at the P2 position is independently selected from:
(a) proline, alanine, leucine, isoleucine, glycine, valine, histidine asparagine, or threonine;
(b) proline, alanine, leucine, isoleucine, glycine, valine, asparagine, threonine;
(c) proline, alanine, leucine, isoleucine, glycine, valine, threonine; and
(d) proline;
and wherein the amino acid residue at the P1 position is independently selected from:
(a) alanine, leucine, valine, isoleucine or serine;
(b) alanine, leucine, valine, isoleucine, asparagine or serine; and
(c) alanine.

In certain aspects, the proelastase proteins of the disclosure have an elastase cleavage domain in which:
the amino acid residue at the P1' position is alanine, leucine, valine, isoleucine or serine, and is most preferably valine;
the amino acid residue at the P2' position is glycine, alanine, or valine, and is most preferably valine;
the amino acid residue at the P3' position is glycine, valine, threonine, phenylalanine, tyrosine or tryptophan, and is most preferably glycine.

In other aspects, the proelastase proteins of the disclosure have an activation peptide in which:
the amino acid residue at the P10 position is threonine;
the amino acid residue at the P9 position is glutamine or histidine;
the amino acid residue at the P8 position is aspartate;
the amino acid residue at the P7 position is leucine; and
the amino acid residue at the P6 position is proline.

In certain preferred embodiments, a proelastase protein of the disclosure has a histidine residue at the P5 position and/or a proline residue at the P2 position and/or an alanine residue at the P1 position.

The present invention provides proelastase proteins comprising (i) optionally, a signal sequence; (ii) an elastase activation peptide sequence comprising an elastase recognition sequence operably linked to (iii) an amino acid sequence of a type I mature elastase.

In certain aspects, the proelastase protein has an elastase recognition sequence of SEQ ID NO:119 or SEQ ID NO:124.

In certain aspects, the proelastase protein has a cleavage domain the propeptide portion of which comprises the amino acid sequence of SEQ ID NO:120.

In certain aspects, the proelastase protein has a cleavage domain of SEQ ID NO:123 or
SEQ ID NO:125.

In certain aspects, the proelastase protein has an activation peptide sequence of SEQ ID NO:121.

In certain aspects, the proelastase proteins of the invention are isolated.

Nucleic acids encoding the elastase proteins of the invention, methods for producing and purifying the proteins, recombinant cells and cell culture supernatants, compositions comprising elastase proteins (e.g., pharmaceutical compositions, unit dosages, formulations), the use of the proteins for therapeutic purposes and kits comprising the proteins, formulations, pharmaceutical compositions and unit doses are encompassed herein.

The present invention provides nucleic acids encoding proelastase proteins, vectors comprising such nucleic acid, and host cells genetically engineered to express proelastase proteins, for example a host cells into which a vector encoding a proelastase protein is introduced.

The present invention provides a solution comprising a proelastase protein. The solution can be a buffer solution and/or contain cell culture components. In a specific embodiment, the solution is a buffer solution comprising phosphate and/or Tris base.

The present invention provides a cell culture supernatant comprising a proelastase protein.

The invention provides methods of producing a mature elastase protein, comprising subjecting a solution containing proelastase protein to conditions that produce mature elastase protein. The invention further provides methods of producing a maturing elastase protein, comprising: (a) culturing a host cell engineered to express a proelastase protein under conditions in which the proelastase protein is produced; (b) recovering, and optionally purifying, the proelastase protein, and (c) subjecting a solution comprising said proelastase protein to conditions that produce mature elastase protein, thereby producing a mature elastase protein. In certain aspects, such conditions do not include contacting the proelastase protein with trypsin and/or contacting said proelastase protein with a catalytic amount of an elastase and/or subjecting the solution to a pH of 6 to 11. In a specific embodiment, the solution comprises cell culture components, e.g., if it is a cell culture supernatant or is made from cell culture supernatant containing proelastase protein. In certain aspects, the methods further comprise the step of lyophilizing the mature elastase protein and/or purifying the mature elastase protein.

Nucleic acids encoding the elastase proteins of the invention are exemplified in embodiments 40-67 in Section 8 below, including vectors (see, e.g., embodiments 70-72). Also exemplified in Section 8 are recombinant cells (see, e.g., embodiments 73-84), cell supernatants containing elastase proteins (see, e.g., embodiment 88). Methods for producing elastase proteins are exemplified in embodiments 89-224, 261-276 and 347-373 in Section 8. Methods for producing elastase formulations are exemplified in embodiments 225-260 in Section 8. Methods of producing pharmaceutical compositions are exemplified in embodiments 374-385 in Section 8. Pharmaceutical compositions comprising elastase proteins are exemplified in embodiments 277-313 and 386 in Section 8, and unit dosages are exemplified in embodiments 413-420 in Section 8. Formulations of elastase proteins are exemplified in embodiments 324-346 in Section 8. The use of the elastase proteins for therapeutic purposes is exemplified in embodiments 387-414 in Section 8. Kits comprising the proteins are exemplified in Section 8 by way of embodiments 421-424.

Various aspects of the invention with respect to proelastase proteins with SEQ ID NOS:64 and 69 are exemplified as Specific Embodiments in Section 8 below; however, such embodiments are applicable to other elastase protein sequences disclosed herein.

The production methods described herein often include an activation step, whereby the activation peptide is removed from the proelastase sequence/separated from the mature elastase sequence, thereby generating a mature elastase protein. The activation steps described herein may be auto activation steps, i.e., carried out by an elastase activity, or non-auto activation step, i.e., non-elastase mediated, e.g., carried out by trypsin.

In certain aspects, the present invention provides a nucleic acid molecule comprising a nucleotide sequence which encodes an elastase protein (including but not limited to a protein of any one of SEQ ID NOS: 6-9, 64-69, 88-91, or 98-103) comprising (i) an elastase propeptide comprising an activation peptide sequence comprising an elastase recognition sequence operably linked to (ii) the amino acid sequence of a protein having elastase activity. The protein optionally further comprises a signal sequence, such as a yeast α-factor signal peptide and exemplified by the amino acid sequence of SEQ ID NO:34, operably linked to said elastase propeptide. The α-factor is sometimes referred to herein as "alpha-factor" or "alpha mating factor" or "α-mating factor." In certain specific embodiments, the protein comprises a non-elastase propeptide such as yeast α-factor propeptide. In certain specific embodiments, the protein can comprise one or more spacer sequences. Spacer sequences can include, but are not limited to, Kex2 and STE13 protease cleavage sites. In a specific embodiment, a Kex2 spacer can be used. In another embodiment, a Kex2 spacer can be operably linked to STE13 spacers as shown in FIG. 1B. A signal peptide sequence and a non-elastase propeptide sequence is exemplified by the amino acid sequences of SEQ IDS NO:51 or 97. A peptide containing a signal peptide sequence, a non-elastase propeptide sequence, and a spacer sequence is exemplified by the amino acid sequences of SEQ IDS NO:50 or 96.

In other specific embodiments, the signal sequence is a mammalian secretion signal sequence, such as a porcine or human type I elastase (used interchangeably with a type I pancreatic elastase) signal sequence.

Preferably, the elastase recognition sequence is a type I pancreatic elastase recognition sequence.

In specific embodiments, the protein having type I elastase activity is a mature human type I elastase, for example a protein of the amino acid sequence of SEQ ID NO:1, 4, 5, 84, or 87.

The present invention also provides a nucleic acid molecule comprising a nucleotide sequence which encodes a protein comprising (i) a signal sequence operable in *Pichia pastoris* operably linked to (ii) an activation sequence (including but not limited to an amino acid sequence of SEQ ID NOS: 23, 72, 73, or 80) comprising a protease recognition sequence (including but not limited to an amino acid sequence of any of SEQ ID NOS:11-23 and 93 which in turn is operably linked to (iii) the amino acid sequence of a mature human type I elastase. In a preferred embodiment, the protease recognition sequence is a human type I elastase recognition sequence, most preferably an elastase recognition sequence of SEQ ID NO:20.

Proelastase proteins (optionally comprising a signal sequence and thus representing preproelastase proteins) and mature elastase proteins encoded by the nucleic acids of the invention are also provided, as are compositions (e.g., pharmaceutical compositions, formulations and unit dosages) comprising said mature elastase proteins.

In a preferred embodiment, the proelastase protein or mature elastase protein does not have an N-terminal methionine residue. In another embodiment, however, the proelastase protein or mature elastase protein does have an N-terminal methionine residue.

Table 1 below summarizes the sequence identifiers used in the present specification. Preferred proteins of the invention comprise or consist of any of SEQ ID NOS:1-32, 34, 37-73, 77, 78, 82-92, and 98-105 listed in Table 1 below, or are encoded in part or entirely by the nucleotide sequences of SEQ ID NO: 33 and SEQ ID NO: 81.

TABLE 1

Summary of amino acid and nucleotide SEQ ID NOS.

| MOLECULE | NUCLEOTIDE OR AMINO ACID | SEQ ID NO |
|---|---|---|
| Mature human elastase I, including first "valine," with possible polymorphism at position 220 (V or L) (numbering refers to position in context of preproprotein) | Amino Acid | 1 |
| Mature human elastase I, minus first "valine," with possible polymorphism at position 220 (V or L) (numbering refers to position in context of preproprotein) | Amino Acid | 2 |
| Mature human elastase I, minus first two "valines," with possible polymorphism at position 220 (V or L) (numbering refers to position in context of preproprotein) | Amino Acid | 3 |
| Mature human elastase I, with first "valine" substituted by "alanine," with possible polymorphism at position 220 (V or L) (numbering refers to position in context of preproprotein) | Amino Acid | 4 |
| Mature human elastase I (isotype 2), including first "valine" | Amino Acid | 5 |

TABLE 1-continued

Summary of amino acid and nucleotide SEQ ID NOS.

| MOLECULE | NUCLEOTIDE OR AMINO ACID | SEQ ID NO |
|---|---|---|
| Engineered elastase proprotein no. 1 (pPROT42 variant), with possible polymorphism at position 220 (V or L) (numbering refers to position in context of preproprotein) | Amino Acid | 6 |
| Engineered elastase proprotein no. 2, with possible polymorphism at position 220 (V or L) (numbering refers to position in context of preproprotein) | Amino Acid | 7 |
| Engineered elastase proprotein no. 3, with possible polymorphism at position 220 (V or L) (numbering refers to position in context of preproprotein) | Amino Acid | 8 |
| Engineered elastase proprotein no. 4, with possible polymorphism at position 220 (V or L) (numbering refers to position in context of preproprotein) | Amino Acid | 9 |
| Engineered elastase proprotein no. 5 (pPROT24 trypsin activated sequence), with possible polymorphism at position 220 (V or L) (numbering refers to position in context of preproprotein) | Amino Acid | 10 |
| Consensus elastase recognition sequence 1 (Positions $Xaa_1$ = P3, $Xaa_2$ = P2, $Xaa_3$ = P1) | Amino Acid | 11 |
| Consensus elastase recognition sequence 2 (Positions P3-P2-P1) | Amino Acid | 12 |
| Consensus elastase recognition sequence 3 (Positions P3-P2-P1) | Amino Acid | 13 |
| Elastase recognition sequence 1 (Positions P3-P2-P1) | Amino Acid | 14 |
| Elastase recognition sequence 2 (Positions P3-P2-P1) | Amino Acid | 15 |
| Elastase recognition sequence 3 (Positions P3-P2-P1) | Amino Acid | 16 |
| Wild-type trypsin recognition sequence (pPROT24) (Positions P3-P2-P1) | Amino Acid | 17 |
| Elastase recognition sequence 5 (Positions P3-P2-P1) | Amino Acid | 18 |
| Elastase recognition sequence 6 (Positions P3-P2-P1) | Amino Acid | 19 |
| Elastase recognition sequence 7 (Positions P3-P2-P1 of Variants 48 and 55) | Amino Acid | 20 |
| Elastase recognition sequence 8 | Amino Acid | 21 |
| Human elastase activation sequence 1 | Amino Acid | 22 |
| Human elastase activation sequence 2 | Amino Acid | 23 |
| pro-PROT-201 cleavage site | Amino Acid | 24 |
| pPROT40 cleavage site | Amino Acid | 25 |
| pPROT41 cleavage site | Amino Acid | 26 |
| pPROT42 cleavage site | Amino Acid | 27 |
| pPROT43 cleavage site | Amino Acid | 28 |
| pPROT44 cleavage site | Amino Acid | 29 |
| pPROT45 cleavage site | Amino Acid | 30 |
| pPROT46 cleavage site | Amino Acid | 31 |
| pPROT47 cleavage site | Amino Acid | 32 |
| Coding region of a human elastase-1 (i.e., human type I pancreatic elastase) (NCBI Accession No. NM_001971) | Nucleotide | 33 |
| Yeast alpha factor signal peptide | Amino Acid | 34 |
| 20F primer | Nucleotide | 35 |
| 24R primer | Nucleotide | 36 |
| pPROT42 P3 Cleavage Site Variant Elastase, with possible polymorphism at position 220 (V or L) (numbering refers to position in context of preproprotein) | Amino Acid | 37 |
| pPROT42 P2 Cleavage Site Variant Elastase, with possible polymorphism at position 220 (V or L) (numbering refers to position in context of preproprotein) | Amino Acid | 38 |
| Mature porcine pancreatic Elastase I (from GenBank Accession P00772.1) | Amino Acid | 39 |
| Elastase Variant Propeptide Cleavage Domain 40 | Amino Acid | 40 |
| Elastase Variant Propeptide Cleavage Domain 41 | Amino Acid | 41 |
| Elastase Variant Propeptide Cleavage Domain 42 | Amino Acid | 42 |
| Elastase Variant Propeptide Cleavage Domain 43 | Amino Acid | 43 |
| Elastase Variant Propeptide Cleavage Domain 44 | Amino Acid | 44 |
| Elastase Variant Propeptide Cleavage Domain 45 | Amino Acid | 45 |
| Elastase Variant Propeptide Cleavage Domain 46 | Amino Acid | 46 |
| Elastase Variant Propeptide Cleavage Domain 47 | Amino Acid | 47 |
| Elastase Variant Propeptide Cleavage Domain 48 | Amino Acid | 48 |
| Elastase Variant Propeptide Cleavage Domain 49 | Amino Acid | 49 |
| Yeast alpha-mating factor signal peptide, propeptide, and spacer sequence 1 | Amino Acid | 50 |
| Yeast alpha-mating factor signal peptide and propeptide sequence 2 | Amino Acid | 51 |
| Elastase Variant Propeptide Cleavage Domain 52 | Amino Acid | 52 |
| Elastase Variant Propeptide Cleavage Domain 53 | Amino Acid | 53 |
| Elastase Variant Propeptide Cleavage Domain 54 | Amino Acid | 54 |
| Elastase Variant Propeptide Cleavage Domain 55 | Amino Acid | 55 |

TABLE 1-continued

Summary of amino acid and nucleotide SEQ ID NOS.

| MOLECULE | NUCLEOTIDE OR AMINO ACID | SEQ ID NO |
|---|---|---|
| Elastase Variant Propeptide Cleavage Domain 56 | Amino Acid | 56 |
| Elastase Variant Propeptide Cleavage Domain 57 | Amino Acid | 57 |
| Elastase Variant Propeptide Cleavage Domain 58 | Amino Acid | 58 |
| Elastase Variant Propeptide Cleavage Domain 59 | Amino Acid | 59 |
| Elastase Variant Propeptide Cleavage Domain 60 | Amino Acid | 60 |
| Elastase Variant Propeptide Cleavage Domain 61 | Amino Acid | 61 |
| Elastase Variant Propeptide Cleavage Domain 62 | Amino Acid | 62 |
| Elastase Variant Propeptide Cleavage Domain 63 | Amino Acid | 63 |
| Elastase Proenzyme with variant Cleavage Domain 48, with possible polymorphism at position 220 (V or L) (numbering refers to position in context of preproprotein) | Amino Acid | 64 |
| Elastase Proenzyme with variant Cleavage Domain 49, with possible polymorphism at position 220 (V or L) (numbering refers to position in context of preproprotein) | Amino Acid | 65 |
| Elastase Proenzyme with variant Cleavage Domain 52, with possible polymorphism at position 220 (V or L) (numbering refers to position in context of preproprotein) | Amino Acid | 66 |
| Elastase Proenzyme with variant Cleavage Domain 53, with possible polymorphism at position 220 (V or L) (numbering refers to position in context of preproprotein) | Amino Acid | 67 |
| Elastase Proenzyme with variant Cleavage Domain 54, with possible polymorphism at position 220 (V or L) (numbering refers to position in context of preproprotein) | Amino Acid | 68 |
| Elastase Proenzyme with variant Cleavage Domain 55, with possible polymorphism at position 220 (V or L) (numbering refers to position in context of preproprotein) | Amino Acid | 69 |
| Wild Type Elastase +AlaArg Cleavage Variant, with possible polymorphism at position 220 (V or L) (numbering refers to position in context of preproprotein) | Amino Acid | 70 |
| Wild Type Elastase +Arg Cleavage Variant, with possible polymorphism at position 220 (V or L) (numbering refers to position in context of preproprotein) | Amino Acid | 71 |
| Variant 48 Human Elastase Activation peptide | Amino Acid | 72 |
| Variant 55 Human Elastase Activation peptide | Amino Acid | 73 |
| Human Elastase Cleavage Domain Consensus Sequence; corresponds to residues P5, P4, P3, P2, P1, P'1, P'2, and P'3 of an elastase cleavage domain | Amino Acid | 74 |
| PCR Mutagenesis Primer for pPROT3 construction | Nucleic Acid | 75 |
| PCR Mutagenesis Primer or pPROT3 construction | Nucleic Acid | 76 |
| Mature ELA1 C-terminal Variant of Talas et al., 2000, Invest Dermatol. 114(1): 165-70. | Amino Acid | 77 |
| Mature ELA-1 variants, with possible polymorphisms at positions 44 (W or R); 59 (M or V); 220 (V or L); and 243 (Q or R) (numbering refers to position in context of preproprotein) | Amino Acid | 78 |
| Activation peptide variants (wild type, trypsin cleavable), with possible polymorphism at position 10 (Q or H) (numbering refers to position in context of preproprotein) | Amino Acid | 79 |
| Activation peptide "consensus" sequence | Amino Acid | 80 |
| Coding region of ELA-1.2A | Amino Acid | 81 |
| Translation Product of ELA-1.2A (Trypsin activated pPROT24 sequence) | Amino Acid | 82 |
| Translation Product of ELA-1.2A (trypsin activated pPROT24 sequence), with possible polymorphisms at positions 44 (W or R); 59 (M or V); 220 (V or L); and 243 (Q or R) (numbering refers to position in context of preproprotein) | Amino Acid | 83 |
| Mature human elastase I, including first "valine," with possible polymorphisms at positions 44 (W or R); 59 (M or V); 220 (V or L); and 243 (Q or R) (numbering refers to position in context of preproprotein) | Amino Acid | 84 |
| mature human elastase I, minus first "valine," with possible polymorphisms at positions 44 (W or R); 59 (M or V); 220 (V or L); and 243 (Q or R) (numbering refers to position in context of preproprotein) | Amino Acid | 85 |
| Mature human elastase I, minus first two "valines," with possible polymorphisms at positions 44 (W or R); 59 (M or V); 220 (V or L); and 243 (Q or R) (numbering refers to position in context of preproprotein) | Amino Acid | 86 |
| mature human elastase I, with first "valine" substituted by "alanine," with possible polymorphisms at positions 44 (W or R); 59 (M or V); 220 (V or L); and 243 (Q or R) (numbering refers to position in context of preproprotein) | Amino Acid | 87 |

TABLE 1-continued

Summary of amino acid and nucleotide SEQ ID NOS.

| MOLECULE | NUCLEOTIDE OR AMINO ACID | SEQ ID NO |
|---|---|---|
| Engineered elastase proprotein no. 1 (pPROT42 variant), with possible polymorphisms at positions 10 (Q or H); 44 (W or R); 59 (M or V); 220 (V or L); and 243 (Q or R) (numbering refers to position in context of preproprotein) | Amino Acid | 88 |
| Engineered elastase proprotein no. 2, with possible polymorphisms at positions 10 (Q or H); 44 (W or R); 59 (M or V); 220 (V or L); and 243 (Q or R) (numbering refers to position in context of preproprotein) | Amino Acid | 89 |
| Engineered elastase proprotein no. 3, with possible polymorphisms at positions 10 (Q or H); 44 (W or R); 59 (M or V); 220 (V or L); and 243 (Q or R) (numbering refers to position in context of preproprotein) | Amino Acid | 90 |
| engineered elastase proprotein no. 4, with possible polymorphisms at positions 10 (Q or H); 44 (W or R); 59 (M or V); 220 (V or L); and 243 (Q or R) (numbering refers to position in context of preproprotein) | Amino Acid | 91 |
| engineered elastase proprotein no. 5 (pPROT24 trypsin activated sequence), with possible polymorphisms at positions 10 (Q or H); 44 (W or R); 59 (M or V); 220 (V or L); and 243 (Q or R) (numbering refers to position in context of preproprotein) | Amino Acid | 92 |
| Consensus elastase recognition sequence 4 (Positions P3-P2-P1) | Amino Acid | 93 |
| pPROT42 P3 Cleavage Site Variant Elastase, with possible polymorphisms at positions 44 (W or R); 59 (M or V); 220 (V or L); and 243 (Q or R) (numbering refers to position in context of preproprotein) | Amino Acid | 94 |
| pPROT42 P2 Cleavage Site Variant Elastase, with possible polymorphisms at positions 44 (W or R); 59 (M or V); 220 (V or L); and 243 (Q or R) (numbering refers to position in context of preproprotein) | Amino Acid | 95 |
| Yeast alpha-mating factor signal peptide, propeptide, and spacer sequence 1 | Amino Acid | 96 |
| Yeast alpha-mating factor signal peptide and propeptide sequence 2 | Amino Acid | 97 |
| Elastase Proenzyme with variant Cleavage Domain 48 Generic to SEQ ID NO: 64, with possible polymorphisms at positions 10 (Q or H); 44 (W or R); 59 (M or V); 220 (V or L); and 243 (Q or R) (numbering refers to position in context of preproprotein) | Amino Acid | 98 |
| Elastase Proenzyme with variant Cleavage Domain 49, with possible polymorphisms at positions 10 (Q or H); 44 (W or R); 59 (M or V); 220 (V or L); and 243 (Q or R) (numbering refers to position in context of preproprotein) | Amino Acid | 99 |
| Elastase Proenzyme with variant Cleavage Domain 52, with possible polymorphisms at positions 10 (Q or H); 44 (W or R); 59 (M or V); 220 (V or L); and 243 (Q or R) (numbering refers to position in context of preproprotein) | Amino Acid | 100 |
| Elastase Proenzyme with variant Cleavage Domain 53, with possible polymorphisms at positions 10 (Q or H); 44 (W or R); 59 (M or V); 220 (V or L); and 243 (Q or R) (numbering refers to position in context of preproprotein) | Amino Acid | 101 |
| Elastase Proenzyme with variant Cleavage Domain 54, with possible polymorphisms at positions 10 (Q or H); 44 (W or R); 59 (M or V); 220 (V or L); and 243 (Q or R) (numbering refers to position in context of preproprotein) | Amino Acid | 102 |
| Elastase Proenzyme with variant Cleavage Domain 55, with possible polymorphisms at positions 10 (Q or H); 44 (W or R); 59 (M or V); 220 (V or L); and 243 (Q or R) (numbering refers to position in context of preproprotein) | Amino Acid | 103 |
| Wild Type Elastase +AlaArg Cleavage Variant, with possible polymorphisms at positions 44 (W or R); 59 (M or V); 220 (V or L); and 243 (Q or R) (numbering refers to position in context of preproprotein) | Amino Acid | 104 |
| Wild Type Elastase +Arg Cleavage Variant, with possible polymorphisms at positions 10 (Q or H); 44 (W or R); 59 (M or V); 220 (V or L); and 243 (Q or R) (numbering refers to position in context of preproprotein) | Amino Acid | 105 |
| Mature human elastase I cleavage variant lacking first four amino acids, with possible polymorphisms at positions 10 (Q or H); 44 (W or R); 59 (M or V); 220 (V or L); and 243 (Q or R) (numbering refers to position in context of preproprotein) | Amino Acid | 106 |

TABLE 1-continued

Summary of amino acid and nucleotide SEQ ID NOS.

| MOLECULE | NUCLEOTIDE OR AMINO ACID | SEQ ID NO |
|---|---|---|
| Mature human elastase I cleavage variant lacking first six amino acids, with possible polymorphisms at positions 44 (W or R); 59 (M or V); 220 (V or L); and 243 (Q or R) (numbering refers to position in context of preproprotein) | Amino Acid | 107 |
| Mature human elastase I cleavage variant lacking first nine amino acids, with possible polymorphisms at positions 44 (W or R); 59 (M or V); 220 (V or L); and 243 (Q or R) (numbering refers to position in context of preproprotein) | Amino Acid | 108 |
| Nucleic acid sequence of FIG. 1A | Nucleic Acid | 109 |
| Amino acid sequence of FIG. 1A | Amino Acid | 110 |
| Nucleic acid sequence of FIG. 1B | Nucleic Acid | 111 |
| Amino acid sequence of FIG. 1B | Amino Acid | 112 |
| Nucleic acid sequence of FIG. 13 | Nucleic Acid | 113 |
| Amino acid sequence of FIG. 14 | Amino Acid | 114 |
| Cleavage domain sequence of trypsin-activated pPROT101-24-V | Amino Acid | 115 |
| Cleavage domain sequence of auto-activated pPROT101-42-V | Amino Acid | 116 |
| Cleavage domain sequence of auto-activated pPROT101-49-V | Amino Acid | 117 |
| Cleavage domain sequence of auto-activated pPROT101-55L-V | Amino Acid | 118 |
| Consensus elastase recognition sequence 5 (Positions P3-P2-P1) | Amino Acid | 119 |
| Consensus sequence 1 for the propeptide portion of the cleavage domain; corresponds to residues P5, P4, P3, P2, and P1 | Amino Acid | 120 |
| Consensus sequence 2 for the activation peptide; corresponds to residues P10 through P1 | Amino Acid | 121 |
| Proelastase consensus sequence 1 for residues P10 through P3' | Amino Acid | 122 |
| Consensus cleavage domain sequence 2; corresponds to residues P5, P4, P3, P2, P1, P'1, P'2, and P'3 | Amino Acid | 123 |
| Consensus elastase recognition sequence 6 (Positions P3-P2-P1) | Amino Acid | 124 |
| Consensus cleavage domain sequence 3; corresponds to residues P5, P4, P3, P2, P1, P'1, P'2, and P'3 | Amino Acid | 125 |

There are at least 5 confirmed polymorphisms in human type I elastase protein, at positions 10 (Q or H); 44 (W or R); 59 (M or V); 220 (V or L); and 243 (Q or R). The full-length (preproelastase) protein is 258 amino acids in length. The first 8 amino acids correspond to the signal or "pre" peptide sequence that is cleaved off to generate an inactive proprotein, and a further "pro" peptide sequence (comprising or consisting of 10 amino acids corresponding to an activation peptide) are cleaved to generate the active, mature protein. Thus, the polymorphism at position 10 is present in the proprotein but not in the mature protein.

Accordingly, in Table 2 below are presented all possible combinations of the 5 polymorphisms of human type I elastase. The present invention provides preproelastase and proelastase proteins (including but not limited to the variant preproelastase and proelastase proteins described herein), such as the proteins exemplified in embodiments 1-39 and 68-69 or the proteins obtained or obtainable by the method of any one of embodiments 89-224, 261-276, and 347-373 in Section 8, comprising the any of the combinations of polymorphisms set forth in Table 2 below.

TABLE 2

Variants of human type I immature elastase (pre-pro) and pro elastase proteins. The position numbering refers to the position in the context of the preproprotein of native human type I elastase.

| | Position | | | | |
|---|---|---|---|---|---|
| Embodiment | 10 Q or H | 44 W or R | 59 M or V | 220 V or L | 243 Q or R |
| 1. | Q | W | M | V | Q |
| 2. | Q | W | M | V | R |
| 3. | Q | W | M | L | Q |
| 4. | Q | W | V | V | Q |
| 5. | Q | R | M | V | Q |
| 6. | Q | W | M | L | R |
| 7. | Q | W | V | L | Q |
| 8. | Q | R | V | V | Q |
| 9. | Q | W | V | V | R |
| 10. | Q | R | M | L | Q |
| 11. | Q | R | M | V | R |
| 12. | Q | R | V | L | Q |
| 13. | Q | R | V | V | R |
| 14. | Q | R | M | L | R |
| 15. | Q | W | V | L | R |
| 16. | Q | R | V | L | R |
| 17. | H | W | M | V | Q |
| 18. | H | W | M | V | R |
| 19. | H | W | M | L | Q |
| 20. | H | W | V | V | Q |
| 21. | H | R | M | V | Q |
| 22. | H | W | M | L | R |
| 23. | H | W | V | L | Q |

TABLE 2-continued

Variants of human type I immature elastase (pre-pro) and pro elastase proteins. The position numbering refers to the position in the context of the preproprotein of native human type I elastase.

| Embodiment | Position | | | | |
|---|---|---|---|---|---|
| | 10 Q or H | 44 W or R | 59 M or V | 220 V or L | 243 Q or R |
| 24. | H | R | V | V | Q |
| 25. | H | W | V | V | R |
| 26. | H | R | M | L | Q |
| 27. | H | R | M | V | R |
| 28. | H | R | V | L | Q |
| 29. | H | R | V | V | R |
| 30. | H | R | M | L | R |
| 31. | H | W | V | L | R |
| 32. | H | R | V | L | R |

Moreover, in Table 3 below are presented all possible combinations of the 4 polymorphisms of human type I elastase that may be present in a mature elastase protein. The present invention provides mature elastase proteins (including but not limited to the variant mature elastase proteins described herein), such as the mature elastase proteins obtained or obtainable by the method of any one of embodiments 89-224, 261-276, and 347-373 in Section 8, comprising the any of the combinations of polymorphisms set forth in Table 3 below.

TABLE 3

Variants of mature human type I elastase proteins. The position numbering refers to the position in the context of the preproprotein of native human type I elastase.

| Embodiment | Position | | | |
|---|---|---|---|---|
| | 44 W or R | 59 M or V | 220 V or L | 243 Q or R |
| 1. | W | M | V | Q |
| 2. | W | M | V | R |
| 3. | W | M | L | Q |
| 4. | W | V | V | Q |
| 5. | R | M | V | Q |
| 6. | W | M | L | R |
| 7. | W | V | L | Q |
| 8. | R | V | V | Q |
| 9. | W | V | V | R |
| 10. | R | M | L | Q |
| 11. | R | M | V | R |
| 12. | R | V | L | Q |
| 13. | R | V | V | R |
| 14. | R | M | L | R |
| 15. | W | V | L | R |
| 16. | R | V | L | R |

The mature type I elastases of the invention can be purified, for example for use in pharmaceutical compositions. In specific embodiments, the elastases are at least 70%, 80%, 90%, 95%, 98% or 99% pure.

The mature type I elastases of the invention preferably have a specific activity of greater than 1, greater than 5, greater than 10, greater than 20, greater than 25, or greater than 30 U/mg of protein, as determined by measuring the rate of hydrolysis of the small peptide substrate N-succinyl-Ala-Ala-Ala-pNitroanilide (SLAP), which is catalyzed by the addition of elastase. One unit of activity is defined as the amount of elastase that catalyzes the hydrolysis of 1 micromole of substrate per minute at 30° C. and specific activity is defined as activity per mg of elastase protein (U/mg). Preferably, a mature human type I elastase has a specific activity within a range in which the lower limit is 1, 2, 3, 4, 5, 7, 10, 15 or 20 U/mg protein and in which the upper limit is, independently, 5, 10, 15, 20, 25, 30, 35, 40 or 50 U/mg protein. In exemplary embodiments, the specific activity is in the range of from 1 to 40 U/mg of protein, from 1 to 5 U/mg of protein, from 2 to 10 U/mg of protein, from 4 to 15 U/mg of protein, from 5 to 30 U/mg of protein, from 10 to 20 U/mg of protein, from 20 to 40 U/mg of protein, or any range whose upper and lower limits are selected from any of the foregoing values. A mature porcine type I elastase preferably has a specific activity within a range in which the lower limit is 1, 2, 3, 4, 5, 7, 10, 15, 20, 30, 40, 50, 60, or 75 U/mg protein and in which the upper limit is, independently, 5, 10, 15, 20, 25, 30, 35, 40, 50, 60, 75, 90, 95 or 100 U/mg protein. In exemplary embodiments, the specific activity of the porcine elastase is in the range of from 10 to 50 U/mg of protein, from 20 to 60 U/mg of protein, from 30 to 75 U/mg of protein, from 30 to 40 U/mg of protein, from 20 to 35 U/mg of protein, from 50 to 95 U/mg of protein, from 25 to 100 U/mg of protein, or any range whose upper and lower limits are selected from any of the foregoing values.

Accordingly, certain aspects of the present invention relate to compositions, such as pharmaceutical compositions, elastase formulations and unit dosages, such as those exemplified in embodiments 277-314, 346, 386, and 413-420 or those obtained or obtainable by the method of any one of embodiments 261-276 and 374-385 in Section 8 below.

In certain embodiments, the compositions of the invention comprise trypsin-activated elastase proteins, e.g., trypsin activated proteins made by any of the methods disclosed herein. In other embodiments, the compositions comprise autoactivated elastase proteins, e.g., autoactivated elastase proteins made by any of the methods disclosed herein. In certain aspects, a composition of the invention is characterized by at least one, at least two, at least three, at least four, at least five, at least six or at least seven of the following properties: (a) the composition is free of trypsin; (b) the composition is substantially free of trypsin; (c) the composition is free of any protein consisting of SEQ ID NOS:70 and 71; (d) the composition is substantially free of any protein consisting of SEQ ID NOS:2 and 3; (e) the composition is free of bacterial proteins; (f) the composition is substantially free of bacterial proteins; (g) the composition is free of mammalian proteins other than said mature elastase protein; (h) the composition is substantially free of mammalian proteins other than said mature elastase protein; (i) the composition is free or substantially free of one, two, three or all four proteins consisting of SEQ ID NO:85, 86, 94 and 95; (j) the composition is free or substantially free of one, two, or all three proteins consisting of SEQ ID NO:106, 107 and 108; (k) the composition contains pharmaceutically acceptable levels of endotoxins (e.g., 10 EU/mg elastase or less, or 5 EU/mg elastase or less); (l) the mature elastase protein in the composition is characterized by a specific activity of 1 to 40 U/mg of protein or any other range of specific activity disclosed herein; (m) the trypsin activity in said composition corresponds to less than 4 ng per 1 mg of mature elastase protein or any other range of trypsin activity disclosed herein; (n) the composition comprises polysorbate-80; (o) the composition comprises dextran; (p) the composition comprises sodium ions, potassium ions, phosphate ions, chloride ions and polysorbate-80; (q) the composition comprises sodium ions, potassium ions, phosphate ions, chloride ions and dextran; (r) the composition comprises sodium ions, potassium ions, phosphate ions, chloride ions, polysorbate-80, and dextran; (s) the mature elastase protein in said composition dispays an amount of stability disclosed herein, e.g., maintains 60% to 100% of its specific activity after at least a week of storage at 4° C., after at least a month of storage at 4° C., after at least two months of storage at 4° C., after at least three months of storage at 4° C., or after at least month six months of storage at 4° C.; and (t) the composition comprises a unit dosage of 0.0033 mg to 200 mg of said mature elastase protein, or any other unit dosage of mature elastase protein disclosed herein.

In certain aspects, the composition is characterized by at least three characteristics, at least four characteristics or five characteristics independently selected from the following groups (i) through (v):

(i) (a), (b) or (m)
(ii) (e) or (f)
(iii) (g) or (h)
(iv) (k)
(v) (l)

In specific embodiments, two of said at least three or at least said four characteristics are selected from groups (i) and (iv) or (v). In other embodiments, three of at least said four characteristics are selected from groups (i), (iv) and (v).

In specific embodiments, the present invention provides a composition, including but not limited to a pharmaceutical composition, elastase formulation or unit dosage, comprising (i) a therapeutically effective amount of human type I elastase that is free of trypsin and (ii) a pharmaceutically acceptable carrier. Alternatively, the present invention provides a composition comprising (i) a therapeutically effective amount of human type I elastase that is substantially free of trypsin and (ii) a pharmaceutically acceptable carrier. In specific embodiments, the human type I elastase and/or the composition comprises less than 5 ng/ml of trypsin activity, less than 4 ng/ml of trypsin activity, less than 3 ng/ml of trypsin activity, less than 2 ng/ml of trypsin activity, or less than 1.56 ng/ml of trypsin activity. In the foregoing examples, the ng/ml trypsin activity can be assayed in a liquid human type I elastase composition or preparation containing 1 mg/ml human type I elastase protein. Thus, the trypsin activities may also be described in terms of milligrams of elastase protein, for example, less than 3 ng trypsin activity/mg elastase protein, less than 1.56 ng trypsin activity/mg elastase protein, etc. The present invention further provides a composition comprising (i) a therapeutically effective amount of human type I elastase and (ii) a pharmaceutically acceptable carrier, wherein the composition comprises less than 5 ng of trypsin activity per mg of elastase, less than 4 ng trypsin activity per mg of elastase, less than 3 ng of trypsin activity per mg of elastase, less than 2 ng of trypsin activity per mg of elastase, or less than 1.56 ng of trypsin activity per mg of elastase.

The present invention further provides methods of improving the quality of mature elastase proteins produced by trypsin activation methods (e.g., the methods of embodiment 145 in Section 8 below), comprising purifying the mature elastase protein on a Macro-Prep High S Resin column. It was found by the present inventors that mature elastase proteins purified on a Macro-Prep High S Resin column yields elastase compositions with trypsin activity levels corresponding 20-25 ng trypsin activity/mg elastase protein, as compared to purification on a Poros (Poly (Styrene-Divinylbenzene)) column which yields elastase compositions with trypsin activity leavels corresponding to approximately 1000 ng trypsin activity/mg elastase protein. The present invention further provides elastase compositions comprising mature elastase proteins produced by purifying trypsin-activated elastase proteins on a Macro-Prep High S Resin column. The Macro-Prep High S Resin is available from Biorad (Hercules, Calif.), according to whom a column of rigid methacrylate supports with little shrinkage and swelling. Other similar cation exchange columns of the same class and/or with the same bead size (around 50 μm) may be used, such as other methacrylate columns, may suitably be used.

Other aspects of the present invention relate to compositions, including but not limited to pharmaceutical compositions, elastase formulations or unit dosages, comprising porcine type I pancreatic elastase. In specific embodiments, the present invention provides a composition comprising (i) a therapeutically effective amount of porcine type I pancreatic elastase that is free of trypsin and (ii) a pharmaceutically acceptable carrier. Alternatively, the present invention provides a composition comprising (i) a therapeutically effective amount of porcine type I pancreatic elastase that is substantially free of trypsin and (ii) a pharmaceutically acceptable carrier. In specific embodiments, the porcine type I pancreatic elastase and/or the composition comprises less than 100 ng/ml of trypsin activity, less than 75 ng/ml of trypsin activity, less than 50 ng/ml of trypsin activity, less than 25 ng/ml of trypsin activity, less than 15 ng/ml of trypsin activity, less than 10 ng/ml of trypsin activity, less than 5 ng/ml of trypsin activity, less than 4 ng/ml of trypsin activity, less than 3 ng/ml of trypsin activity, less than 2 ng/ml of trypsin activity, or less than 1.56 ng/ml of trypsin activity. In the foregoing examples, the ng/ml trypsin activity can be assayed in a liquid porcine type I pancreatic elastase composition or preparation containing 1 mg/ml porcine type I pancreatic elastase. Thus, the trypsin activities may also be described in terms of milligrams of elastase protein, for example, less than 25 ng trypsin activity/mg elastase protein, less than 5 ng trypsin activity/mg elastase protein, etc. The present invention further provides a composition comprising (i) a therapeutically effective amount of porcine type I elastase and (ii) a pharmaceutically acceptable carrier, wherein the composition comprises than 100 ng of trypsin activity per mg of elastase, less than 75 ng trypsin activity per mg of elastase, less than 50 ng of trypsin activity per mg of elastase, less than 25 ng of trypsin activity per mg of elastase, less than 15 ng of trypsin activity per mg of elastase, less than 10 ng or trypsin activity per mg of elastase, less than 5 ng of trypsin activity per mg of elastase, less than 4 ng trypsin activity per mg of elastase, less than 3 ng of trypsin activity per mg of elastase, less than 2 ng of trypsin activity per mg of elastase, or less than 1.56 ng of trypsin activity per mg of elastase.

In other embodiments, the present invention provides compositions of elastase proteins, such as mature elastase proteins, including but not limited to pharmaceutical compositions, elastase formulations or unit dosages, that are free of N-terminal variants corresponding to one, two, three or all four of SEQ ID NOS: 70, 71, 104, 105. In certain embodiments, the present invention provides a pharmaceutical composition comprising (i) a therapeutically effective amount of mature human type I elastase (ii) a pharmaceutically acceptable carrier, which pharmaceutical composition is free of any protein with SEQ ID NOS:70, 71, 104, 105.

In other embodiments, the present invention provides a composition, including but not limited to a pharmaceutical composition, an elastase formulation or unit dosage, comprising (i) a therapeutically effective amount of human type I elastase that is free or substantially free of variant proteins containing specific additional amino acids on the N-terminal end of the mature elastase protein (SEQ ID NOS: 37, 38, 70, 71, 94, 95, 104, 105) and (ii) a pharmaceutically acceptable carrier. In other embodiments, the present invention provides a composition comprising (i) a therapeutically effective amount of human type I elastase that is free or substantially free of variant proteins lacking N-terminal amino acids of the mature elastase protein (SEQ ID NOS: 2, 3, 37, 38, 70, 71, 85, 86, 94, 95, 104, 105, 106, 107, 108) and (ii) a pharmaceutically acceptable carrier. In specific embodiments, the human type I elastase and/or the composition comprises less than 25% N-terminal variants, less than 20% N-terminal variants, less than 15% N-terminal variants, less than 10% N-terminal variants, less than 5% N-terminal variants, less than 4% N-terminal variants, less than 3% N-terminal variants, less than 2% N-terminal variants, less than 1% N-terminal variants, less than 0.5% N-terminal variants, 0% N-terminal variants, or comprises N-terminal variants in an amount ranging between any two of the foregoing percentages (e.g., 2%-25% N-terminal variants, 0.5%-10% N-terminal variants, 5%-15% N-terminal variants, 0%-2% N-terminal variants, etc.). As used herein, the term "less than X % N-terminal variants" refers to the amount of N-terminal variants as a percentage of total elastase protein.

In other embodiments, the present invention provides a composition, including but not limited to a pharmaceutical composition, an elastase formulation or unit dosage, comprising (i) a therapeutically effective amount of mature human type I elastase (ii) a pharmaceutically acceptable carrier, which pharmaceutical composition is substantially free of bacterial proteins and/or is substantially free of mammalian proteins other than said mature human type I elastase. In specific embodiments, the human type I elastase and/or the composition comprises less than 25% bacterial proteins and/or mammalian proteins other than said mature human type I elastase, less than 20% bacterial proteins and/or mammalian proteins other than said mature human type I elastase, less than 15% bacterial proteins and/or mammalian proteins other than said mature human type I elastase, less than 10% bacterial proteins and/or mammalian proteins other than said mature human type I elastase, less than 5% bacterial proteins and/or mammalian proteins other than said mature human type I elastase, less than 4% bacterial proteins and/or mammalian proteins other than said mature human type I elastase, less than 3% bacterial proteins and/or mammalian proteins other than said mature human type I elastase, less than 2% bacterial proteins and/or mammalian proteins other than said mature human type I elastase, less than 1% bacterial proteins and/or mammalian proteins other than said mature human type I elastase, less than 0.5% bacterial proteins and/or mammalian proteins other than said mature human type I elastase, 0% bacterial proteins and/or mammalian proteins other than said mature human type I elastase, or comprises bacterial proteins and/or mammalian proteins other than said mature human type I elastase in an amount ranging between any two of the foregoing percentages (e.g., 2%-25% bacterial proteins and/or mammalian proteins other than said mature human type I elastase, 0.5%-10% bacterial proteins and/or mammalian proteins other than said mature human type I elastase, 5%-15% bacterial proteins and/or mammalian proteins other than said mature human type I elastase, 0%-2% bacterial proteins and/or mammalian proteins other than said mature human type I elastase, etc.). As used herein, the term "less than X % bacterial proteins and/or mammalian proteins other than said mature human type I elastase" refers to the amount of such proteins as a percentage of total protein in an elastase preparation or in said composition. In certain embodiments, the elastase represents at least 95%, at least 96%, at least 97%, at least 98%, at least 99%, at least 99.5% or at least 99.8% of the total protein in such compositions or preparations.

Methods for the treatment and prevention of diseases of biological conduits, comprising administration of compositions (e.g., pharmaceutical compositions, elastase formulations or unit dosages) comprising a purified mature human type I elastase of the invention to a patient in need thereof, are also provided.

Further provided are vectors comprising nucleic acids encoding any of the elastase proteins of the invention ("nucleic acids of the invention"), host cells engineered to express the nucleic acids of the invention. In specific embodiments, the vectors further comprise a nucleotide sequence which regulates the expression of the elastase protein. For example, the nucleotide sequence encoding the protein of the invention can be operably linked to a methanol-inducible promoter. Other suitable promoters are exemplified in Section 5.3 below.

In a specific embodiment, the present invention provides a vector comprising a nucleotide sequence encoding an open reading frame, the open reading frame comprising a yeast α-factor signal peptide or a type I elastase signal peptide (e.g., porcine elastase signal peptide) operably linked to a human type I elastase proprotein sequence. Optionally, the vector further comprises a methanol-inducible promoter operably linked to the open reading frame.

Host cells comprising the nucleic acids and vectors of the invention are also provided. In certain embodiments, the vector or nucleic acid is integrated into the host cell genome; in other embodiments, the vector or nucleic acid is extrachromosomal. A preferred host cell is a *Pichia pastoris* cell. Other suitable host cells are exemplified in Section 5.3 below.

In a specific embodiment, the present invention provides a *Pichia pastoris* host cell genetically engineered to encode an open reading frame comprising a yeast α-factor signal peptide or a porcine elastase signal peptide operably linked to a human type I elastase proenzyme sequence. Optionally, the open reading frame is under the control of a methanol-inducible promoter.

The present invention further provides methods for producing an immature or mature elastase protein of the invention comprising culturing a host cell engineered to express a nucleic acid of the invention under conditions in which the proelastase protein is produced. In certain embodiments, the mature elastase protein is also produced.

Preferred culture conditions for producing the proelastase and mature proteins of the invention, particularly for the host cell *Pichia pastoris*, include a period of growth at a low pH. Typically, the low pH is 2.0, 2.5, 3.0, 3.5, 4.0, 4.5, 5.0, 5.5, 6.0, or any range between any pair of the foregoing values. In specific embodiments, the low pH is a pH ranging from 2.0 to 6.0, from 2.0 to 5.0, from 3.0 to 6.0, from 3.0 to 5.0, from 4.0 to 6.0, or from 3.0 to 4.0. At the end of the culture period, the pH of the culture can be raised, preferably to a pH of 7.0, 7.5, 8.0, 8.5, 9.0, 9.5, 10.0, 10.5, 11.0 or a pH ranging between any two of the foregoing values for the purpose of separating or removing the activation sequence from the mature elastase protein. In specific embodiments, the pH of the culture is raised to a pH ranging from 7.5 to 10.0 or 8.0 to 9.0 and most preferably to a pH of 8.0.

Where the expression of a proelastase protein of the invention is under the control of a methanol-inducible promoter, conditions for producing an immature or mature elastase protein of the invention may also comprise a period of methanol induction.

The elastase production methods of the invention may further comprise the step of recovering the protein expressed by the host cell. In certain instances, the protein recovered is a proelastase comprising the activation sequence. In other instances, the protein recovered is a mature elastase lacking the activation sequence. Under certain conditions, both proelastase and mature elastase proteins are recovered.

Preferably, particularly where it is desired to circumvent auto-activation of an auto-activated proelastase, culture conditions for proelastase expression may comprise a period of growth and induction at low pH. Typically, the low pH is 2.0, 2.5, 3.0, 3.5, 4.0, 4.5, 5.0, 5.5, or 6.0, or any range between any pair of the foregoing values. In specific embodiments, the low pH is a pH ranging from 2.0 to 3.0, from 4.0 to 5.0, from 5.0 to 6.0, or from 6.0 to 7.0. In particular embodiments, the pH ranges from 4.0 to 6.0 and is most preferably a pH of 5.5.

Preferably, particularly where it is desired to circumvent auto-activation of an auto-activated proelastase, culture conditions for proelastase expression comprise a period of growth and induction in sodium citrate, sodium succinate, or sodium acetate. In specific embodiments, a concentration of 5-50 mM, 7.5-100 mM, 10-15 mM, 50-200 mM, 75-175 mM, 100-150 mM, 75-125 mM, or of any range whose upper and lower limits are selected from any of the foregoing values (e.g., 50-75 mM, 75-100 mM, etc.) is used. In a preferred embodiment, the sodium citrate, sodium succinate, or sodium acetate concentration is 90-110 mM and most preferably is 100 mM.

Additionally, particularly where it is desired to circumvent auto-activation of an auto-activated proelastase or auto-degradation by mature elastase, culture conditions for expression of an immature elastase protein may comprise a period of growth and induction at the lower end of the temperature range suitable for the host cell in question. For example, where the host cell is a *Pichia pastoris* host cell, the preferred range is about 22-28° C. In a specific embodiment, the *Pichia pastoris* host cell is cultured at 28° C.

Additionally, particularly where it is desired to circumvent protein degradation by host cell proteases, culture conditions for expression of an immature elastase protein may comprise a period of growth and induction at the lower end of the temperature range suitable for the host cell in question. For example, where the host cell is a *Pichia pastoris* host cell, the preferred range is about 22-28° C. In a specific embodiment, the *Pichia pastoris* host cell is cultured at 28° C.

The activation of an auto-activated proelastase protein of the invention may be initiated by the addition of extrinsic elastase in a small (catalytic) amount. In certain embodiments, a catalytic amount of extrinsic elastase represents less than 10%, less than 5%, less than 2%, less than 1%, less than 0.5% or less than 0.1%, on either a molar or molecular weight basis, of the elastase in the sample to which the catalytic elastase is added.

Alternatively or concurrently, the auto-activated proelastase may be subjected to pH 7-11 (most preferably pH 8), upon which the auto-activated proelastase activation peptide is removed without requiring trypsin and resulting in mature, active elastase. In specific embodiments, Tris base is added to a concentration of 50-200 mM, 75-175 mM, 100-150 mM, 75-125 mM, or any range whose upper and lower limits are selected from any of the foregoing values (e.g., 50-75 mM, 75-100 mM, etc.) during the activation step. In a preferred embodiment, Tris base is added to a concentration 90-110 mM, most preferably 100 mM. The pH of the Tris base is preferably 7-11; in specific embodiments, the Tris base is at a pH of 7.0-11.0, 7-9, 7.5 to 9.5, 7.5 to 10, 8-10, 8-9, or any range whose upper and lower limits are selected from any of the foregoing values. In a preferred embodiment, the Tris base is at a pH of 7.5-8.5, most preferably 8.0.

Expression of an immature elastase sequence can in some instances yield a mixture of proelastase proteins and mature elastase proteins, as well as N-terminal variant elastase proteins. Thus, the present invention provides a composition comprising at least two of (1) a proelastase protein, (2) a mature elastase protein, and (3) N-terminal variant elastase proteins.

Once a mature elastase is produced, it can be lyophilized, for example for pharmaceutical formulations. In an exemplary embodiment, the present invention provides methods of isolating a lyophilized mature type I elastase comprising steps:

(a) culturing a host cell, such as a *Pichia pastoris* host cell, engineered to express a nucleic acid molecule encoding a preproelastase open reading frame under conditions in which the open reading frame is expressed, wherein, in a specific embodiment, said open reading frame comprises nucleotide sequences encoding, in a 5' to 3' direction (i) a signal peptide, e.g., a singal peptide operable in *Pichia pastoris*; (ii) an activation sequence comprising an elastase recognition sequence; and (iii) the sequence of a mature type I elastase protein, thereby producing a proelastase protein;

(b) subjecting the proelastase protein to autoactivation conditions, thereby producing a mature type I elastase, wherein the autoactivation conditions include, one or a combination of the following:
  (i) changing the pH of a solution (which can be a cell culture supernatant) containing the proelastase protein, e.g., to a pH of 6.5-11, preferably 8-9;
  (ii) purifying the proelastase protein, for example, by ion exchange chromatography, and subjecting the solution extended conversion to remove N-terminal variants, thereby producing mature human type I elastase;
  (iii) concentrating the proelastase protein (e.g., 2-fold, 3-fold, 5-fold, 8-fold, 10-fold, 12-fold, or a range in which the upper and lower limits are independently selected from the foregoing levels of concentrations);
  (iv) subjecting the proelastase protein to increased temperature (e.g., 29° C., 30° C., 32° C., 35° C., 40° C., 45° C., or 40° C., or a range in which the upper and lower limits are independently selected from the foregoing temperatures);
  (v) purifying the proelastase protein (e.g., using Macro-Prep High S Resin) from a cell culture supernatant and incubating a solution comprising the purified proelastase protein at ambient temperatures (e.g., 22° C. to 26° C.) for a period of at least one day (e.g., one day, two days, three days, four days five days, or six days, a range of days in which the upper and lower limits are independently selected from the foregoing values) (this is influenced by the presence of citrate/acetate, concentration, temperature, and pH in the solution, and can readily be determined by one of skill in the art).

(c) optionally, purifying the mature human type I elastase, e.g., ion exchange chromatography step for polish chromatography; and (d) lyophilizing the mature type I elastase, thereby isolating a lyophilized mature human type I elastase. The mature type I elastase is preferably a human type I elastase. In certain aspects, the lyophilized mature type I elastase is preferably more than 95% pure; in specific embodiments, the lyophilized mature type I elastase is more than 98% or more than 99% pure.

The mature elastase proteins of the invention can be formulated into pharmaceutical compositions. Thus, in exemplary embodiments, the present invention provides a method of generating a pharmaceutical composition comprising a mature human type I elastase, said method comprising (i) isolating a lyophilized mature human type I elastase according to the methods described above; and (ii) reconstituting the lyophilized mature human type I elastase in a pharmaceutically acceptable carrier. The mature human type I elastases of the invention preferably have a specific activity of greater than 1, greater than 5, greater than 10, greater than 20, greater than 25, or greater than 30 U/mg of protein, as determined by measuring the rate of hydrolysis of the small peptide substrate N-succinyl-Ala-Ala-Ala-pNitroanilide (SLAP), which is catalyzed by the addition of elastase. One unit of activity is defined as the amount of elastase that catalyzes the hydrolysis of 1 micromole of substrate per minute at 30° C. and specific activity is defined as activity per mg of elastase protein (U/mg). Preferably, a mature human type I elastase of the invention has a specific activity within a range in which the lower limit is 1, 2, 3, 4, 5, 7, 10, 15 or 20 U/mg protein and in which the upper limit is, independently, 5, 10, 15, 20, 25, 30, 35, 40 or 50 U/mg protein. In exemplary embodiments, the specific activity is in the range of 1-40 U/mg of protein, 1-5 U/mg protein, 2-10 U/mg protein, 4-15 U/mg protein, 5-30 U/mg of protein, 10-20 U/mg of protein, 20-40 U/mg of protein, or any range whose upper and lower limits are selected from any of the foregoing values (e.g., 1-10 U/mg, 5-40 U/mg, etc.).

The pharmaceutical compositions of the invention are preferably stable. In specific embodiments, a pharmaceutical composition (for example a pharmaceutical composition prepared by lyophilization and reconstitution as described above) maintains at least 50%, more preferably at least 60%, and most preferably at least 70% of its specific activity after a week of storage at 4° C. In specific embodiments, the pharmaceutical composition maintains at least 75%, at least 80%, at least 85% or at least 95% of its specific activity after reconstitution and a week of storage at 4° C.

This invention also provides proteins comprising a type I elastase proprotein amino acid sequence containing an elastase cleavage domain sequence. Other cleavage domains that can be used in this invention are any of the sequences described by the consensus cleavage domain sequence (SEQ ID NO:74) $Xaa_1\ Xaa_2\ Xaa_3\ Xaa_4\ Xaa_5\ Xaa_6\ Xaa_7\ Xaa_8$, where $Xaa_1$=P5, $Xaa_2$=P4, $Xaa_3$=P3, $Xaa_4$=P2, $Xaa_5$=P1, $Xaa_6$=P'1, $Xaa_7$=P'2, and $Xaa_8$=P'3, where:

$Xaa_1$ is glutamate, histidine, proline, glycine, asparagine, lysine, or alanine, or, optionally, an analog thereof;

$Xaa_2$ is threonine, alanine, proline or histidine or, optionally, an analog thereof;

$Xaa_3$ is alanine, leucine, isoleucine, methionine, lysine, asparagine or valine, or, optionally, an analog thereof, but is preferably not glycine or proline;

$Xaa_4$ is proline, alanine, leucine, isoleucine, glycine, valine, or threonine, or, optionally, an analog thereof;

$Xaa_5$ is alanine, leucine, valine, isoleucine, or serine but not glycine, tyrosine, phenylalanine, proline, arginine, glutamate, or lysine, or, optionally, an analog thereof;

$Xaa_6$ is alanine, leucine, valine, isoleucine or serine, or, optionally, an analog thereof;

$Xaa_7$ is glycine, alanine, or valine, or, optionally, an analog thereof; and $Xaa_8$ is valine, threonine, phenylalanine, tyrosine, or tryptophan, or, optionally, an analog thereof.

This invention also provides proteins comprising a type I elastase proprotein amino acid sequence containing an elastase cleavage domain sequence. Other cleavage domains that can be used in this invention are any of the sequences described by the consensus cleavage domain sequence (SEQ ID NO:123) $Xaa_1 Xaa_2\ Xaa_3\ Xaa_4\ Xaa_5\ Xaa_6\ Xaa_7\ Xaa_8$, where $Xaa_1$=P5, $Xaa_2$=P4, $Xaa_3$=P3, $Xaa_4$=P2, $Xaa_5$=P1, $Xaa_6$=P'1, $Xaa_7$=P'2, and $Xaa_8$=P'3, where:

$Xaa_1$ is glutamate, histidine, proline, glycine, asparagine, lysine, or alanine, or, optionally, an analog thereof;

$Xaa_2$ is threonine, alanine, proline or histidine or, optionally, an analog thereof $Xaa_3$ is alanine, leucine, isoleucine, methionine, lysine, asparagine or valine, or, optionally, an analog thereof, but is preferably not glycine or proline;

$Xaa_4$ is proline, alanine, leucine, isoleucine, glycine, valine, or threonine, or, optionally, an analog thereof;

$Xaa_5$ is alanine, leucine, valine, isoleucine, or serine but not glycine, tyrosine, phenylalanine, proline, arginine, glutamate, or lysine, or, optionally, an analog thereof;

$Xaa_6$ is alanine, leucine, valine, isoleucine or serine, or, optionally, an analog thereof;

$Xaa_7$ is glycine, alanine, or valine, or, optionally, an analog thereof; and $Xaa_8$ is glycine, valine, threonine, phenylalanine, tyrosine, or tryptophan, or, optionally, an analog thereof.

This invention also provides proteins comprising a type I elastase proprotein amino acid sequence containing an elastase cleavage domain sequence. Other cleavage domains that can be used in this invention are any of the sequences described by the consensus cleavage domain sequence (SEQ ID NO:125) $Xaa_1 Xaa_2\ Xaa_3\ Xaa_4\ Xaa_5\ Xaa_6\ Xaa_7\ Xaa_8$, where $Xaa_1$=P5, $Xaa_2$=P4, $Xaa_3$=P3, $Xaa_4$=P2, $Xaa_5$=P1, $Xaa_6$=P'1, $Xaa_7$=P'2, and $Xaa_8$=P'3, where:

$Xaa_1$ is glutamate, histidine, proline, glycine, asparagine, lysine, or alanine, or, optionally, an analog thereof;

$Xaa_2$ is threonine, alanine, proline or histidine or, optionally, an analog thereof;

$Xaa_3$ is alanine, leucine, isoleucine, methionine, lysine, asparagine, threonine or valine, or, optionally, an analog thereof, but is preferably not glycine or proline;

$Xaa_4$ is proline, alanine, leucine, isoleucine, glycine, valine, asparagine, or threonine, or, optionally, an analog thereof;

$Xaa_5$ is alanine, leucine, valine, isoleucine, or serine but not glycine, tyrosine, phenylalanine, proline, arginine, glutamate, asparagine, or lysine, or, optionally, an analog thereof;

$Xaa_6$ is alanine, leucine, valine, isoleucine or serine, or, optionally, an analog thereof;

$Xaa_7$ is glycine, alanine, or valine, or, optionally, an analog thereof; and $Xaa_8$ is glycine, valine, threonine, phenylalanine, tyrosine, or tryptophan, or, optionally, an analog thereof.

In certain embodiments relating SEQ ID NO:74, SEQ ID NO:123, or SEQ ID NO:125, $Xaa_1$ is histidine and/or $Xaa_4$ is proline and/or $Xaa_5$ is alanine.

This invention also provides a method of isolating a mature human type I elastase comprising: (a) culturing, under culturing conditions, a host cell comprising a nucleotide sequence which encodes a proprotein comprising (i) an activation sequence comprising a trypsin recognition sequence operably linked to (ii) the amino acid sequence of a protein having elastase activity under said culturing conditions, wherein said culturing conditions comprise a period of growth or induction at pH of 2 to 6; (b) recovering the expressed proprotein; (c) contacting the recovered protein with a catalytic amount of trypsin under pH conditions in which the trypsin is active; and (d) isolating mature human type I elastase. In this method the mature human type I elastase may consist essentially of SEQ ID NO: 1, 4, 5, 84, or 87. In certain embodiments, the conditions may comprise (a) a period of growth or induction at pH of 4 to 6; (b) a period of growth or induction at 22° C. to 28° C.; or (c) sodium citrate, sodium succinate, or sodium acetate concentrations of about 50 mM to about 200 mM or a sodium citrate concentration is 90 mM to about 110 mM in the culture media of said host cells.

It should be noted that the indefinite articles "a" and "an" and the definite article "the" are used in the present application, as is common in patent applications, to mean one or more unless the context clearly dictates otherwise. Further, the term "or" is used in the present application, as is common in patent applications, to mean the disjunctive "or" or the conjunctive "and."

All publications mentioned in this specification are herein incorporated by reference. Any discussion of documents, acts, materials, devices, articles or the like that has been included in this specification is solely for the purpose of providing a context for the present invention. It is not to be taken as an admission that any or all of these matters form part of the prior art base or were common general knowledge in the field relevant to the present invention as it existed anywhere before the priority date of this application.

The features and advantages of the invention will become further apparent from the following detailed description of embodiments thereof.

BRIEF DESCRIPTION OF THE DRAWINGS

FIG. 1A-1B: FIG. 1A shows the synthetic (i.e., recombinant) human ELA-1.2A sequence (SEQ ID NO:130). The recombinant human elastase-1 (i.e., human type I pancreatic elastase) sequence contains a 750-base pair coding region. Selected restriction enzyme sites are underlined. Base substitutions are in double underlined, bolded text and the codons containing them are double underlined. Stop codons are shaded in gray (but not underlined). The propeptide sequence is italicized. The coding region results in a 250-amino acid protein (SEQ ID NO:82). After cleavage of the 10-amino acid propeptide, the resulting mature enzyme is 240 amino acids. FIG. 1B shows the pPROT24 translational fusion region. The translational fusion between the vector and the ELA-1 coding region is depicted. The PCR amplification of the ELA-1 sequence provided for the incorporation of the Kex2 and STE13 signal cleavage domains to yield a secreted product with an expected N-terminus of the first amino acid (in bold text) of the activation sequence (italicized). FIG. 1B discloses SEQ ID NOS:111 and 112, respectively, in order of appearance.

FIG. 4: SDS-PAGE analysis of fractions from capture chromatography of a 201-24-266-VU culture containing trypsin-activated pro-PRT-201. Lane numbers correspond to fraction numbers. Fractions 6-18 primarily consist of glycosylated proenzyme (upper band) and non-glycosylated proenzyme (lower band). Fractions 19-35 primarily consist of non-glycosylated proenzyme. M=molecular weight markers. FT=column flow through.

FIGS. 5A-5F: FIG. 5A shows an auto-activated proprotein data table. Propeptide sequences are listed in the first column. SDS-PAGE of supernatants after 1, 2 and 3 days of induction (lanes 1, 2 and 3, respectively) are shown in the second column. Relative proprotein yields based on SDS-PAGE are listed in the third column. Relative stabilities of the proprotein over 3 days of induction based on SDS-PAGE are listed in the fourth column. Proproteins with 42 and 48 propeptide sequences are ranked as having low stability because of the presence of mature protein during induction (observed after 1, 2 and 3 days for the 42 variant and after 2 and 3 days for the 48 variant). Relative conversion rates of the proproteins as determined by time to achieve maximal SLAP reaction velocity are listed in the fifth column. The estimated percentages of converted protein that comprised N-terminal variants of the mature elastase protein are listed in the sixth column. FIGS. 5B-5F show conversion rate data for propeptide sequences 24, 42, 48, 49 and 55, respectively.

FIG. 7A shows samples induced at 22° C. and FIG. 7B shows samples induced at 25° C. In both FIG. 7A and FIG. 7B, lanes 1-3 are supernatants after 1, 2 and 3 days of induction, respectively, containing 0% sodium citrate; lanes 4-6 are similar except with 12.5% sodium citrate; lanes 7-9 are similar except with 25% sodium citrate; and lanes 10-12 are similar except with 50 mM sodium citrate.

FIG. 13: Concentration dependence of pro conversion. Purified pro-PRT-201 from the 201-55M3-003-VU clone (pro-PRT-201-55M3-003-VU) was subjected to conversion at concentrations of 0.2, 1.0, 1.6, and 1.8 mg/mL. Conversion reactions were monitored by HIC-HPLC in real-time until the proprotein was ≤1% of the total protein. The graph shows the relative amounts of mature (full-length) PRT-201 (lightly shaded bars) and N-terminal variants (darkly shaded bars) produced during the conversions.

FIG. 14. DNA sequence of synthetic (i.e., recombinant) porcine pancreatic elastase type 1 (SEQ ID NO:113). The recombinant sequence contains a 750 base pair coding region. SacII and XbaI restriction sites as underlined were incorporated to facilitate cloning. Stop codons are highlighted. The pro-peptide sequence is in bold-face type.

FIG. 15. Amino acid sequence of synthetic (i.e., recombinant) porcine type I pancreatic elastase (SEQ ID NO:114). The pro-peptide region is in bold-face type while the trypsin cleavage site is highlighted. After cleavage of the 10 amino acid pro-peptide, the resulting mature enzyme is 240 amino acids.

DETAILED DESCRIPTION OF THE INVENTION

Figure 2:
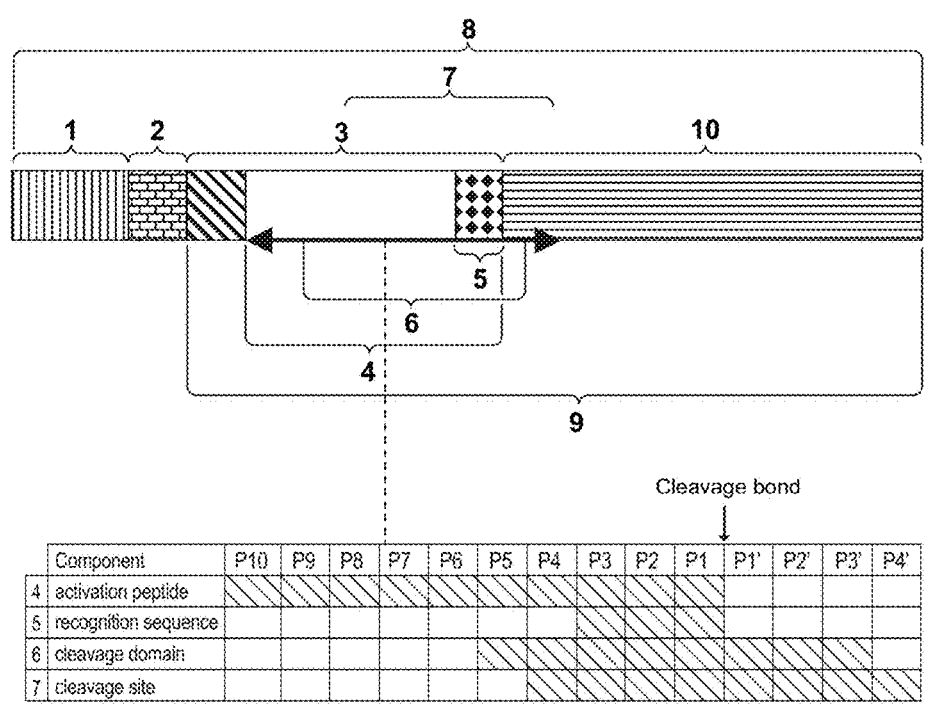
FIG. 2: A N-terminal to C-terminal schematic of the (overlapping) core components of the elastase proteins of the invention, wherein the numbered components depict: (1) signal sequence (vertical stripes); (2) optional propeptide/ spacer sequence (bricks); (3) elastase propeptide (diagonal stripes, gray fill and diamond pattern combined); (4) activation peptide (gray fill and diamond pattern combined); (5) recognition sequence (diamond pattern); (6) cleavage domain (gray fill, diamond pattern and the left portion of the horizontal stripes); (7) cleavage site (gray fill, diamond pattern and the left portion of the horizontal stripes); (8) preproelastase protein (entire scheme); (9) proelastase protein (diagonal stripes, gray fill, diamond pattern and horizontal stripes combined); and (10) mature elastase protein (horizontal stripes). The table shows the amino acid designations of the region in the schematic spanned by the arrow. Not drawn to scale. The nomenclature is for reference purposes only and is not intended to connote a particular function, activity or mechanism.

The present invention is directed to methods for recombinant expression and production of mature, biologically active elastase proteins. The present invention provides novel, efficient methods of making recombinant elastase proteins by culturing host cells, including the preferred host cell, *Pichia pastoris*, comprising nucleic acids encoding proelastase proteins and preproelastase proteins. The use of the recombinant proteins to manufacture pharmaceutical compositions for the treatment and prevention of diseases of biological conduits (including arteries or veins) is also provided.

In certain aspects, the present invention is directed to recombinant auto-activated proelastase proteins and related nucleic acids, host cells, and methods of manufacture. Such auto-activated proelastase proteins are engineered to contain an elastase recognition site immediately N-terminal to the first residue of the mature elastase protein. Under specified culture conditions, such as those described in Section 6 below, it is possible to reduce auto-activation until activation is desired. It is also possible to reduce auto-activation until the pro-elastase is removed from the cell culture.

The present invention provides efficient expression and purification processes for producing pharmaceutical grade elastase proteins. The present invention also provides methods for treating or preventing diseases of biological conduits using the elastase proteins of the invention.

The description in Section 5 herein is applicable to the embodiments of Section 8. Thus, for example, a reference to an elastase protein of the invention includes, but is not limited to, a reference to an elastase protein according to any one of embodiments 1-39 and 68-69, or an elastase protein obtained or obtainable by the method of any one of embodiments 89-224, 261 to 276, and 347 to 373. Likewise, a reference to a nucleic acid of the invention refers, inter alia, to a nucleic acid according to any one of embodiments 40-67; reference to a vector refers, inter alia, a reference to a vector according to any one of embodiments 70-72; reference to a cell refers, inter alia, to a cell according to any one of embodiments 73-87, reference to a cell culture supernatant refers, inter alia, to a cell culture supernatant according to embodiment 88; reference to compositions, such as pharmaceutical compositions, elastase formulations and unit dosages, includes, for example, those exemplified in embodiments 277-314, 346, 386, and 413-420 or those obtained or obtainable by the method of any one of embodiments 261-276 and 374-385; and references to therapeutic methods also includes a reference to therapeutic methods according to any one of embodiments 387-414; and reference to a kit includes a reference to, inter alia, a reference to a kit of embodiments 421-425 of Section 8.

5.1 Elastase Proteins

The present invention is directed to, inter alia, methods for recombinant expression and production of mature, biologically active elastase proteins. The elastase proteins are generally expressed as preproproteins, containing, among other sequences, a signal peptide, an activation peptide, and a mature portion with biological activity. Suitable mature elastase protein sequences are described in Section 5.1.1 below. Suitable activation peptide sequences are described in Section 5.1.2 below. Suitable signal sequences are described in Section 5.1.3 below.

Accordingly, in certain aspects, the elastase proteins of the invention are preproelastase proteins. Removal of the signal sequence from the preproprotein upon secretion generally yields an inactive proprotein containing an activation peptide and a mature protein. The phrases "activation sequence" and "activation peptide" are used interchangeably herein. Thus, in other aspects, the elastase proteins of the invention are proelastase proteins comprising an activation peptide that is operably linked to a mature elastase protein. In an exemplary embodiment, an activation peptide or sequence of a wild-type human type I pancreatic elastase comprises the first 10 N-terminal amino acids of the human type I elastase proprotein (SEQ ID NO:22). In certain embodiments, the activation peptide is a peptide of SEQ ID NO:80 or SEQ ID NO:121. Activation peptides or sequences useful in the practice of this invention also include, but are not limited to, SEQ ID NO: 23, 72 and 73. Still other activation sequences useful in the practice of this invention can be obtained from the N-terminal residues 1-10 of SEQ ID NO:64-69 and 98-103.

Removal of the activation peptide from the proelastase sequence generates a mature elastase protein. The step by which the activation peptide is removed from the proelastase sequence/separated from the mature elastase sequence to generate a mature elastase protein is referred to herein as an activation step. Thus, in yet other aspects, the elastase proteins of the invention are mature elastase proteins.

Amino acid residues comprising the C-terminus (i.e., carboxy terminus) of the activation peptide and the N-terminus (i.e., amino terminus) of the mature protein that surround the cleavage bond are depicted in FIG. 2 and also identified herein as follows. First, residues located at the C-terminus of the activation peptide are designated PX, ... P5, P4, P3, P2, and P1, where P1 is the C-terminal residue of the activation peptide. Residues located at the N-terminus of the mature protein are designated P1', P2', P3', ... PX', where P1' is the N-terminal amino acid residue of the mature protein. The scissile bond that is cleaved by proteolysis (referred to as the "cleavage bond" in FIG. 2) is the peptide bond between the P1 residue of the activation peptide and P1' residue of the mature protein.

In certain preferred embodiments, a proelastase protein of the disclosure has a histidine residue at the P5 position and/or a proline residue at the P2 position and/or an alanine residue at the P1 position.

The region spanning 4 amino acids of the C-terminus of the activation peptide (residues P4 to P1) through to the first 4 amino acids of the N-terminus of the mature protein (residues P1' to P4') is referred to herein as the "cleavage site."

The region spanning approximately 5 amino acids of the C-terminus of the activation peptide (i.e., residues P5 to P1) through to approximately the first 3 amino acids of the N-terminus of the mature protein (i.e., residues P1' to P3') is referred to herein as the "cleavage domain." Examples of cleavage domains that can be used in the context of this invention include, but are not limited to, SEQ ID NOS: 42, 43, 48, 49, 52, 53, 54 or 55. Other cleavage domains that can be used in this invention are any of the sequences described by the consensus cleavage domain sequence (SEQ ID NO:123) $Xaa_1 Xaa_2 Xaa_3 Xaa_4 Xaa_5 Xaa_6 Xaa_7 Xaa_8$, where $Xaa_1$=P5, $Xaa_2$=P4, $Xaa_3$=P3, $Xaa_4$=P2, $Xaa_5$=P1, $Xaa_6$=P1', $Xaa_7$=P2', and $Xaa_8$=P3', where:

Xaa$_1$ is glutamate, histidine, proline, glycine, asparagine, lysine, or alanine, or, optionally, an analog thereof;

Xaa$_2$ is threonine, alanine, proline or histidine or, optionally, an analog thereof;

Xaa$_3$ is alanine, leucine, isoleucine, methionine, lysine, asparagine or valine, or, optionally, an analog thereof, but is preferably not glycine or proline;

Xaa$_4$ is proline, alanine, leucine, isoleucine, glycine, valine, or threonine, or, optionally, an analog thereof;

Xaa$_5$ is alanine, leucine, valine, isoleucine, or serine but not glycine, tyrosine, phenylalanine, proline, arginine, glutamate, or lysine, or, optionally, an analog thereof;

Xaa$_6$ is alanine, leucine, valine, isoleucine or serine, or, optionally, an analog thereof;

Xaa$_7$ is glycine, alanine, or valine, or, optionally, an analog thereof; and

Xaa$_8$ is glycine, valine, threonine, phenylalanine, tyrosine, or tryptophan, or, optionally, an analog thereof.

In specific embodiments, the proelastase cleavage domain is any sequence described by the consensus cleavage domain sequence of SEQ ID NO:74, SEQ ID NO:123, or SEQ ID NO:125.

In certain aspects, the proelastase proteins have a propeptide portion of the cleavage domain of are any of the sequences described by the consensus cleavage domain sequence (SEQ ID NO:126) Xaa$_1$Xaa$_2$ Xaa$_3$ Xaa$_4$ Xaa$_5$, where Xaa$_1$=P5, Xaa$_2$=P4, Xaa$_3$=P3, Xaa$_4$=P2, Xaa$_5$=P1, where:

Xaa$_1$ is any natural amino acid;

Xaa$_2$ is any natural amino acid except glycine, lysine, phenylalanine, tyrosine, tryptophan, or arginine;

Xaa$_3$ is any natural amino acid;

Xaa$_4$ is proline, alanine, leucine, isoleucine, glycine, valine, histidine, asparagine, or threonine, and Xaa$_5$ is alanine, leucine, valine, isoleucine, asparagine, or serine.

In certain aspects, Xaa$_1$ is glutamate or histidine, preferably histidine and/or Xaa$_4$ is proline and/or Xaa$_5$ is alanine.

The three amino acid region spanning residues P3, P2, and P1 of the activation peptide is referred to herein as an "elastase recognition site". Examples of recognition sites that can be used in the context of this invention include, but are not limited to, SEQ ID NOS: 14-16, and 18-21. Other recognition sites contemplated by this invention include any recognition site described by the consensus recognition sites of SEQ ID NO: 11, 12, 13, or 93. The SEQ ID NO:11 consensus elastase recognition sequence 1 is represented by the peptide sequence Xaa$_1$Xaa$_2$ Xaa$_3$, wherein Xaa$_1$=P3, Xaa$_2$=P2, Xaa$_3$=P1, wherein:

Xaa$_1$ is alanine, leucine, isoleucine, methionine, lysine, asparagine or valine, or, optionally, an analog thereof but is preferably not glycine or proline;

Xaa$_2$ is proline, alanine, leucine, isoleucine, glycine, valine, or threonine, or, optionally, an analog thereof;

Xaa$_3$ is alanine, leucine, valine, isoleucine, or serine, or, optionally, an analog thereof, but is preferably not glycine, tyrosine, phenylalanine, proline, arginine, glutamate, or lysine.

The SEQ ID NO:12 consensus elastase recognition sequence 2 is represented by the sequence Xaa$_1$Pro Xaa$_2$, wherein:

Xaa$_1$ is alanine, leucine, isoleucine, methionine, lysine, or valine, or, optionally, an analog thereof, but is preferably not glycine or proline;

Pro is proline, or, optionally, an analog thereof;

Xaa$_2$ is alanine, leucine, valine, isoleucine, or serine, or, optionally, an analog thereof, but is preferably not glycine, tyrosine, phenylalanine, proline, arginine, glutamate, or lysine.

The SEQ ID NO:13 consensus elastase recognition sequence 3 is represented by the peptide sequence Xaa$_1$Xaa$_2$ Xaa$_3$, wherein Xaa$_1$=P3, Xaa$_2$=P2, Xaa$_3$=P1, wherein Xaa$_1$ is asparagine or alanine, or, optionally, an analog thereof; wherein Xaa$_2$ is proline or alanine, or, optionally, an analog thereof, and wherein Xaa$_3$ is alanine, leucine, or valine, or, optionally, an analog thereof.

The SEQ ID NO:93 consensus elastase recognition sequence 4 is represented by the sequence Xaa$_1$Pro Xaa$_2$, wherein:

Xaa$_1$ is alanine, leucine, isoleucine, methionine, lysine, asparagine or valine, or, optionally, an analog thereof, but is preferably not glycine or proline;

Pro is proline, or, optionally, an analog thereof;

Xaa$_2$ is alanine, leucine, valine, isoleucine, or serine, or, optionally, an analog thereof, but is preferably not glycine, tyrosine, phenylalanine, proline, arginine, glutamate, or lysine.

The SEQ ID NO:119 consensus elastase recognition sequence 5 is represented by the sequence Xaa$_1$Xaa$_2$ Xaa$_3$, wherein:

Xaa$_1$ is any natural amino acid, but is preferably not glycine or proline;

Xaa$_2$ is proline, alanine, leucine, isoleucine, glycine, valine, histidine or threonine;

Xaa$_3$ is alanine, leucine, valine, isoleucine, or serine.

The SEQ ID NO:124 consensus elastase recognition sequence 5 is represented by the sequence Xaa$_1$Xaa$_2$ Xaa$_3$, wherein:

Xaa$_1$ is alanine, leucine, isoleucine, methionine, lysine, asparagine, histidine, or valine;

Xaa$_2$ is proline, alanine, leucine, isoleucine, glycine, valine, or threonine;

Xaa$_3$ is alanine, leucine, valine, isoleucine, or serine.

In certain aspects, a proelastase protein of the disclosure has a sequence for P10 through P3' described by the consensus sequence of SEQ ID NO:122.

Reference to a sequence as a "cleavage sequence," "cleavage domain," "activation sequence," "elastase recognition sequence," etc., is solely for ease of reference and is not intended to imply any function of the sequence or mechanism by which the sequence is recognized or processed.

The proteins of the invention are generally composed of amino acids and may in addition include one or more (e.g., up to 2, 3, 4, 5, 6, 7, 8, 9, 10, 12 or 15) amino acid analogs. Generally, as used herein, an amino acid refers to a naturally-occurring L stereoisomer. An amino acid analog refers to a D-stereoisomer, a chemically modified amino acid, or other unnatural amino acid. For example, unnatural amino acids include, but are not limited to azetidinecarboxylic acid, 2-aminoadipic acid, 3-aminoadipic acid, β-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. A chemically modified amino acid includes an amino acid that is chemically blocked, reversibly or irreversibly, and/or modified at one or more of its side groups, α-carbon atoms, terminal amino group, or terminal carboxylic acid group. A chemical modification includes adding chemical moieties, creating new bonds, and removing chemical moieties. Examples of chemically modified amino acids include, for example, methionine sulfoxide, methionine sulfone, S-(carboxymethyl)-cysteine, S-(carboxymethyl)-cysteine sulfoxide and S-(carboxymethyl)-cysteine sulfone. Modifications at amino acid side groups include acylation of lysine ε-amino groups, N-alkylation of arginine, histidine, or lysine, alkylation of glutamic or aspartic carboxylic acid groups, and deamidation of glutamine or asparagine. Modifications of the terminal amino include the des-amino, N-lower alkyl, N-di-lower alkyl, and N-acyl modifications. Modifications of the terminal carboxy group include the amide, lower alkyl amide, dialkyl amide, and lower alkyl ester modifications. A lower alkyl is a $C_1$-$C_4$ alkyl. Furthermore, one or more side groups, or terminal groups, may be protected by protective groups known to the ordinarily-skilled protein chemist. The α-carbon of an amino acid may be mono- or di-methylated.

The proteins of the invention may be modified or derivatized, such as modified by phosphorylation or glycosylation, or derivatized by conjugation, for example to a lipid or another protein (e.g., for targeting or stabilization), or the like.

The present invention often relates to an "isolated" or "purified" elastase protein. An isolated elastase protein is one that is removed from its cellular milieu. A purified elastase protein is substantially free of cellular material or other contaminating proteins from the cell or tissue source from which the elastase protein is derived, or substantially free of chemical precursors or other chemicals when chemically synthesized. The language "substantially free of cellular material" includes preparations of elastase protein in which the protein is separated from cellular components of the cells from which it is recombinantly produced. Thus, elastase protein that is substantially free of cellular material includes preparations of elastase protein having less than about 30%, 20%, 10%, or 5% (by dry weight) of heterologous protein (also referred to herein as a "contaminating protein"). When the elastase protein is produced by a process in which it is secreted into culture medium, it is also preferably substantially free of the culture medium, i.e., culture medium represents less than about 20%, 10%, or 5% of the volume of the elastase protein preparation.

In certain embodiments, an isolated or purified elastase is additionally free or substantially free of cellular DNA. In specific embodiments, host cell genomic DNA is present in an amount of less than 10 picogram, less than 5 picograms, less than 3 picograms, less than 2 picograms, or less than 1 picogram of DNA per milligram of elastase protein in a preparation of isolated or purified elastase protein, or in a composition comprising isolated or purified elastase protein. In one embodiment, the host cell DNA is *Pichia pastoris* DNA.

Useful elastase protein sequences are provided in Table 1. In a specific embodiment, the invention provides a proelastase protein (including but not limited to a protein of any one of SEQ ID NOS:6-9, 64-69, 88-91 and 98-103) comprising (i) an activation sequence comprising an elastase recognition sequence operably linked to (ii) the amino acid sequence of a protein having type I elastase activity. Several polymorphisms of human type I elastase are known. Any combination of polymorphisms is contemplated in the proelastase protein sequences of the present invention, including but not limited to the combinations of polymorphisms set forth in Table 2. The protein optionally further comprises a signal sequence operably linked to said activation sequence. In certain specific embodiments, the signal sequence is operable in *Pichia pastoris*, such as a yeast α-factor signal peptide, exemplified by the amino acid sequence of SEQ ID NO:34. Alternative signal peptide containing sequences are exemplified in SEQ ID NOS:50 and 96 (containing a signal peptide, a non-elastase propeptide and a spacer sequence) and SEQ ID NOS:51 and 97 (containing the signal peptide and a non-elastase propeptide). In other specific embodiments, the signal sequence is a mammalian secretion signal sequence, such as a porcine elastase signal sequence. Preferably, the elastase recognition sequence is a type I elastase recognition sequence, most preferably a human type I elastase recognition sequence.

The present invention further encompasses variants of the elastase proteins of the invention. Variants may contain amino acid substitutions at one or more predicted non-essential amino acid residues. Preferably, a variant includes no more than 15, no more than 12, no more than 10, no more than 9, no more than 8, no more than 7, no more than 6, no more than 5, no more than 4, no more than 3, no more than 2 or no more than 1 conservative amino acid substitution relative to a naturally occurring mature elastase and/or no more than 5, no more than 4, no more than 3, or no more than 2 non-conservative amino acid substitutions, or no more than 1 non-conservative amino acid substitution, relative to a naturally occurring mature elastase.

In a specific embodiments, the variant has no more than 10 or more preferably no more than five conservative amino acid substitutions relative to a mature elastase, a proelastase or a preproelastase of the invention, such as with respect to a mature elastase of SEQ ID NO:1 or SEQ ID NO:84 or a proelastase protein of SEQ ID NOS:6-9, 64-69, 88-91, and 98-103. The amino acid sequences of SEQ ID NOS:1 and 84 contain one or more positions corresponding to potential polymorphisms in the mature elastase sequence, at positions 44 (W or R); 59 (M or V); 220 (V or L); and 243 (Q or R) (positions refer to preproprotein). The invention thus encompasses mature elastase proteins with any combination of the four polymorphisms identified in SEQ ID NO:84. Each of such combinations is outlined in Table 3 above. The sequence of SEQ ID NOS:88-91 and 98-103 further contain a potential polymorphism in the propeptide sequence, at position 10 (Q or H). The invention thus encompasses preproelastase and proelastase sequences containing any combination of the five polymorphisms identified in SEQ ID NOS:88-91 and 98-103. Each of such combinations is outlined in Table 2 above.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan).

The variant elastase proteins of the invention may include amino acid substitutions with amino acid analogs as well as amino acids, as described herein.

In specific embodiments, the protein of the invention comprises or consists essentially of a variant of a mature human type I elastase, e.g., a variant which is at least about 75%, 85%, 90%, 93%, 95%, 96%, 97%, 98% or 99% identical to the elastase proproteins or mature elastase proteins listed in Table 1, such as, but not limited to, the elastase proproteins of SEQ ID NOS: 6-9, 64-69, 88-91, and 98-103, and retain elastase activity when expressed to produce a mature elastase protein of SEQ ID NO: 1, 4, 5, 84 or 87.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (% identity=(# of identical positions/total # of overlapping positions)×100). In one embodiment, the two sequences are the same length. In other embodiments, the two sequences differ in length by no more than 1%, 2%, 3%, 4%, 5%, 6%, 7%, 8%, 9% or 10% of the length of the longer of the two sequences.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and) XBLAST programs of Altschul, et al. (1990)*J. Mol. Biol.* 215:403-410. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See www.ncbi.nlm.nih.gov.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci.* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see bioweb.pasteur.fr/docs/man/man/fasta.1.html#sect2, the contents of which are incorporated herein by reference.

The percent identity between two sequences can be determined using techniques similar to those described above, with or without allowing gaps. In calculating percent identity, typically exact matches are counted.

The elastase proteins of the invention can exhibit post-translational modifications, including, but not limited to glycosylations (e.g., N-linked or O-linked glycosylations), myristylations, palmitylations, acetylations and phosphorylations (e.g., serine/threonine or tyrosine). In one embodiment, the elastase proteins of the invention exhibit reduced levels of O-linked glycosylation and/or N-linked glycosylation relative to endogenously expressed elastase proteins. In another embodiment, the elastase proteins of the invention do not exhibit O-linked glycosylation or N-linked glycosylation.

5.1.1. The Mature Elastase Sequence

The mature elastase sequences of the present invention are preferably mammalian elastase sequences, most preferably human elastase sequences. In other embodiments, the mature mammalian elastase sequences are from other mammals such as mouse, rat, pig, cow, or horse.

In the methods and compositions of the invention, the mature elastase sequence employed is preferably that of a type I pancreatic elastase, which preferentially cleaves hydrophobic protein sequences, preferable on the carboxy side of small hydrophobic residues such as alanine. Examples of type I pancreatic elastases include the human elastase I enzyme (NCBI Accession Number NP_001962) that is expressed in skin and the porcine pancreatic elastase I enzyme (NCBI Accession Number CAA27670) that is expressed in the pancreas. SEQ ID NO:1 and SEQ ID NO:84 are examples of mature human type I elastase sequences.

Alternatively, a type II elastase that can cleave hydrophobic protein sequences, preferably on the carboxy side of medium to large hydrophobic amino acid residues, may be used. Examples of type II elastases include the human elastase IIA enzyme (NCBI Accession Number NP254275) and the porcine elastase II enzyme (NCBI Accession Number A26823) that are both expressed in the pancreas.

Variants of a mature elastase protein of the invention are also encompassed. Variants include proteins comprising amino acid sequences sufficiently identical to or derived from the amino acid sequence of the mature elastase protein of the invention and exhibit elastase biological activity. A biologically active portion of a mature elastase protein of the invention can be a protein which is, for example, at least 150, 160, 175, 180, 185, 190, 200, 210, 220, 230, 231, 232, 233, 234, 235, 236, 237, 238, or 239 amino acids in length. Moreover, other biologically active portions, in which other regions of the protein are deleted, can be prepared by recombinant techniques and evaluated for one or more of the functional activities of the native form of a mature elastase protein of the invention.

In addition, mature elastase proteins comprising any combination of the four human type I elastase polymorphisms are represented by SEQ ID NO:84. Possible combinations are set forth in Table 3 above.

5.1.2. Proelastase Activation Sequences

The elastase activation sequence is any sequence whose removal from a proelastase protein results in a biologically active mature elastase protein.

Activation sequences generally contain protease recognition sites adjacent to where proproteins are cleaved to produce mature, biologically active proteins. An activation sequence may be engineered to add a protease or elastase recognition site, or it may be engineered to replace an existing protease recognition site with another protease recognition site. Activation peptides or sequences useful in the practice of this invention include, but are not limited to, SEQ ID NO: 23, 72 and 73. Still other activation sequences useful in the practice of this invention can be obtained from the N-terminal residues 1-10 of SEQ ID NO:64-68. In preferred aspects, the proelastase activation sequence is engineered to contain a recognition sequence for a type I or type II elastase. Most preferably, the elastase recognition sequence is recognized by the mature elastase to which it is operably linked. Thus, in embodiments directed to a type II elastase, the recognition sequence is most preferably a type II elastase recognition sequence. Conversely, in embodiments directed to a type I elastase, the recognition sequence is most preferably a type I elastase recognition sequence. In a preferred embodiment, the recognition sequence is a human type I elastase recognition sequence. Exemplary type I recognition sequences include the amino acid sequence of SEQ ID NOS: 14-16, and 18-21. Other recognition sites contemplated by this invention include any recognition site described by the consensus recognition sites of SEQ ID NO: 11, 12, or 13.

5.1.3. Signal Sequences

The proelastase proteins of the invention may further contain a signal sequence which increases the secretion of a proelastase protein into the culture medium of the host cell in which it is expressed.

The native signal sequence of the elastase protein may be used, particularly for expression in a mammalian host cell. In other embodiments, the native signal sequence of an elastase protein of the invention can be removed and replaced with a signal sequence from another protein, such as the porcine type I elastase signal sequence, the human type I elastase signal sequence, or the yeast α-factor signal sequence. In certain specific embodiments, the yeast α-factor signal peptide can further comprise (1) a yeast α-factor propeptide or (2) a yeast α-factor propeptide and spacer sequence, each respectively exemplified by the amino acid sequence of SEQ ID NOS:50 and 96 or SEQ ID NOS:51 and 97. Alternatively, the gp67 secretory sequence of the baculovirus envelope protein can be used as a heterologous signal sequence (Current Protocols in Molecular Biology (Ausubel et al., eds., John Wiley & Sons, 1992)). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

5.2 Elastase Nucleic Acids

One aspect of the invention pertains to recombinant nucleic acid molecules that encode a recombinant elastase protein of the invention. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The present invention is directed to nucleic acids encoding the elastase proteins of the invention. Thus, in certain embodiments, the present invention provides a nucleic acid molecule comprising a nucleotide sequence which encodes a proelastase protein (including but not limited to a protein of any one of SEQ ID NOS:6-9, 64-69, 88-91, or 98-103) comprising (i) an activation sequence comprising an elastase recognition sequence operably linked to (ii) the amino acid sequence of a protein having type I elastase activity. In other embodiments, the present invention also provides a nucleic acid molecule comprising a nucleotide sequence which encodes a protein comprising (i) a signal sequence operable in *Pichia pastoris* operably linked to (ii) an activation sequence (including but not limited to an amino acid sequence of SEQ ID NOS: 23, 72, or 73) comprising a protease recognition sequence which in turn is operably linked to (iii) the amino acid sequence of a mature human type I elastase.

A nucleic acid of the invention may be purified. A "purified" nucleic acid molecule, such as a cDNA molecule, can be substantially free of other cellular material, or culture medium when produced by recombinant techniques, or substantially free of chemical precursors or other chemicals when chemically synthesized.

In instances wherein the nucleic acid molecule is a cDNA or RNA, e.g., mRNA, molecule, such molecules can include a poly A "tail," or, alternatively, can lack such a 3' tail.

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

5.3 Recombinant Expression Vectors and Host Cells

Further provided are vectors comprising any of the nucleic acids of the invention or host cells engineered to express the nucleic acids of the invention. In specific embodiments, the vectors comprise a nucleotide sequence which regulates the expression of the protein encoded by the nucleic acid of the invention. For example, the nucleotide sequence encoding the protein of the invention can be operably linked to a methanol-inducible promoter.

Host cells comprising the nucleic acids and vectors of the invention are also provided. In certain embodiments, the vector or nucleic acid is integrated into the host cell genome; in other embodiments, the vector or nucleic acid is extra-chromosomal. A preferred host cell is a *Pichia pastoris* cell.

As used herein, the term "vector" refers to a nucleic acid molecule capable of transporting another nucleic acid to which it has been linked. One type of vector is a "plasmid," which refers to a circular double-stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of coding sequences to which they are operably linked. In general, expression vectors of utility in recombinant DNA techniques are often in the form of plasmids (vectors).

The recombinant expression vectors of the invention comprise nucleotide sequence encoding a mature elastase, a proelastase or a preproelastase of the invention in a form suitable for expression in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185 (Academic Press, San Diego, Calif., 1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of elastase protein desired, etc. The expression vectors of the invention can be introduced into host cells to thereby produce elastase proteins encoded by nucleic acids as described herein.

The recombinant expression vectors of the invention can be designed for expression of an elastase protein of the invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of the recombinant elastase protein; 2) to increase the solubility of the recombinant elastase protein; and 3) to aid in the purification of the recombinant elastase protein by acting as a ligand in affinity purification. Often, in fusion expression vectors, a proteolytic cleavage domain is introduced at the junction of the fusion moiety and the recombinant protein to enable separation of the recombinant protein from the fusion moiety subsequent to purification of the fusion protein. Thus, the fusion moiety and proteolytic cleavage domain together can act as an activation sequence, including a protease recognition site, for recombinant expression of an elastase protein. Enzymes capable of activating such fusion proteins, and their cognate recognition sequences, include Factor Xa, thrombin and enterokinase. Typical fusion expression vectors include pGEX (Pharmacia Biotech Inc.; Smith and Johnson, 1988, Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, Gene 69:301-315) and pET-11d (Studier et al., 1990, Gene Expression Technology: Methods in Enzymology 185, Academic Press, San Diego, Calif., 185:60-89).

Target gene expression from the pTrc vector relies on host RNA polymerase transcription from a hybrid trp-lac fusion promoter. Target gene expression from the pET-11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant elastase protein expression in *E. coli* is to express the protein in a host bacteria with an impaired capacity to proteolytically cleave the recombinant protein (Gottesman, 1990, Gene Expression Technology: Methods in Enzymology 185, Academic Press, San Diego, Calif. 185:119-129). Another strategy is to alter the nucleic acid sequence of the nucleic acid to be inserted into an expression vector so that the individual codons for each amino acid are those preferentially utilized in *E. coli* (Wada et al., 1992, Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* or *P. pastoris* include pYepSec1 (Baldari et al., 1987, *EMBO J.* 6:229-234), pMFa (Kurjan and Herskowitz, 1982, *Cell* 30:933-943), pJRY88 (Schultz et al., 1987, Gene 54:113-123), pYES2 (Invitrogen Corporation, San Diego, Calif.), and pPicZ (Invitrogen Corp, San Diego, Calif.). For expression in yeast, a methanol-inducible promoter is preferably used. Alteration of the nucleic acid sequence of the nucleic acid to be inserted into an expression vector so that the individual codons for each amino acid are those preferentially utilized in *P. pastoris* is also contemplated herein. More specifically, the codons of SEQ ID NO:33 or SEQ ID NO:81 can be substituted for codons that are preferentially utilized in *P. pastoris*.

Alternatively, the expression vector is a baculovirus expression vector. Baculovirus vectors available for expression of proteins in cultured insect cells (e.g., Sf 9 cells) include the pAc series (Smith et al., 1983, Mol. Cell Biol. 3:2156-2165) and the pVL series (Lucklow and Summers, 1989, Virology 170:31-39). Another strategy is to alter the nucleic acid sequence of the nucleic acid to be inserted into an expression vector so that the individual codons for each amino acid are those preferentially utilized in insect cells.

In yet another embodiment, an elastase protein is expressed in mammalian cells using a mammalian expression vector. Examples of mammalian expression vectors include pCDM8 (Seed, 1987, Nature 329(6142):840-2) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1:268-277), lymphoid-specific promoters (Calame and Eaton, 1988, Adv. Immunol. 43:235-275), in particular promoters of T cell receptors (Winoto and Baltimore, 1989, EMBO J. 8:729-733) and immunoglobulins (Banerji et al., 1983, Cell 33:729-740; Queen and Baltimore, 1983, Cell 33:741-748), neuron-specific promoters (e.g., the neurofilament promoter; Byrne and Ruddle, 1989, Proc. Natl. Acad. Sci. USA 86:5473-5477), pancreas-specific promoters (Edlund et al., 1985, Science 230:912-916), and mammary gland-specific promoters (e.g., milk whey promoter; U.S. Pat. No. 4,873,316 and European Application Publication No. EP264166). Developmentally-regulated promoters are also encompassed, for example the mouse hox promoters (Kessel and Gruss, 1990, Science 249:374-379) and the beta-fetoprotein promoter (Campes and Tilghman, 1989, Genes Dev. 3:537-546).

In certain aspects of the invention, expression of a protein of the invention may be increased by increasing the dosage of the corresponding gene, for example by the use of a high copy expression vector or gene amplification. Gene amplification can be achieved in dihydrofolate reductase- ("dhfr-") deficient CHO cells by cotransfection of the gene of interest with the dhfr gene and exposure to selective medium with stepwise increasing concentrations of methotrexate. See, e.g., Ausubel et al., Current Protocols in Molecular Biology Unit 16.14, (John Wiley & Sons, New York, 1996). An alternative method for increasing gene copy number is to multimerize an expression cassette (e.g., promoter with coding sequence) encoding the elastase protein of interest in a vector prior to introducing the vector into the host cell. Methods and vectors for achieving expression cassette multimerization are known in yeast and mammalian host cell systems (see, e.g., Monaco, Methods in Biotechnology 8:Animal Cell Biotechnology, at pp. 39-348 (Humana press, 1999); Vassileva et al., 2001, Protein Expression and Purification 21:71-80; Mansur et al., 2005, Biotechnology Letter 27(5):339-45. In addition, kits for multi-copy gene expression are commercially available. For example, a multi-copy *Pichia* expression kit can be obtained from Invitrogen (Carlsbad, Calif.). The multimerization of an expression cassette is exemplified in Example 6, infra.

Accordingly, other aspects of the invention pertain to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a coding sequence for a selectable marker (e.g., for resistance to antibiotics) is generally introduced into the host cells along with the open reading frame of interest. Preferred selectable markers include those which confer resistance to drugs, such as G418, hygromycin, zeocin and methotrexate. Cells stably transfected with the introduced nucleic acid can be identified by drug selection (e.g., cells that have incorporated the selectable marker coding sequence will survive, while the other cells die).

In another embodiment, the expression characteristics of an endogenous elastase coding seqence within a cell, cell line or microorganism may be modified by inserting a DNA regulatory element heterologous to the elastase coding sequence into the genome of a cell, stable cell line or cloned microorganism such that the inserted regulatory element is operatively linked with the endogenous gene A heterologous sequence, containing a regulatory element, may be inserted into a stable cell line or cloned microorganism, such that it is operatively linked with and activates expression of an endogenous elastase gene, using techniques, such as targeted homologous recombination, which are well known to those of skill in the art, and described e.g., in Chappel, U.S. Pat. No. 5,272,071; PCT publication No. WO 91/06667, published May 16, 1991. The heterologous sequence may further include the signal peptides, cleavage sequences and/or activation sequences of the present invention.

5.4 Methods of Manufacturing Mature Elastase Proteins

A host cell of the invention, such as a prokaryotic or eukaryotic host cell in culture, can be used to produce an elastase protein of the invention. Accordingly, the invention further provides methods for producing an elastase protein of the invention using the host cells of the invention. In one embodiment, the method comprises culturing the host cell of invention (into which a recombinant expression vector encoding an elastase protein of the invention has been introduced) in a suitable medium such that the elastase protein is produced. In another embodiment, the method further comprises isolating the elastase protein from the medium or the host cell.

The present invention further provides methods for producing immature elastase proteins of the invention comprising culturing a host cell engineered to express a nucleic acid of the invention under conditions in which the proelastase protein is produced. In certain embodiments, the pre-proelastase protein is also produced. The present invention further provides methods for producing mature elastase proteins of the invention comprising culturing a host cell engineered to express a nucleic acid of the invention under conditions in which a proelastase protein is produced and subjecting the proelastase protein to activation conditions such that the mature elastase protein is produced.

Preferred culture conditions for producing the immature and mature proteins of the invention, particularly for the host cell *Pichia pastoris*, include a period of growth at a low pH. In specific embodiments, the low pH is a pH of 2-6, a pH of 2-5, a pH of 3-6, a pH of 3-5, a pH of 4-6, a pH of 3-4 or any range whose upper and lower limits are selected from any of the foregoing values. At the end of the culture period, the pH of the culture can be raised, preferably to a pH of 7-11, most preferably to a pH of 8.

Where the expression of a proelastase protein of the invention is under the control of a methanol-inducible promoter, conditions for producing an immature or mature elastase protein of the invention may also comprise a period of methanol induction.

The elastase production methods of the invention may further comprise the step of recovering the protein expressed by the host cell. In certain instances, the protein recovered is a proelastase, containing the activation sequence. In other instances, the protein recovered is a mature elastase lacking the activation sequence. Under certain conditions, both proelastase and mature elastase proteins are produced. In other instances, the preproelastase is produced.

Preferably, particularly where it is desired to circumvent auto-activation of an auto-activated proelastase, culture conditions for proelastase expression comprise a period of growth in sodium citrate, sodium succinate, or sodium acetate. In specific embodiments, a concentration of about 5-50 mM, 7.5-100 Mm, 10-150 mM, 50-200 mM, 75-175 mM, 100-150 mM, 75-125 mM, or of any range whose upper and lower limits are selected from any of the foregoing values is used. In a preferred embodiment, the sodium citrate, sodium succinate, or sodium acetate concentration is 90-110 mM, most preferably 100 mM.

Additionally, particularly where it is desired to circumvent protein degradation, culture conditions for proelastase expression comprise a period of growth and induction at the lower end of the temperature range suitable for the host cell in question. For example, where the host cell is a *Pichia pastoris* host cell, the preferred range is about 22-28° C. In specific embodiments, the *Pichia pastoris* host cell is cultured at a temperature of about 28° C. The growth and induction need not be performed at the same temperature; for example, in an embodiment where *Pichia pastoris* is utilized as a host cell, growth can be performed at 28° C. while induction can be performed at 22° C.

The activation of an auto-activated proelastase protein of the invention may be initiated by the addition of extrinsic elastase in a small (catalytic) amount. Alternatively or concurrently, the activation of an auto-activated proelastase protein of the invention may be initiated by raising the pH of the solution containing the auto-activated proelastase protein. The pH is preferably 7-11; in specific embodiments, the solution is at a pH of 7-10, 7-9, 8-10, 8-9, or any range whose upper and lower limits are selected from any of the foregoing values. In a preferred embodiment, the pH of the solution 7-9, most preferably 8.

In specific embodiments, the auto-activated proelastase may be subjected to Tris base, during the activation step. In specific embodiments, Tris base is added to a concentration of 5-50 mM, 7.5-100 Mm, 10-150 mM, 50-200 mM, 75-175 mM, 100-150 mM, 75-125 mM, or of any range whose upper and lower limits are selected from any of the foregoing values. In a preferred embodiment, Tris base is added to a concentration 90-110 mM, most preferably 100 mM. The pH of the Tris base is preferably 7-11; in specific embodiments, the Tris base is at a pH of 7-10, 7-9, 8-10, 8-9, or any range whose upper and lower limits are selected from any of the foregoing values. In a preferred embodiment, the Tris base is at a pH of 7-9, most preferably 8.

In certain aspects of the invention, the temperature for elastase autoactivation is ambient temperature, e.g., a temperature ranging from 22° C. to 26° C. In certain embodiments, the elastase activation step is preferably performed with the proelastase at a low initial concentration, e.g., 0.1-0.3 mg/ml, for optimal accuracy of the cleavage reaction and minimal formation of N-terminal variants.

In certain embodiments of the invention, addition of catalytic amounts of elastase is not required to convert the auto-activated proelastase to mature elastase, as the proelastase can undergo autoproteolysis. In certain embodiments, the rate of autoproteolysis is concentration independent. Without seeking to be limited by theory, it is believed that concentration independent autoproteolysis of certain auto-activated proelastase proteins is mediated via an intramolecular process where the proelastase molecule cleaves itself via an intramolecular reaction. However, in other embodiments, activation of the auto-activated proelastase is concentration dependent. Without seeking to be limited by theory, it is believed that concentration dependent autoproteolysis of certain auto-activated proelastase proteins is mediated via an intermolecular reaction where proelastase is cleaved by another proelastase and/or by a mature elastase. In still other embodiments, certain auto-activated elastase proproteins display a combination of concentration dependent and concentration independent activation. In those instances where auto-activation is concentration dependent, the proprotein can be maintained in a more dilute form to reduce activation if desired. Activation of elastase proproteins comprising the elastase propeptide cleavage domain of SEQ ID NO:55 that include but are not limited to the proprotein of SEQ ID NO:69 can be controlled by maintaining such proproteins in a dilute form. The binding cleft of mature type I elastases is hydrophobic. Activation of elastase proproteins can also be controlled by placing amino acids (such as histidine) in the activation peptide that have side chains that are charged at a lower pH but are not charged at higher pH. In this way, such pro-proteins can be expressed and purified in low pH solutions where activation is very slow and then activated quickly by raising the pH to a level where elastase activity is high and the side chain of the amino acid (such as histidine) is not charged.

It is also recognized that certain undesirable N-terminal sequence variants of mature elastase can accumulate in the course of producing mature elastase proteins of this invention. More specifically, proelastase proteins containing the SEQ ID NO:42 elastase propeptide cleavage domain that include the proprotein of SEQ ID NO:6 can yield N-terminal sequence variants where cleavage has occurred at the peptide bond that is C-terminal to any of the residues at positions P3 or P2. However, the occurrence of such undesirable N-terminal variants can be reduced by placing certain amino acids in certain locations in the activation sequence. For example, when a proline in present in the P2 position, the production of N-terminal variants with one or two additional N-terminal amino acids is reduced or eliminated. Also, elimination of the need for trypsin for activation reduces or eliminates the production of the variant that lacks nine N-terminal residues. Additionally, the occurrence of undesirable N-terminal variants can be reduced or eliminated by conducting the activation reaction under certain conditions.

More specifically, in certain embodiments activation conditions include an "extended conversion" step during which N-terminal variants produced during the initial portion of the conversion reaction are subsequently selectively degraded. The relative amounts of protein species during "extended conversion" can be monitored in real-time by HIC-HPLC. The selective degradation of undesired N-terminal variants increases the proportion of full-length, mature PRT-201 in the conversion reaction and reduces the proportion of N-terminal variants. For proelastase proteins containing the SEQ ID NO:55 elastase propeptide cleavage domain, the extended conversion step is performed for 4 to 8 hours, and preferably about 6 hr. For other proelastase proteins, the externded conversion step may be increased or decreased, depending on the proportion of N-terminal variants relative to mature (full length) elastase immediately after all of the proelastase has been converted. When the conversion occurs in complex media, such as fermentation broth, the period of extended conversion may be increased due to competition at the active site of mature elastase by other proteins and peptides in solution. Alternatively, a mixture of mature elastase and N-terminal variant elastase can be recovered from the complex media prior to the extended conversion step, thereby reducing the active site competitition and the time required to remove the N-terminal variant species.

As mentioned above, during a conversion reaction for pro-PRT-201-55M3-003-VU, there is a side-reaction that leads to the production of N-terminal variants. In the specific case of pro-PRT-201-55M3-003-VU, these N-terminal variants are missing the first two valines and have little or no elastase activity. For other mutant pro-proteins there are additional N-terminal variants produced, some with additions and others with different deletions. An N-terminal removal step has been developed which reduces the N-terminal variants to a range of 0-2%. The development of this removal step evolved from a variety of experiments and observations. As mentioned previously, during optimization of conversion condition experiments with pro-PRT-201-42 it was observed that longer conversion reactions often led to a very low percentage of N-terminal variants. It was subsequently determined that the longer conversion reactions allowed mature PRT-201 to selectively degrade N-terminal variants. The discovery of PRT-201's ability to selectively degrade N-terminal variants under certain conditions had a tremendous benefit by helping to produce a more purified PRT-201 product with less N-terminal variants. This N-terminal variant removal step was implemented into a large scale production process by establishing conditions that would allow the pro-PRT-201 to convert to mature PRT-201 and then allow the PRT-201 to degrade the N-terminal variants.

Figure 10:
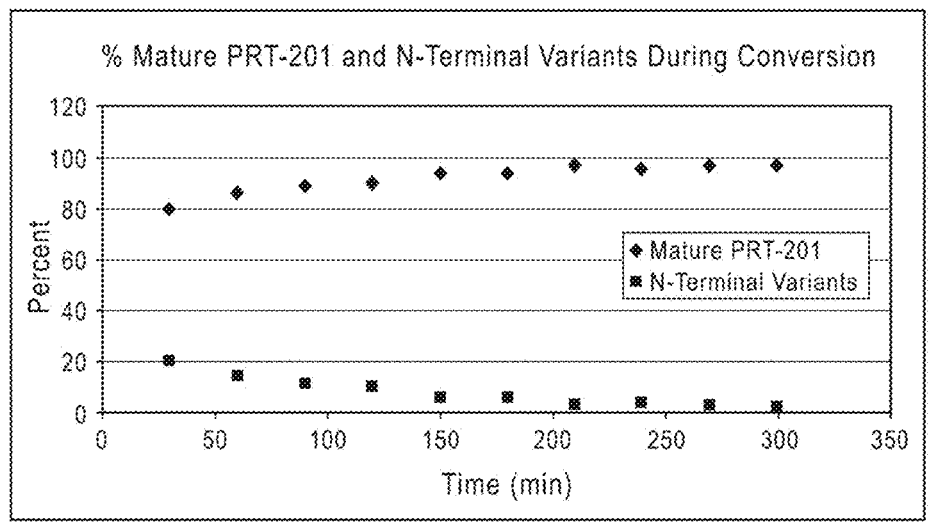
FIG. 10: HIC-HPLC analysis of purified proprotein conversion. Purified pro-PRT-201-55M3-003-VU was subjected to conversion at 26° C. The graph shows relative amounts of mature (full-length) PRT-201 and N-terminal variants produced during the conversion.

A representative example of such a step is shown in FIG. 10 as it was monitored in real-time by HIC-HPLC. At approximately 50 minutes, the 100% pro-PRT-201-55M3 had completely converted to approximately 86% mature PRT-201 and 14% N-terminal variants. The conversion reaction was extended which allowed mature PRT-201 to selectively degrade the N-terminal variants resulting in a decrease of variants from 14% to 2%. With longer incubations, the N-terminal variants can be selectively degraded to an undetectable level. When the N-terminal variant level is sufficiently low, the activity of PRT-201 is suppressed with sodium citrate and adjustment of the reaction pH to 5.0.

Once purified mature elastase has been obtained, the active enzyme can be brought into a solution at which the elastase protein is relatively inactive and placed into a buffer for further column chromatography, e.g., cation exchange chromatography, purification steps. In general, the elastase protein can be placed in sodium citrate at a concentration of about 5 to 25 mM and a pH of about 2 to 5. In a specific embodiment, the elastase is placed in 20 mM sodium citrate, pH 5. The eluted fractions are then optionally analyzed by one, more than one, or all of the following methods: (1) spectrophotometry at A280 to determine concentration, (2) SDS-PAGE to assess purity, (3) activity assay, e.g., SLAP assay, to assess elastase specific activity, and (4) HIC-HPLC to detect mature elastase and N-terminal variants, and fractions with suitable characteristics (e.g., acceptable specific activity, acceptably low levels (preferably absence) of detectable glycoforms, and acceptably low levels (preferably absence) of detectable N-terminal variants) are pooled.

Once purified mature elastase has been obtained, the active enzyme can be brought into a suitable solution for lyophilization. In general, the elastase protein can be placed into a buffer of 1× phosphate buffered saline ("PBS") (137 mM sodium chloride, 10 mM sodium phosphate, 2.7 mM potassium phosphate pH 7.4) prior to lyophilization. In certain embodiments, the elastase protein can be placed into a buffer of 0.1×PBS (13.7 mM sodium chloride, 1.0 mM sodium phosphate, 0.27 mM potassium phosphate pH 7.4) prior to lyophilization.

Expression of a proelastase sequence can in some instances yield a mixture of proelastase and mature elastase proteins. Thus, the present invention provides a composition comprising both a proelastase protein and a mature elastase protein.

5.5 Pharmaceutical Compositions

The mature elastase proteins of the invention can be incorporated into pharmaceutical compositions suitable for administration. Such compositions typically comprise the elastase protein and pharmaceutically inert ingredients, for example a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Also contemplated as pharmaceutically inert ingredients are conventional excipients, vehicles, fillers, binders, disintegrants, solvents, solubilizing agents, and coloring agents. The use of such media and agents for pharmaceutically active substances is well known in the art. Except insofar as any conventional media or agent is incompatible with a mature elastase protein, use thereof in the compositions is contemplated. Supplementary active compounds can also be incorporated into the compositions.

Accordingly, certain aspects of the present invention relate to pharmaceutical compositions. In specific embodiments, the present invention provides a composition comprising (i) a therapeutically effective amount of a mature human type I elastase and (ii) a pharmaceutically acceptable carrier. The mature human type I elastase that can be used in the composition include but are not limited to the proteins of SEQ ID NO:1, 4, 5, 84, 87. The mature human type I elastase may contain any of the combinations of polymorphisms set forth in Table 3 above.

In other embodiments, the present invention provides a pharmaceutical composition comprising (i) a therapeutically effective amount of mature human type I elastase (ii) a pharmaceutically acceptable carrier, which pharmaceutical composition is free of trypsin, or fragments of trypsin. In other embodiments, the pharmaceutical composition is substantially free of trypsin or fragments of trypsin. As used herein, the phrase "free of trypsin" refers to a composition in which trypsin is not used in any portion of the production process. As used herein, the phrase "substantially free of trypsin" refers to a composition wherein trypsin is present at a final percent (i.e., weight trypsin/total composition weight) of no more than about 0.0025% or more preferably, less than about 0.001% on a weight/weight basis. As used herein, the phrase "free of" trypsin refers to a composition in which the variant is undetectable, e.g., by means of an enzymatic assay or ELISA.

In certain aspects, a composition of the invention has less trypsin activity than the equivalent of 3 ng/ml of trypsin as measured by a BENZ assay, preferably less trypsin activity than the equivalent of 2.5 ng/ml of trypsin as measured by a BENZ assay, and even more preferably less trypsin activity than the equivalent of 2 ng/ml of trypsin as measured by a BENZ assay. In a specific embodiment, the present invention provides a composition comprising a therapeutically effective amount of elastase protein in which the trypsin activity is the equivalent of less than 1.6 ng/ml of trypsin as measured by a BENZ assay. Examples of elastase compositions with less trypsin activity than the equivalent of 1.6 ng/ml of trypsin as measured by a BENZ assay are provided in Example 8 below. In certain embodiments, the ng/ml trypsin activity can be assayed in a liquid human type I elastase composition or preparation containing 1 mg/ml human type I elastase protein. Thus, the trypsin activities may also be described in terms of milligrams of elastase protein, for example, less than 3 ng trypsin activity/mg elastase protein, less than 1.56 ng trypsin activity/mg elastase protein, etc.

The present invention further provides pharmaceutical compositions that are either free or substantially free of undesirable N-terminal variants of mature elastase. Undesirable N-terminal variants include, but are not limited to, variants produced by cleavage at the peptide bond that is C-terminal to any of the residues at the P5, P4, P3, P2, P'1, P'2, P'3, P'4, P'6, and/or P'9 positions. Certain undesirable N-terminal variants are produced by trypsin activation; others are produced by autoactivation of proelastase sequences that do not contained optimized activation sequences.

In certain embodiments, the pharmaceutical composition is free or substantially free of one, more than one or all N-terminal variants of mature elastase that include but are not limited to SEQ ID NOS: 2, 3, 37, 38, 70, 71, 85, 86, 94, 95, 104, 105, 106, 107, 108. In certain embodiments, the present invention provides a pharmaceutical composition comprising (i) a therapeutically effective amount of mature human type I elastase (ii) a pharmaceutically acceptable carrier, which pharmaceutical composition is free or substantially free of any protein with SEQ ID NOS: 2, 3, 37, 38, 70, 71, 85, 86, 94, 95, 104, 105, 106, 107, or 108. In other embodiments, the pharmaceutical composition is substantially free of N-terminal variants of mature elastase that include but are not limited to SEQ ID NOS: 2, 3, 37, 38, 70, 71, 85, 86, 94, 95, 104, 105, 106, 107, or 108. As used herein, the phrase "free of" a particular variant refers to a composition in which the variant is undetectable, e.g., by means of cation exchange HPLC assay, hydrophobic interaction HPLC assay, or mass spectrometry combined with liquid chromatography. As used herein, the phrase "substantially free" refers to a composition wherein the N-terminal variant is present at a final percent (i.e. weight N-terminal variant/total composition weight) of at least less than about 0.5%. In certain preferred embodiments, the composition that is substantially free of N-terminal variant is a composition where the concentration of N-terminal variant is less than about 0.1% or less than about 0.01% or, more preferably, even less than about 0.001% on a weight/weight basis. In certain aspects, the presence of N-terminal variants is detected by means of cation exchange HPLC assay, hydrophobic interaction HPLC assay, or mass spectrometry combined with liquid chromatography.

In certain specific embodiments, a pharmaceutical composition that is free of N-terminal variants of SEQ ID NO:70, 71, 104 and 105 is produced by activation of a proelastase which does not contain an arginine in the P1 postion and/or an alanine in the P2 position.

In other embodiments, the present invention provides a pharmaceutical composition comprising (i) a therapeutically effective amount of mature human type I elastase (ii) a pharmaceutically acceptable carrier, which pharmaceutical composition is substantially free of bacterial proteins and/or is substantially free of mammalian proteins other than said mature human type I elastase. As used herein, the phrase "substantially free of mammalian proteins" or "substantially free of bacterial proteins" refers to a composition wherein such proteins are present at a final percent (i.e. weight mammalian proteins (other than elastase and, optionally, a carrier protein such as albumin) or bacterial proteins/total composition weight) of at least less than about 0.5%. In certain preferred embodiments, the composition that is substantially free of such proteins is a composition where the concentration of the undesirable protein is less than about 0.1% or less than about 0.01%, or, more preferably, even less than about 0.001% on a weight/weight basis.

In certain aspects, a pharmaceutical composition that is "free of mammalian proteins" (other than elastase) contains elastase that is produced from a recombinant cell line that is not a mammalian cell and where no protein with a mammalian sequence or substantially a mammalian sequence is present in any portion of the production process. In certain aspects, a pharmaceutical composition that is "free of bacterial proteins" contains elastase that is produced from a recombinant cell line that is not a bacterial cell and where no protein with a bacterial sequence or substantially a bacterial sequence is present in any portion of the production process.

The mature human type I elastases (including variants) of the invention are most preferably purified for use in pharmaceutical compositions. In specific embodiments, the elastases are at least 70%, 80%, 90%, 95%, 96%, 97%, 98% or 99% pure. In other specific embodiments, the elastases are up to 98%, 98.5%, 99%, 99.2%, 99.5% or 99.8% pure.

For formulating into pharmaceutical compositions, the mature human type I elastases of the invention preferably have a specific activity of greater than greater than 1, greater than 5, greater than 10, greater than 20, greater than 25, or greater than 30 U/mg of protein, as determined by measuring the rate of hydrolysis of the small peptide substrate N-succinyl-Ala-Ala-Ala-pNitroanilide (SLAP), which is catalyzed by the addition of elastase. One unit of activity is defined as the amount of elastase that catalyzes the hydrolysis of 1 micromole of substrate per minute at 30° C. and specific activity is defined as activity per mg of elastase protein (U/mg). Preferably, a pharmaceutical composition comprises a mature human type I elastase which has a specific activity within a range in which the lower limit is 1, 2, 3, 4, 5, 7, 10, 15 or 20 U/mg protein and in which the upper limit is, independently, 5, 10, 15, 20, 25, 30, 35, 40 or 50 U/mg protein. In exemplary embodiments, the specific activity is in the range of 1-40 U/mg of protein, 1-5 U/mg protein, 2-10 U/mg protein, 4-15 U/mg protein, 5-30 U/mg of protein, 10-20 U/mg of protein, 20-40 U/mg of protein, or any range whose upper and lower limits are selected from any of the foregoing values.

The pharmaceutical compositions of the invention are preferably stable. In specific embodiments, a pharmaceutical composition (for example a pharmaceutical composition prepared by lyophilization above) maintains at least 50%, more preferably at least 60%, and most preferably at least 70% of its specific activity after a week, more preferably after a month, yet more preferably after 3 months, and most preferably after 6 months of storage at 4° C. In specific embodiments, the pharmaceutical composition maintains at least 75%, at least 80%, at least 85%, at least 90% or at least 95% of its specific activity after a week, more preferably after a month, yet more preferably after 3 months, and most preferably after 6 months of storage at 4° C.

A pharmaceutical composition of the invention is formulated to be compatible with its intended route of administration. Methods for administering elastases to treat or prevent diseases of biological conduits are described in WO 2001/21574; WO 2004/073504; and WO 2006/036804. The most preferred route of administration is parenteral, for example direct administration to the vessel wall, including local administration to the external adventitial surface of surgically exposed vessels and local administration to the vessel wall using a drug delivery catheter. Solutions or suspensions used for parenteral administration can include the following components: a sterile diluent such as water for injection, saline solution, phosphate buffered saline solution, sugars such as sucrose or dextrans, fixed oils, polyethylene glycols, glycerine, propylene glycol, polysorbate-80 (also known as TWEEN® 80), or other synthetic solvents; antibacterial agents such as methyl parabens; antioxidants such as ascorbic acid or sodium bisulfite; chelating agents such as ethylenediaminetetraacetic acid; buffers such as phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or single or multiple dose vials made of glass or plastic. The parenteral preparation can also be enclosed in a drug delivery catheter. In all cases, the composition must be sterile.

In specific embodiments, a pharmaceutical composition of the invention is a liquid formulation comprising one or more of the following excipients: dextrose (e.g., 2-10% w/v); lactose (e.g., 2-10% w/v); mannitol (e.g., 2-10% w/v); sucrose (e.g., 2-10% w/v); trehalose (e.g., 2-10% w/v); ascorbic acid (e.g., 2-10 mM); calcium chloride (e.g., 4-20 mM); dextran-70 (e.g., 2-10% w/v); poloxamer 188 (e.g., 0.2-1% w/v); polysorbate-80 (e.g., 0.001-5% w/v, more preferably 0.1-5%); glycerin (e.g., 0.2-5% w/v); arginine (e.g., 2-10% w/v); glycine (e.g., 2-10% w/v); dextran-44 (e.g., 2-10% w/v); and dextran-18 (e.g., 2-10% w/v). In certain embodiments, the concentration, singly or in the aggregate, of dextrose, lactose, mannitol, sucrose, trehalose, dextran-70, glycerin, arginine, glycine, dextran-44 or dextran-18 is within a range in which the lower limit is 2.5, 4, 5, or 7% w/v and in which the upper limit is, independently, 4, 5, 6, 8, or 10% w/v.

A liquid formulation can be made by adding water to a dry formulation containing a mature elastase protein, one or more buffer reagents and/or one or more excipients. The dry formulation can be made by lyophilizing a solution comprising mature elastase protein, one or more buffer reagents, and/or one or more excipients.

A liquid formulation can be made, for example, by reconstituting lyophilized elastase proteins of the invention with sterilized water or a buffer solution. Examples of a buffer solution include sterile solutions of saline or phosphate-buffered saline. In a specific embodiment, after reconstitution of a dry formulation comprising mature elastase protein to the desired protein concentration, the solution contains approximately 137 mM sodium chloride, 2.7 mM potassium phosphate, 10 mM sodium phosphate (a phosphate buffered saline concentration that is considered 1×) and the pH of the solution is approximately 7.4. In certain aspects, the dry formulation comprising mature elastase protein also contains sodium, chloride, and phosphate ions in amounts such that only water is needed for reconstitution.

A liquid formulation can be also be made, for example, by reconstituting lyophilized elastase proteins with a buffer solution containing one or more excipients. Examples of excipients include polysorbate-80 and dextran. In a specific embodiment, after reconstitution of a dry formulation comprising mature elastase protein to the desired protein concentration, the resulting solution contains approximately 137 mM sodium chloride, 2.7 mM potassium phosphate, 10 mM sodium phosphate, 0.01% polysorbate-80, and the pH of the solution is approximately 7.4. The one or more excipients can be mixed with the mature elastase protein before lyophilization or after lyophilization but before reconstitution. Thus, in certain aspects, the dry formulation comprising mature elastase protein also contains excipients such as polysorbate-80 or dextran.

In certain aspects, the present invention provides a liquid formulation comprising: 0.001-50 mg/ml of mature elastase protein in a solution of 137 mM sodium chloride, 2.7 mM potassium phosphate, 10 mM sodium phosphate and comprising 5-10%, more preferably 6-9%, of an excipient selected from dextrose, lactose, mannitol, sucrose, trehalose, dextran-70, glycerin, arginine, glycine, dextran-44 or dextran-18.

In a specific embodiment, the present invention provides a liquid formulation comprising: 0.001-50 mg/ml of mature elastase protein in a solution of 137 mM sodium chloride, 2.7 mM potassium phosphate, 10 mM sodium phosphate with a pH of 7.4.

In another specific embodiment, the present invention provides a liquid formulation comprising: 0.001-50 mg/ml of mature elastase protein in a solution of 137 mM sodium chloride, 2.7 mM potassium phosphate, 10 mM sodium phosphate and comprising 0.01% polysorbate-80, with a pH of 7.4.

In another specific embodiment, the present invention provides a liquid formulation comprising: 0.001-50 mg/ml of mature elastase protein in a solution of 137 mM sodium chloride, 2.7 mM potassium phosphate, 10 mM sodium phosphate and comprising 0.01% polysorbate-80 and 8% dextran-18, with a pH of 7.4.

In another specific embodiment, the present invention provides a liquid formulation comprising: 0.001-50 mg/ml of mature elastase protein in a solution of 137 mM sodium chloride, 2.7 mM potassium phosphate, 10 mM sodium phosphate and comprising 8% dextran-18, with a pH of 7.4.

The liquid formulations of the invention preferably contain a final concentration of mature elastase proteins within a range in which the lower limit is 0.1, 0.5, 1, 2.5, 5, 10, 15 or 20 mg/ml and in which the upper limit is, independently, 0.5, 1, 2.5, 5, 10, 25, 50, 100, 250, 500, 1000, or 1500 mg/ml.

In certain aspects, the present invention provides a liquid formulation comprising: 0.0001-500 mg/ml (more preferably 1-100 mg/ml, and yet more preferably 0.5-20 mg/ml) of mature elastase protein in a solution of 0.5×PBS-1.5×PBS (more preferably 1×PBS), the solution comprising 5-10% (more preferably 6-9%) of an excipient selected from dextrose, lactose, mannitol, sucrose, trehalose, dextran-70, glycerin, arginine, glycine, dextran-44 or dextran-18 and having a pH of 6.5-8.5. In a specific embodiment, the liquid formulation comprises 0.5 mg/ml mature elastase protein and 8% dextran-18 in 1×PBS, pH 7.4. In a specific embodiment, the liquid formulation comprises 5 mg/ml mature elastase protein and 8% dextran-18 in 1×PBS, pH 7.4.

A liquid formulation of the invention preferably has an osmolality within a range in which the lower limit is 100, 125, 150, 175, 200, 250 or 275 mOsm/kg and in which the upper limit is, independently, 500, 450, 400, 350, 325, 300, 275 or 250 mOsm/kg. In specifc embodiments, the osmolarity of a liquid formulation of the invention preferably has an osmolality of approximately 125 to 500 mOsm/kg, more preferably of approximately 275 to 325 mOsm/kg, for example as measured by the freezing point depression method.

It is especially advantageous to formulate parenteral compositions, such as compositions that can be made into the liquid formulations of the invention, in dosage unit form for ease of administration and uniformity of dosage. Dosage unit form as used herein refers to physically discrete units suited as unitary dosages for the subject to be treated; each unit containing a predetermined quantity of mature elastase protein calculated to produce the desired therapeutic effect in association with the required pharmaceutical carrier.

As defined herein, a therapeutically effective amount of mature elastase protein (i.e., an effective dosage) ranges from about 0.0033 mg-200 mg. For vessels with smaller diameter and thinner walls, such as those in a radiocephalic arteriovenous fistula, smaller doses (such as of 0.0033 mg-2.0 mg) are preferable. For vessels with a larger diameter and thicker walls such as femoral arteries, larger doses (such as 2.05-100 mg) are preferable.

In certain embodiments, the pharmaceutical compositions can be included in a container, pack, dispenser, or catheter. In still other embodiments, the pharmaceutical compositions can be included in a container, pack, dispenser, or catheter together with instructions for administration. Instructions for administration can be included in printed form either within or upon a container, pack, dispenser, or catheter. Alternatively, instructions for administration can be included either within or upon a container, pack, dispenser, or catheter in the form of a reference to another printed or internet accessible document that provides the instructions.

In certain embodiments, the pharmaceutical compositions can be included in a container, pack, or dispenser. In still other embodiments, the pharmaceutical compositions can be included in a container, pack, or dispenser together with instructions for administration. Instructions for administration can be included in printed form either within or upon a container, pack, or dispenser. Alternatively, instructions for administration can be included either within or upon a container, pack, or dispenser in the form of a reference to another printed or internet accessable document that provides the instructions.

The invention includes methods for preparing pharmaceutical compositions. Once a mature elastase is produced according to the invention, it can be lyophilized and stored until it is reconstituted into a pharmaceutical formulation suitable for administration. In an exemplary embodiment, the present invention provides a method of isolating a lyophilized mature human type I elastase comprising: (a) culturing a host cell, such as a *Pichia pastoris* host cell, engineered to express a nucleic acid molecule encoding a preproelastase open reading frame under conditions in which the open reading frame is expressed, wherein said open reading frame comprises nucleotide sequences encoding, in a 5' to 3' direction (i) a signal peptide operable in *Pichia pastoris*; (ii) an activation sequence comprising an elastase recognition sequence; and (iii) the sequence of a mature type I elastase protein, thereby producing a proelastase protein; (b) subjecting the proelastase protein to autoactivation conditions, thereby producing a mature type I elastase, wherein the autoactivation conditions include, for example: (i) changing the pH of a solution containing the proelastase protein, e.g., to a pH of 6.5-11, preferably 8-9; or (ii) purifying the proelastase protein, for example, by ion exchange chromatography, and subjecting the solution extended conversion to remove N-terminal variants, thereby producing mature human type I elastase; (c) optionally, purifying the mature human type I elastase, e.g., ion exchange chromatography step for polish chromatography; and (d) lyophilizing the mature type I elastase, thereby isolating a lyophilized mature human type I elastase. The mature type I elastase is preferably a human type I elastase. In certain aspects, the lyophilized mature type I elastase is preferably more than 95% pure; in specific embodiments, the lyophilized mature type I elastase is more than 98% or more than 99% pure.

The mature elastase proteins of the invention can be formulated into pharmaceutical compositions. Thus, in an exemplary embodiments, the present invention provides a method of generating a pharmaceutical composition comprising a mature human type I elastase, said method comprising (i) isolating a lyophilized mature human type I elastase according to the methods described above (e.g., in Section 5.4); and (ii) reconstituting the lyophilized mature human type I elastase in a pharmaceutically acceptable carrier.

5.6 Effective Dose

The present invention generally provides the benefit of parenteral, preferably local, administration of recombinant elastase proteins, alone or in combination with other agents, for treating or preventing disease in biological conduits.

In certain embodiments, as an alternative to parenteral administration, oral administration of agents for treating or preventing disease in biological conduits may be used.

Toxicity and therapeutic efficacy of the elastase proteins utilized in the practice of the methods of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Such information can be used to more accurately determine useful doses in humans.

5.7 Methods of Administration

The invention relates to pharmaceutical compositions comprising novel elastase proteins and methods of use thereof for preventing or treating disease in biological conduits. Such pharmaceutical compositions can be formulated in a conventional manner as described in Section 5.5 above.

The elastase compositions of the present invention can be administered to the desired segment of the biological conduit being treated by a device known to one of skill in the art to be acceptable for delivery of solutions to the wall of an artery or vein, e.g., a syringe, a drug delivery catheter, a drug delivery needle, an implanted drug delivery polymer, such as a sheet or microsphere preparation, an implantable catheter, or a polymer-coated vascular stent, preferably a self-expanding stent.

In certain embodiments, the administration to the desired segment may be guided by direct visualization, ultrasound, CT, fluoroscopic guidance, MRI or endoscopic guidance.

In certain aspects of the present invention, administration of an elastase to a biological conduit comprises applying a liquid formulation of elastase directly to the external adventitial surface of a surgically exposed artery or vein. In specific aspects of this invention, the administration is performed with a syringe.

In certain aspects of the present invention, administration of an elastase to a biological conduit comprises localizing a delivery apparatus in close proximity to the segment of the biological conduit to be treated. In some embodiments, during delivery of the elastase protein by a delivery apparatus, a portion of the delivery apparatus can be inserted into the wall of the biological conduit. In some embodiments, the lumen of the biological conduit can be pressurized while the elastase protein is delivered to the pressurized segment of the biological conduit. In some embodiments, the lumen of the biological conduit is pressurized by mechanical action. In some embodiments, the lumen of the biological conduit is pressurized with a balloon catheter. In some embodiments, pressure is applied to the inner wall of the biological conduit by a self-expanding member which is part of a catheter or device. In some embodiments, the elastase protein is administered and the pressurizing is performed by the same device. In some embodiments, the biological conduit is surgically exposed and the elastase protein is delivered into the lumen or is applied to the external surface of the biological conduit in vivo. In embodiments involving luminal delivery, blood flow through the vessel may be stopped with a clamp or to allow the elastase to contact the vessel wall for longer time periods and to prevent inhibition of the elastase by serum. In some embodiments, the biological conduit is surgically removed and the elastase is delivered to the luminal surface and/or to the external surface of the conduit in vitro. The treated conduit may then, in certain embodiments, be returned to the body.

In other aspects of the present invention, administration of an elastase to a biological conduit entails the use of a polymer formulation that is placed as a stent within the vessel to be treated, a clamp or strip applied to the external surface of the biological conduit, or a wrap on or around the vessel to be treated, or other device in, around or near the vessel to be treated.

In yet other aspects of the present invention, an elastase is percutaneously injected into a tissue region for purpose of dilating arteries and/or vein within that region, including collateral arteries. In other aspects, an elastase is percutaneously injected directly into the wall of an artery or vein or into the surrounding tissues for the purpose of dilating a specific segment of vessel. In embodiments aimed at treatment of heart vessels, an elastase protein can be either percutaneously delivered to the pericardial space or directly applied to surgically exposed coronary vessels.

Medical devices that can be used to administer the elastase proteins of the invention to blood vessels are described in Section 5.9 below.

5.8 Kits

The present invention provides kits for practicing the methods of the present invention. A "therapeutic" kit of the invention comprises in one or more containers one or more of the agents described herein as useful for treating or preventing disease in biological conduits, optionally together with any agents that facilitate their delivery. An alternative kit of the invention, the "manufacturing" kit, comprises in one or more containers one or more of the agents described herein as useful for making recombinant elastase proteins.

The therapeutic kit of the invention may optionally comprise additional components useful for performing the methods of the invention. By way of example, the therapeutic kit may comprise pharmaceutical carriers useful for formulating the agents of the invention. The therapeutic kit may also comprise a device or a component of a device for performing the therapeutic methods of the invention, for example a syringe or needle. The inclusion of devices such as an intramural or perivascular injection catheters or intraluminal injection catheters in the therapeutic kits is also contemplated. In certain embodiments, the agents of the invention can be provided in unit dose form. In addition or in the alternative, the kits of the invention may provide an instructional material which describes performance of one or more methods of the invention, or a notice in the form prescribed by a governmental agency regulating the manufacture, use or sale of pharmaceuticals or biological products, which notice reflects approval by the agency of manufacture, use or sale for human administration. Instructional materials can be included in printed form either within or upon one or more containers of the kit. Alternatively, instructional materials can be included either within or upon one or more containers of the kit in the form of a reference to another printed or internet accessable document that provides the instructional materials.

In specific embodiments, a kit of the invention comprises a medical device as described in Section 5.9 below.

The manufacturing kit of the invention may optionally comprise additional components useful for performing the methods of the invention.

5.9 Medical Devices Useful for Administration of Elastase Proteins

Provided herein are medical devices that can be used to administer the elastase proteins of the present invention to a biological conduit, such as an artery or vein. Such devices are described below and in provisional application No. 61/025,084, filed Jan. 31, 2008, provisional application No. 61/025,463, filed Feb. 1, 2008, and provisional application No. 61/075,710, filed Jun. 25, 2008, each of which is incorporated by reference herein in its entirety. The elastase proteins of the present invention can also be administered to biological conduits via conventional catheters.

In one embodiment, a medical device useful for administration of elastase proteins has a central longitudinal axis, and comprises one or more actuators, wherein the one or more actuators can exist in a constrained configuration in which a length of said one or more actuators is oriented substantially parallel to the longitudinal axis of said medical device and an unconstrained configuration in which at least a portion of the length of said one or more actuators is oriented substantially non-parallel to the device's central longitudinal axis. After the device is positioned at a target site adjacent to the wall of a biological conduit, one or more actuators (and if desired, all of the actuators) may be released from a constrained configuration and permitted to adopt an unconstrained configuration, thereby making contact with the wall of the biological conduit. The one or more actuators may be of any shape, and in preferred embodiments, the movement of the one or more actuators from the constrained configuration to the unconstrained configuration occurs upon release of a constraining force by the device operator but without the input by the operator of any deforming forces to the device or the target tissue.

Figure 22:
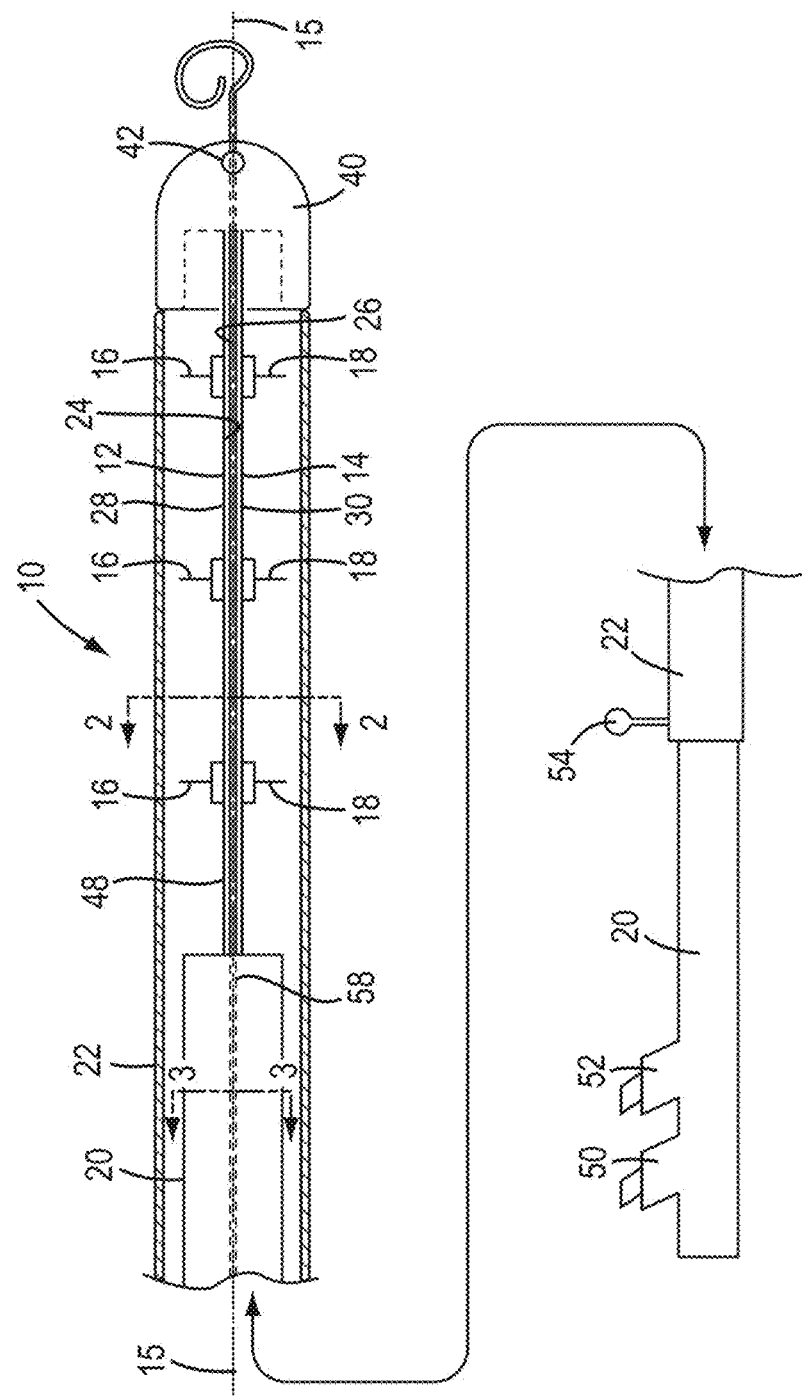
FIG. 22. A side, partially sectioned view of one embodiment of the medical device described in Section 5.9.
Figure 23:
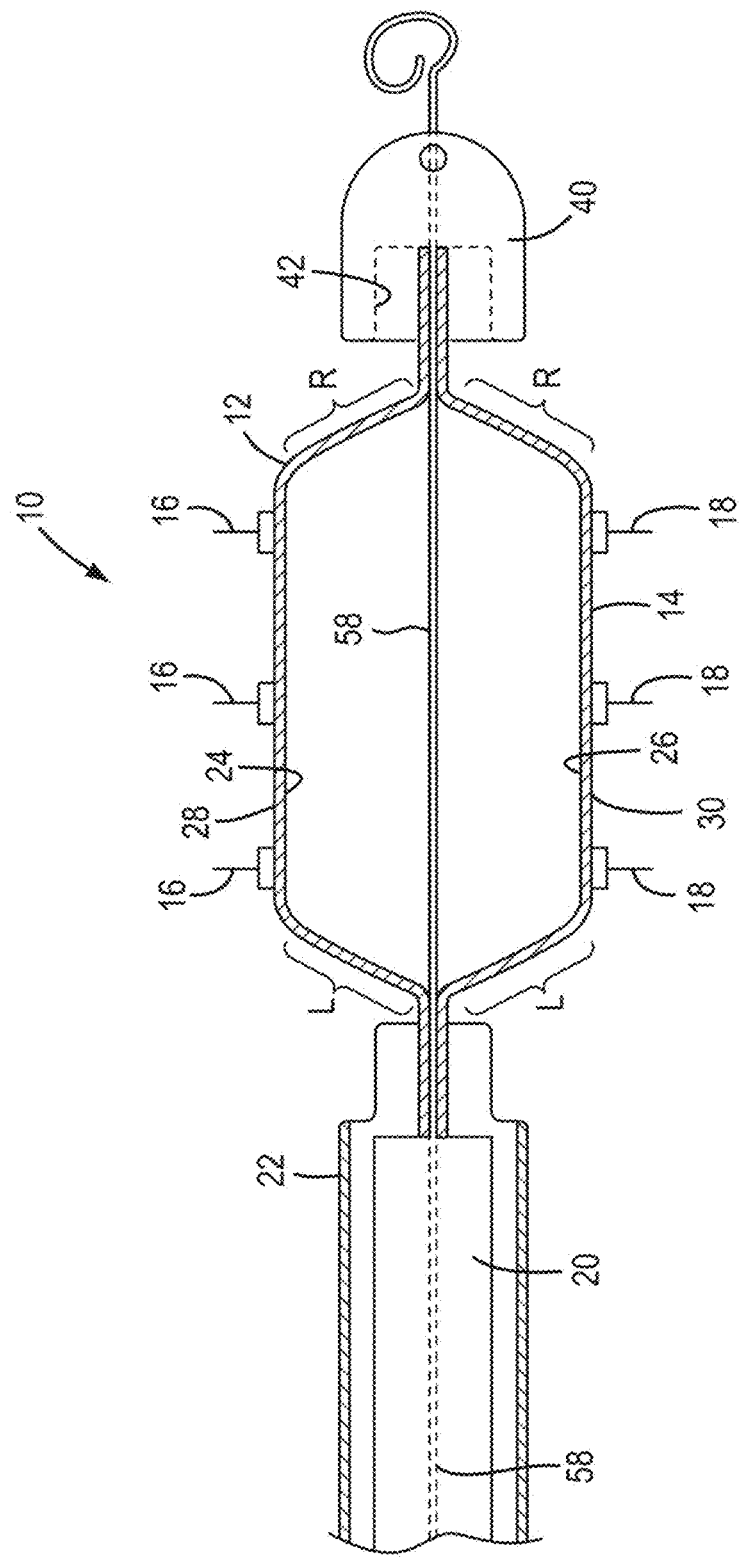
FIG. 23. A view similar to FIG. 22 that illustrates the movement of the actuators of the medical device.

In a first specific embodiment, shown in FIG. 22, the device is a fluid delivery catheter 10 comprising one or more actuators that are formed as a pair of elongate splines 12, 14, the intermediate regions of which are movable between a constrained configuration which is oriented substantially parallel to the central longitudinal axis 15 of the catheter assembly and an unconstrained configuration in which at least a portion of the pair of splines is oriented substantially non-parallel to said central longitudinal axis (see the left L and right R portions of the spline lengths in FIG. 23). The one or more splines 12, 14 may be constructed as elongate bands or wires that each have opposite proximal and distal ends. In a preferred embodiment, the splines have flat, opposing interior surfaces 24, 26, and flat opposite facing exterior surfaces 28, 30. In this embodiment, the splines 12, 14 can translate between constrained positions and unconstrained positions, as shown respectively in FIGS. 22 and 23. In one embodiment, the pair of splines is positioned back-to-back in their constrained configurations as shown in FIG. 22.

The catheter 10 further comprises one or more tissue penetrators 16, 18 secured to one or more surfaces of the one or more splines 12, 14, a central catheter component 20 having an elongate length, and an exterior catheter component 22 that can shield the tissue penetrator or penetrators during catheter movement within the biological conduit.

The tissue penetrators 16, 18 may be constructed of any suitable material. Preferred examples of such materials include, but are not limited to, nickel, aluminum, steel and alloys thereof. In a specific embodiment, the tissue penetrators are constructed of nitinol.

The central catheter component 20 and the exterior catheter component 22 may be constructed of materials typically employed in constructing catheters. Examples of such materials include, but are not limited to, silicone, polyurethane, nylon, Dacron, and PEBAX™.

The actuators are preferably constructed of a flexible, resilient material. In a preferred embodiment, the flexible, resilient material is capable of being constrained upon the application of a constraining force, e.g., when the actuators are in the constrained configuration, and adopts its original unconstrained shape when the constraining force is removed, e.g., when the actuators are in the unconstrained configuration. Any such flexible, resilient material can be used, including but not limited to surgical steel, aluminum, polypropylene, olefinic materials, polyurethane and other synthetic rubber or plastic materials. The one or more actuators are most preferably constructed of a shape memory material. Examples of such shape memory materials include, but are not limited to, copper-zinc-aluminum-nickel alloys, copper-aluminum-nickel alloys, and nickel-titanium (NiTi) alloys. In a preferred embodiment, the shape memory material is nitinol. In a preferred embodiment, when the pair of splines assumes the unconstrained configuration, the shape memory properties of the material from which each spline is formed cause the splines, without the application of any external deforming force, to bow radially away from each other in a single plane as shown in FIG. 23.

Figure 24:
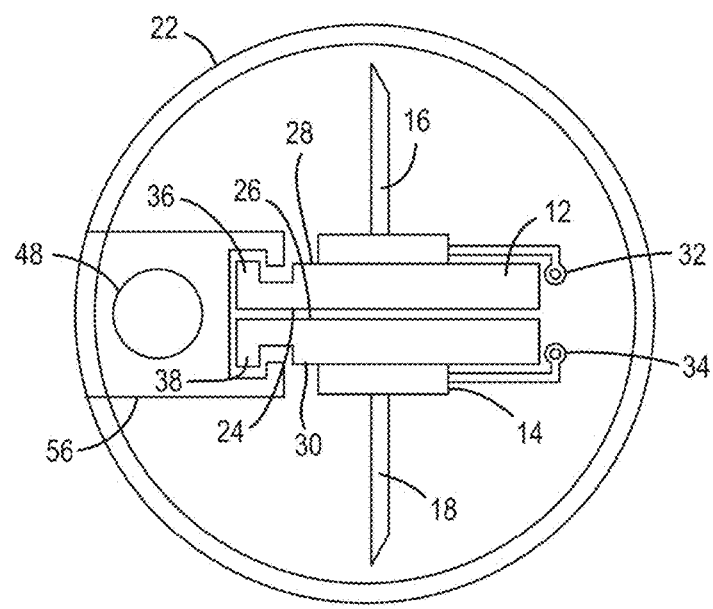
FIG. 24. An end section view in the plane of line 2-2 in FIG. 22.

One or more of the splines (and preferably each of the splines) has a flexible fluid delivery conduit 32, 34 that extends along the length of the spline, or within the spline, as shown in FIG. 24. As the splines 12, 14 move from their straight, constrained configurations to their bowed, unconstrained configurations, the fluid delivery conduits 32, 34 also move from straight configurations to bowed configurations. In one embodiment, the fluid delivery conduits 32, 34 are separate tubular conduits that are secured along the lengths of the pair of splines 12, 14. In another embodiment, the fluid delivery conduits are conduits formed into or within the material of the splines.

One or more of the splines (and preferably each of the splines 12,14) is also formed with a zipper rail 36, 38 that extends along a length of the spline (FIG. 24). The zipper rails 36, 38 are formed of either the same material as the splines 12, 14, or a material that flexes with the splines 12, 14.

One or more of the tissue penetrators 16, 18 is secured to the exterior surfaces 28, 30 of the pair of splines 12, 14 (FIG. 24). The tissue penetrators 16, 18 are connected to and communicate with the fluid delivery conduits 32, 34 that extend along the lengths of the splines 12, 14. The tissue penetrators 16, 18 are positioned to project substantially perpendicular from the exterior surfaces 28, 30 of the splines 12, 14. The tissue penetrators 16, 18 have hollow interior bores that communicate with the fluid delivery conduits 32, 34 of the splines. The distal ends of the tissue penetrators have fluid delivery ports that communicate with the interior bores of the tissue penetrators.

The device permits delivery of fluids into or through one or more distinct layers of a wall of a biological conduit, for example a vascular wall. The vascular wall comprises numerous structures and layers, including the endothelial layer and basement membrane layer (collectively the intimal layer), the internal elastic lamina, the medial layer, and the adventitial layer. These layers are arranged such that the endothelium is exposed to the lumen of the vessel and the basement membrane, the internal elastic lamina, the media, and the adventitia are each successively layered over the endothelium, as described in U.S. Pat. App. Publication No. 2006/0189941A1. With the medical devices of the present invention, the depth to which the tissue penetrators 16, 18 can penetrate is determined by the length of each tissue penetrator 16, 18. For example, if the target layer is the adventitial layer, tissue penetrators 16, 18 having a defined length sufficient for penetration to the depth of the adventitial layer upon deployment of the device are used. Likewise, if the target layer is the medial layer, tissue penetrators 16, 18 having a defined length sufficient for penetration to the depth of the medial layer upon deployment of the device are used.

In specific embodiments, the length of tissue penetrators 16, 18 may range from about 0.3 mm to about 5 mm for vascular applications, or up to about 20 mm or even 30 mm for applications involving other biological spaces or conduits, for example in colonic applications. Tissue penetrators 16, 18 preferably have a diameter of about 0.2 mm (33 gauge) to about 3.4 mm (10 gauge), more preferably 0.2 mm to 1.3 mm (about 33 to 21 gauge). The distal tips of the tissue penetrators may have a standard bevel, a short bevel, or a true short bevel. In an alternative embodiment, the tissue penetrators attached to any one spline are not of identical lengths, but may be configured such that their distal ends align so as to be equidistant from the wall of the biological conduit when the medical device is in the unconstrained position, e.g., during use.

The central catheter component 20 has an elongate length with opposite proximal and distal ends, shown to the left and right respectively in FIG. 22. In one embodiment, the central catheter component 20 has a cylindrical exterior surface that extends along its elongate length. The proximal ends of the splines 12, 14 are attached e.g., soldered or glued, to the distal end of the central catheter component 20, while the distal ends of the splines 12, 14 are attached, e.g., soldered or glued, to a catheter guide tip 40. The tip 40 has a smooth exterior surface that is designed to move easily in the biological conduit. A guide wire bore 48 extends through the length of the central catheter 20 and tip 40. The guide wire bore is dimensioned to receive a guide wire in sliding engagement through the bore.

Figure 25:
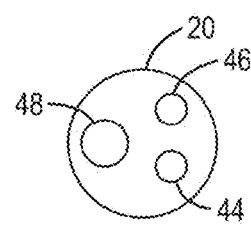
FIG. 25. An end section view in the plane of line 3-3 in FIG. 22.
Figure 26:
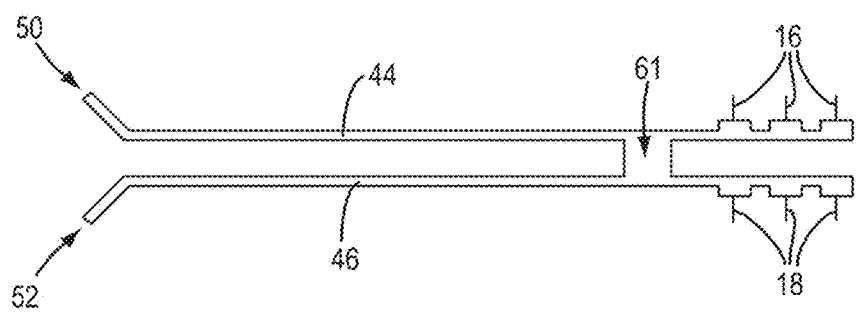
FIG. 26. A diagram of the fluid path of the medical device of FIG. 22, extending from the Luer hubs through the fluid delivery conduits to the reservoir and then to the tissue penetrators.
Figure 32:
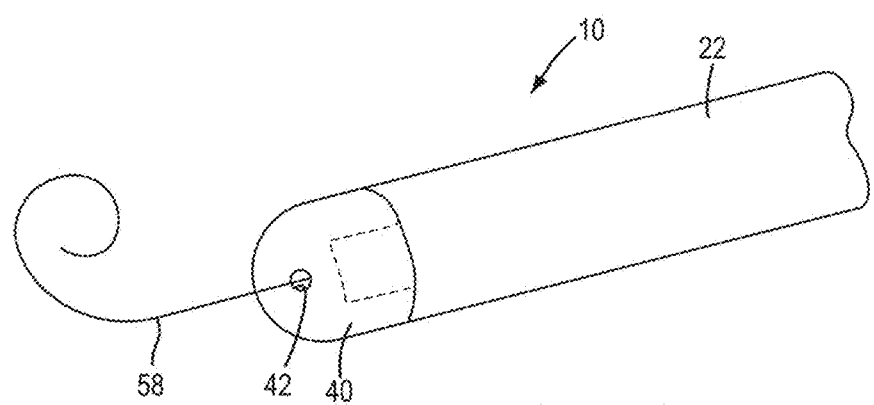
FIG. 32. A partial view of the exterior of the medical device of FIG. 22 in its constrained position.

A pair of fluid delivery lumens 44, 46 extends through the interior of the central catheter component 20 for the entire length of the catheter component (FIG. 25). At the distal end of the central catheter component 20 the pair of fluid delivery lumens 44, 46 communicates with the pair of fluid delivery conduits 32, 34 that extend along the lengths of the splines 12, 14 to the tissue penetrators 16, 18. A guide wire bore 48 also extends through the interior of the central catheter component 20 from the proximal end to the distal end of the central catheter component (FIG. 25). The proximal end of the central catheter component 20 is provided with a pair of Luer hubs 50, 52 (FIG. 22). In one embodiment, each Luer hub 50, 52 communicates with one of the fluid delivery lumens 44, 46 extending through the length of the central catheter. Each Luer hub 50, 52 is designed to be connected with a fluid delivery source to communicate a fluid through each Luer hub 50, 52, then through each fluid delivery lumen 44, 46 extending through the central catheter component 20, then through each fluid delivery conduit 32, 34 extending along the lengths of the pair of splines 12, 14, and then through the tissue penetrators 16, 18 secured to each of the pair of splines. In another embodiment, each Luer hub 50, 52 independently communicates with both of the fluid delivery lumens 44, 46 extending through the length of the central catheter component. In this configuration, a first fluid can be delivered through a first Luer hub to both tissue penetrators 16, 18 and a second fluid can be delivered through a second Luer hub to both tissue penetrators 16, 18. Delivery of fluid to both tissue penetrators from each Luer hub can be achieved by an independent conduit extending from each Luer hub to a distal common reservoir 61 as shown in FIG. 32. This reservoir communicates with both tissue penetrators 16, 18. Alternatively, in another embodiment, the medical device of the instant invention comprises only a single Luer hub connected to a single fluid delivery lumen extending through the central catheter, which then is attached to a distal common reservoir, permitting the delivery of a single fluid to both tissue penetrators 16, 18.

The exterior catheter component 22 has a tubular configuration that surrounds the pair of splines 12, 14 and a majority of the central catheter 20 (FIG. 22). The catheter component 22 has an elongate length that extends between opposite proximal and distal ends of the catheter component shown to the left and right, respectively in FIG. 22. The catheter component distal end is dimensioned to engage in a secure engagement with the guide tip 40, where the exterior surface of the tip 40 merges with the exterior surface of the catheter component 22 when the catheter component distal end is engaged with the tip. The tubular configuration of the catheter component 22 is dimensioned so that an interior surface of the catheter component 22 is spaced outwardly of the plurality of tissue penetrators 16, 18 on the pair of splines 12, 14 in the constrained positions of the pair of splines. The proximal end of the central catheter 20 extends beyond the proximal end of the catheter component 22 when the catheter component distal end engages with the catheter guide tip 40.

A mechanical connection 54 is provided between the exterior catheter component 22 proximal end and the central catheter component 20 proximal end that enables the exterior catheter component to be moved rearwardly along the lengths of the pair of splines 12, 14 and the central catheter component 20 causing the exterior catheter component 22 distal end to separate from the guide tip 40 and pass over the pair of splines 12, 14, and forwardly over the length of the central catheter component 20 and over the lengths of the pair of splines 12, 14 to engage the exterior catheter component 22 distal end with the tip 40 (FIG. 22). The mechanical connection 54 could be provided by a handle or button that manually slides the exterior catheter component 22 over the central catheter component 20. The connection 54 could also be provided by a thumbwheel or trigger mechanism. In addition, the connection 54 could be provided with an audible or tactile indicator (such as clicking) of the incremental movement of the exterior catheter component 22 relative to the central catheter component 20.

In one embodiment, the exterior catheter component 22 is provided with a single zipper track 56 that extends along the entire length of one side of the exterior catheter component 22 on the interior surface of the exterior catheter component (FIG. 24). The zipper track 56 in the interior of the exterior catheter component 22 engages in a sliding engagement with the zipper rails 36, 38 at one side of each of the splines 12, 14. Advancing the exterior catheter component 22 forwardly along the lengths of the central catheter component 20 and the pair of splines 12, 14 toward the guide tip 40 of the catheter assembly causes the zipper track 56 of the exterior catheter component to slide along the rails 36, 38 of the pair of splines 12, 14. This moves the pair of splines 12, 14 from their bowed, unconstrained configuration shown in FIG. 23 toward their back-to-back, constrained configuration shown in FIG. 22. The engagement of the spline rails 36, 38 in the zipper track 56 of the exterior catheter component 22 holds the pair of splines 12, 14 in their back-to-back relative positions shown in FIG. 22. With the exterior catheter component 22 pushed forward over the central catheter component 20 and the pair of splines 12, 14 to where the distal end of the exterior catheter component 22 engages with the guide tip 40, the tissue penetrators 16, 18 are covered and the catheter assembly of the present invention can be safely moved forward or backward in a biological conduit. The exterior catheter component 22 covers the tissue penetrators 16, 18 projecting from the pair of splines 12, 14 and the engagement of the exterior catheter component 22 with the distal guide tip 40 provides the catheter assembly with a smooth exterior surface that facilitates the insertion of the catheter assembly into and through a biological conduit such as a blood vessel. In another embodiment, the exterior catheter component 22 is provided with two zipper tracks at 180 degrees from each other that extend along the entire length of the exterior catheter component 22 on the interior surface and the splines have rails on both sides.

A guide wire 58 is used with the catheter assembly (FIG. 22). The guide wire 58 extends through the central catheter component guide wire bore 48, along the splines 12, 14, and through the guide tip outlet 42. In certain embodiments, the guide wire 58 has a solid core, e.g., stainless steel or superelastic nitinol. The guide wire may be constructed of radiopaque material, either in its entirety or at its distal portions (e.g., the most distal 1 mm to 25 mm or the most distal 3 mm to 10 mm). The guide wire 58 may optionally be coated with a medically inert coating such as TEFLON®.

In use of this device, the guide wire 58 is positioned in the biological conduit by methods well known in the art. The guide wire 58 extends from the biological conduit, through the guide wire outlet 42 in the tip 40 of the assembly, through the exterior shielding catheter 22 past the tissue penetrators 16, 18, and through the guide wire bore 48 of the central catheter 20. In other embodiments, the catheter assembly is a rapid-exchange catheter assembly, wherein the guide wire lumen is present in the distal end of the guide tip 40 of the catheter, but does not extend throughout the entire length of the medical device.

After positioning of the guide wire, the device is advanced into the biological conduit along the previously positioned guide wire 58. One or more radiopaque markers may optionally be provided on the device to monitor the position of the device in the biological conduit. Any material that prevents passage of electromagnetic radiation is considered radiopaque and could be used. Preferred radiopaque materials include, but are not limited to, platinum, gold, or silver. The radiopaque material can be coated on the surface of all or a part of the tip 40, on all or part of the splines 12, 14 or other actuators, on the guide wire 58, or on some combination of the foregoing strucutres. Alternatively, a ring of radiopaque material can be attached to the tip 40. The device may optionally be provided with onboard imaging, such as intravascular ultrasound or optical coherence tomography. The tip of the device may optionally be provided with optics that are used to determine the position of the device or characteristics of the surrounding biological conduit.

When the device is at its desired position in the biological conduit, the operator uses mechanical connection 54 to retract the exterior catheter component 22 rearwardly away from the guide tip 40. In a preferred embodiment, as the exterior catheter component 22 is withdrawn from over the tissue penetrators 16, 18, the zipper track 56 of the exterior catheter component 22 is withdrawn over the rails 36, 38 of the pair of splines 12, 14. This movement releases the pair of splines 12, 14 from their constrained, back-to-back configuration shown in FIG. 22, and allows the shape memory material of the splines 12, 14 to adopt their unconstrained, bowed configurations shown in FIG. 23. As the splines 12, 14 move to their unconstrained, bowed configurations, the splines come into contact with the inner surface of the wall(s) of the biological conduit and the tissue penetrators 16, 18 on the exterior surfaces 28, 30 of the splines 12, 14 are pressed into the interior surface of the biological conduit at the position of the device.

After the tissue penetrators 16, 18 have entered the desired layer of the wall of a biological conduit, a fluid can be delivered through the fluid delivery lumens 44, 46 in the central catheter component 20, through the fluid delivery conduits 32, 34 on the pair of splines 12, 14, and through the tissue penetrators 16, 18. When the delivery of the fluid is complete, the operator uses the mechanical connection 54 to move the exterior catheter component 22 (which may also be referred to as a shielding component) forward over the central catheter component 20 and over the pair of splines 12, 14 toward the guide tip 40. As the exterior catheter component 22 moves forward over the pair of splines 12, 14, the zipper track 56 on the interior of the exterior catheter component 22 passes over the rails 36, 38 on the pair of splines 12, 14, causing the splines 12, 14 to move from their unconstrained, bowed configuration back to their constrained configuration. When the exterior catheter component 22 has been entirely advanced over the pair splines 12, 14 and again engages with the guide tip 40, the zipper track 56 in the exterior catheter component 22 holds the splines 12, 14 in their constrained configuration. The device then can be repositioned for release at another location in the biological conduit or another biological conduit, or withdrawn from the body.

The shape and length of the splines 12, 14 are selected such that various embodiments of the device can be used in biological spaces or conduits of various sizes or diameters. In certain embodiments, the splines may be flat or rounded. Flat splines preferably have a width ranging from about 0.2 mm to about 20 mm, a height ranging from about 0.2 mm to about 5 mm, and a length ranging from about 10 mm to about 200 mm, depending on the particular application. Rounded splines preferably have a diameter ranging from about 0.2 mm to about 20 mm and a length ranging from about 10 mm to about 200 mm, depending on the particular application. In specific embodiments, flat splines are 3.5 mm to 5 mm, 5 mm to 10 mm, 10 mm to 15 mm, 15 mm to 20 mm in width, or any range therewithin (e.g., 3.5 mm to 10 mm); 3.5 mm to 5 mm, 5 mm to 10 mm. 10 mm to 15 mm, 15 mm to 20 mm in height, or any range therewithin (e.g., 3.5 mm to 10 mm); and 10 mm to 20 mm, 20 mm to 40 mm, 40 mm to 80 mm, 80 mm to 120 mm, 120 mm to 150 mm or 150 to 200 mm in length, or any range therewithin (e.g., 10 mm to 40 mm), or any permutation of the foregoing (e.g., a width of 5 mm to 10 mm, a height or 3.5 to 5 mm, and a length of 20 to 40 mm). In other embodiments, rounded splines are 3.5 mm to 5 mm, 5 mm to 10 mm, 10 mm to 15 mm, 15 mm to 20 mm in diameter, or any range therewithin (e.g., 3.5 mm to 10 mm) and 10 mm to 20 mm, 20 mm to 40 mm, 40 mm to 80 mm, 80 mm to 120 mm, 120 mm to 150 mm or 150 to 200 mm in length, or any range therewithin (e.g., 10 mm to 40 mm), or any permutation of the foregoing (e.g., a diameter of 5 mm to 10 mm and a length of 20 to 40 mm).

Figures 27, 28:
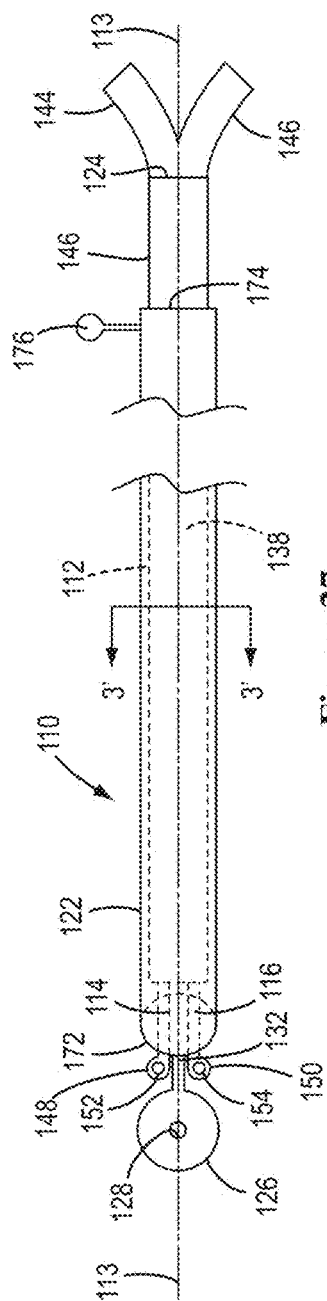
FIG. 27. A side, partially sectioned view of a second embodiment of the medical device of the present invention showing the actuators in their constrained configurations.
FIG. 28. A view similar to FIG. 27, but showing the actuators in their unconstrained configurations.

In a second specific embodiment, shown in FIG. 27, the device of the present invention is a fluid delivery catheter 110 comprising a central catheter component 112 having an elongate length with a longitudinal axis 113, one or more (and preferably two) flexible, resilient actuators that, in this specific embodiment, are formed as tissue penetrator presentation tubes 114, 116 that extend from the distal portion of the central catheter component 112. At least a portion of the tissue presentation tubes 114, 116 are movable between a constrained configuration which is oriented substantially parallel to the central longitudinal axis 113 of the catheter assembly and an unconstrained configuration which is oriented substantially non-parallel to the central longitudinal axis 113 of the catheter.

The catheter further comprises one or more (and preferably two) flexible, elongate tissue penetrators 118, 120 that extend through the two tissue penetrator presentation tubes 114, 116, and an exterior deployment tube 122 that extends over portions of the lengths of the central catheter component 112, the tissue penetrator presentation tubes 114, 116, and the middle rail 132.

The central catheter component 112 and the exterior deployment tube 122 may be constructed of any materials suitable for constructing catheters. Examples of such materials include, but are not limited to, silicone, polyurethane, nylon, Dacron, and PEBAX™.

Figure 31:
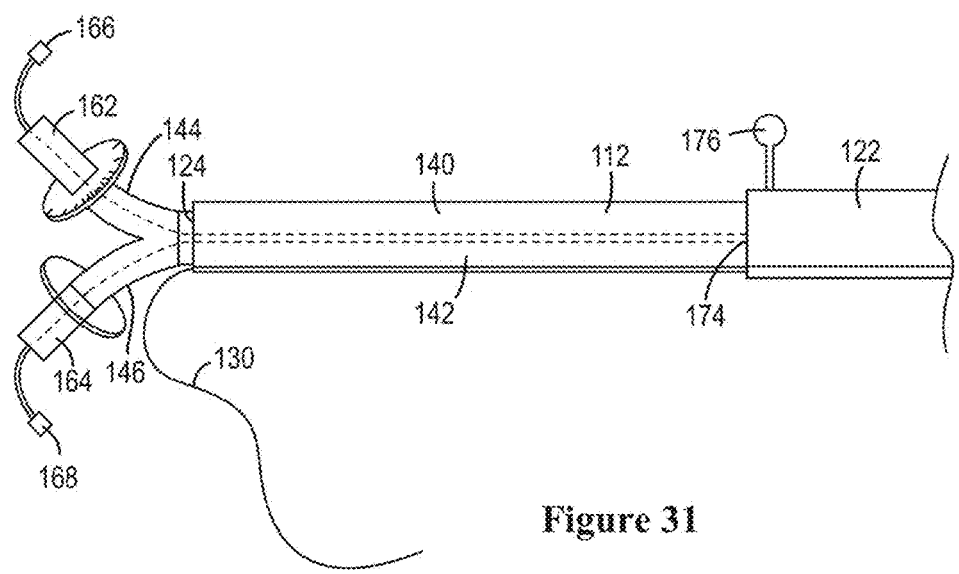
FIG. 31. A side view showing the detail of the proximal end of the device, shown to the right in FIGS. 27 and 28.

The tissue penetrators 118, 120 connect to respective hubs 166, 168 (FIG. 31). One or more of the pair of tissue penetrators 118, 120 preferably has a diameter of about 0.2 mm (33 gauge) to about 3.4 mm (10 gauge), more preferably 0.8 mm to 1.3 mm (about 18 to 21 gauge). One or more of the pair of tissue penetrators may have a standard bevel, a short bevel or a true short bevel. The pair of tissue penetrators 118, 120 are preferably constructed of materials that allow the tissue penetrators to flex along their lengths. Examples of such materials include, but are not limited to, nickel, aluminum, steel and alloys thereof. In a specific embodiment, the tissue penetrators are constructed of nitinol. The full length of the tissue penetrators 118, 120 can be constructed of a single material, or the distal ends (e.g., the distal 1 mm to the distal 20 mm), including the tips 156, 158, of the tissue penetrators 118, 120 may be constructed of one material and connected to the respective hubs 166, 168 via a tubing constructed of a different material, e.g., plastic.

One or more of the pair of tissue penetrator presentation tubes 114, 116 is preferably constructed of a flexible, resilient material. Such flexible, resilient material can be deformed, e.g., when the tissue penetrator presentation tubes 114, 116 are in the straight, constrained configuration of FIG. 27, but returns to its original shape when the deformation force is removed, e.g., when the tissue penetrator presentation tubes 114, 116 are in the curved, unconstrained configuration shown in FIG. 28. Any such flexible, resilient material can be used, including but not limited to surgical steel, aluminum, polypropylene, olefinic materials, polyurethane and other synthetic rubber or plastic materials. The pair of tissue penetrator presentation tubes 114, 116 is most preferably constructed of a shape memory material. Examples of such shape memory materials include, but are not limited to, copper-zinc-aluminum-nickel alloys, copper-aluminum-nickel alloys, and nickel-titanium (NiTi) alloys. In a preferred embodiment, the shape memory material is nitinol.

Figure 29:
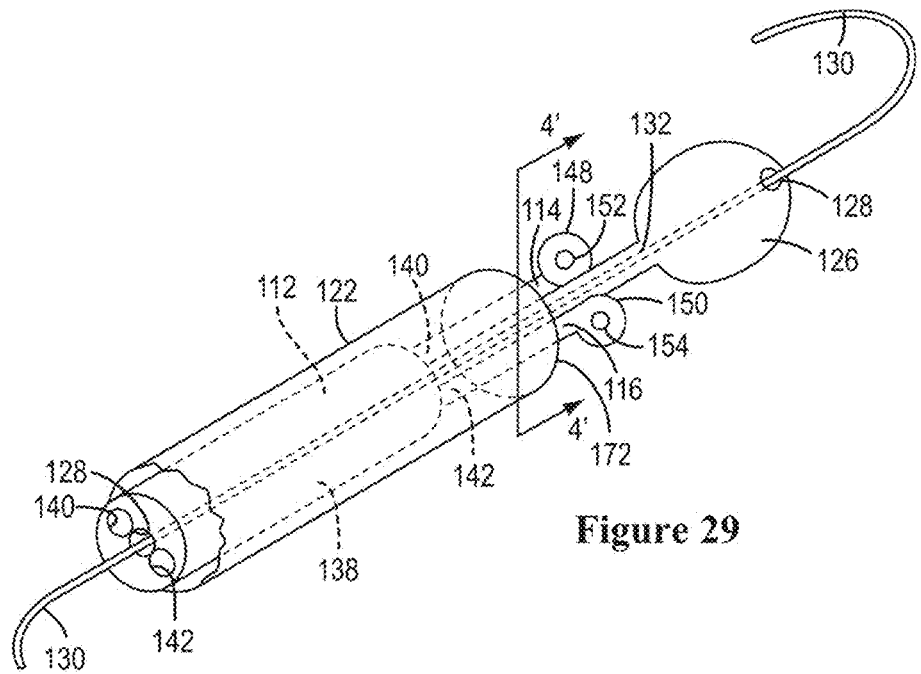
FIG. 29. An end perspective view of the assembly along the line 3'-3' of FIG. 27.

The central catheter component 112 has a flexible elongate length with opposite proximal 124 and distal 126 ends (FIG. 27). The distal end 126 of the central catheter component is formed as a guide tip that has an exterior shape configuration that will guide the distal end 126 through a biological conduit. A guide wire bore 128 within middle rail 132 extends through the center of the central catheter 112 from the proximal end 124 to the distal end 126. The guide wire bore 128 receives a flexible, elongate guide wire 130 for sliding movement of the bore 128 over the wire (FIG. 29). The guide wire 130 is used to guide the catheter assembly through a biological conduit. In certain embodiments, the guide wire 130 has a solid core, e.g., stainless steel or superelastic nitinol. The guide wire may optionally be constructed of radiopaque material, either in its entirety or at its distal portions (e.g., the most distal 1 mm to 25 mm or the most distal 1 mm to 3 mm). The guide wire 130 may optionally be coated with a medically inert coating such as TEFLON®. In other embodiments, the catheter assembly is a rapid-exchange catheter assembly wherein a guide wire is positioned on the distal end of the guide tip 126 and extends therefrom.

A narrow middle rail 132 surrounding the guide wire bore 128 extends from the guide tip of the catheter distal end 126 toward the catheter proximal end 124. The middle rail 132 connects the guide tip 126 to a base portion 138 of the central catheter component.

The central catheter component base portion 138 has a cylindrical exterior surface that extends along the entire length of the base portion. The base portion 138 extends along a majority of the overall length of the central catheter component 112. As shown in FIG. 29, the guide wire bore 128 extends through the center of the central catheter component base portion 138. In addition, a pair of tissue penetrator lumens 140, 142 also extend through the length of the central catheter component base portion 138 alongside the guide wire bore 128. At the proximal end 124 of the central catheter component, a pair of ports 144, 146 communicate the pair of lumens 140, 142 with the exterior of the central catheter component 112 (FIG. 27).

In an alternative embodiment, the medical device of FIG. 27 also may comprise a single flexible, resilient actuator that is formed as a tissue penetrator presentation tube, a single flexible, elongate tissue penetrator that extends through the tissue penetrator presentation tube and connects to a hub, and an exterior deployment tube that extends over portions of the lengths of the central catheter component, the tissue penetrator presentation tube, and the middle rail.

The pair of first and second tissue penetrator presentation tubes 114, 116 project from the catheter central component base portion 138 toward the catheter distal end 126. Each of the tissue penetrator presentation tubes is formed as a narrow, elongate tube having a proximal end that is secured to the central catheter component base portion 138, and an opposite distal end 148, 150. Each of the first and second tissue penetrator presentation tubes 114, 116 has an interior bore 152, 154 that communicates with the respective first tissue penetrator lumen 140 and second tissue penetrator lumen 142 in the central catheter component base portion 138.

Figure 30:
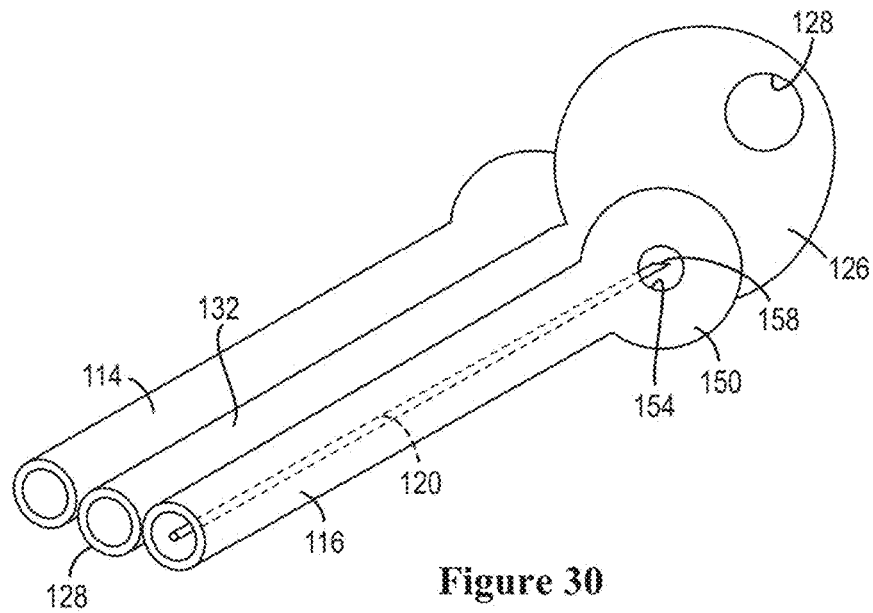
FIG. 30. An end perspective view of the assembly along the line 4'-4' of FIG. 29 showing the tissue penetrators.

As shown in FIGS. 29 and 30, the exterior configurations of the tissue penetrator presentation tubes 114, 116 are matched to the middle rail 132 so that the lengths of the tissue penetrator presentation tubes 114, 116 may be positioned side-by-side on opposite sides of the middle rail 132. The tissue penetrator tube distal ends 148, 150 can be formed as guide tip surfaces that also facilitate the passage of the catheter through a vascular system. The tissue penetrator tube distal ends 148, 150 are preferably larger in diameter than the tissue penetrator presentation tubes 114, 116. In a specific embodiment, the tissue penetrator tube distal tips 148, 150 are rounded and bulbous tips. Such tips are atraumatic and the tubes will not inadvertently puncture the wall of a biological conduit. The tips 148, 150 are exposed and do not extend outwardly beyond the diameter of the guide tip 126.

Each of the tissue penetrator tubes 114, 116 is preferably constructed of a shape memory material, such as nitinol. The tubes 114, 116 are formed with curved, unconstrained configurations shown in FIG. 28. The tubes 114, 116 move to the curved, unconstrained configurations shown in FIG. 28 when no constraining force is applied against the tubes. In order for the presentation tubes 114, 116 to lie in straight, constrained configurations along the middle rail 132, a constraining force must be applied to the tubes to keep them in their straight, constrained positions shown in FIG. 27. As each of the tubes 114, 116 moves from its straight, constrained configuration shown in FIG. 28 to its curved, unconstrained configuration shown in FIG. 28, the tissue penetrator bores 152, 154 extending through the tubes also move from straight configurations to curved configurations.

The pair of tissue penetrators 118, 120, from their distal tips to the hubs 166, 168, have lengths that are slightly longer than the combined lengths of the tissue penetrator lumens 140, 142 extending through the central catheter base portion 138 and the tissue penetrator bores 152, 154 extending through the tissue penetrator presentation tubes 114, 116. The tips 156, 158 of the tissue penetrators 118, 120 are positioned adjacent to the distal ends 148, 150 of the tissue penetrator presentation tubes 114, 116 and are positioned inside of the bores 152, 154 of the tubes in the constrained configuration of FIG. 27. The opposite, proximal ends of the tissue penetrators 118, 120 project out through the side ports 144, 146 of the central catheter 112. The pair of tissue penetrators 118, 120 are dimensioned to easily slide through the tissue penetrator lumens 140, 142 of the central catheter component 112 and the tissue penetrator bores 152, 154 of the tissue penetrator presentation tubes 114, 116. The side ports 144, 146 of the central catheter component 112 are preferably at 20° to 90° angles to the central catheter proximal end 124, most preferably at 30° to 60° angles to the central catheter proximal end 124.

A pair of manual operator movement to linear movement controllers 162, 164 can be connected to the proximal ends of the tissue penetrators 118, 120 and can be secured to the central catheter ports 144, 146 (FIG. 31). The controllers 162, 164 can be constructed to convert operator movement into controlled linear movement of the tissue penetrators 118, 120 through the central catheter tissue penetrator lumens 140, 142 and through the tissue penetrator presentation tube bores 152, 154. In one embodiment, there are rotating controllers 162, 164 that can be manually moved in one direction, such that the tissue penetrator injection tips 156, 158 at the tissue penetrator distal ends can be adjustably positioned to extend a desired length out from the tissue penetrator tube bores 152, 154 at the tissue penetrator tube distal ends 148, 150. By rotating the controllers in the opposite direction, the tissue penetrators 118, 120 can be retracted back into the tissue penetrator tube bores 152, 154. Each of the operator movement to linear movement controllers 162, 164 can be provided with a hub 166, 168 that communicates with the interior bore extending through the tissue penetrators 118, 120 and can be used to connect a syringe or tubing containing a solution of a diagnostic or therapeutic agent.

The exterior deployment tube 122 has a tubular length that surrounds the central catheter 112, the tissue penetrator presentation tubes 114, 116, and the middle rail 132. The deployment tube 122 can be mounted on the central catheter component 112 and the pair of tissue penetrator presentation tubes 114, 116 for sliding movement to a forward position of the deployment tube 122 where an open distal end 172 of the deployment tube is positioned adjacent the distal ends 148, 150 of the tissue penetrator presentation tubes 114, 116 as shown in FIG. 27, and a rearward position of the deployment tube 122 where the tube distal end 172 is positioned adjacent to the connection of the tissue penetrator presentation tubes 114, 116 with the central catheter component 112 as shown in FIG. 28. The opposite proximal end 174 of the deployment tube 122 can be provided with a mechanical connection 176 to the central catheter 112. The mechanical connection 176 enables the deployment tube 122 to be moved between its forward and rearward positions relative to the central catheter 112 and the tissue penetrator presentation tubes 114, 116 (FIGS. 27 and 28). Such a connection could be provided by a thumbwheel, a sliding connection, a trigger or push button or some other connection that is manually operable to cause the deployment tube 122 to move relative to the central catheter 112 and the presentation tubes 114, 116. When the deployment tube 122 is moved to its forward position shown in FIG. 27, the tube distal end 172 passes over the lengths of the tissue penetrator presentation tubes 114, 116 and moves the presentation tubes to their constrained positions extending along the opposite sides of the central catheter middle rail 132. When the deployment tube 122 is moved to its rearward position shown in FIG. 28, the distal end 172 of the deployment tube is retracted from over the length of the tissue penetrator presentation tubes 114, 116 and gradually allows the presentation tubes 114, 116 to release their constrained energy and move to their curved, unconstrained configurations shown in FIG. 28.

In use of the catheter 110, the deployment tube 122 is in the forward position shown in FIG. 27. The guide wire 130 is positioned in a biological conduit (such as an artery or vein) in a known manner. The catheter is then advanced into the biological conduit over the guide wire. The guide wire 130 extends from the biological conduit, and enters the central catheter component distal end 126 through the guide wire lumen 128. The wire 130 passes through the length of the central catheter 112 and emerges at the proximal end of the central catheter component adjacent to the catheter ports 144, 146, where the guide wire 130 can be manually manipulated.

The catheter 110 can be advanced through the biological conduit and can be guided by the guide wire 130. Radiopaque markers may optionally be provided on the assembly to monitor the position of the assembly in the biological conduit. Any material that prevents passage of electromagnetic radiation is considered radiopaque and may be used. Useful radiopaque materials include, but are not limited to, platinum, gold, or silver. The radiopaque material can be coated on the surface of all or a part of the tip 126, on all or part of the presentation tubes 114, 116, on all or part of the tissue penetrators 118, 120, on the guide wire 130, or on any combination of the foregoing structures. Alternatively, a ring of radiopaque material can be attached to the tip 126. The assembly may optionally be provided with onboard imaging, such as intravascular ultrasound or optical coherence tomography. The tip of the assembly may optionally be provided with optics that are useful for determining the position of the assembly or the characteristics of the surrounding biological conduit. When the assembly is at a desired position, the exterior deployment tube 122 can be moved from its forward position shown in FIG. 27 toward its rearward position shown in FIG. 28 by manual manipulation of the mechanical connection 176.

As the deployment tube 122 is withdrawn from over the pair of tissue penetrator presentation tubes 114, 116, the constrained energy of the tissue penetrator presentation tubes 114, 116 is released and the tubes move toward their unconstrained, curved configurations shown in FIG. 28. This movement positions the tissue penetrator bores 152, 154 at the tissue penetrator tube distal ends 148, 150 against the interior surfaces of the biological conduit into which the assembly 110 has been inserted.

The operator movement to linear movement controllers 162, 164 then can be manually operated to extend the tissue penetrator distal ends 156, 158 from the tissue penetrator bores 152, 154 at the tissue penetrator presentation tube distal ends 148, 150. A gauge may be provided on each of the operator movement to linear movement controllers 162, 164 that provides a visual indication of the extent of the projection of the tissue penetrator tips 156, 158 from the tissue penetrator tube ends 148, 150 as the controllers 162, 164 are rotated. The controllers also could provide an audible sound or tactile feel such as clicking to indicate incremental distance steps of the tissue penetrator movements. This deploys the tissue penetrator tips 156, 158 a desired distance into the walls of the biological conduit.

In a third specific embodiment, a medical device of the instant invention is a fluid delivery catheter comprising one or more tissue penetrators constructed of a flexible, resilient material. In certain aspects, the medical device of the present invention has a central longitudinal axis, and comprises one or more tissue penetrators, wherein the one or more tissue penetrators can exist in a constrained configuration in which a length of said one or more tissue penetrators is oriented substantially parallel to the longitudinal axis of said medical device and an unconstrained configuration in which at least a portion of the length of said one or more tissue penetrators is oriented substantially non-parallel to the device's central longitudinal axis. After the device is positioned at a target site adjacent to the wall of a biological conduit, one or more tissue penetrators (and if desired, all of the tissue penetrators) may be released from a constrained configuration and permitted to adopt an unconstrained configuration, thereby making contact with the wall of the biological conduit. The one or more tissue penetrators may be of any shape, and in preferred embodiments, the movement of the one or more tissue penetrators from the constrained configuration to the unconstrained configuration occurs upon release of a constraining force by the device operator but without the input by the operator of any deforming forces to the device or the target tissue.

In a preferred embodiment, tissue penetrators are constructed of flexible, resilient material that is capable of being constrained upon the application of a constraining force, e.g., when the tissue penetrators are in the constrained configuration, and adopts its original unconstrained shape when the constraining force is removed, e.g., when the tissue penetrators are in the unconstrained configuration. Any such flexible, resilient material can be used, including but not limited to surgical steel, aluminum, polypropylene, olefinic materials, polyurethane and other synthetic rubber or plastic materials. The one or more tissue penetrators are most preferably constructed of a shape memory material. Examples of such shape memory materials include, but are not limited to, copper-zinc-aluminum-nickel alloys, copper-aluminum-nickel alloys, and nickel-titanium (NiTi) alloys. In a preferred embodiment, the shape memory material is nitinol. In a preferred embodiment, when the tissue penetrators assume the unconstrained configuration, the shape memory properties of the material from which each tissue penetrator is formed cause the tissue penetrators, without the application of any external deforming force, to move from a position substantially parallel to the longitudinal axis of the medical device to a position substantially perpendicular to the longitudinal axis of the medical device.

In a preferred embodiment, the tissue penetrators are maintained in the constrained configuration by an exterior catheter component having a tubular configuration that surrounds the tissue penetrators. A mechanical connection is provided between the exterior catheter component and the central catheter component to which the tissue penetrators are attached. The mechanical connection enables the exterior catheter component to be moved rearwardly along the length of the central catheter component, thereby uncovering the constrained one or more tissue penetrators and permitting the one or more tissue penetrators to assume an unconstrained configuration wherein they make contact with the target delivery site. One of ordinary skill in the art would appreciate that this specific embodiment may be readily adapted to incorporate radiopaque markers to facilitate positioning of the device or rapid-exchange features to facilitate the use of the device.

The medical device of the present invention, in its various embodiments, permits delivery of fluids into distinct layers of a vascular wall. The vascular wall consists of numerous structures and layers, structures and layers, including the endothelial layer and the basement membrane layer (collectively the intimal layer), the internal elastic lamina, the medial layer, and the adventitial layer. These layers are arranged such that the endothelium is exposed to the lumen of the vessel and the basement membrane, the intima, the internal elastic lamina, the media, and the adventitia are each successively layered over the endothelium as described in U.S. Pat. App. Publication No. 2006/0189941A1. With the medical devices of the present invention, the depth to which the tissue penetrator tips 156, 158 can penetrate into the target tissue can be controlled by rotating the controllers 162, 164. For example, if the target layer is the adventitial layer, the constrained energy of the tubes 114, 116 is released, the tubes adopt their unconstrained, curved configurations shown in FIG. 28, and the tissue penetrator tips 156, 158 are advanced with the controllers to a length sufficient for penetration to the depth of the adventitial layer. Likewise, if the target layer is the medial layer, the constrained energy of the tubes 114, 116 is released, the tubes adopt their unconstrained, curved configurations shown in FIG. 28, and the tissue penetrator tips 156, 158 are advanced with the controllers to a length sufficient for penetration to the depth of the medial layer.

With the tissue penetrators embedded in the desired layer of the wall of the biological conduit, a fluid can then be delivered through the tissue penetrators 118, 120. When the delivery of the fluid is complete, the controllers 162, 164 can be operated to withdraw the tissue penetrator tips 156, 158 back into the interior bores 152, 154 of the tissue penetrator presentation tubes 114, 116. The deployment tube 122 can then be moved to its forward position where the deployment tube distal end 172 moves the tissue penetrator presentation tubes 114, 116 back to their constrained positions shown in FIG. 27. When the deployment tube 122 has been moved to its full forward position shown in FIG. 27, the assembly can then be repositioned or withdrawn from the body.

The medical device of the instant invention also permits delivery of fluids to plaque deposits on the inside of the wall of the biological conduit or within the wall of the biological conduit.

The medical device of the instant invention also permits delivery of fluids to extracellular spaces or tissues located outside of the outer wall of the biological conduit (e.g., to the exterior surface of a blood vessel or to muscle positioned against the outer surface of vessel such as myocardium).

One advantageous feature of the devices of the present invention is that the actuators, by virtue of their design, make contact with less than the complete circumference of the inner wall of a biological conduit following their deployment therein. In preferred embodiments, the actuators make contact with less than 100% of the circumference of the inner wall of a biological conduit in which they are deployed. More preferably, the actuators make contact with less than 75%, 50% or 25% of the circumference of the inner wall of a biological conduit in which they are deployed. Most preferably, the actuators make contact with less than 10%, 5%, 2.5%, 1%, 0.5% or 0.1% of the circumference of the inner wall of a biological conduit in which they are deployed.

The devices can be used to deliver fluids comprising a variety of therapeutic and/or diagnostic agents to a wall of a biological conduit. Therapeutic agents include, but are not limited to proteins, chemicals, small molecules, cells and nucleic acids. A therapeutic agent delivered by the device may either comprise a microparticle or a nanoparticle, be complexed with a microparticle or a nanoparticle, or be bound to a microparticle or a nanoparticle. Protein agents include elastases, antiproliferative agents, and agents that inhibit vasospasm. The use of the devices for delivery of an elastase is specifically contemplated. Several published patent applications (WO 2001/21574; WO 2004/073504; and WO 2006/036804) teach that elastase, alone and in combination with other agents, is beneficial in the treatment of diseases of biological conduits, including obstruction of biological conduits and vasospasm. Diagnostic agents include, but are not limited to, contrast, microparticles, nanoparticles or other imaging agents.

A variety of distinct fluid delivery methods can be practiced with the device. In certain applications, distinct fluids can be delivered through each tissue penetrator of the device either simultaneously or sequentially. In other applications, the same fluid can be delivered through both tissue penetrators either simultaneously or sequentially. Embodiments and/or methods where a first fluid is delivered through both tissue penetrators followed by delivery of a second fluid through both tissue penetrators are also contemplated.

Methods of using the devices to deliver fluids into or through a wall of a biological conduit are also specifically contemplated. These methods comprise the steps of introducing the device into the biological conduit, advancing the device to a target site within the conduit, releasing the actuators from their constrained positions, optionally advancing the tissue penetrators through lumens in the actuators to penetrate to a desired depth into the wall of a biological conduit, delivering at least one fluid into or through the wall, optionally returning the tissue penetrators back into the lumens of the actuators, retracting the actuators to their constrained position, repositioning the device in the same or a different conduit for the delivery of additional fluid if so desired, and removing the device from the conduit.

EXAMPLES

This section describes methods of production of recombinant type I elastase for clinical use, for example as an agent to enlarge the diameter of blood vessels and thereby the lumen of blood vessels. Human type I pancreatic elastase displays 89% amino acid identity across the entire length of the porcine type I pancreatic elastase, with complete conservation of the "catalytic triad" and substrate specificity determining residues. Porcine type I elastase is initially synthesized as an enzymatically inactive proenzyme that is activated by trypsin to yield the mature enzyme that contains four internal disulfide bonds and no glycosylation (see Shotton, 1970, Methods Enzymol 19:113-140, Elastase; and Hartley and Shotton, 1971, Biochem. J. 124(2): 289-299, Pancreatic Elastase. The Enzymes 3:323-373 and references therein).

The examples below demonstrate the development of efficient and scalable recombinant porcine and human type I elastase expression and purification schemes suitable for cGMP manufacture of these enzymes for non-clinical and clinical studies, and commercial pharmaceutical use. The mature porcine elastase has been given the name PRT-102. The mature human type I elastase has been given the name PRT-201.

6.1 Terminology and Abbreviations

As used herein, the terms PRT-101, PRT-102, PRT-201 and pro-PRT-201 shall mean the following:

PRT-101: porcine pancreatic elastase. Unless otherwise indicated, the porcine pancreatic elastase employed in the examples is highly purified porcine pancreatic elastase purchased from Elastin Products Company, Inc, Owensville, Mo., catalog # EC134.

PRT-102: mature recombinant type I porcine pancreatic elastase. It should be noted that vectors with the designation "pPROT101-XXX" encode PRT-102.

PRT-201: mature recombinant type I human pancreatic elastase.

pro-PRT-201: proenzyme form of recombinant human type I pancreatic elastase containing a propeptide sequence.

The following abbreviations are used in Section 6 of the application:

BKGY: buffered glycerol-complex medium
BKME: buffered methanol-complex medium
CHO: Chinese hamster ovary
E. coli: Escherichia coli
ELA-1: type I pancreatic elastase
HEK: human embryonic kidney
hELA-1: human ELA-1
HIC: hydrophobic interaction chromatography
MBP: maltose binding protein
pELA-1: porcine ELA-1
P. pastoris: Pichia pastoris
PCR: polymerase chain reaction
PMSF: phenylmethylsulphonyl fluoride
RP: reversed phase
S. cerevisiae: Saccharomyces cerevisiae
SDS-PAGE: sodium dodecyl sulfate-polyacrylamide gel electrophoresis
SEC: size exclusion chromatography
USP: United States Pharmacopeia
YPDS: yeast extract peptone dextrose sorbitol medium 6.2 Example 1: Elastase DNA Synthesis The human elastase-1 coding sequence was obtained from U.S. Pat. No. 5,162,205 (Takiguichi et al., 1992). Several sequence changes were made to facilitate cloning into expression vectors (FIG. 1A). The base changes fell within the degeneracy of the genetic code so that no amino acid residues were changed. A second stop codon was added immediately after the native stop codon to minimize potential ribosome read through.

The modified coding sequence was synthesized by Blue Heron Biotechnology (Bothell, Wash.) using a non-PCR "long oligo" technique under license from Amgen (Thousand Oaks, Calif.). The recombinant DNA, named ELA-1.2A (SEQ ID NO:81), was cloned into the vector Blue Heron pUC, a derivative of pUC119, and the resulting plasmid was named pPROT1. pPROT1 was sequenced on both strands to confirm the correct sequence. High quality sequencing data with extensive overlap on both strands permitted unambiguous base assignments across the entire sequence, which was covered by a minimum of four sequencing reactions with at least one reaction for each strand.

6.3 Example 2: Expression of Prt-201 in E. Coli

A variety of expression strategies were attempted in an effort to obtain soluble and enzymatically active human elastase in E. coli.

One set of E. coli expression vectors comprised in frame fusions of human type I pancreatic elastase (ELA-1) to the carboxy terminus of a Maltose Binding Protein (MBP) that was in turn fused to an N-terminal secretory peptide. Both the human ELA-1 mature and proenzyme coding sequences were cloned as in-frame C-terminal fusions to the MBP coding sequence of plasmid pMAL-p2G (New England Biolabs, Inc., Beverly, Mass.) to yield either pPROT3 (mature ELA-1) or pPROT5 (ELA-1 proenzyme). Construction of pPROT3 was effected by first obtaining by PCR mutagenesis a 6.6 kb mature human ELA-1 encoding fragment with a SnaBI site at the N-terminal valine codon of mature human ELA-1 and a HindIII site located 3' to the mature ELA-1 termination codons. This PCR mutagenesis used a pPROT1 template comprising the ELA-1.2A coding sequence (SEQ ID NO:81) and two oligonucleotide primers (5' ATC TAC GTA GTC GGA GGG ACT GAG GCC, SEQ ID NO:75; and 5' gtc gac aag ctt atc agt tgg agg cga t, SEQ ID NO:76). The resultant 6.6 kb PCR fragment was isolated, digested with SnaBI and HindIII, and subsequently cloned into the XmaI/HindIII digested pMAL-p2G vector to yield pPROT3. Construction of pPROT5 was effected by cloning the ScaI/HindIII fragment from pPROT1 and ligating into the pMAL p2G vector that had been digested with SnaBI and HindIII. The resultant fusion operably links the N-terminus of the human ELA-1 proenzyme coding region to the C-terminus of the MBP of pMAL-p2G in pPROT5. The trypsin cleavage domain of the human ELA-1 proprotein is preserved in pPROT5.

E. coli strain TB1 was transformed with pPROT3 and pPROT5 and subsequently induced with IPTG to determine if either the fusion protein or enzymatically active human ELA-1 could be produced. In the case of pPROT3, all of the MBP-ELA-1 fusion protein produced was insoluble. No soluble or enzymatically active MBP-ELA-1 fusion protein was detected in the periplasmic material obtained by osmotic shock of induced pPROT3-containing E. coli. In the case of pPROT5, low levels of soluble recombinant MBP-proELA-1 protein could be detected in the periplasmic material obtained by osmotic shock of induced pPROT5-containing E. coli through use of SDS-PAGE and Coomassie stain or by use of anti-MBP antibodies on a Western blot (New England Biolabs, Inc., Beverly, Mass.). The soluble recombinant MBP-proELA-1 protein could be digested with trypsin to yield both MBP and mature human ELA-1. Mature human ELA-1 obtained from inductions of pPROT5 was subsequently assayed for elastase activity with SLAP peptide substrate. Elastase activity was observed in pPROT5 periplasmic extracts. This elastase enzymatic activity was dependent on trypsin activation (i.e., no activity was observed in absence of trypsin and amount of activity is increased by increasing the time period of trypsin activation). Moreover, the elastase activity was dependent on pPROT5 in as much as no activity was observed in pMAL-p2G vector control extracts treated in parallel with trypsin. Finally, the pPROT5 elastase activity was inhibited by PMSF (a known serine protease inhibitor).

The recombinant MBP-proELA-1 fusion protein was subsequently purified and cleaved with trypsin to obtain an enzymatically active pPROT5-derived mature human ELA-1. The fusion protein was first purified on amylose affinity chromatography followed by elution with maltose. The purified MBP-proELA-1 was then treated with immobilized trypsin. Following the trypsin activation step, the cleaved MBP-proELA-1 was purified by cationic SP Sepharose chromatography. However, subsequent experiments with affinity purified pPROT5-derived mature human ELA-1 indicated that only very limited amounts of soluble and enzymatically active elastase could be obtained from E. coli containing pPROT5. Moreover, the specific activity of the affinity purified, pPROT5-derived mature human ELA-1 was very low, ranging from 0.27 to 0.38 U/mg (U=micromole of SLAP substrate hydrolyzed per min).

An alternative strategy of obtaining soluble and enzymatically active ELA-1 in E. coli was also pursued. In brief, the pPROT8 vector that encodes a protein fusion comprising the first 8 amino acid residues of the E. coli lacZ alpha subunit plus 5 amino acids of poly linker encoded residues followed by the human ELA-1 N-terminal proenzyme was constructed. This vector was constructed by ligating a BamHI/NcoI fragment containing the human ELA-1 coding sequence from pPROT1 (i.e., a vector containing the ELA-1.2A sequence; SEQ ID NO: 81) into pBlueHeron pUC (Blue Heron Biotechnology, Bothell, Wash., USA) that was digested with BamHI/NcoI.

E. coli strain EC100 (EPICENTRE Biotechnologies, Madison, Wis.) was transformed with pPROT8 and subsequently induced with IPTG to determine if either the fusion protein or enzymatically active human ELA-1 could be produced. In the case of EC100 transformed cells, all of the pPROT8 derived LacZ-proELA-1 fusion protein produced was insoluble (i.e., found in inclusion bodies). An E. coli strain containing mutations in the trxB and gor genes (the Origami™ strain, Takara Minis Bio, Inc., Madison, Wis.) was subsequently transformed with pPROT8 as E. coli strains with mutations in these coding sequences are known to promote recovery of soluble and enzymatically active recombinant proteins. Although some soluble pPROT8 derived LacZ-proELA-1 fusion protein in the trxB/gor E. coli strain was recovered upon induction with IPTG, it could not be converted to enzymatically active human ELA-1 with trypsin.

6.4 Example 3: Expression of Prt-201 in Mammalian Cell Lines

Several expression strategies were attempted in an effort to obtain soluble and enzymatically active human type I pancreatic elastase (ELA-1) in mammalian cell lines. The high copy mammalian expression vector pcDNA3.1 (Invitrogen) containing the CMV promoter was used as a backbone for two human ELA-1 elastase expression vectors, pPROT30 and pPROT31. To construct pPROT30, the human ELA-1 proenzyme sequence was amplified by PCR and fused to a porcine pancreatic elastase signal sequence incorporated in the forward PCR primer. Using restriction sites incorporated into the PCR primers, the PCR product was digested and ligated using the corresponding restriction sites in the pcDNA3.1 vector. pPROT31 was constructed in a similar fashion, except that the human ELA-1 mature coding sequence was used instead of the proenzyme coding sequence in an attempt at direct expression of the mature enzyme. E. coli was transformed with the ligation reactions and clones were selected for miniprep screening. One clone for each expression vector was selected based on expected restriction digest patterns for the correct insert. Plasmid DNA was prepared for each clone and the expression vector coding sequences were confirmed by DNA sequencing.

The mammalian cell lines CHO, COS, HEK293 and HEK293T were transiently transfected separately with pPROT30 and pPROT31. After several days, cell culture supernatants were harvested and analyzed for human ELA-1 proprotein (pPROT30) or mature protein (pPROT31) expression by Western blot. An anti-porcine pancreatic elastase polyclonal antibody cross-reacted with a band of the expected molecular weight for the human ELA-1 proprotein in pPROT30 supernatants and for the mature human ELA-1 protein in pPROT31 supernatants.

The pPROT30 and pPROT31 supernatants were analyzed for elastase activity by SLAP assay. For pPROT30, the supernatants were first treated with trypsin to convert the proenzyme to mature PRT-201. No elastase activity was detected in any of the supernatants for either vector using the SLAP assay.

6.5 Example 4: Expression of Trypsin-Activated Prt-201 in P. pastoris

The vector for P. pastoris secreted expression, PV-1, was synthesized by Blue Heron and used to first clone the wild-type human ELA-1 coding sequence. The PV-1 vector was designed for simple cloning, selection and high-level expression of the recombinant protein. The vector contains the Zeocin™ resistance gene for direct selection of multicopy integrants. Fusion of the N-terminus of the elastase propeptide to a yeast α-mating type sequence comprising the yeast secretion signal, propeptide and spacer sequences as shown in FIG. 1B permits secretion of the expressed protein in the culture media. The secreted elastase proprotein can be easily separated from the cell pellet, a substantial first step towards purification. Additionally, the proenzyme form of human ELA-1 containing the trypsin cleavage site was selected for expression to avoid directly expressing the mature, activated enzyme which may lead to protein misfolding or toxicity to the cells expressing the recombinant enzyme.

Figure 3:
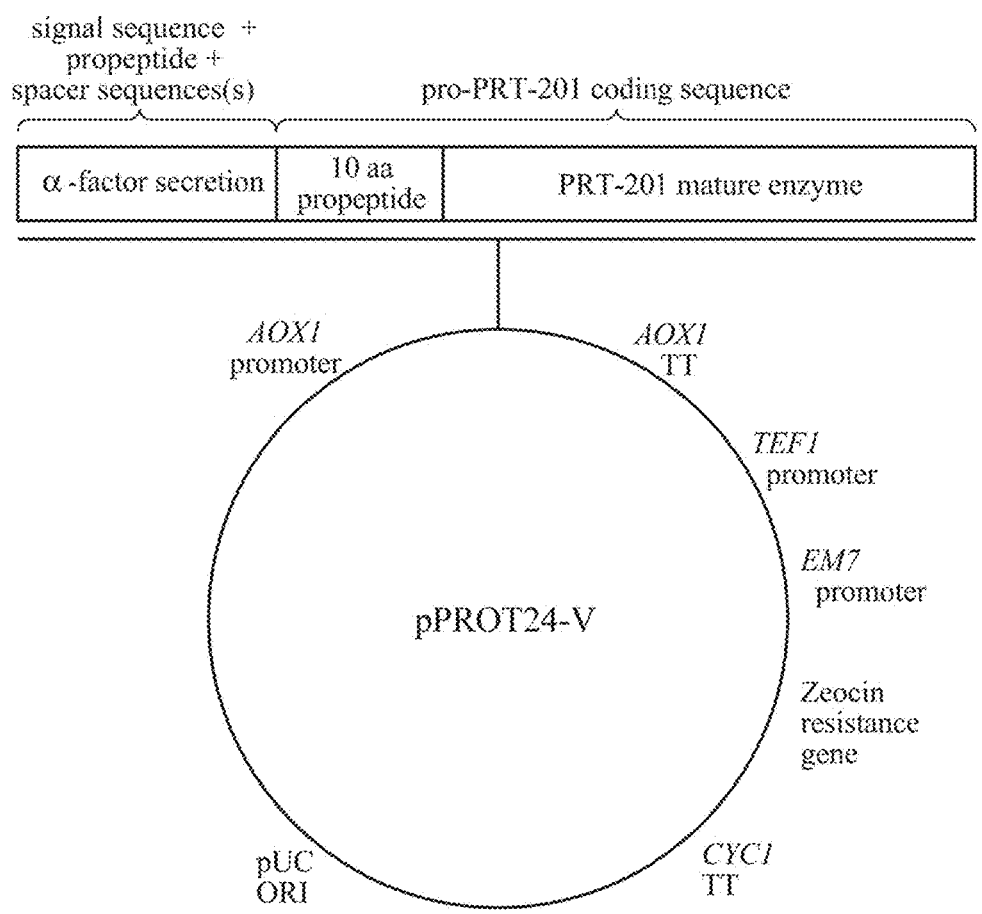
FIG. 3. Diagram of the pPROT24-V Vector. "α-factor secretion" refers to a cassette containing the yeast α-factor signal peptide and propeptide, followed by a Kex2 site and STE13 repeats.

Cloning of the expression construct pPROT24-V to direct the expression of ELA-1 proenzyme was accomplished as follows. The human ELA-1 coding region (SEQ ID NO:81) was amplified from Blue Heron pUC ELA-1 by PCR (Expand High Fidelity PCR System, Roche, Indianapolis, Ind.). The 20F forward primer incorporated an XhoI site (5'-ggctcgagaaaagagaggctgaagctactcaggaccttccggaaaccaat-gcccgg-3; SEQ ID NO:35). The 24R primer incorporated a SacII site (5'-gggccgcggcttatcagttggaggcgatgacat-3'; SEQ ID NO:36). The resulting PCR product was gel-purified and cloned into pCR2.1-TOPO (Invitrogen). The ELA-1 coding sequence was isolated using XhoI and SacII, gel-purified, and cloned into PV-1 vector at those sites to yield pPROT24-V (FIG. 3).

The pPROT24-V ligated product was amplified in E. coli strain TOP10. The cell mixture was plated on low salt LB plates supplemented with 25 microgram/mL Zeocin. DNA plasmid was prepared (Qiagen, Valencia, Calif.) and the human ELA-1 insert was identified by restriction digestion. The pPROT24 coding sequence was verified by sequencing both strands of purified maxiprep DNA with multiple overlapping reactions. High quality sequencing data allowed unambiguous base assignments and confirmed the correct coding sequence. Glycerol stocks of pPROT24-V/TOP10 were made and stored at −80° C.

The wild-type NRRL Y-11430 P. pastoris strain obtained from the United States Department of Agriculture (USDA, Peoria, Ill., USA) was used for transformation. Plasmid DNA from pPROT24-V was linearized with SacI and complete digestion was confirmed by running a small aliquot of the reaction on an agarose gel. Electroporation was used to transform P. pastoris with pPROT24-V plasmid DNA. Cell mixtures were plated onto YPDS plates containing 100 microgram/mL Zeocin. After three days, colonies began to form and were selected over several more days for re-streaking on fresh plates.

In general, drug-resistant transformants were screened for expression in a 1 L baffled flask. A single colony was used to inoculate 200 mL of BKGY medium. The composition of the BKGY solution was the following: 10 g/L glycerol, 13.4 g/L yeast nitrogen base with ammonium sulfate and without amino acids (Invitrogen), 20 g/L soy peptone, 10 g/L yeast extract, 0.4 mg/L biotin in 0.1 M potassium-phosphate buffer (pH 5.0). The culture was grown for two days at 28° C. with shaking at 275 rpm. The cultures were pelleted by centrifugation at 650×g for 10 min at room temperature. The cell pellets were resuspended with BKME induction media, pH 5.0, by resuspending the pellets at a ratio of 1 g wet cells to 5 mL induction media. A 50 mL cell suspension was placed in a 500 mL non-baffled flask to obtain a 1:10 ratio of cell suspension to flask volume. The cells were incubated at 22° C. with shaking at 275 rpm for 1-3 days. Methanol in the induction media was replenished to a final concentration of 0.5% twice daily over the course of induction.

To screen for expression, 1 mL aliquots were taken, transferred to 1.5 mL microfuge tubes and centrifuged for 5 min at 20,000×g in a microcentrifuge. Supernatants were transferred to fresh tubes and stored at −80° C. For SDS-PAGE analysis, supernatant aliquots were thawed and mixed with 4× Laemmli buffer supplemented to 5% volume with the reducing agent beta-mercaptoethanol. Samples were boiled for 5 min, gently centrifuged, and loaded onto an 8-16% gradient Tris-HCl pre-cast gel in a Criterion electrophoresis system (Bio-Rad). After electrophoresis, the gel was stained with Coomassie and analyzed for human ELA-1 proenzyme expression. Clone 201-24-266-VU was selected as a high-yield clone for further evaluation. A development cell bank consisting of 201-24-266-VU glycerol stocks was prepared and stored at −80° C.

For scale-up production of human ELA-1 proenzyme using clone 201-24-266-VU, multiple production runs were performed that generally followed the methods described below. Where applicable, run-to-run variations in the methods are noted.

For cell culture, a series of 2 L baffled shaker flasks (typically ranging from 20 to 40 flasks) containing 500 mL BKGY growth medium were inoculated with 250 microliters of thawed 201-24-266-VU glycerol stock. Cultures were grown at 28° C. for 2 days in a shaking incubator at 250-300 rpm. After 2 days, the cells were pelleted by centrifugation and the supernatant was discarded. The cells were resuspended in BKME induction media, pH 5.0, at a ratio of 1 g of weight cells to 5 mL media. A volume of 200-400 mL cell suspension was placed in 2 L non-baffled flasks and cultured for 3 days in a shaking incubator (250-300 rpm) at 22° C. Methanol in the media was replenished to 0.5% volume twice daily during the course of induction. At the end of induction, the shake flask cultures were centrifuged to pellet the cells. The supernatant was removed and immediately filtered at room temperature through a 0.22 um polyether-sufone membrane using 1 L vacuum filtration units to remove any remaining cell debris. The filtrate was stored at 2-8° C. for up to 1.5 months. Based on HIC-HPLC analysis, the yield of human ELA-1 proenzyme from clone pro-PRT-201-24-266-VU in the clarified supernatant was typically 200 to 250 mg/L.

Capture of pro-PRT-201-24-266-VU from the supernatant was effected as follows. First, supernatant from multiple rounds of shaker flask cultures (typically 4 to 10 rounds) was combined (typically 8 to 25 L total), diluted 8-fold with water and adjusted to pH 5.0 with 1 M HCl. The diluted supernatant was then loaded onto an equilibrated 2 L bed volume Macro-Prep High S ionic exchange capture column at 2-8° C. at a rate of 100 mL/min (linear flow rate 76 cm/hr). The chromatography program comprised the following steps: 1. Wash column with 10 L (5 column volumes [CVs]) of Buffer A (20 mM sodium citrate, pH 5.0.) at 100 mL/min (76 cm/hr); 2. Wash column with 4 L (2 CVs) of a mixture of 90% Buffer A and 10% Buffer B (500 mM sodium chloride; 20 mM sodium citrate, pH 5.0) for a final buffer composition of 50 mM sodium chloride; 20 mM sodium citrate, pH 5.0 at 100 mL/min (76 cm/hr); 3. Wash column with 6 L (3 CVs) of a mixture of 80% Buffer A and 20% Buffer B for a final buffer composition of 100 mM sodium chloride; 20 mM sodium citrate, pH 5.0 at 100 ml/min (76 cm/hr); 4. Wash column with 6 L (3 CVs) of a linear gradient, starting from 75% Buffer A and 25% Buffer B to 68% Buffer A and 32% Buffer B, at 100 ml/min (153 cm/hr); 5. Elute with a linear gradient of 30 L (15 CVs) starting from 68% Buffer A and 32% Buffer B to 0% Buffer A and 100% Buffer B, at 100 ml/min (76 cm/hr). The eluate was collected in fractions of 500-1000 mL each.

Figure 4:
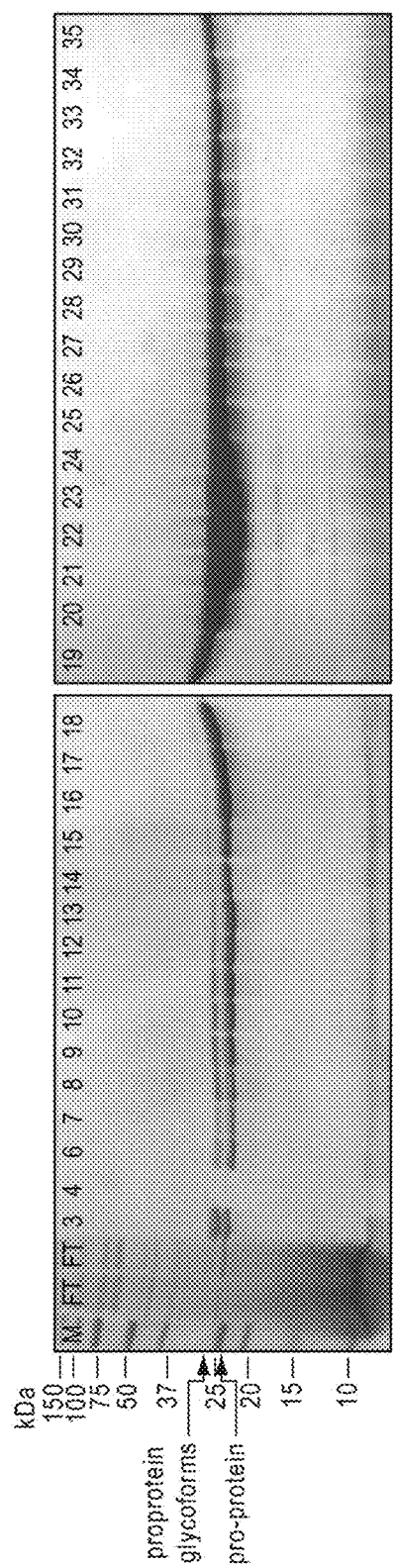
Figure 5B:
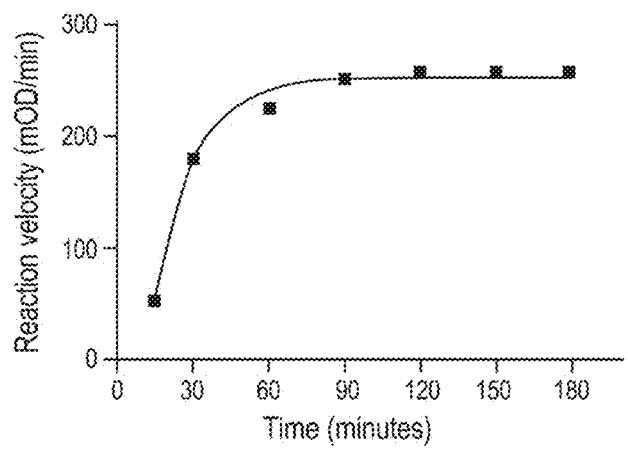
Figure 5C:
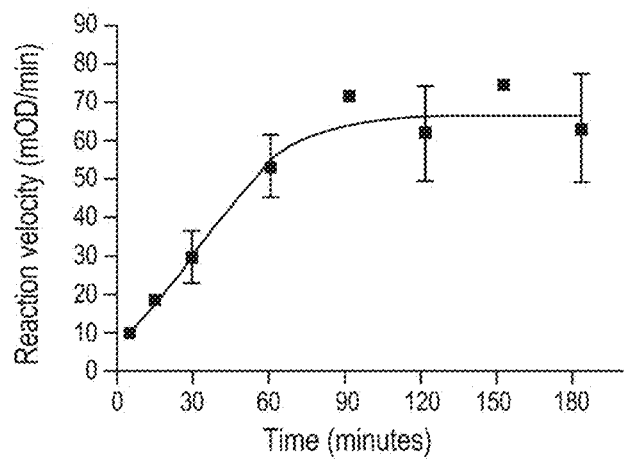
Figure 5D:
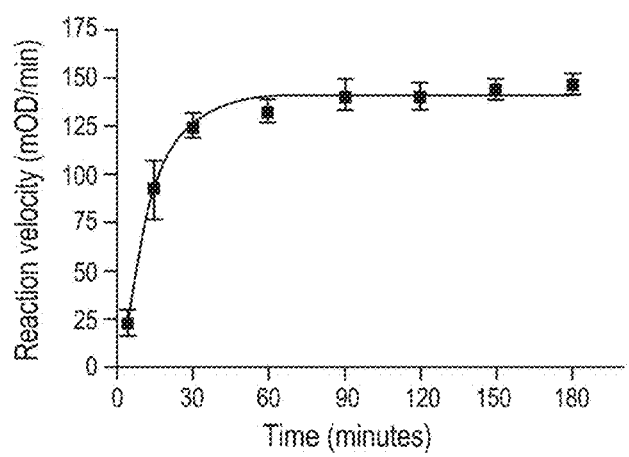
Figure 5E:
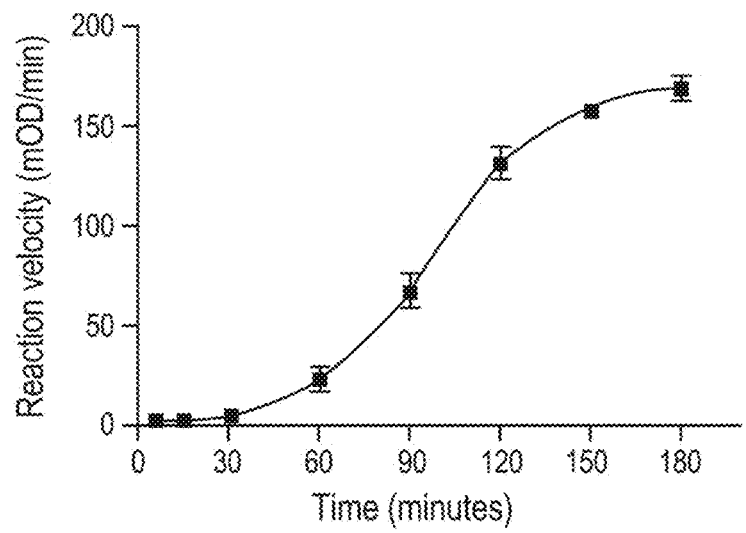
Figure 5F:
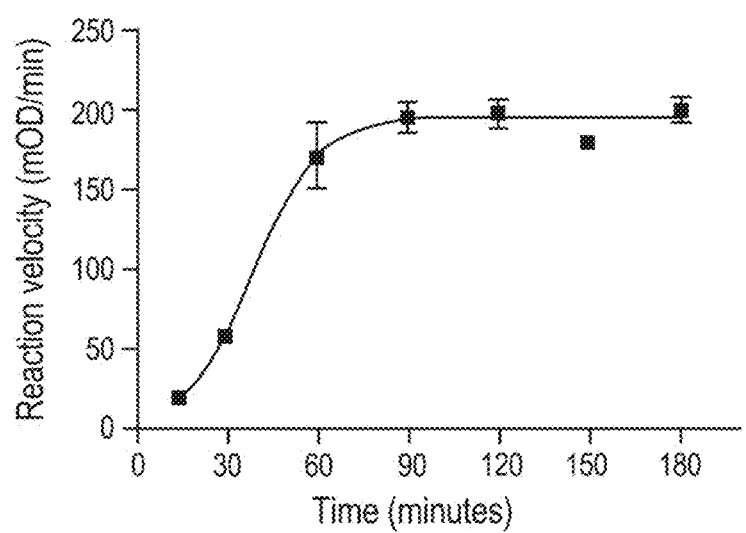

Typically, two predominant protein species were observed by SDS-PAGE followed by Coomassie staining: the glycosylated human ELA-1 proenzyme and the non-glycosylated human ELA-1 proenzyme, as determined by subsequent LC/MS analysis, typically eluting at about 320 mM sodium chloride, shown in FIG. 4. In some production runs a protein slightly smaller than the human ELA-1 proenzyme was observed as a minor species. Subsequent LC/MS analysis of these fractions showed that most of the protein was not full-length proenzyme but instead was lacking several amino acids at the N-terminus. These N-terminal variants were purified and subjected to elastase activity analysis, which revealed that they had lower elastase activity than full length PRT-201. N-terminal variants could arise from the human ELA-1 proenzyme exhibiting a low level of elastase activity during cell culture and capture chromatography operations and either cleaving itself through an intramolecular reaction or cleaving another human ELA-1 proenzyme molecule through an intermolecular reaction. Suboptimal cleavage conditions during these operations could lead to a high level of inaccurate cleavage of the proenzyme (sometimes referred to as spontaneous or uncontrolled conversion) resulting in mostly N-terminal variants, rather than intact, full length PRT-201.

After inspection of SDS-PAGE results, a subset of fractions was pooled to obtain purified non-glycosylated pro-PRT-201 for further processing. Fractions containing glycosylated proenzyme or full-length PRT-201 and/or N-terminal variants (which co-migrate on SDS-PAGE) were typically excluded from the pooling. The pooled pro-PRT-201 was typically stored in a 5 L plastic beaker at 2-8° C. for several hours to overnight prior to conversion from proenzyme to mature enzyme.

Conversion of pro-PRT-201 to mature PRT-201 by immobilized trypsin was effected as follows. The pooled pro-PRT-201 fractions were dialyzed in 20 mM sodium phosphate, pH 5.0, overnight at 2-8° C. This step provides for the removal of citrate, which inhibits trypsin. Following dialysis, the pro-PRT-201 was passed over a column of recombinant trypsin (TrypZean) immobilized to agarose beads pre-equilibrated with 20 mM sodium phosphate, pH 5.0. Typically, the contact time between pro-PRT-201 and the immobilized TrypZean was between 3.5 to 5 min. The resulting post-conversion material was analyzed by SDS-PAGE to confirm conversion and subsequently loaded onto a Macro-Prep High S polish column. The column was washed sequentially with 5 CVs of 20 mM sodium citrate, pH 5.0; 2 CVs of 20 mM sodium citrate, 50 mM sodium chloride, pH 5.0; and 3 CVs of 20 mM sodium citrate, 100 mM sodium chloride, pH 5.0. The column was further washed with a linear gradient from 125 mM sodium chloride to 160 mM sodium chloride in 20 mM sodium citrate, pH 5.0. PRT-201 was eluted in a linear gradient from 165 mM to 500 mM sodium chloride in 20 mM sodium citrate, pH 5.0 and collected in fractions. Fractions were analyzed for protein by SDS-PAGE followed by Coomassie staining and for elastase activity by SLAP assay. Typically, fractions having a specific activity of 90% or greater than that of the fraction with the highest specific activity were pooled. In subsequent LC/MS analysis, late-eluting fractions having lower specific activity were found to be enriched in PRT-201 N-terminal variants.

Pooled fractions with high specific activity were diafiltered into formulation buffer composed of 0.1×PBS (13.7 mM sodium chloride, 1 mM sodium phosphate, 0.27 mM potassium phosphate) at pH 5.0. After concentration of PRT-201 to 1 mg/mL, the pH was adjusted to 7.4. The solution was then aliquoted into glass serum vials with an elastomer stopper, and lyophilized. Lyophilization was typically performed with a primary drying cycle at −30 to −50° C. and a secondary drying cycle at −15° C. After lyophilization, the vials were stoppered under vacuum and crimped with an aluminum seal. The vials were then typically stored at 2-8° C. or −80° C.

To evaluate the stability of lyophilized PRT-201 in vials, two lots that were manufactured into sterile GMP drug product have been placed on a stability program. The stability program consists of storage of the drug product at −15° C. and periodic removal of a subset of vials for testing by the following stability-indicating analytical methods (specifications are in parentheses): appearance of lyophilized material (white to off-white powder), appearance after reconstitution (clear, colorless solution free of particles), specific activity by SLAP assay (25-45 U/mg), purity by RP-HPLC (total purity: not less than 93%; individual impurity: not more than 2%), purity by reduced SDS-PAGE (not less than 93%), purity by non-reduced SDS-PAGE (not less than 93%), particulate matter injections (conforms to USP), aggregates by SEC-HPLC (not more than 3%), content per vial (4.5-5.5 mg), pH (6.5-8.5), moisture (does not exceed 5%) and sterility (conforms to USP). To date, both lots have met the indicated specifications at all time points tested (lot C0807117 through 12 months and lot C1007132 through 9 months). These results indicate that PRT-201 is stable for at least 12 months when stored lyophilized in vials at −15° C.

The use of sodium citrate, pH 5.0, during both capture chromatography of pro-PRT-201 and polish chromatography of converted PRT-201 was based on data showing that sodium citrate inhibited elastase activity of purified PRT-201 and therefore might also inhibit elastase activity of pro-PRT-201 and PRT-201 during processing operations. Such inhibition could minimize the spontaneous conversion of pro-PRT-201 to N-terminal variants and minimize auto-degradation of PRT-201. In an experiment where SLAP assay buffer contained 115 mM sodium citrate, pH 5.0, the specific activity of PRT-201 was inhibited by 91%.

Occasionally, eluted material from the pro-PRT-201 capture column was not subjected to conversion by trypsin as described above but instead used to obtain preparations enriched in various protein species. For example, pools of fractions containing primarily glycosylated pro-PRT-201, non-glycosylated pro-PRT-201 or proteins arising from spontaneous conversion were made from the capture column eluate. Typically, these fraction pools were diafiltered into 10 mM sodium phosphate, pH 5.0, lyophilized, and stored at −80° C.

A study was performed to determine the effect of pH and temperature on the stability of purified pro-PRT-201 over time. Lyophilized pro-PRT-201 was reconstituted in 10 mM sodium phosphate at pHs ranging from 3.0 to 8.4, followed by incubation at 4° C. or 25° C. for 7 days. After 7 days, the pro-PRT-201 samples under conditions of pH 4.0-8.0 and 25° C. showed an enrichment in mature PRT-201 that increased with increasing pH as shown by SDS-PAGE and Coomassie staining. Under the conditons of pH 8.4 and 25° C., complete conversion of pro-PRT-201 to mature PRT-201 was observed. The samples at 4° C., from pH 4.0 to 8.4 showed little to no conversion. At pH 3.0, no conversion was observed at either 4° C. and 25° C. It has been reported in the literature (Hartley and Shotton, 1971, Pancreatic Elastase. Enzymes 3:323-373) that porcine pancreatic elastase is irreversibly inactivated after prolonged storage at pHs lower than 3.0. Thus, based these results of this study and to avoid irreversibly inactivating PRT-201, useful conditions to minimize conversion of purified pro-PRT-201 are storage at 4° C. between pH 3.0-4.0.

6.6 Example 5: Expression of Auto-Activated Prt-201 in *P. pastoris*

To obtain a variant proenzyme capable of auto-activation, thereby eliminating the need for trypsin activation, a variety of elastase cleavage domain variant vectors were constructed and analyzed in small-scale culture and conversion experiments. The variant vectors were created by site-directed PCR mutagenesis of the pPROT24-V vector and subsequent derivative vectors. Site-directed mutagenesis was performed using Pfu Turbo DNA polymerase (Stratagene). The *E. coli* XL10-Gold strain was transformed with the resulting plasmids. The transformed cell mixtures were plated on low salt LB plates supplemented with 25 microgram/mL Zeocin. Drug-resistant clones were picked and plasmid DNA was prepared (Qiagen, Valencia, Calif.). Clones were confirmed for the expected codon changes by sequencing both strands of plasmid DNA in the propeptide region with multiple overlapping reactions. *P. pastoris* was transformed with the variant vectors and clones were selected as described in the preceding Example.

A summary of the elastase cleavage domain variants that were created is provided in Table 4 below:

TABLE 4

Elastase cleavage domain variants

| Pro-peptide sequence name | P5 | P4 | P3 | P2 | P1 | P'1 | P'2 | P'3 |
|---|---|---|---|---|---|---|---|---|
| 24 | Glu | Thr | Asn | Ala | Arg | Val | Val | Gly |
| 40 | Glu | Thr | Ala | Ala | Ala | Val | Val | Gly |
| 41 | Glu | Thr | Asn | Ala | Ala | Ala | Val | Gly |
| 42 | Glu | Thr | Asn | Ala | Ala | Val | Val | Gly |
| 43 | Glu | Thr | Asn | Ala | Pro | Val | Val | Gly |
| 44 | Glu | Thr | Gly | Ala | Gly | Ile | Val | Gly |
| 45 | Glu | Thr | Val | Pro | Gly | Val | Val | Gly |
| 46 | Glu | Thr | Ala | Pro | Gly | Val | Val | Gly |
| 47 | Glu | Thr | Asn | Pro | Gly | Val | Val | Gly |
| 48 | Glu | Thr | Asn | Pro | Ala | Val | Val | Gly |
| 49 | Glu | Thr | Asn | His | Ala | Val | Val | Gly |
| 52 | Glu | Thr | Lys | Pro | Ala | Val | Val | Gly |
| 53 | Glu | Thr | His | Pro | Ala | Val | Val | Gly |
| 54 | Glu | His | Asn | Pro | Ala | Val | Val | Gly |
| 55 | His | Thr | Asn | Pro | Ala | Val | Val | Gly |
| 56 | Pro | Thr | His | Pro | Ala | Val | Val | Gly |
| 57 | Pro | Thr | Asn | Pro | Ala | Val | Val | Gly |
| 58 | His | Thr | His | Pro | Ala | Val | Val | Gly |
| 59 | Glu | Thr | Phe | Pro | Ala | Val | Val | Gly |
| 60 | His | Thr | Phe | Pro | Ala | Val | Val | Gly |
| 61 | Gly | Thr | Phe | Pro | Ala | Val | Val | Gly |
| 62 | His | Thr | Gly | Pro | Ala | Val | Val | Gly |
| 63 | His | Thr | Lys | Pro | Ala | Val | Val | Gly |

For Table 4 above, the first column listing of the "Pro-Peptide Sequence Name" corresponds to the SEQ ID NO for the indicated elastase cleavage domain. Thus, 24 corresponds to the wild-type trypsin cleavage domain of SEQ ID NO:24. Numbers 40-49, 52-63 correspond respectively to the variant elastase cleavage domains of SEQ ID NOS: 40-49, and 52-63.

To culture the variant clones, shaker flask culture conditions developed for the trypsin-activated 201-24-266-VU clone described in the preceding Example were generally followed. Several methods of converting the variant proproteins secreted into the shaker flask supernatant to mature PRT-201 were tested. The first conversion strategy consisted of chromatographically purifying the variant proenzyme first, followed by controlled cleavage in a specific conversion buffer. Because the amino acid changes in the variant proproteins resulted in only small changes in the theoretical isoelectric points compared to the wild-type proenzyme, cation exchange chromatography was carried out generally as described in the preceding Example. Supernatants from the variant clone cultures were prepared for chromatography either by dilution with water generally as described in the preceding Example or by concentration followed by diafiltration of the supernatant using tangential flow filtration into the column loading buffer. After chromatographic purification, eluted fractions were analyzed by SDS-PAGE followed by Coomassie staining. Gel analysis demonstrated greater amounts of converted mature protein to proprotein in the fractions compared to the starting supernatant, indicating that a considerable amount of spontaneous proprotein conversion had occurred. Upon subsequent purification, the spontaneously converted protein was determined by LC/MS to consist of mainly N-terminal variants which were shown to have little or no elastase activity in the SLAP assay.

The second conversion strategy consisted of converting the variant proprotein prior to purifying from the culture supernatant, followed by chromatographic purification of the mature enzyme. This conversion strategy was first tested in a small-scale assay and subsequently scaled up to accommodate larger conversion volumes. For small-scale conversion, clarified supernatant from variant clone cultures was typically concentrated 5-fold by centrifugation at 2-8° C. in an ultracentrifugal filter device. After concentration, the retentate was diluted 5-fold with Tris buffer to a final concentration of 100 mM of Tris-HCl typically in a pH range of 8.0 to 9.0. Samples were incubated at room temperature on a rocking platform. Elastase activity was monitored by SLAP assay typically until the activity reaction velocity reached a plateau. In some cases, the reaction velocity increased so slowly that SLAP monitoring was halted before a plateau was achieved. Converted samples were analyzed for protein species (e.g., proprotein and PRT-201/N-terminal variants) by SDS-PAGE. To scale up this conversion strategy, supernatant containing variant proprotein was concentrated 10-fold using tangential flow filtration followed by diafiltration with 100 mM Tris-HCl ranging in pH from 6.0 to 9.0. The progress of the conversion reaction was monitored over time by HIC-HPLC analysis in which proprotein, PRT-201, and N-terminal variant species were quantified. When the pH of the diafiltration buffer was between 8.0 and 9.0 there were generally higher rates of conversion.

The elastase proproteins listed in Table 5 were expressed in *P. pastoris* as described and tested for their capacity to undergo auto-conversion in small-scale conversion assays as described in the second conversion strategy above. The results of those studies are summarized in Table 5 below:

TABLE 5

Results of expression of elastase proproteins in *P. pastoris*.

| Pro-Peptide Sequence Name | Shaker Flask Yield | Shaker Flask Stability | Conversion Rate | % N-Terminal Variants | Trypsin Used in Processing |
|---|---|---|---|---|---|
| 24 | High | High | Fast | 20% | Yes |
| 40 | None | Not Applicable | Not Applicable | Not Applicable | No |
| 41 | Intermediate | High | Slow | Not Tested | No |
| 42 | Low | Low | Intermediate | 25% | No |
| 43 | Intermediate | High | Slow | Not Tested | No |
| 44 | Intermediate-High | High | No Conversion Detected | Not Applicable | No |
| 45 | Intermediate | High | No Conversion Detected | Not Applicable | No |

TABLE 5-continued

Results of expression of elastase proproteins in *P. pastoris*.

| Pro-Peptide Sequence Name | Shaker Flask Yield | Shaker Flask Stability | Conversion Rate | % N-Terminal Variants | Trypsin Used in Processing |
|---|---|---|---|---|---|
| 46 | Intermediate | High | No Conversion Detected | Not Applicable | No |
| 47 | Intermediate | High | No Conversion Detected | Not Applicable | No |
| 48 | Intermediate | Low | Fast | 15% | No |
| 49 | High | High | Slow | 35% | No |
| 52 | Intermediate | Low | Fast | Not Tested | No |
| 53 | Intermediate | Intermediate | Fast | 25% | No |
| 54 | Intermediate | Low | Fast | Not Tested | No |
| 55 | Intermediate-High | Intermediate | Fast | 15% | No |
| 56 | Low | Low | Not Tested | Not Tested | No |
| 57 | Low | Low | Not Tested | Not Tested | No |
| 58 | Intermediate-High | Intermediate | Slow | Not Tested | No |
| 59 | Intermediate-High | Intermediate | Slow | Not Tested | No |
| 60 | Intermediate-High | High | Slow | Not Tested | No |
| 61 | None | Not Applicable | Not Applicable | Not Applicable | No |
| 62 | High | High | No Conversion Detected | Not Applicable | No |
| 63 | None | Not Applicable | Not Applicable | Not Applicable | No |

In Table 5 above, the first column listing of the "Pro-Peptide Sequence Name" corresponds to the SEQ ID NO for the indicated elastase cleavage domain. Thus, 24 corresponds to the wild-type trypsin activated elastase cleavage domain of SEQ ID NO:24. Numbers 40-49, and 52-63 correspond respectively to the variant elastase cleavage domains of SEQ ID NOS: 40-49, and 52-63. The column labeled "Shaker Flask Yield" corresponds to the amount of the corresponding proprotein in the culture supernatant over 3 days of induction as determined by SDS-PAGE analysis. The column labeled "Shaker Flask Stability" corresponds to the stability of the corresponding proprotein in the supernatant of the shaker flask culture media over 3 days of induction as determined by the amount of PRT-201/N-terminal variants seen on SDS-PAGE analysis. The column labeled "Conversion Rate" corresponds to the relative rate of conversion of proprotein to PRT-201, as indicated by the time to achieve maximal SLAP reaction velocity (Fast: less than 60 minutes; Intermediate: 60 to 120 minutes; and Slow: greater than 120 minutes). Conversion time courses of the variant proproteins were determined using the small-scale conversion assay described above and compared to the conversion time course of the 24 proprotein determined by activation using immobilized trypsin. The column labeled "% N-Terminal Variants" refers to the percentage of converted protein that comprised N-terminal variants of the mature elastase protein (i.e. variants comprising cleavage at the bond C-terminal to any site other than P1). To illustrate the relative ranking systems used in Table 5, examples of SDS-PAGE, conversion rate and N-terminal variant analyses for a subset of auto-activated variants are shown in FIG. 5.

Analysis of the various variants revealed that elastase proproteins comprising either the SEQ ID NO:48 or SEQ ID NO:55 variant elastase cleavage domain provided auto-activated elastases with superior qualities including intermediate to high shaker flask yields and low percentages of variants upon conversion. Further analysis of elastase proproteins comprising either the SEQ ID NO:48 and SEQ ID NO:55 variant elastase cleavage domain revealed that auto-activation of the corresponding proproteins (i.e. the elastase proenzymes of SEQ ID NO:64 and SEQ ID NO:69, respectively) produced just one class of N-terminal variant with a cleavage at the peptide bond C-terminal to the P'2 residue. Further analysis of elastase proproteins revealed that the proprotein comprising SEQ ID NO:55 variant elastase cleavage domain was more stable than the proprotein comprising the SEQ ID NO:48 variant elastase cleavage domain.

Initial experiments to optimize conditions for controlled cleavage of purified pro-PRT-201 were performed using the proprotein with the 42 pro-peptide sequence (SEQ ID NO:6). This purified proprotein was subjected to conversion in a matrix of conditions including pH (7.7 to 8.9), buffer composition (0.4 to 10 mM sodium citrate), protein concentration (0.14 to 0.23 mg/mL), and reaction time (5 to 24 hours). At the end of the conversion period, the reactions were quenched by adding formic acid to reduce the pH to 3.0. The relative amounts of protein species in each reaction were determined by mass spectrometry. Based on these results, the conversion conditions that resulted in the lowest percentage of N-terminal variants included a pH of 8.3, a buffer composition of 100 mM Tris and less than 1 mM sodium citrate, a protein concentration of 0.2 mg/mL, and a reaction time of 5 to 24 hours. In this study, only the reaction end points were analyzed. Thus real-time data on conversion quality was not obtained, and the final result may have reflected both the initial production of N-terminal variants and a substantial amount of time for those variants to have been degraded. Subsequently, an HIC-HPLC assay was developed to enable real-time monitoring of the conversion reaction. Further conversion optimization studies, including those using real-time HIC-HPLC monitoring, are described in Example 6.

6.7 Example 6: Expression of Auto-Activated Prt-201 in *P. pastoris* Using a Multicopy Variant Vector Multicopy integration of recombinant genes in *P. pastoris* has been utlized to increase expression of the desired protein (see, e.g., Sreekrishna et al., 1989, Biochemistry 28:4117-4125; Clare et al., 1991, Bio/Technology 9:455-460; Romanos et al., 1991, Vaccine 9:901-906). However, in certain instances, expression levels obtained from single copy vector integrants was efficient and was not improved by the multicopy vector integrants (Cregg et al., 1987, Bio/Technology 5:479-485). Spontaneous multicopy plasmid integration events occur in vivo at a low frequency in *P. pastoris*. To obtain genomic integration of multiple copies of a gene and possibly increase the protein expression, an in vitro ligation method can be used to produce tandem inserts of the gene in an expression vector, followed by *P. pastoris* transformation.

To obtain a multicopy integrant of the pPROT55-V variant, an in vitro ligation method was used to construct a vector containing multiple copies of the pPROT55-V that was subsequently used for *P. pastoris* transformation. To make the multicopy vector, the pPROT55-V vector was digested with BglII and BamHI to release the 2.3 kb expression cassette encoding the pro-PRT-201 gene, the AOX1 promoter, and the AOX1 transcription termination sequence. The expression cassette was then ligated with a preparation of the pPROT55-V vector that had been linearized with BamHI and treated with calf intestinal alkaline phosphatase (New England Biolabs, MA, USA) to prevent self-ligating. The ligation mixture was incubated overnight at 16° C. The *E. coli* TOP10 strain (Invitrogen, CA, USA) was transformed with the ligation reaction. The transformation mix was plated out on low salt LB in the presence of 25 microgram/mL of Zeocin. Drug-resistant transformants were picked and plasmid DNA was prepared.

Figure 6:
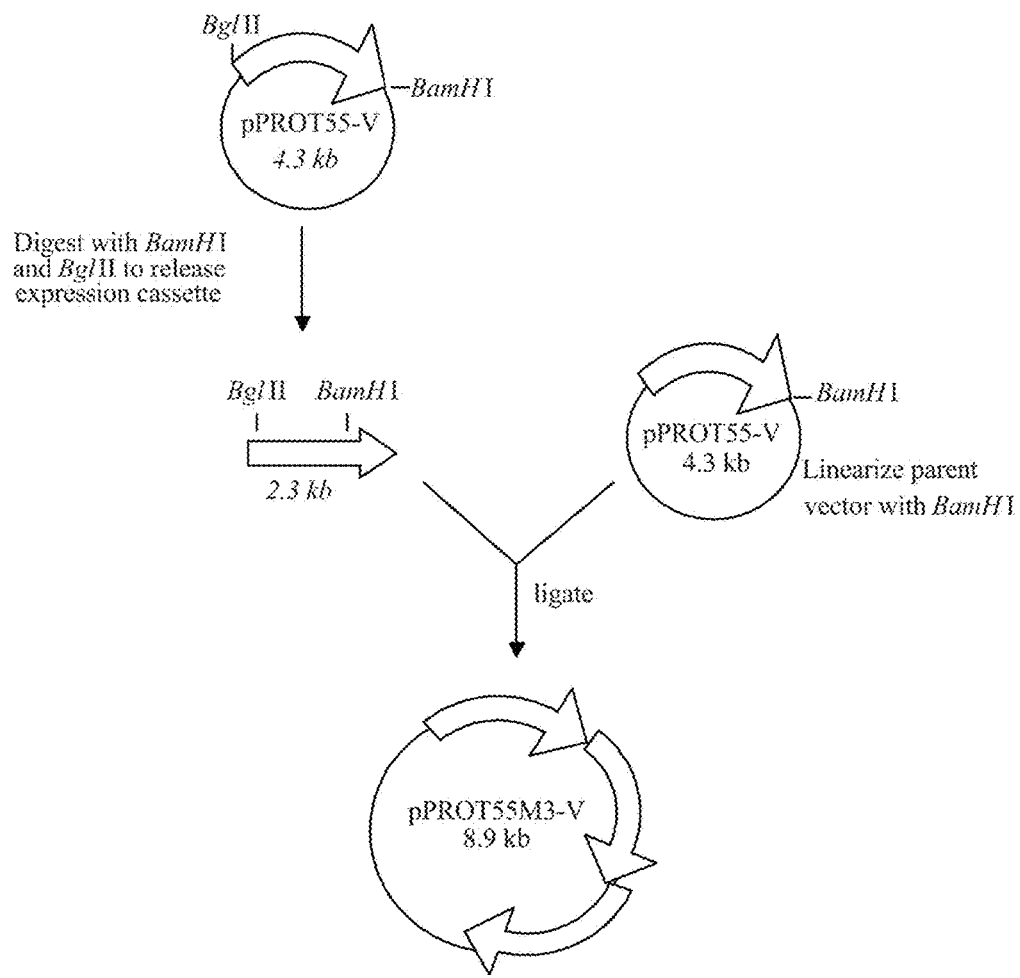
FIG. 6. pPROT55M3-V cloning scheme. pPROT55M3-V was engineered by in vitro ligation of two additional expression cassettes to the 4.3 kb pPROT55-V vector backbone, giving a total of three tandem expression cassettes. The 2.3 kb expression cassette fragment was released from pPROT55-V with a BglII and BamHI restriction digest and purified, followed by ligation of two copies of the expression cassette to pPROT55-V linearized with BamHI.

To determine the number of expression cassettes in the resulting clones, plasmid DNA was digested with BglII and BamHI and analyzed by agarose gel electrophoresis with a DNA size standard marker. A clone containing a single defined insert band with the size consistent with three 2.3 kb expression cassettes was identified and named pPROT55M3-V. Restriction enzyme mapping was used to confirm the orientation of a linear head-to-tail multimer formation for the pPROT55M3-V vector. FIG. 6 depicts the pPROT55M3-V cloning scheme.

The wild-type *P. pastoris* strain NRRL Y-11430 was used for transformation, which was carried out as described in Example 4 except that the pPROT55M3-V vector was linearized with BglII instead of SacI prior to transformation. Drug-resistant transformants were cultured and screened for expression of the pPROT55M3 proprotein as described in Example 4.

Figure 7A:
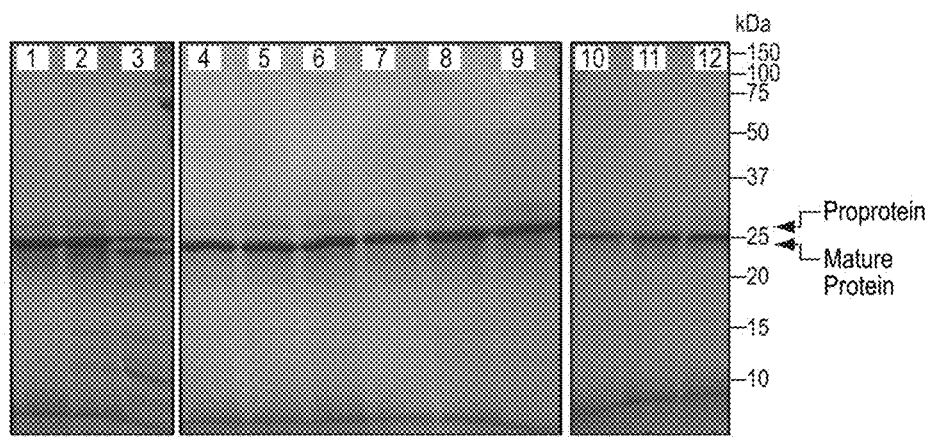
FIGS. 7A-B: Shaker flask optimization of clone 201-55M3-006-VU. The standard induction media, BKME, was prepared and supplemented with sodium citrate to achieve final concentrations of 0, 12.5, 25 and 50 mM sodium citrate, pH 5.5. The media was used to resuspend growth phase cell pellets using a ratio of 1 g wet cell weight to 10 mL of induction media. Cell suspensions of 25 mL each were placed in a 250 mL non-baffled flasks and incubated at 22° C. or 25° C. for 3 days with shaking at 275 rpm. Methanol was added twice daily to a final concentration of 0.5% by volume. Supernatant aliquots were taken during the 3-day period and analyzed for protein expression by SDS-PAGE and Coomassie staining.
Figure 7B:
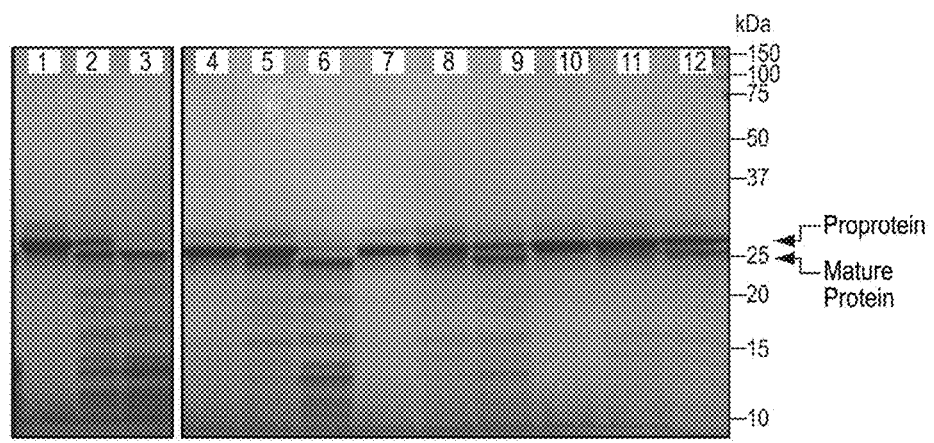

Optimization of shaker flask culture conditions was performed to minimize spontaneous cleavage during induction. Shaker flask optimization focused on two variables, induction temperature and induction media composition. First, it was found that performing induction at 22° C. compared to 25° C. resulted in a higher ratio of proenzyme to mature enzyme in the culture supernatant for all media compositions tested. Second, addition of sodium citrate to increase the buffering strength of the induction media resulted in the absence of spontaneously converted mature enzyme in the culture supernatant across all sodium citrate concentrations tested (12.5 to 50 mM). The effects of these variables on proprotein expression yield and stability in shaker flask supernatant over time are illustrated in FIG. 7.

The high-expressing three-copy clone 201-55M3-003-VU was selected for scale-up fermentation analysis using fermentation procedures established for the 201-55-001-VU clone described as follows. Fermentation of the 201-55-001-VU clone was effected by thawing one cell bank vial and using it to inoculate a shaker flask containing 500 ml of BKGY growth medium at pH 5.7. The seed culture was grown for 24 hours with shaking at 28° C. until the wet cell weight was approximately 40 g/L. The fermentor containing BKGY growth medium at pH 5.7 was sterilized in the autoclave. After the media was cooled to 28° C., supplements including yeast nitrogen base and biotin were added. The fermentor was inoculated at a ratio of 1:33 of seed culture to BKGY growth medium.

The fermentation procedure started with a fed-batch of glycerol and glycerol feed at pH 5.7 at 28° C. The pH was controlled by 10% phosphoric acid and 30% ammonium sulfate solutions. The culture was agitated from 300-1000 rpm with aeration to control the dissolved oxygen at 40%. After the initial glycerol batch was depleted and dissolved oxygen spiked, indicating the depletion of glycerol from the system, additional 50% glycerol was fed at 131 g/h until the wet cell weight reached preferably between 200 g/L to 300 g/L. After the wet cell weight reached 200 g/L-300 g/L, the induction was immediately initiated with a methanol bolus of 0.025 mL per gram of wet biomass. After depletion of the methanol bolus and the rise of dissolved oxygen, induction was continued by the addition of limiting amounts of methanol with a constant feed rate of 0.0034 g methanol/g wet cell weight/hr. At the start of constant methanol feed, the pH of the fermentation broth was changed from 5.7 to 5.5 and the temperature was changed from 28° C. to 22° C. The fermentation was harvested after 70 hours of induction.

Figure 8:
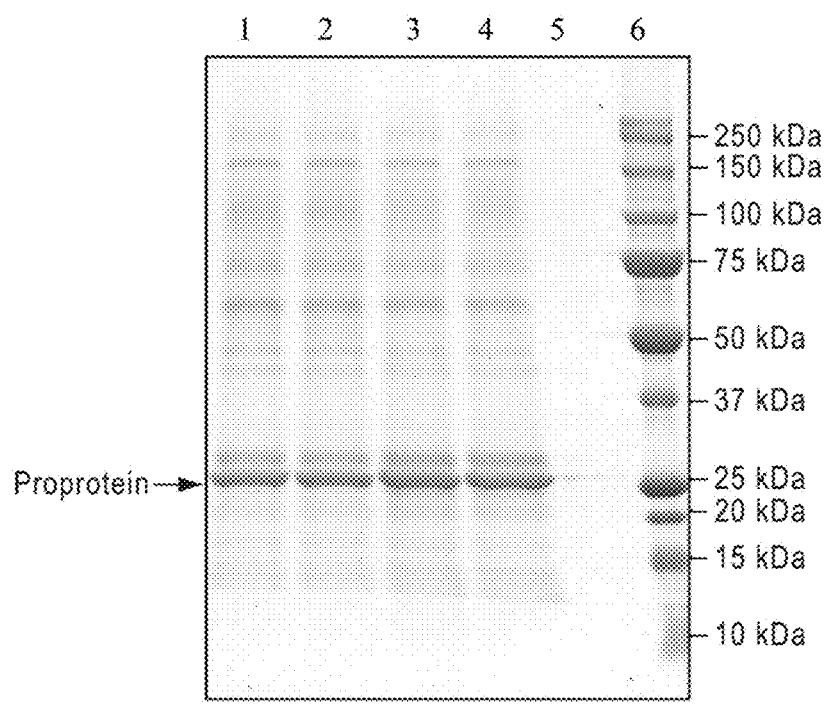
FIG. 8. SDS-PAGE analysis of 201-55-001-VU and 201-55M3-003-VU fermentation supernatants. Lanes 1, 2: 201-55-001-VU supernatant; lanes 3, 4: 201-55M3-003-VU supernatant; lane 5: empty; lane 6: molecular weight markers.

To determine the relative yields of single and 3-copy clones, clone 201-55-001-VU, containing one genomic integrant of the single copy pPROT55-V vector, was fermented in parallel with clone 201-55M3-003-VU, containing one genomic integrant of the 3-copy pPROT55M3-V vector. The fermentations were carried out as described above except that the pH of the culture was maintained at 5.7 throughout induction. The harvested supernatants from 201-55-001-VU and 201-55M3-003-VU fermentations were analyzed by gradient SDS-PAGE followed by Colloidal Blue staining (FIG. 8), which showed that higher proprotein expression was obtained from the multicopy 201-55M3-003-VU clone compared to the single copy 201-55-001-VU clone. SDS-PAGE results were confirmed with HIC-HPLC analysis of proprotein concentration in the fermentation supernatants, demonstrating that the 201-55M3-003-VU clone produced approximately 600 mg/L of the secreted proprotein while the 201-55-001-VU clone produced approximately 400 mg/L. Thus, the multicopy 201-55M3-003-VU clone containing three expression cassettes produced approximately 50% more proprotein compared to single copy 201-55-001-VU clone containing a single expression cassette.

Two conversion strategies were tested using the 201-55M3-003-VU supernatant produced from the fermentation. These strategies generally follow the strategies described for other proprotein variants in Example 5, except that they were performed on a larger scale. In the first strategy, the proprotein was captured from the supernatant by cation exchange chromatography, followed by conversion to the mature protein and polish chromatography. In the second strategy, the proprotein was converted to the mature protein prior to purification, followed by capture using cation exchange chromatography, extended conversion to remove the N-terminal variants, and further polish chromatography. Both strategies also included an extended incubation step in a buffer at pH 8.0 after conversion to effect the selective degradation of N-terminal variants.

Figure 9:
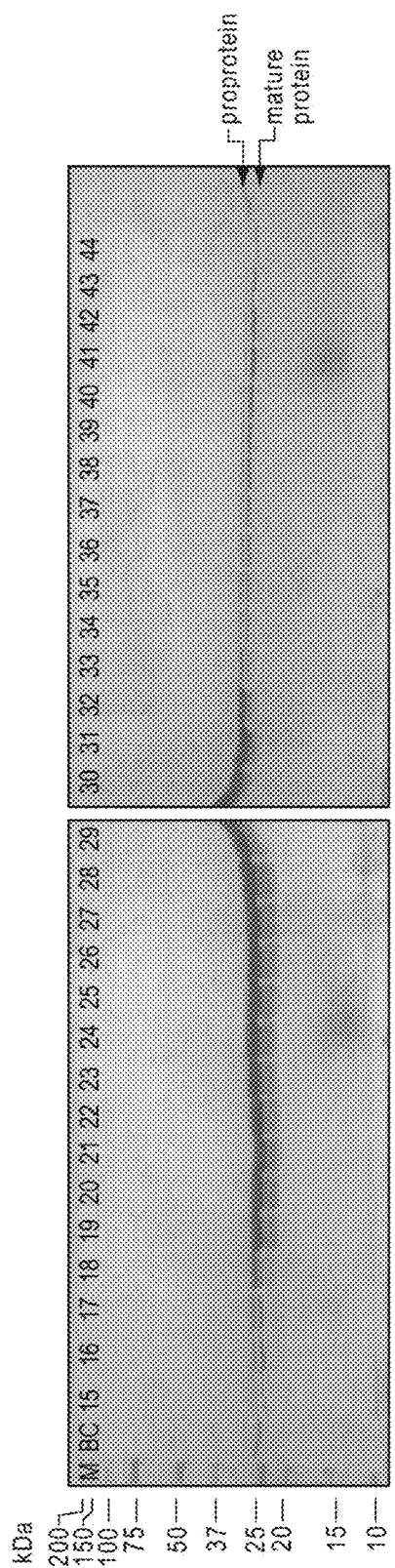
FIG. 9. SDS-PAGE analysis of fractions from pPROT55M3-V proprotein capture chromatography. A total of 30 microliters from each elution fraction was mixed with 10 microliters 4× Laemmli sample loading buffer supplemented with beta-mercaptoethanol. The proteins were electrophoresed on an 8-16% linear gradient gel followed by Coomassie staining. Two predominant forms of PRT-201 were observed: the proprotein (fractions 15-43) and spontaneously converted mature PRT-201 (fractions 15-44). Lane numbers correspond to fraction numbers. M, molecular weight marker. BC, before column (pre-load) sample.

Using the first strategy, capture of the proprotein followed by conversion and PRT-201 polish purification were effected as follows. The 201-55M3-003-VU supernatant was harvested from the fermentation culture and frozen at −80° C. Approximately 7 L of frozen clarified supernatant (3.5 L from the 201-55M3-003-VU fermentation described above and 3.5 L from 201-55M3-003-VU shaker flask cultures prepared generally as described in Examples 4 and 5) was thawed and diluted 8-fold with deionized water and 1 M sodium citrate, pH 4.3, at 2-8° C. to obtain a final concentration of 25 mM sodium citrate. The pH of the solution was adjusted to 4.7. The solution was loaded onto a 2.3 L bed Macroprep High S cation exchange column at 76 cm/hr at 2-8° C. The column was washed with 5 CVs of 25 mM sodium citrate, pH 4.7, followed by 5 CVs of 160 mM sodium chloride, 25 mM sodium citrate, pH 4.7. The proprotein was eluted with 15 CVs of a linear gradient starting from 160 mM sodium chloride to 500 mM sodium chloride in 25 mM sodium citrate, pH 4.7, at 87 ml/min (67 cm/hr). The eluate was collected in fractions. Fractions were analyzed by SDS-PAGE for protein content (FIG. 9). A small amount of spontaneously converted protein was observed by SDS-PAGE. Fractions containing the proprotein were pooled for further processing. The pooled material was subjected to HIC-HPLC analysis, which showed that it consisted of 92% proprotein and 8% mature PRT-201.

To initiate conversion, the pooled material was buffer exchanged using tangential flow filtration into 100 mM sodium chloride, 20 mM Tris, pH 4.0, using constant volume diafiltration at 10-12° C. Tangential flow filtration was performed with regenerated cellulose membranes, a transmembrane pressure of 15 psi, a crossflow rate of 20 L/min and a flux of 800 mL/min. Three diavolumes of the buffer at 2-8° C. was added at the same rate as the flux. Subsequently, three additional volumes of buffer at ambient temperature were added at the same rate as the flux to raise the temperature of the conversion solution to the target of 26° C. Tangential flow filtration was used to concentrate the conversion solution to the target of 1.5 mg/mL using the conditions of 15 psi transmembrane pressure, 1.2 L/min crossflow rate, and 76 ml/min flux. However, after approximately 2 minutes of starting the concentration procedure, unexpected precipitation was observed and the concentration process was halted. The protein concentration of the conversion solution was determined to be 1.1 mg/mL by UV absorbance at 280 nm in a volume of 570 mL. To minimize further precipitation, the conversion solution was diluted to 1 mg/mL with 100 mM sodium chloride, 20 mM Tris, pH 4.0, and filtered through a 0.22 micron membrane. Sixteen mL of 3 M Tris, pH 9.0 was added to the conversion solution. The conversion solution was placed in a water bath at 26° C. The conversion reaction was monitored by HIC-HPLC analysis. After 30 minutes, HIC-HPLC showed that the majority of the proprotein had been converted to PRT-201 and some N-terminal variants (FIG. 10). After 1 hour, the conversion reaction consisted of 0% proprotein, 86% full-length PRT-201 and 14% N-terminal variants. The conversion material was incubated further for 4 more hours, at which time HIC-HPLC analysis showed that the conversion material consisted of 98% full-length PRT-201 and 2% N-terminal variants.

The conversion material was diluted 4-fold with deionized water and 1 M sodium citrate, pH 4.3, to a final concentration of 25 mM sodium citrate. The pH of the solution was adjusted to 5.0 in preparation for loading onto the polish column. The solution was loaded onto a 600 mL bed Macroprep High S cation exchange column at 27 mL/min (83 cm/hr). The column was washed with 5 CVs of 20 mM sodium citrate, pH 5.0 followed by 5 CVs of 160 mM sodium chloride, 20 mM sodium citrate, pH 5.0. PRT-201 was eluted with 15 CVs of a linear gradient starting from 160 mM to 500 mM sodium chloride in 25 mM sodium citrate, pH 5.0, at 87 mL/min (67 cm/hr). The eluate was collected in fractions. Fractions were analyzed by SDS-PAGE for protein content and by SLAP assay for specific activity. Fractions containing PRT-201 with a specific activity of >30 U/mg were pooled. The pooled PRT-201 fractions were diafiltered by tangential flow filtration into formulation buffer (0.1×PBS, pH 5.0). The pH of diafiltered PRT-201 was adjusted to pH 7.4 and the protein concentration was adjusted to 1 mg/mL by tangential flow filtration. Vials were filled and lyophilized as described for PRT-201 produced from the 201-24-266-VU clone in Example 4.

Using the second strategy, proprotein conversion followed by purification of PRT-201 was effected as follows. Approximately 7 L of the frozen clarified supernatant from the 201-55M3-003-VU fermentation described above was thawed and the conversion reaction was initiated by tangential flow filtration with a conversion buffer containing 100 mM Tris, pH 8.0, using constant volume diafiltration at ambient temperature with regenerated cellulose membranes. Two diavolumes of 100 mM Tris-HCl, pH 8.0 were sufficient to change the pH of the retentate from pH 5.0 to 8.0 and effect conversion. An experiment was also performed by directly adjusting the pH of the clarified supernatant to 8.0 by adding a Tris base to a final concentration of 100 mM and adjusting the pH to 8.0 with 1 N sodium hydroxide. This resulted in the formation of precipitates and a cloudy supernatant, possibly due to precipitation of broth components, which was undesirable. The preferred method of conversion using tangential flow filtration did not result in precipitation.

Figure 11:
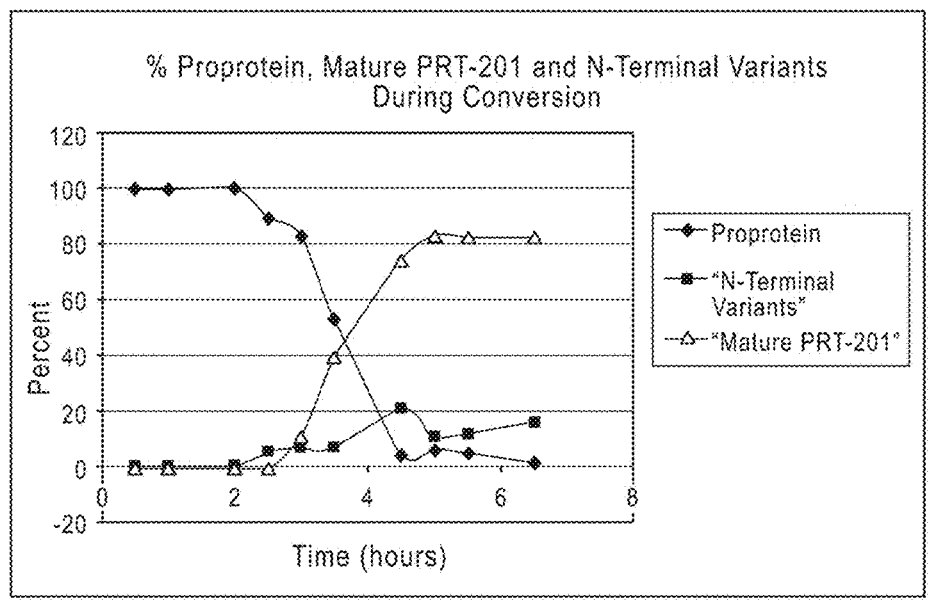
FIG. 11: HIC-HPLC analysis of proprotein conversion in fermentation supernatant effected by tangential flow filtration. Clarified 201-55M3-003-VU fermentation supernatant was subjected to tangential flow filtration with 100 mM Tris, pH 8.0, using constant volume diafiltration at ambient temperature with regenerated cellulose membranes. The graph shows relative amounts of proprotein, mature (full-length) PRT-201 and N-terminal variants present at various time points during the conversion.

The conversion reaction was monitored by real-time HIC-HPLC analysis. After initiation of conversion, pro-PRT-201 converted to mature PRT-201 slowly over the first two hours, followed by an acceleration of conversion (FIG. 11). At 4.5 hours, the conversion reaction consisted of approximately 4% pro-PRT-201, 75% mature PRT-201 and 21% N-terminal variants. At 6.5 hours, the conversion reaction consisted of approximately 1% pro-PRT-201, 83% mature PRT-201 and 16% N-terminal variants. The reduction in N-terminal variants from 21% to 16% from 4.5 hrs to 6.5 hrs may be due to degradation of N-terminal variants by full length, active PRT-201, but this was not complete and not as rapid as the reduction in N-terminal variants seen during conversion of purified pro-PRT 201. In this second strategy, extending the conversion reaction may not entirely remove the N-terminal variants due to the competing proteins in the supernatant that compete for the active site of elastase. To improve the conversion reaction, the postconversion material was captured and subsequently diafiltered into an appropriate buffer to initiate extended conversion at pH 8.0 for selective degradation of N-terminal variants as described below.

Figure 12:
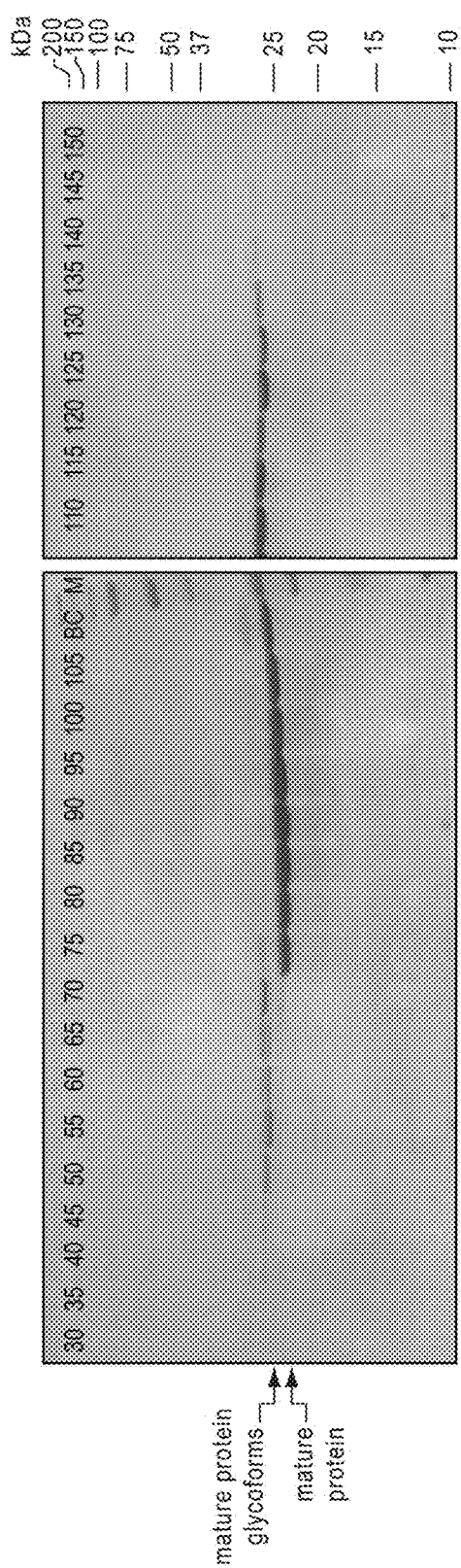
FIG. 12. SDS-PAGE analysis of fractions from pPROT55M3-V conversion capture chromatography. A total of 30 microliters from each elution fraction was mixed with 10 microliters 4× Laemmli sample loading buffer supplemented with beta-mercaptoethanol. The proteins were electrophoresed on an 8-16% linear gradient gel followed by Coomassie staining. Two predominant forms of PRT-201 were observed: the glycosylated mature form (fractions 35-70), and the non-glycosylated mature form (fractions 75-160). Lane numbers correspond to fraction numbers. M, molecular weight marker. BC, before column (pre-load) sample.

Capture of PRT-201 from the conversion material was effected as follows. The conversion material was buffer exchanged into 20 mM sodium citrate, pH 5.0 and loaded onto a Macro-Prep High S cation-exchange chromatography column. The column was washed with 5 CVs of 20 mM sodium citrate, pH 5.0 followed by 5 CVs of 20 mM sodium citrate, 160 mM sodium chloride, pH 5.0. PRT-201 was eluted with a linear gradient from 160 mM to 500 mM sodium chloride in 20 mM sodium citrate, pH 5.0. The fractions were analyzed by SDS-PAGE for protein content, HIC-HPLC for N-terminal variants, UV absorbance at 280 nm for protein concentraton, and SLAP assay for elastase activity. Two predominant proteins bands were detected by SDS-PAGE, corresponding to PRT-201 and PRT-201 glycoforms, as shown in FIG. 12. Fractions that contained PRT-201 glycoforms as determined by SDS-PAGE or N-terminal variants as determined by HIC-HPLC were excluded from pooling. Fractions that exhibited relatively low specific activity (less than 30 U/mg) as determined by SLAP assay were also excluded from pooling. The remaining fractions containing PRT-201 were pooled for further processing. HIC-HPLC analysis of the pooled fractions revealed that this material consisted of approximately 98% full-length PRT-201 and 1-2% N-terminal variants. The pooled material was stored at 2-8° C. for 12-16 hrs.

Given the prior observation that N-terminal variants appeared to decrease over a prolonged conversion period as described above, the pooled PRT-201 material was subjected to an extended incubation step at pH 8.0. The extended incubation was performed by diafiltration and tangential flow filtration with 100 mM Tris, 300 mM sodium chloride, pH 8.0 for 2.5 hours at ambient temperature. After 2.5 hours, the conversion material consisted of 100% mature PRT-201 as shown by HIC-HPLC analysis. The conversion material was subjected to diafiltration and tangential flow filtration into 20 mM sodium citrate, pH 5.0 to suppress elastase activity and prepare for column chromatography. The diafiltered PRT-201 material was stored for approximately 64 hours at 2-8° C.

Polish chromatographic purification of PRT-201 was effected as follows. The diafiltered PRT-201 material was loaded onto a Macro-Prep High S cation exchange column and washed with 5 CVs of Buffer C (20 mM sodium citrate, pH 5.0) followed by 5 CVs of 160 mM sodium chloride, 20 mM sodium citrate, pH 5.0. Elution of PRT-201 was performed with a linear gradient of 15 CVs starting from 68% Buffer C and 32% Buffer D (160 mM sodium chloride, 25 mM sodium citrate, pH 5.0) to 0% Buffer C and 100% Buffer D (500 mM sodium chloride, 25 mM sodium citrate, pH 5.0), at 50 ml/min (153 cm/hr). The eluate was collected in fractions. PRT-201 eluted as a symmetrical peak at 37 mS/cm (330 mM sodium chloride). Fractions were analyzed by SDS-PAGE analysis for protein content, UV absorbance at 280 nm for protein concentration and SLAP assay for specific activity. Fractions containing PRT-201 that had a specific activity of 30.1-38.8 U/mg were pooled. The pooled PRT-201 fractions were diafiltered by tangential flow filtration into formulation buffer (0.1×PBS, pH 5.0). The pH of diafiltered PRT-201 was adjusted to pH 7.4 and the protein concentration was adjusted to 1 mg/mL by tangential flow filtration. Vials were filled and lyophilized as described for PRT-201 produced from the 201-24-266-VU clone in Example 4.

The conditions for the conversion procedures described above were chosen based on conversion optimization studies that examined protein concentration, temperature, buffer composition, diavolume and pH variables. In the first study, the effect of proprotein concentration on the production of N-terminal variants during conversion was analyzed. Purified pro-PRT-201 from the 201-55M3-003-VU clone (pro-PRT-201-55M3-003-VU) at a starting concentration of 0.2 mg/mL in 20 mM sodium phosphate, pH 5.0 was aliquotted and concentrated to 1.0, 1.6, and 1.8 mg/mL using centrifugal concentrating devices as determined by UV absorbance at 280 nm. Conversion of the proprotein was effected by adding Tris and sodium chloride to 100 mM each of the four concentration samples, adjusting the pH from 5.0 to 8.0, and incubating the samples at ambient temperature. The conversion reaction was monitored by HIC-HPLC in real-time until the proprotein was ≤1% of the total protein (FIG. 13). At this endpoint, the 0.2 mg/mL sample consisted of approximately 8% N-terminal variants, whereas the 1.0 mg/mL, 1.6 and 2.0 mg/mL samples consisted of approximately 14%, 19% and 29% N-terminal variants, respectively. The remainder of the protein in each sample consisted of full-length PRT-201. These results demonstrate that increasing concentrations of pro-PRT-201-55-003-VU during conversion leads to the formation of more N-terminal variants and less full-length PRT-201. Other studies have suggested that pro-PRT-201-55M3-003-VU conversion occurs through both intramolecular and intermolecular reactions. Thus, for this variant proprotein, it is likely that intramolecular reactions, which are favored in more dilute proprotein solutions, give rise to more accurate conversion whereas intermolecular reactions, favored in more concentrated proprotein solutions, result in less accurate conversion, i.e., the formation of a higher percentage of the N-terminal variants relative to full-length PRT-201.

In the second study, the effect of temperature on the production of N-terminal variants during conversion was analyzed. Purified pro-PRT-201 from the 201-55M3-VU clone (named pro-PRT-201-55M3-003-VU) was produced at a concentration of 1.6 mg/mL was subjected to conversion as described above at either 15° C. or 26° C. The conversion reactions were monitored in real-time by HIC-HPLC and allowed to progress until the proprotein comprised <1% of total protein. The time required to reach this reduction in proprotein was approximately 30 minutes at 26° C. and approximately 90 minutes at 15° C. At these times, a similar percentage of N-terminal variants (about 20% of total protein) for both temperatures was observed. Thus, the higher temperature of 26° C. resulted in a more rapid conversion reaction compared to the lower temperature of 15° C. while producing an essentially identical reaction product profile.

The third study examined the effect of buffer composition on proprotein solubility during the conversion reaction. Purified pro-PRT-201 (pro-PRT-201-55M3-003-VU) at a concentration of 1.0 mg/mL was subjected to conversion under the conditions listed in Table 6. The conversion reactions were performed at ambient temperature except for one (buffer composition of 20 mM Tris-HCl, 100 mM sodium chloride, pH 4.0) that was performed at 2 to 8° C. Conversion reactions were inspected visually for precipitation. As noted in Table 6, buffer compositions that did not result in precipitation included 100 mM Tris-HCl, pH 8.0; 100 mM Tris-HCl, 100 mM sodium chloride, pH 5.0; and 100 mM Tris-HCl, 300 mM sodium chloride, pH 8.0. Buffer compositions with lower concentrations of Tris or without sodium chloride at lower pH (i.e., pH 5.0) exhibited precipitation.

TABLE 6

Effect of buffer composition on precipitation during conversion.

| Buffer Composition | Temperature | Precipitation Observed | Soluble (No Precipitation Observed) |
|---|---|---|---|
| 1 mM Tris-HCl, pH 5.0 | Ambient | + | |
| 25 mM Tris-HCl, pH 5.0 | Ambient | + | |
| 100 mM Tris-HCl, pH 5.0 | Ambient | + | |
| 100 mM Tris-HCl, pH 8.0 | Ambient | | + |
| 20 mM Tris-HCl, 100 mM sodium chloride, pH 4.0 | 2-8° C. | + | |
| 100 mM Tris-HCl, 100 mM sodium chloride, pH 5.0 | Ambient | | + |
| 100 mM Tris-HCl, 300 mM sodium chloride, pH 8.0 | Ambient | | + |

In the fourth study, the effect of tangential flow filtration diavolume number on precipitation during conversion of supernatant containing proprotein (pro-PRT-201-55M3-003-VU) was analyzed. The solution used for buffer exchange was 100 mM Tris-HCl, 100 mM sodium chloride, pH 8.0. Additionally, a direct pH adjustment of the supernatant from pH 5.0 to 8.0 without tangential flow filtration was tested. As noted in Table 7, direct pH adjustment of the supernatant resulted in a large amount of precipitation. With 1 diavolume of exchange, some precipitation was observed. No precipitation was observed when 2 to 5 diavolumes were used.

TABLE 7

Effect of diavolume number on precipitation during buffer exchange.

| Diavolumes | Precipitation Observed |
|---|---|
| 0 | Major precipitation |
| 1 | Minor precipitation |
| 2 | No precipitation |
| 3 | No precipitation |
| 5 | No precipitation |

In the fifth study, the effect of pH on elastase activity of mature PRT-201 was analyzed. This study was designed to identify a useful pH range for conversion that would not result in an irreversible loss of elastase activity of the mature PRT-201 conversion product. Solutions of 1 mg/mL PRT-201 in 20 mM Tris-HCl, 20 mM potassium phosphate were prepared from pH 1 to 14. Solutions were kept at ambient temperature for 0.5, 2, 24 and 48 hours. At the indicated time points, the solutions were tested for elastase activity in the SLAP assay. Elastase activity was largely stable from pH 3 to 8 at all time points. At pHs less than 3 and greater 8, elastase activity was reduced at all time points, with a correlation between longer time points and lower elastase activity. These results indicated that a conversion reaction performed outside a pH range of 3 to 8 could negatively impact elastase activity of the PRT-201 conversion product.

6.8 Example 7: Production of Auto-Activated Recombinant Porcine Type I Pancreatic Elastase A vector encoding auto-activated porcine ELA-1 proenzyme was expressed *P. pastoris*. The resulting auto-activated porcine ELA-1 was compared to a porcine ELA-1 protein expressed as a trypsin-activated wild-type proprotein.

To construct the trypsin-activated porcine ELA-1 vector, the porcine ELA-1 coding region was synthesized by Blue Heron Biotechnology (Bothell, Wash.) using a non-PCR "long oligo" technique under license from Amgen (Thousand Oaks, Calif.). The recombinant gene was cloned into the Blue Heron pUC vector, a derivative of pUC119. The porcine ELA-1 gene was sequenced on both strands to confirm the correct sequence. SacII and XbaI restriction sites were incorporated as potential cloning sites flanking the porcine ELA-1 gene as shown in FIG. 14. A second stop codon was also added immediately after the native stop codon to minimize potential ribosome read through. FIG. 15 shows the nature identical amino acid sequence of porcine ELA-1 proenzyme, which contains the trypsin-activated site.

Figure 16:
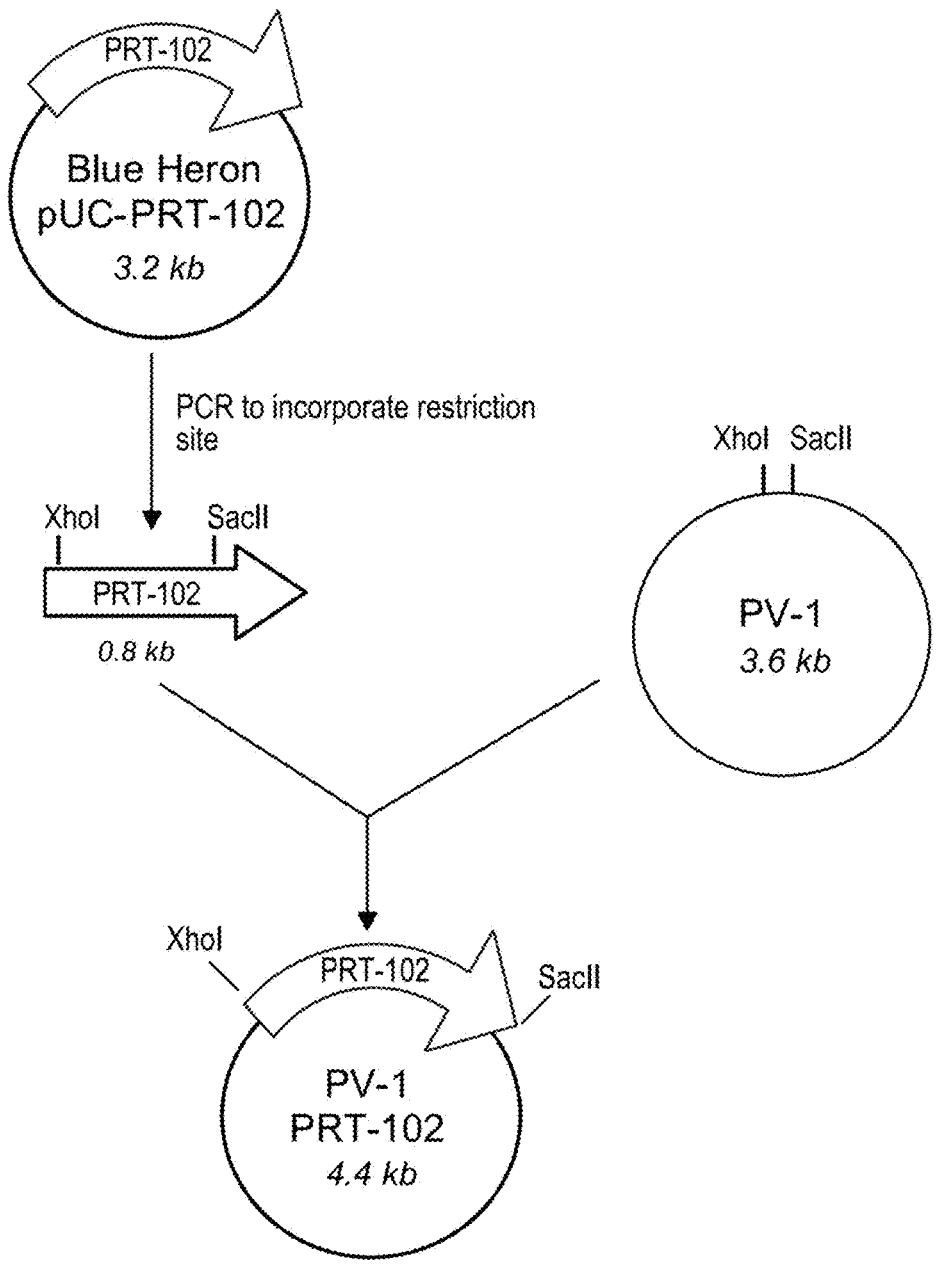
FIG. 16. Cloning scheme of porcine type I pancreatic elastase into PV-1 vector. After synthesis of the porcine type I pancreatic elastase proprotein coding region, it was cloned in the Blue Heron pUC vector. In addition to amplifying the coding sequence of porcine type I pancreatic elastase, PCR was used to incorporate XhoI and SacII restriction sites for cloning into the PV-1 vector. The PCR product was digested, gel-purified and ligated with PV-1 vector digested with XhoI and SacII, thus resulting in a pPROT101-24-V expression vector encoding trypsin-activated porcine type I pancreatic elastase proprotein.

The coding region of porcine ELA-1 was amplified by PCR using a pair of oligonucleotides containing XhoI and SacII restriction sites to facilitate cloning. The PCR product was digested with XhoI and SacII and purified by agarose gel electrophoresis. The porcine ELA-1 fragment was cloned into the PV-1 vector at XhoI and SacII restriction sites. The *E. coli* TOP10 strain was transformed with the ligation mixture. The cell mixture was plated on low salt LB plates supplemented with 25 mg/mL Zeocin. Drug-resistant clones were picked and plasmid DNA was prepared (Qiagen, CA). Based on restriction analysis, a clone containing the porcine ELA-1 gene insert was identified and the vector was named pPROT101-24-V. The coding sequence of this vector was confirmed by DNA sequencing. The cloning scheme for pPROT101-24-V is depicted in FIG. 16.

Using the trypsin-activated pPROT101-24-V vector, three different auto-activated clones were engineered by changing the trypsin cleavage site in the pro-peptide region of porcine ELA-1 to elastase cleavage sites. Site-directed mutagenesis was performed generally as described in Example 4 using synthetic oligonucleotide primers containing the desired mutations as described in Table 8. All the mutations in the pro-peptide region were confirmed by double-stranded DNA sequencing.

TABLE 8

Cleavage domain sequences of trypsin-activated and auto-activated porcine ELA-1 vectors. Mutagenized codons are shaded. The cleaved bond is between P1 and P'1.

| Construct name | Pro-peptide sequence | | | | | | | Mature sequence | | | SEQ ID NO. |
|---|---|---|---|---|---|---|---|---|---|---|---|
| | P7 | P6 | P5 | P4 | P3 | P2 | P1 | P'1 | P'2 | P'3 | |
| Trypsin-activated pPROT101-24-V | Phe | Pro | Glu | Thr | Asn | Ala | Arg | Val | Val | Gly | 115 |
| Auto-activated pPROT101-42-V | Phe | Pro | Glu | Thr | Asn | Ala | Ala | Val | Val | Gly | 116 |
| Auto-activated pPROT101-49-V | Phe | Pro | Glu | Thr | Asn | His | Ala | Val | Val | Gly | 118 |
| Auto-activated pPROT101-55L-V | Leu | Pro | His | Thr | Asn | pro | Ala | Val | Val | Gly | 117 |

Figure 17:
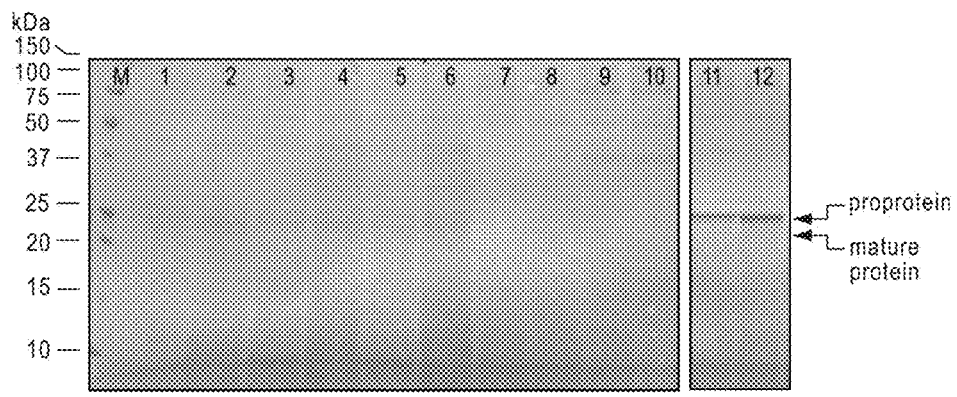
FIG. 17. Expression analysis of auto-activated pPROT101-42-V and trypsin-activated pPROT101-24-V clones during methanol induction by SDS-PAGE. Shaker flask supernatants after 1 day of induction were analyzed on an 8-16% gradient gel followed by staining with Coomassie staining. Lanes 1-10 contain supernatants from ten different clones transformed with pPROT101-42-V. Lanes 11-12 contain supernatants from two different clones transformed with pPROT101-24-V. M, molecular weight markers.
Figure 18:
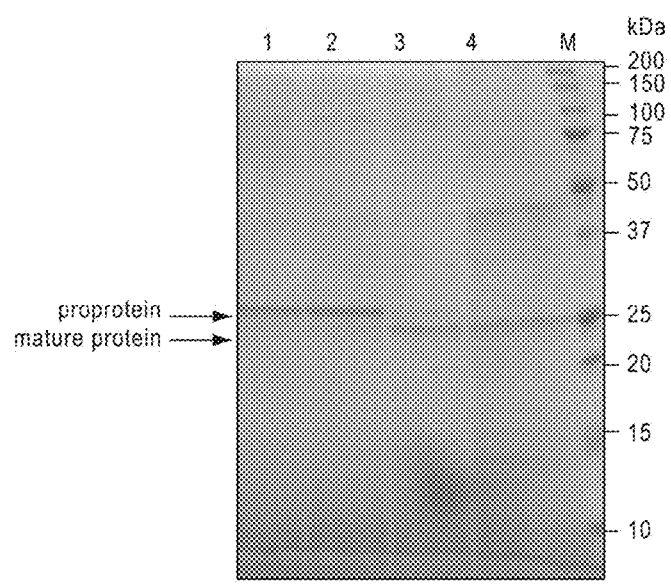
FIG. 18. Expression analysis of auto-activated pPROT101-49-V and pPROT101-55L-V clones during methanol induction by SDS-PAGE. Shaker flask supernatants after 1 and 2 days of induction were analyzed on an 8-16% gradient gel followed by Coomassie staining. Lanes 1-2 contain supernatants from a pPROT101-49-V clone after 1 and 2 days of induction, respectively. Lanes 3-4 contain supernatants from a pPROT101-55L-V clone after 1 and 2 days of induction, respectively. M, molecular weight markers.

The wild-type NRRL Y-11430 *P. pastoris* strain was transformed and drug-resistant transformants were cultured and screened for expression of the porcine ELA-1 proteins as described in Example 3. Based on analysis by SDS-PAGE and Coomassie staining (see FIG. 17 and FIG. 18), the wild-type trypsin-activated pPROT101-24-V clones had the highest levels of expression compared to the auto-activated clones. Of the auto-activated clones, the pPROT101-49-V clones had the highest level of expression, followed by the pPROT101-55L-V clones and then the pPROT101-49-V clones. Auto-activated pPROT101-42-V and pPROT101-55L-V proproteins exhibited substantial spontaneous conversion during induction, while the trypsin-activated pPROT101-24-V and auto-activated pPROT101-49-V proproteins showed greater stability in the induction media.

Studies of the elastase activity of PRT-102 produced by trypsin activation of proelastase protein expressed from pPROT101-24-V showed higher specific activity than PRT-201 as shown in Table 9 below:

TABLE 9

Elastase activity of three different samples of mature porcine type I pancreatic elastase (trypsin activated) as compared to mature human type I pancreatic elastase.

| Sample Name | PRT-201 | PRT-102 | PRT-102 | PRT-102 |
|---|---|---|---|---|
| Activity as measured by SLAP (U/mg protein) (Replicates) | 34.6 | 91.8 | 99.4 | 100.7 |
| | 32.9 | 88.3 | 91.3 | 88.6 |

TABLE 9-continued

Elastase activity of three different samples of mature
porcine type I pancreatic elastase (trypsin activated)
as compared to mature human type I pancreatic elastase.

| Sample Name | PRT-201 | PRT-102 | PRT-102 | PRT-102 |
|---|---|---|---|---|
| Average of Replicates | 33.6 | 88.5 | 93.5 | 92.9 |
| Standard Deviation | 0.9 | 3.2 | 5.2 | 6.7 |

Figure 19:
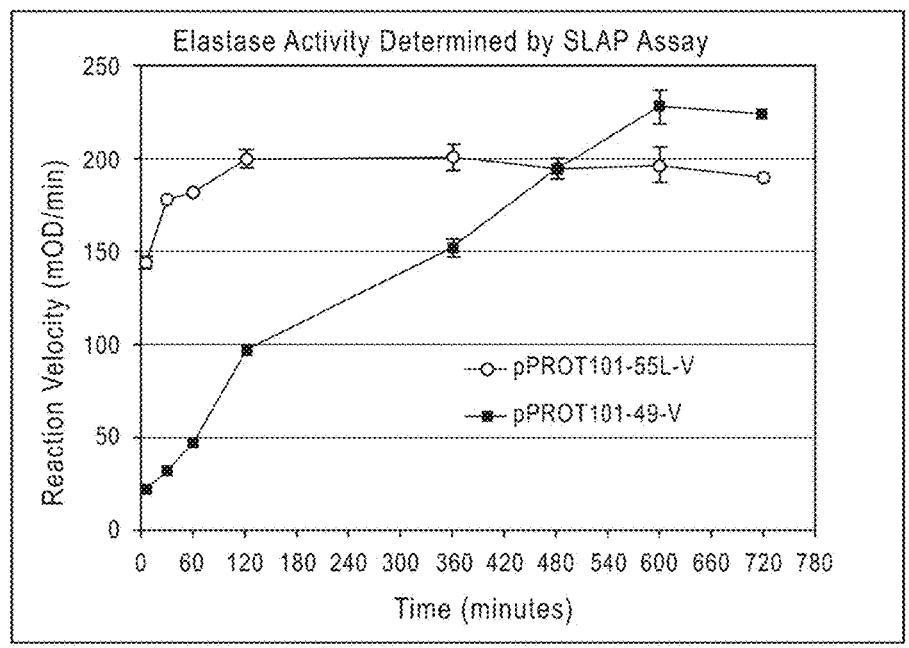
FIG. 19. Time course activation of pPROT101-49-V and pPROT101-55L-V proteins by small-scale conversion assay as determined by SLAP elastase activity. Error bars represent ±SD of the mean (n=4).
Figure 20:
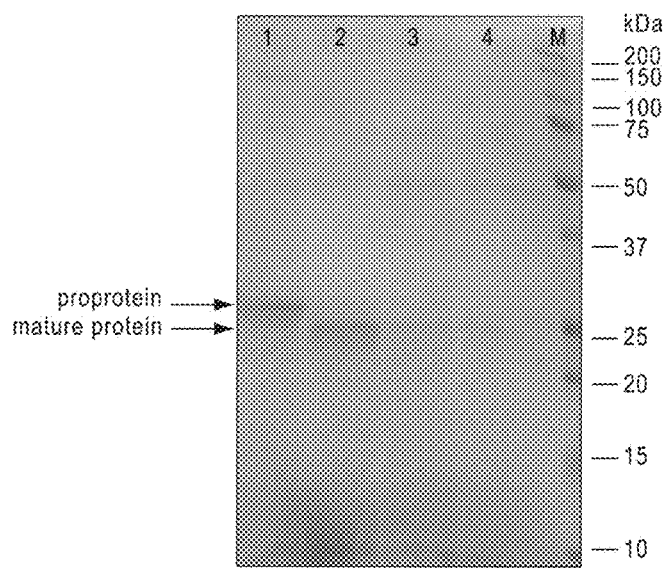
FIG. 20. SDS-PAGE analysis of pPROT101-49-V and pPROT101-55L-V supernatants before and after small-scale conversion assay. Prior to electrophoresis, the samples were mixed with citric acid, the reducing agent TCEP, and LDS sample buffer (Invitrogen, CA). The samples were heated at 70° C. for 10 minutes. Lanes 1-2: pPROT101-49-V pre- and post-conversion assay supernatant, respectively; lanes 3-4: pPROT101-55L-V pre- and post-conversion assay supernatant, respectively. M, molecular weight markers.

A small-scale conversion experiment was used to determine if pPROT101-55L-V and pPROT101-49-V proproteins could be converted to mature enzymes exhibiting elastase activity. pPROT101-55L-V and pPROT101-49-V shaker flask supernatants were concentrated 10-fold with an centrifugal filter unit and diluted 5-fold with 100 mM Tris-HCl, pH 9.0. The conversion was allowed to proceed at room temperature and elastase activity was monitored over time by SLAP assay. The average change in absorbance per minute was determined from each time point and reported as non-normalized reaction velocity (FIG. 19). Conversion of both pPROT101-49-V and pPROT101-55L-V supernatants resulted in an increase in elastase activity. The final time point samples from each clone were analyzed by SDS-PAGE followed by Coomassie staining and compared to pre-conversion samples (FIG. 20). The SDS-PAGE results confirmed that nearly all of the pPROT101-49-V proprotein was converted to mature protein by the end of the conversion assay. The SDS-PAGE results also showed that nearly all of the pPROT101-55L-V had been spontaneously converted to mature protein prior to the conversion assay.

Purified preparations of pPROT101-24-V and pPROT101-49-V proproteins and mature enzymes were submitted to Danforth Plant Science Center, MO for intact molecular weight analysis. The proproteins were purified by cation exchange chromatography (Macroprep High S, Bio-Rad). For mature enzyme analysis, the proproteins from both clones were first treated to produce mature enzymes and then purified by cation exchange chromatography. The trypsin-activated proprotein was treated with trypsin while the auto-activated proprotein was converted in the presence of 100 mM Tris-HCl, pH 9.0, followed by cation exchange chromatography. The major peaks obtained from mass spectrometry analysis are listed in Table 10.

TABLE 10

Expected and observed molecular weights
for porcine ELA-1 proteins.

| Protein | Expected MW | Observed MW |
|---|---|---|
| Trypsin-activated pPROT101-24-V proprotein | 27068 | 27064 |
| Trypsin-activated pPROT101-24-V mature enzyme | 25908 | 25898 |
| Auto-activated pPROT101-49-V proprotein | 27049 | 27047 |
| Auto-activated pPROT101-49-V mature enzyme | 25908 | 25910 |

SDS-PAGE, elastase activity and mass spectrometry results demonstrated that auto-activated forms of type I porcine pancreatic elastase can be produced by engineering the pro-peptide sequence to replace the trypsin cleavage site with an elastase cleavage site. The expression levels of these auto-activated forms of type I porcine pancreatic elastase are lower than the wild-type trypsin-activated form. Of the autoactivated clones tested, those with the pPROT101-49-V pro-peptide sequence showed the highest level of expression and the least spontaneous conversion. Conversion of the pPROT101-49-V and pPROT101-55L-V clones resulted in the production of mature proteins with substantial elastase activity. Mass spectrometry analysis revealed that the molecular weights of pPROT101-49-V proprotein and mature porcine type I corresponded to the expected masses.

6.9 Example 8: Trypsin Activity Analysis of Mature Recombinant Human Elastase-1 by Benz Colorimetric Peptide Substrate Assay A colorimetric hydrolysis assay using the small peptide substrate N-benzoyl-Phe-Val-Arg-pNitroanilide (BENZ) was performed to determine if purified mature elastase protein produced by the auto-activated clone 201-55M3-003-VU possesses trypsin activity. Three vials of lyophilized PRT-201 purified from clone 201-55M3-003-VU were retrieved from −80° C. storage and reconstituted with water to obtain 1 mg/mL PRT-201 in 0.1×PBS, pH 7.4. Protein concentrations were confirmed by measuring UV absorbance at 280 nm. A TrypZean stock solution (10 mg/mL) was used to generate a standard curve for trypsin activity. A previously tested trypsin-activated PRT-201 sample was included as a positive control. In addition, some experimental and control samples were spiked with TrypZean to determine trypsin activity recovery in the presence of PRT-201. A subset of the spiked and unspiked samples was treated with soybean trypsin inhibitor (SBTI) to determine the ability of SBTI to inhibit any intrinsic or spiked trypsin activity. TrypZean standards were also treated with SBTI to confirm the effectiveness of the inhibitor. See Table 11 below for a summary of the samples included in this study.

TABLE 11

Figure 21:
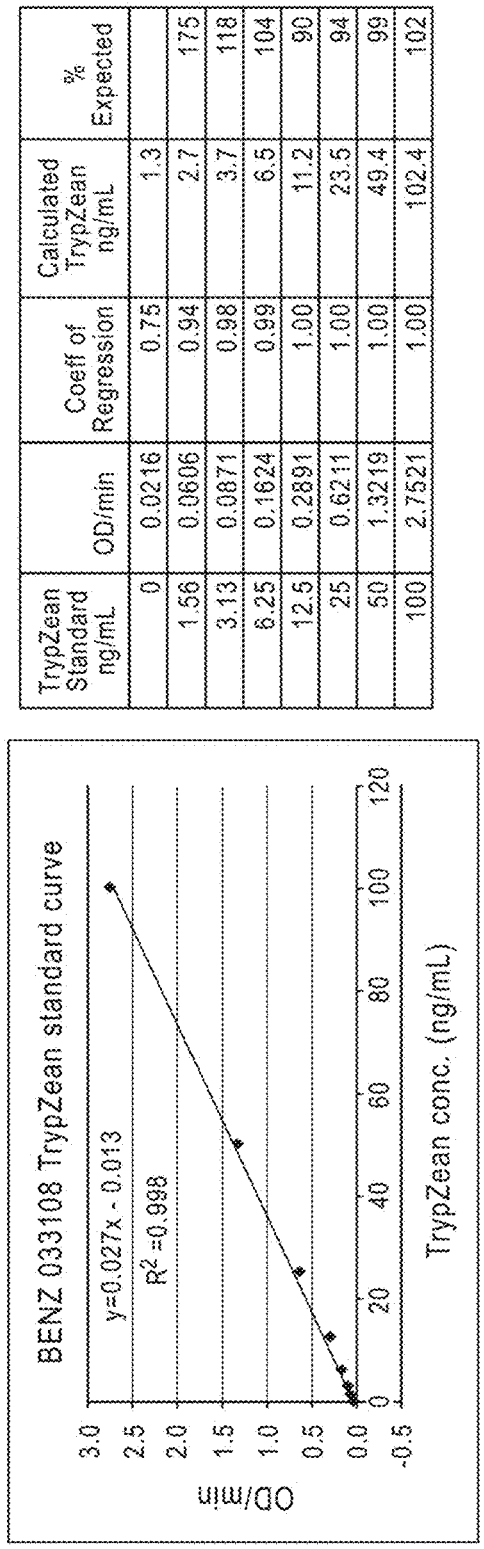
FIG. 21. TrypZean standard curve.

TrypZean dilutions for the standard curve were prepared using the assay buffer (0.1M
Tris, pH 8.3). The standard curve for TrypZean solutions is shown in FIG. 21.

| Description | No addition | Plus TrypZean spike (to 100 ng/mL) | Plus SBTI (to 10 ug/mL) | Plus TrypZean spike and SBTI |
|---|---|---|---|---|
| PRT-201 from clone 55M3 Vial #1 | ✓ | ✓ | ✓ | ✓ |
| PRT-201 from clone 55M3 Vial #2 | ✓ | ✓ | ✓ | ✓ |
| PRT-201 from clone 55M3 Vial #3 | ✓ | ✓ | ✓ | ✓ |
| PRT-201 from trypsin activated clone | ✓ | ✓ | ✓ | ✓ |
| Buffer only (0.1M Tris, pH 8.3) | ✓ | Not done | ✓ | Not done |
| TrypZean standard, 1.56 ng/mL | ✓ | Not done | ✓ | Not done |
| TrypZean standard, 3.13 ng/mL | ✓ | Not done | ✓ | Not done |
| TrypZean standard, 6.25 ng/mL | ✓ | Not done | ✓ | Not done |
| TrypZean standard, 12.5 ng/mL | ✓ | Not done | ✓ | Not done |
| Tr5ypZean standard, 25 ng/mL | ✓ | Not done | ✓ | Not done |

TABLE 11-continued

TrypZean dilutions for the standard curve were prepared using the assay buffer (0.1M Tris, pH 8.3). The standard curve for TrypZean solutions is shown in FIG. 21.

| Description | No addition | Plus TrypZean spike (to 100 ng/mL) | Plus SBTI (to 10 ug/mL) | Plus TrypZean spike and SBTI |
|---|---|---|---|---|
| TrypZean standard, 50 ng/mL | ✓ | Not done | ✓ | Not done |
| TrypZean standard, 100 ng/mL | ✓ | Not done | ✓ | Not done |

The substrate solution was prepared (0.4 mg/mL N-benzoyl-Phe-Val-Arg-pNitroanilide Lot 7733 in 0.1 M Tris, pH 8.3) and prewarmed to 30° C. in a water bath. In triplicate, 100 microliters of each sample was pipetted into a 96-well microplate. Using a multichannel pipettor, 200 microliters of substrate solution was pipetted into each well and the microplate was immediately placed into a microplate reader preheated to 30° C. The microplate reader recorded the absorbance at 405 nm for each well once per minute for 60 minutes.

The PRT-201 samples were also tested for elastase activity in the SLAP assay. The SLAP substrate solution was prepared (4.5 mg/mL SLAP in 0.1 M Tris, pH 8.3) and prewarmed to 30° C. in a water bath. The 1 mg/mL PRT-201 samples were diluted 20× with water to 0.05 mg/mL. In triplicate, 10 microliters of each sample dilution was pipetted into a 96-well microplate. Using a multichannel pipettor, 300 microliters of SLAP substrate solution was pipetted into each well and the microplate was immediately placed into a microplate reader preheated to 30° C. The microplate reader recorded the absorbance at 405 nm for each well once per minute for 5 minutes.

The results of the BENZ and SLAP activity assays are respectively presented in Tables 11 and 12 below.

curve in the trypsin activity assay (<1.56 ng/mL). Additionally, the coefficients of regression for the triplicate hydrolysis reactions were poor (<0.8), further supporting the absence of trypsin activity in this auto-activated mature elastase protein. In contrast, the level of trypsin activity of the control trypsin-activate sample was determined to be 8.7 ng/mL.

6.10 Example 9: Drug Product Formulation

A study was conducted to identify lyophilized PRT-201 formulations that had the following characteristics: strong ionic strength buffer upon reconstitution; pH stability at 7.4; capable of one-step reconstitution; improved stability; and improved cake appearance. A screen conducted to assess various pre-formulation buffers and excipients. Formulations with sodium phosphate buffer and trehalose and mannitol as excipients were found to meet the study objectives. One specific lyophilized formulation having these characteristics produces upon reconstitution with water a 4 mg/mL pH 7.4 solution of PRT-201 in 25 mM sodium phosphate, 3% mannitol, and 1% trehalose.

TABLE 12

Mean trypsin activity, reported as TrypZean concentration equivalent (ng/mL).

| Description | No addition | Plus TrypZean spike (to 100 ng/mL) | Plus SBTI (to 10 ug/mL) | Plus TrypZean spike and SBTI |
|---|---|---|---|---|
| PRT-201 from clone 55M3 Vial #1 | <1.56 [a] | 118.7 | <1.56 [a] | <1.56 [a] |
| PRT-201 from clone 55M3 Vial #2 | <1.56 [a] | 122.4 | <1.56 [a] | <1.56 [a] |
| PRT-201 from clone 55M3 Vial #3 | <1.56 [a] | 122.8 | <1.56 [a] | <1.56 [a] |
| PRT-201 from trypsin activated clone | 8.7 | 130.0 | <1.56 [a] | <1.56 [a] |
| Buffer only (0.1M Tris, pH 8.3) | 1.3 | Not done | <1.56 [a] | Not done |
| TrypZean standard, 1.56 ng/mL | 2.7 | Not done | <1.56 [a] | Not done |
| TrypZean standard, 3.13 ng/mL | 3.7 | Not done | <1.56 [a] | Not done |
| TrypZean standard, 6.25 ng/mL | 6.5 | Not done | <1.56 [a] | Not done |
| TrypZean standard, 12.5 ng/mL | 11.2 | Not done | <1.56 [a] | Not done |
| Tr5ypZean standard, 25 ng/mL | 23.5 | Not done | <1.56 [a] | Not done |
| TrypZean standard, 50 ng/mL | 49.4 | Not done | <1.56 [a] | Not done |
| TrypZean standard, 100 ng/mL | 102.4 | Not done | <1.56 [a] | Not done |

[a] Coefficient of regression <0.8.

TABLE 13

Mean SLAP activity, reported as U/mg

| Description | No addition |
|---|---|
| PRT-201 from clone 55M3 Vial #1 | 34.9 |
| PRT-201 from clone 55M3 Vial #2 | 36.6 |
| PRT-201 from clone 55M3 Vial #3 | 35.7 |
| PRT-201 from trypsin activated clone | 32.1 |

The level of trypsin activity of PRT-201 from clone 201-55M3-003-VU was below the range of the standard Thus, in certain embodiments, a formulation of the disclosure contains sodium phosphate buffer and/or trehalose and/or mannitol. Such formulations can be modified, e.g., by the addition of sodium chloride, so as to produce a more isotonic solution upon reconstitution. Alternatively, the formulation can be modified following reconstitution so as to produce a more isotonic solution. In specific embodiments, the formulation is a unit dosage. In other embodiments, the formulation has a molarity ranging from 120 to 150 mmol/L, more preferably ranging from 135 to 140 mmol/L (for example 138 mmol/L).

SEQUENCE LISTING

| SEQ ID NO. | Description | Type of sequence | Sequence |
|---|---|---|---|
| 1 | Mature human elastase I, including first "valine" | Amino acid, single letter format, wherein: X = V or L | VVGGTEAGRNSWPSQISLQYRSGGSRYHTCGGTL IRQNWVMTAAHCVDYQKTFRVVAGDHNLSQNDGT EQYVSVQKIVVHPYWNSDNVAAGYDIALLRLAQSV TLNSYVQLGVLPQEGAILANNSPCYITGWGKTKTN GQLAQTLQQAYLPSVDYAICSSSSYWGSTVKNTM VCAGGDGVRSGCQGDSGGPLHCLVNGKYSXHGV TSFVSSRGCNVSRKPTVFTQVSAYISWINNVIASN |
| 2 | Mature human elastase I, minus first "valine" | Amino acid, single letter format, wherein: X = V or L | VGGTEAGRNSWPSQISLQYRSGGSRYHTCGGTLI RQNWVMTAAHCVDYQKTFRVVAGDHNLSQNDGT EQYVSVQKIVVHPYWNSDNVAAGYDIALLRLAQSV TLNSYVQLGVLPQEGAILANNSPCYITGWGKTKTN GQLAQTLQQAYLPSVDYAICSSSSYWGSTVKNTM VCAGGDGVRSGCQGDSGGPLHCLVNGKYSXHGV TSFVSSRGCNVSRKPTVFTQVSAYISWINNVIASN |
| 3 | Mature human elastase I, minus first two "valines" | Amino acid, single letter format, wherein: X = V or L | GGTEAGRNSWPSQISLQYRSGGSRYHTCGGTLIR QNWVMTAAHCVDYQKTFRVVAGDHNLSQNDGTE QYVSVQKIVVHPYWNSDNVAAGYDIALLRLAQSVT LNSYVQLGVLPQEGAILANNSPCYITGWGKTKTNG QLAQTLQQAYLPSVDYAICSSSSYWGSTVKNTMV CAGGDGVRSGCQGDSGGPLHCLVNGKYSXHGVT SFVSSRGCNVSRKPTVFTQVSAYISWINNVIASN |
| 4 | Mature human elastase I, with first "valine" substituted by "alanine" | Amino acid, single letter format, wherein: X = V or L | AVGGTEAGRNSWPSQISLQYRSGGSRYHTCGGTL IRQNWVMTAAHCVDYQKTFRVVAGDHNLSQNDGT EQYVSVQKIVVHPYWNSDNVAAGYDIALLRLAQSV TLNSYVQLGVLPQEGAILANNSPCYITGWGKTKTN GQLAQTLQQAYLPSVDYAICSSSSYWGSTVKNTM VCAGGDGVRSGCQGDSGGPLHCLVNGKYSXHGV TSFVSSRGCNVSRKPTVFTQVSAYISWINNVIASN |
| 5 | Mature human elastase I (isotype 2), including first "valine" | Amino acid, single letter format | VVGGTEAGRNSWPSQISLQYRSGGSRYHTCGGTL IRQNWVMTAAHCVDYQKTFRVVAGDHNLSQNDGT EQYVSVQKIVVHPYWNSDNVAAGYDIALLRLAQSV TLNSYVQLGVLPQEGAILANNSPCYITGWGKTKTN GQLAQTLQQAYLPSVDYAICSSSSYWGSTVKNTM VCAGGDGSSLWMPG |
| 6 | Engineered elastase proprotein no. 1 (pPROT42 variant) | Amino acid, single letter format, wherein X = V or L | TQDLPETNAAVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |
| 7 | Engineered elastase proprotein no. 2 | Amino acid, single letter format, wherein: X = V or L | TQDLPETNAAAVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |
| 8 | Engineered elastase proprotein no. 3 | Amino acid, single letter format, wherein: X = V or L | TQDLPETAAAVVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |
| 9 | Engineered elastase proprotein no. 4 | Amino acid, single letter format, wherein: X =V or L | TQDLPETNNAPVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |

| SEQ ID NO. | Description | Type of sequence | Sequence |
|---|---|---|---|
| 10 | Wild-type elastase proprotein no. 5 (produced from pPROT24 trypsin activated sequence) | Amino acid, single letter format, wherein: X = V or L | TQDLPETNARVVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |
| 11 | Consensus elastase recognition sequence 1 (Positions $Xaa_1$ = P3, $Xaa_2$ = P2, $Xaa_3$ = P1) | Amino acid, three letter format | $Xaa_1$ $Xaa_2$ $Xaa_3$<br>$Xaa_1$ = alanine, leucine, isoleucine, methionine, lysine, asparagine or valine<br>$Xaa_2$ = proline, alanine, leucine, isoleucine, glycine, valine, or threonine<br>$Xaa_3$ = alanine, leucine, valine, isoleucine, or serine |
| 12 | Consensus elastase recognition sequence 2 (Positions P3-P2-P1) | Amino acid, three letter format | $Xaa_1$ Pro $Xaa_2$<br>$Xaa_1$ = alanine, leucine, isoleucine, methionine, lysine, or valine<br>$Xaa_2$ = alanine, leucine, valine, isoleucine, or serine |
| 13 | Consensus elastase recognition sequence 3 (Positions P3-P2-P1) | Amino acid, three letter format | $Xaa_1$ $Xaa_2$ $Xaa_3$<br>$Xaa_1$ = asparagine or alanine<br>$Xaa_2$ = proline or alanine<br>$Xaa_3$ = alanine or leucine or valine |
| 14 | Elastase recognition sequence 1 (Positions P3-P2-P1) | Amino acid, three letter format | Ala Ala Ala |
| 15 | Elastase recognition sequence 2 (Positions P3-P2-P1) | Amino acid, three letter format | Asn Ala Ala |
| 16 | Elastase recognition sequence 3 (Positions P3-P2-P1) | Amino acid, three letter format | Asn Ala Pro |
| 17 | Wild-type trypsin recognition sequence (pPROT24) (Positions P3-P2-P1) | Amino acid, three letter format | Asn Ala Arg |
| 18 | Elastase recognition sequence 5 (Positions P3-P2-P1) | Amino acid, three letter format | Ala Pro Ala |
| 19 | Elastase recognition sequence 6 (Positions P3-P2-P1) | Amino acid, three letter format | Ala Ala Pro |
| 20 | Elastase recognition sequence 7 | Amino acid, three letter format | Asn Pro Ala |

| SEQ ID NO. | Description | Type of sequence | Sequence |
|---|---|---|---|
| | (Positions P3-P2-P1 of Variants 48 and 55) | | |
| 21 | Elastase recognition sequence 8 | Amino acid, three letter format | Leu Pro Ala |
| 22 | Human elastase activation sequence 1 (Wild-type) | Amino acid, three letter format | Thr Gln Asp Leu Pro Glu Thr Asn Ala Arg |
| 23 | Human elastase activation sequence 2 | Amino acid, three letter format | Thr Gln Asp Leu Pro Glu Thr Asn Ala Ala |
| 131 | pro-PROT-201 cleavage site | Amino acid, three letter format | Thr Asn Ala Arg Val Val Gly Gly |
| 25 | pPROT40 cleavage site | Amino acid, three letter format | Thr Ala Ala Ala Val Val Gly Gly |
| 26 | pPROT41 cleavage site | Amino acid, three letter format | Thr Asn Ala Ala Val Val Gly Gly |
| 27 | pPROT42 cleavage site | Amino acid, three letter format | Thr Asn Ala Val Val Gly Gly |
| 28 | pPROT43 cleavage site | Amino acid, three letter format | Thr Asn Ala Pro Val Val Gly Gly |
| 29 | pPROT44 cleavage site | Amino acid, three letter format | Thr Gly Ala Gly Ile Val Gly Gly |
| 30 | pPROT45 cleavage site | Amino acid, three letter format | Thr Val Pro Gly Val Val Gly Gly |
| 31 | pPROT46 cleavage site | Amino acid, three letter format | Thr Ala Pro Gly Val Val Gly Gly |
| 32 | pPROT47 cleavage site | Amino acid, three letter format | Thr Asn Pro Gly Val Val Gly Gly |
| 33 | Coding region of a human elastase-1 (NCBI Accession No. NM_001971) | Nucleotide | ACCCAGGACCTTCCGGAAACCAATGCCCGCGTA GTCGGAGGGACTGAGGCCGGGAGGAATTCCTG GCCCTCTCAGATTTCCCTCCAGTACCGGTCTGG AGGTTCCCGGTATCACACCTGTGGAGGGACCCT TATCAGACAGAACTGGGTGATGACAGCTGCTCA CTGCGTGGATTACCAGAAGACTTTCCGCGTGGT GGCTGGAGACCATAACCTGAGCCAGAATGATGG CACTGAGCAGTACGTGAGTGTGCAGAAGATCGT GGTGCATCCATACTGGAACAGCGATAACGTGGC TGCCGGCTATGACATCGCCCTGCTGCGCCTGGC CCAGAGCGTTACCCTCAATAGCTATGTCCAGCTG GGTGTTCTGCCCCAGGAGGGAGCCATCCTGGCT AACAACAGTCCCTGCTACATCACAGGCTGGGGC AAGACCAAGACCAATGGGCAGCTGGCCCAGACC CTGCAGCAGGCTTACCTGCCCTCTGTGGACTAC GCCATCTGCTCCAGCTCCTCCTACTGGGGCTCC ACTGTGAAGAACACCATGGTGTGTGCTGGTGGA GATGGAGTTCGCTCTGGATGCCAGGGTGACTCT GGGGGCCCCCTCCATTGCTTGGTGAATGGCAAG TATTCTGTCCATGGAGTGACCAGCTTTGTGTCCA GCCGGGGCTGTAATGTCTCCAGGAAGCCTACAG TCTTCACCCAGGTCTCTGCTTACATCTCCTGGAT AAATAATGTCATCGCCTCCAACTGA |
| 34 | Yeast alpha factor signal peptide | Amino acid, three letter format | Met-Arg-Phe-Pro-Ser-Ile-Phe-Thr-Ala-Val-Leu-Phe-Ala-Ala-Ser-Ser-Ala-Leu-Ala-Ala-Pro-Val-Asn-Thr- |

| SEQ ID NO. | Description | Type of sequence | Sequence |
|---|---|---|---|
| 35 | 20F primer | Nucleotide | Ggctcgagaaaagagaggctgaagctactcaggaccttccggaaac caatgcccgg |
| 36 | 24R primer | Nucleotide | gggccgcggcttatcagttggaggcgatgacat |
| 37 | pPROT42 P3 cleavage site variant elastase | Amino acid, single letter format, wherein: X = V or L | AAVVGGTEAGRNSWPSQISLQYRSGGSRYHTCG GTLIRQNWVMTAAHCVDYQKTFRVVAGDHNLSQN DGTEQYVSVQKIVVHPYWNSDNVAAGYDIALLRLA QSVTLNSYVQLGVLPQEGAILANNSPCYITGWGKT KTNGQLAQTLQQAYLPSVDYAICSSSSYWGSTVK NTMVCAGGDGVRSGCQGDSGGPLHCLVNGKYSX HGVTSFVSSRGCNVSRKPTVFTQVSAYISWINNVIA SN |
| 38 | pPROT42 P2 cleavage site variant elastase | Amino acid, single letter format, wherein: X = V or L | AVVGGTEAGRNSWPSQISLQYRSGGSRYHTCGGT LIRQNWVMTAAHCVDYQKTFRVVAGDHNLSQNDG TEQYVSVQKIVVHPYWNSDNVAAGYDIALLRLAQS VTLNSYVQLGVLPQEGAILANNSPCYITGWGKTKT NGQLAQTLQQAYLPSVDYAICSSSSYWGSTVKNT MVCAGGDGVRSGCQGDSGGPLHCLVNGKYSXHG VTSFVSSRGCNVSRKPTVFTQVSAYISWINNVIASN |
| 39 | Mature porcine pancreatic elastase I (from GenBank Accession P00772.1) | Amino acid, single letter format | VVGGTEAQRNSWPSQISLQYRSGSSWAHTCGGTL IRQNWVMTAAHCVDRELTFRVVVGEHNLNQNDGT EQYVGVQKIVVHPYWNTDDVAAGYDIALLRLAQSV TLNSYVQLGVLPRAGTILANNSPCYITGWGLTRTN GQLAQTLQQAYLPTVDYAICSSSSYWGSTVKNSM VCAGGDGVRSGCQGDSGGPLHCLVNGQYAVHGV TSFVSRLGCNVTRKPTVFTRVSAYISWINNVIASN |
| 40 | Elastase variant propeptide cleavage domain 40 | Amino acid, three letter format | Glu Thr Ala Ala Ala Val Val Gly |
| 41 | Elastase variant propeptide cleavage domain 41 | Amino acid, three letter format | Glu Thr Asn Ala Ala Ala Val Gly |
| 42 | Elastase variant propeptide cleavage domain 42 | Amino acid, three letter format | Glu Thr Asn Ala Ala Val Val Gly |
| 43 | Elastase variant propeptide cleavage domain 43 | Amino acid, three letter format | Glu Thr Asn Ala Pro Val Val Gly |
| 44 | Elastase variant propeptide cleavage domain 44 | Amino acid, three letter format | Glu Thr Gly Ala Gly Ile Val Gly |
| 45 | Elastase variant propeptide cleavage domain 45 | Amino acid, three letter format | Glu Thr Val Pro Gly Val Val Gly |
| 46 | Elastase variant propeptide cleavage domain 46 | Amino acid, three letter format | Glu Thr Ala Pro Gly Val Val Gly |

| SEQ ID NO. | Description | Type of sequence | Sequence |
|---|---|---|---|
| 47 | Elastase variant propeptide cleavage domain 47 | Amino acid, three letter format | Glu Thr Asn Pro Gly Val Val Gly |
| 48 | Elastase variant propeptide cleavage domain 48 | Amino acid, three letter format | Glu Thr Asn Pro Ala Val Val Gly |
| 49 | Elastase variant propeptide cleavage domain 49 | Amino acid, three letter format | Glu Thr Asn His Ala Val Val Gly |
| 50 | Yeast alpha-mating factor signal peptide, propeptide, and spacer sequence 1 | Amino acid, three letter format | Met-Arg-Phe-Pro-Ser-Ile-Phe-Thr-Ala-Val-Leu-Phe-Ala-Ala-Ser-Ser-Ala-Leu-Ala-Ala-Pro-Val-Asn-Thr-Thr-Thr-Glu-Asp-Glu-Thr-Ala-Gln-Ile-Pro-Ala-Glu-Ala-Val-Ile-Gly-Tyr-Leu-Asp-Leu-Glu-Gly-Asp-Phe-Asp-Val-Ala-Val-Leu-Pro-Phe-Ser-Asn-Ser-Thr-Asn-Asn-Asn-Gly-Leu-Leu-Phe-Ile-Asn-Thr-Thr-Ile-Ala-Ser-Ile-Ala-Ala-Lys-Glu-Glu-Gly-Val-Ser-Leu-Asp-Lys-Arg-Glu-Ala-Glu-Ala |
| 51 | Yeast alpha-mating factor signal peptide and propeptide sequence 2 | Amino acid, three letter format | Met-Arg-Phe-Pro-Ser-Ile-Phe-Thr-Ala-Val-Leu-Phe-Ala-Ala-Ser-Ser-Ala-Leu-Ala-Ala-Pro-Val-Asn-Thr-Thr-Thr-Glu-Asp-Glu-Thr-Ala-Gln-Ile-Pro-Ala-Glu-Ala-Val-Ile-Gly-Tyr-Leu-Asp-Leu-Glu-Gly-Asp-Phe-Asp-Val-Ala-Val-Leu-Pro-Phe-Ser-Asn-Ser-Thr-Asn-Asn-Asn-Gly-Leu-Leu-Phe-Ile-Asn-Thr-Thr-Ile-Ala-Ser-Ile-Ala-Ala-Lys-Glu-Glu-Gly-Val-Ser-Leu-Asp- |
| 52 | Elastase variant propeptide cleavage domain 52 | Amino acid, three letter format | Glu Thr Lys Pro Ala Val Val Gly |
| 53 | Elastase variant propeptide cleavage domain 53 | Amino acid, three letter format | Glu Thr His Pro Ala Val Val Gly |
| 54 | Elastase variant propeptide cleavage domain 54 | Amino acid, three letter format | Glu His Asn Pro Ala Val Val Gly |
| 55 | Elastase variant propeptide cleavage domain 55 | Amino acid, three letter format | His Thr Asn Pro Ala Val Val Gly |
| 56 | Elastase variant propeptide cleavage domain 56 | Amino acid, three letter format | Pro Thr His Pro Ala Val Val Gly |
| 57 | Elastase variant propeptide cleavage domain 57 | Amino acid, three letter format | Pro Thr Asn Pro Ala Val Val Gly |
| 58 | Elastase variant propeptide | Amino acid, three letter format | His Thr His Pro Ala Val Val Gly |

| SEQ ID NO. | Description | Type of sequence | Sequence |
|---|---|---|---|
| | cleavage domain 58 | | |
| 59 | Elastase variant propeptide cleavage domain 59 | Amino acid, three letter format | Glu Thr Phe Pro Ala Val Val Gly |
| 60 | Elastase variant propeptide cleavage domain 60 | Amino acid, three letter format | His Thr Phe Pro Ala Val Val Gly |
| 61 | Elastase variant propeptide cleavage domain 61 | Amino acid, three letter format | Gly Thr Phe Pro Ala Val Val Gly |
| 62 | Elastase variant propeptide cleavage domain 62 | Amino acid, three letter format | His Thr Gly Pro Ala Val Val Gly |
| 63 | Elastase variant propeptide cleavage domain 63 | Amino acid, three letter format | His Thr Lys Pro Ala Val Val Gly |
| 64 | Elastase proenzyme with variant cleavage domain 48 | Amino acid, single letter format, wherein: X = V or L | TQDLPETNPAVVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |
| 65 | Elastase proenzyme with variant cleavage domain 49 | Amino acid, single letter format, wherein: X = V or L | TQDLPETNHAVVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |
| 66 | Elastase proenzyme with variant cleavage domain 52 | Amino acid, single letter format, wherein: X = V or L | TQDLPETKPAVVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |
| 67 | Elastase proenzyme with variant cleavage domain 53 | Amino acid, single letter format, wherein: X = V or L | TQDLPETHPAVVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |
| 68 | Elastase proenzyme with variant cleavage domain 54 | Amino acid, single letter format, wherein: X = V or L | TQDLPEHNPAVVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV |

| SEQ ID NO. | Description | Type of sequence | Sequence |
|---|---|---|---|
| | | | NGKYSXHGVTSFVSSRGCNVSRKPTVFTQVSAYIS WINNVIASN |
| 69 | Elastase proenzyme with variant cleavage domain 55 | Amino acid, single letter format, wherein: X = V or L | TQDLPHTNPAVVGGTEAGRNSWPSQISLQYRSGG SRYHTCGGTLIRQNWVMTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTQVSAYIS WINNVIASN |
| 70 | Wild-type elastase + AlaArg cleavage variant | Amino acid, single letter format, wherein: X = V or L | ARVVGGTEAGRNSWPSQISLQYRSGGSRYHTCG GTLIRQNWVMTAAHCVDYQKTFRVVAGDHNLSQN DGTEQYVSVQKIVVHPYWNSDNVAAGYDIALLRLA QSVTLNSYVQLGVLPQEGAILANNSPCYITGWGKT KTNGQLAQTLQQAYLPSVDYAICSSSSYWGSTVK NTMVCAGGDGVRSGCQGDSGGPLHCLVNGKYSX HGVTSFVSSRGCNVSRKPTVFTQVSAYISWINNVIA SN |
| 71 | Wild-type elastase + Arg cleavage variant | Amino acid, single letter format, wherein: X = V or L | RVVGGTEAGRNSWPSQISLQYRSGGSRYHTCGG TLIRQNWVMTAAHCVDYQKTFRVVAGDHNLSQND GTEQYVSVQKIVVHPYWNSDNVAAGYDIALLRLAQ SVTLNSYVQLGVLPQEGAILANNSPCYITGWGKTK TNGQLAQTLQQAYLPSVDYAICSSSSYWGSTVKNT MVCAGGDGVRSGCQGDSGGPLHCLVNGKYSXHG VTSFVSSRGCNVSRKPTVFTQVSAYISWINNVIASN |
| 72 | Variant 48 human elastase activation peptide | Amino acid, three letter format | Thr Gln Asp Leu Pro Glu Thr Asn Pro Ala |
| 73 | Variant 55 human elastase activation peptide | Amino acid, three letter format | Thr Gln Asp Leu Pro His Thr Asn Pro Ala |
| 74 | Human elastase cleavage domain consensus sequence; corresponds to residues P5, P4, P3, P2, P1, P'1, P'2, and P'3 of an elastase cleavage domain mutagenesis primer | Amino acid, three letter format | Xaa$_1$ Xaa$_2$ Xaa$_3$ Xaa$_4$ Xaa$_5$ Xaa$_6$ Xaa$_7$ Xaa$_8$<br>Xaa$_1$ = glutamate, histidine, proline, glycine, asparagine, lysine, or alanine<br>Xaa$_2$ = threonine, alanine, proline or histidine<br>Xaa$_3$ = alanine, leucine, isoleucine, methionine, lysine, asparagine or valine<br>Xaa$_4$ = proline, alanine, leucine, isoleucine, glycine, valine, or threonine<br>Xaa$_5$ = alanine, leueine, valine, isoleucine, or serine<br>Xaa$_6$ = alanine, leucine, valine, isoleucine or serine<br>Xaa$_7$ = glycine, alanine, or valine<br>Xaa$_8$ = valine, threonine, phenylalanine, tyrosine, or tryptophan |
| 75 | PCR mutagenesis primer | Nucleic Acid | ATC TAC GTA GTC GGA GGG ACT GAG GCC |
| 76 | PCR mutagenesis primer | Nucleic Acid | gtc gac aag ctt atc agt tgg agg cga t |
| 77 | Mature ELA1 C-terminal variant of Talas et al. | Protein, single letter format | VVGGTEAGRNSWPSQISLQYRSGGSRYHTCGGTL IRQNWVMTAAHCVDYQKTFRVVAGDHNLSQNDGT EQYVSVQKIVVHPYWNSDNVAAGYDIALLRLAQSV TLNSYVQLGVLPQEGAILANNSPCYITGWGKTKTN GQLAQTLQQAYLPSVDYAICSSSSYWGSTVKNTM VCAGGDGVRSGCQGDSGGPPPLLGEWQVFSPW SDQLCVQPGL |

| SEQ ID NO. | Description | Type of sequence | Sequence |
|---|---|---|---|
| 78 | Mature ELA-1 variants | Protein, single letter format, wherein:<br>B = W or R<br>J = M or V<br>X = V or L<br>Z = Q or R | VVGGTEAGRNSWPSQISLQYRSGGSBYHTCGGTL<br>IRQNWVJTAAHCVDYQKTFRVVAGDHNLSQNDGT<br>EQYVSVQKIVVHPYWNSDNVAAGYDIALLRLAQSV<br>TLNSYVQLGVLPQEGAILANNSPCYITGWGKTKTN<br>GQLAQTLQQAYLPSVDYAICSSSSYWGSTVKNTM<br>VCAGGDGVRSGCQGDSGGPLHCLVNGKYSXHGV<br>TSFVSSRGCNVSRKPTVFTZVSAYISWINNVIASN |
| 79 | Activation peptide variants (wild-type, trypsin cleavable) | Protein, single letter format, wherein<br>U = Q or H | TUDLPETNAR |
| 80 | Activation peptide variant consensus | Protein, three letter format | Thr Xaa$_1$ Asp Leu Pro Xaa$_2$ Xaa$_3$ Xaa$_4$ Xaa$_5$ Xaa$_6$<br>Xaa$_1$ = glutamine or histidine<br>Xaa$_2$ = glutamate, histidine, proline, glycine, asparagine, lysine, or alanine<br>Xaa$_3$ = threonine, alanine, proline or histidine<br>Xaa$_4$ = alanine, leucine, isoleucine, methionine, lysine, asparagine or valine<br>Xaa$_5$ = proline, alanine, leucine, isoleucine, glycine, valine, or threonine<br>Xaa$_6$ = alanine, leucine, valine, isoleucine, or serine |
| 81 | Coding region of ELA-1.2A | Nucleotide | ACTCAGGACCTTCCGGAAACCAATGCCCGGGTA<br>GTCGGAGGGACTGAGGCCGGGAGGAACTCCTG<br>GCCCTCTCAGATTTCCCTCCAGTACCGGTCTGG<br>AGGTTCCTGGTATCACACCTGTGGAGGGACCCT<br>TATCAGACAGAACTGGGTGATGACAGCTGCACA<br>CTGCCGTGGATTACCAGAAGACTTTCCGCGTGGT<br>GGCTGGAGACCATAACCTGAGCCAGAATGATGG<br>CACTGAGCAGTACGTGAGTGTGCAGAAGATCGT<br>GGTGCATCCATACTGGAACAGCGATAACGTGGC<br>TGCAGGCTATGACATCGCCCTGCTGCGCCTGGC<br>CCAGAGCGTTACCCTCAATAGCTATGTCCAGCTG<br>GGTGTTCTGCCCCAGGAGGGAGCCATCCTGGCT<br>AACAACAGTCCCTGCTACATCACAGGCTGGGGC<br>AAGACCAAGACCAATGGGCAGCTGGCCCAGACC<br>TTGCAGCAGGCTTACCTGCCCTCTGTGGACTAT<br>GCCATCTGCTCCAGCTCCTCCTACTGGGGCTCC<br>ACTGTGAAGAACACTATGGTGTGTGCTGGTGGA<br>GATGGAGTTCGCTCTGGATGTCAGGGTGACTCT<br>GGGGGCCCCCTCCATTGCTTGGTGAATGGCAAG<br>TATTCTCTTCATGGAGTGACCAGCTTTGTGTCCA<br>GCCGGGGCTGTAATGTCTCTAGAAAGCCTACAG<br>TCTTCACACGGGTCTCTGCTTACATCTCCTGGAT<br>AAATAATGTCATCGCCTCCAACTGATAA |
| 82 | Translation product of ELA-1.2A (trypsin activated pPROT24 sequence) | Protein, single letter format | TQDLPETNARVVGGTEAGRNSWPSQISLQYRSGG<br>SWYHTCGGTLIRQNWVMTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSLHGVTSFVSSRGCNVSRKPTVFTRVSAYIS<br>WINNVIASN |
| 83 | Variants of translation product of ELA-1.2A (trypsin activated pPROT24 sequence) | Protein, single letter format, wherein:<br>U = Q or H<br>B = W or R<br>J = M or V<br>X = V or L<br>Z = Q or R | TUDLPETNARVVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSXHGVTSFVSSRGCNVSRKPTVFTZVSAYIS<br>WINNVIASN |
| 84 | Mature human elastase I, including first "valine" | Amino acid, single letter format, wherein:<br>B = W or R<br>J = M or V<br>X = V or L<br>Z = Q or R | VVGGTEAGRNSWPSQISLQYRSGGSBYHTCGGTL<br>IRQNWVJTAAHCVDYQKTFRVVAGDHNLSQNDGT<br>EQYVSVQKIVVHPYWNSDNVAAGYDIALLRLAQSV<br>TLNSYVQLGVLPQEGAILANNSPCYITGWGKTKTN<br>GQLAQTLQQAYLPSVDYAICSSSSYWGSTVKNTM<br>VCAGGDGVRSGCQGDSGGPLHCLVNGKYSXHGV<br>TSFVSSRGCNVSRKPTVFTZVSAYISWINNVIASN |

| SEQ ID NO. | Description | Type of sequence | Sequence |
|---|---|---|---|
| 85 | Mature human elastase I, minus first "valine" | Amino acid, single letter format, wherein:<br>B = W or R<br>J = M or V<br>X = V or L<br>Z = Q or R | VGGTEAGRNSWPSQISLQYRSGGSBYHTCGGTLI<br>RQNWVJTAAHCVDYQKTFRVVAGDHNLSQNDGTE<br>QYVSVQKIVVHPYWNSDNVAAGYDIALLRLAQSVT<br>LNSYVQLGVLPQEGAILANNSPCYITGWGKTKTNG<br>QLAQTLQQAYLPSVDYAICSSSSYWGSTVKNTMV<br>CAGGDGVRSGCQGDSGGPLHCLVNGKYSXHGVT<br>SFVSSRGCNVSRKPTVFTZVSAYISWINNVIASN |
| 86 | Mature human elastase I, minus first two "valines" | Amino acid, single letter format, wherein:<br>B = W or R<br>J = M or V<br>X = V or L<br>Z = Q or R | GGTEAGRNSWPSQISLQYRSGGSBYHTCGGTLIR<br>QNWVJTAAHCVDYQKTFRVVAGDHNLSQNDGTE<br>QYVSVQKIVVHPYWNSDNVAAGYDIALLRLAQSVT<br>LNSYVQLGVLPQEGAILANNSPCYITGWGKTKTNG<br>QLAQTLQQAYLPSVDYAICSSSSYWGSTVKNTMV<br>CAGGDGVRSGCQGDSGGPLHCLVNGKYSXHGVT<br>SFVSSRGCNVSRKPTVFTZVSAYISWINNVIASN |
| 87 | Mature human elastase I, with first "valine" substituted by "alanine" | Amino acid, single letter format, wherein:<br>B = W or R<br>J = M or V<br>X = V or L<br>Z = Q or R | AVGGTEAGRNSWPSQISLQYRSGGSBYHTCGGTL<br>IRQNWVJTAAHCVDYQKTFRVVAGDHNLSQNDGT<br>EQYVSVQKIVVHPYWNSDNVAAGYDIALLRLAQSV<br>TLNSYVQLGVLPQEGAILANNSPCYITGWGKTKTN<br>GQLAQTLQQAYLPSVDYAICSSSSYWGSTVKNTM<br>VCAGGDGVRSGCQGDSGGPLHCLVNGKYSXHGV<br>TSFVSSRGCNVSRKPTVFTZVSAYISWINNVIASN |
| 88 | Engineered elastase proprotein no. 1 (pPROT42 variant) | Amino acid, single letter format, wherein:<br>U = Q or H<br>B = W or R<br>J = M or V<br>X = V or L<br>Z = Q or R | TUDLPETNAAVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSXHGVTSFVSSRGCNVSRKPTVFTZVSAYIS<br>WINNVIASN |
| 89 | Engineered elastase proprotein no. 2 | Amino acid, single letter format, wherein:<br>U = Q or H<br>B = W or R<br>J = M or V<br>X = V or L<br>Z = Q or R | TUDLPETNAAAVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSXHGVTSFVSSRGCNVSRKPTVFTZVSAYIS<br>WINNVIASN |
| 90 | Engineered elastase proprotein no. 3 | Amino acid, single letter format, wherein:<br>U = Q or H<br>B = W or R<br>J = M or V<br>X = V or L<br>Z = Q or R | TUDLPETAAAVVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSXHGVTSFVSSRGCNVSRKPTVFTZVSAYIS<br>WINNVIASN |
| 91 | Engineered elastase proprotein no. 4 | Amino acid, single letter format, wherein:<br>U = Q or H<br>B = W or R<br>J = M or V<br>X = V or L<br>Z = Q or R | TUDLPETNNAPVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSXHGVTSFVSSRGCNVSRKPTVFTZVSAYIS<br>WINNVIASN |
| 92 | Engineered elastase proprotein no. 5 (pPROT24 trypsin activated sequence) | Amino acid, single letter format, wherein:<br>U = Q or H<br>B = W or R<br>J = M or V<br>X = V or L<br>Z = Q or R | TUDLPETNARVVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSXHGVTSFVSSRGCNVSRKPTVFTZVSAYIS<br>WINNVIASN |

-continued

| SEQ ID NO. | Description | Type of sequence | Sequence |
|---|---|---|---|
| 93 | Consensus elastase recognition sequence 2 (Positions P3-P2-P1) | Amino acid, three letter format | $Xaa_1$ Pro $Xaa_2$<br>$Xaa_1$ = alanine, leucine, isoleucine, methionine, lysine, asparagine or valine<br>$Xaa_2$ = alanine, leucine, valine, isoleucine, or serine |
| 94 | pPROT42 P3 cleavage site variant elastase | Amino acid, single letter format, wherein:<br>B = W or R<br>J = M or V<br>X = V or L<br>Z = Q or R | AAVVGGTEAGRNSWPSQISLQYRSGGSBYHTCG<br>GTLIRQNWVJTAAHCVDYQKTFRVVAGDHNLSQN<br>DGTEQYVSVQKIVVHPYWNSDNVAAGYDIALLRLA<br>QSVTLNSYVQLGVLPQEGAILANNSPCYITGWGKT<br>KTNGQLAQTLQQAYLPSVDYAICSSSSYWGSTVK<br>NTMVCAGGDGVRSGCQGDSGGPLHCLVNGKYSX<br>HGVTSFVSSRGCNVSRKPTVFTZVSAYISWINNVIA<br>SN |
| 95 | pPROT42 P2 cleavage site variant elastase | Amino acid, single letter format, wherein:<br>B = W or R<br>J = M or V<br>X = V or L<br>Z = Q or R | AVVGGTEAGRNSWPSQISLQYRSGGSBYHTCGGT<br>LIRQNWVJTAAHCVDYQKTFRVVAGDHNLSQNDG<br>TEQYVSVQKIVVHPYWNSDNVAAGYDIALLRLAQS<br>VTLNSYVQLGVLPQEGAILANNSPCYITGWGKTKT<br>NGQLAQTLQQAYLPSVDYAICSSSSYWGSTVKNT<br>MVCAGGDGVRSGCQGDSGGPLHCLVNGKYSXHG<br>VTSFVSSRGCNVSRKPTVFTZVSAYISWINNVIASN |
| 96 | Yeast alpha-mating factor signal peptide, propeptide, and spacer sequence | Amino acid, three letter format | Met-Arg-Phe-Pro-Ser-Ile-Phe-Thr-Ala-Val-Leu-Phe-<br>Ala-Ala-Ser-Ser-Ala-Leu-Ala-Ala-Pro-Val-Asn-Thr-<br>Thr-Thr-Glu-Asp-Glu-Thr-Ala-Gln-lle-Pro-Ala-Glu-<br>Ala-Val-Ile-Gly-Tyr-Ser-Asp-Leu-Glu-Gly-Asp-Phe-<br>Asp-Val-Ala-Val-Leu-Pro-Phe-Ser-Asn-Ser-Thr-Asn-<br>Asn-Gly-Leu-Leu-Phe-Ile-Asn-Thr-Thr-Ile-Ala-Ser-Ile-<br>Ala-Ala-Lys-Glu-Glu-Gly-Val-Ser-Leu-Glu-Lys-Arg-<br>Glu-Ala-Glu-Ala |
| 97 | Yeast alpha-mating factor signal peptide and propeptide sequence | Amino acid, three letter format | Met-Arg-Phe-Pro-Ser-Ile-Phe-Thr-Ala-Val-Leu-Phe-<br>Ala-Ala-Ser-Ser-Ala-Leu-Ala-Ala-Pro-Val-Asn-Thr-<br>Thr-Thr-Glu-Asp-Glu-Thr-Ala-Gln-lle-Pro-Ala-Glu-<br>Ala-Val-Ile-Gly-Tyr-Ser-Asp-Leu-Glu-Gly-Asp-Phe-<br>Asp-Val-Ala-Val-Leu-Pro-Phe-Ser-Asn-Ser-Thr-Asn-<br>Asn-Gly-Leu-Leu-Phe-Ile-Asn-Thr-Thr-Ile-Ala-Ser-Ile-<br>Ala-Ala-Lys-Glu-Glu-Gly-Val-Ser-Leu-Glu- |
| 98 | Elastase proenzyme with variant cleavage domain 48 | Amino acid, single letter format, wherein:<br>U = Q or H<br>B = W or R<br>J = M or V<br>X = V or L<br>Z = Q or R | TUDLPETNPAVVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSXHGVTSFVSSRGCNVSRKPTVFTZVSAYIS<br>WINNVIASN |
| 99 | Elastase proenzyme with variant cleavage domain 49 | Amino acid, single letter format, wherein:<br>U = Q or H<br>B = W or R<br>J = M or V<br>X = V or L<br>Z = Q or R | TUDLPETNHAVVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSXHGVTSFVSSRGCNVSRKPTVFTZVSAYIS<br>WINNVIASN |
| 100 | Elastase proenzyme with variant cleavage domain 52 | Amino acid, single letter format, wherein:<br>U = Q or H<br>B = W or R<br>J = M or V<br>X = V or L<br>Z = Q or R | TUDLPETKPAVVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV<br>NGKYSXHGVTSFVSSRGCNVSRKPTVFTZVSAYIS<br>WINNVIASN |
| 101 | Elastase proenzyme with variant cleavage domain 53 | Amino acid, single letter format, wherein:<br>U = Q or H<br>B = W or R<br>J = M or V<br>X = V or L | TUDLPETHPAVVGGTEAGRNSWPSQISLQYRSGG<br>SBYHTCGGTLIRQNWVJTAAHCVDYQKTFRVVAG<br>DHNLSQNDGTEQYVSVQKIVVHPYWNSDNVAAGY<br>DIALLRLAQSVTLNSYVQLGVLPQEGAILANNSPCYI<br>TGWGKTKTNGQLAQTLQQAYLPSVDYAICSSSSY<br>WGSTVKNTMVCAGGDGVRSGCQGDSGGPLHCLV |

| SEQ ID NO. | Description | Type of sequence | Sequence |
|---|---|---|---|
| | | Z = Q or R | NGKYSXHGVTSFVSSRGCNVSRKPTVFTZVSAYIS WINNVIASN |
| 102 | Elastase proenzyme with variant cleavage domain 54 | Amino acid, single letter format, wherein: U = Q or H B = W or R J = M r X = V or L Z = Q or R | TUDLPEHNPAVVGGTEAGRNSWPSQISLQYRSGG SBYHTCGGTLIRQNWVJTAAHCVDYQKTFRVVAG DHNLSQNDGTEQYVSVQKIVVHPYWNSDNVAAGY DIALLRLAQSVTLNSYVQLGVLPQEGAILANNSPCYI VTGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTZVSAYIS WINNVIASN |
| 103 | Elastase proenzyme with variant cleavage domain 55 | Amino acid, single letter format, wherein: U = Q or H B = W or R J = M or V X = V or L Z = Q or R | TUDLPHTNPAVVGGTEAGRNSWPSQISLQYRSGG SBYHTCGGTLIRQNWVJTAAHCVDYQKTFRVVAG DHNLSQNDGTEQYVSVQKIVVHPYWNSDNVAAGY DIALLRLAQSVTLNSYVQLGVLPQEGAILANNSPCYI TGWGKTKTNGQLAQTLQQAYLPSVDYAICSSSSY WGSTVKNTMVCAGGDGVRSGCQGDSGGPLHCLV NGKYSXHGVTSFVSSRGCNVSRKPTVFTZVSAYIS WINNVIASN |
| 104 | Wild-type elastase + AlaArg cleavage variant | Amino acid, single letter format, wherein: B = W or R J = M or V X = V or L Z = Q or R | ARVVGGTEAGRNSWPSQISLQYRSGGSBYHTCG GTLIRQNWVJTAAHCVDYQKTFRVVAGDHNLSQN DGTEQYVSVQKIVVHPYWNSDNVAAGYDIALLRLA QSVTLNSYVQLGVLPQEGAILANNSPCYITGWGKT KTNGQLAQTLQQAYLPSVDYAICSSSSYWGSTVK NTMVCAGGDGVRSGCQGDSGGPLHCLVNGKYSX HGVTSFVSSRGCNVSRKPTVFTZVSAYISWINNVIA SN |
| 105 | Wild-type elastase + Arg cleavage variant | Amino acid, single letter format, wherein: B = W or R J = M or V X = V or L Z = Q or R | RVVGGTEAGRNSWPSQISLQYRSGGSBYHTCGGT LIRQNWVJTAAHCVDYQKTFRVVAGDHNLSQNDG TEQYVSVQKIVVHPYWNSDNVAAGYDIALLRLAQS VTLNSYVQLGVLPQEGAILANNSPCYITGWGKTKT NGQLAQTLQQAYLPSVDYAICSSSSYWGSTVKNT MVCAGGDGVRSGCQGDSGGPLHCLVNGKYSXHG VTSFVSSRGCNVSRKPTVFTZVSAYISWINNVIASN |
| 106 | Mature human elastase 1, minus N terminal "VVGG" sequence (SEQ ID NO: 127) | Amino acid, single letter format, wherein: B = W or R J = M or V X = V or L Z = Q or R | TEAGRNSWPSQISLQYRSGGSBYHTCGGTLIRQN WVJTAAHCVDYQKTFRVVAGDHNLSQNDGTEQYV SVQKIVVHPYWNSDNVAAGYDIALLRLAQSVTLNS YVQLGVLPQEGAILANNSPCYITGWGKTKTNGQLA QTLQQAYLPSVDYAICSSSSYWGSTVKNTMVCAG GDGVRSGCQGDSGGPLHCLVNGKYSXHGVTSFV SSRGCNVSRKPTVFTZVSAYISWINNVIASN |
| 107 | Mature human elastase 1, minus N terminal "VVGGTE" sequence (SEQ ID NO: 128) | Amino acid, single letter format, wherein: B = W or R J = M or V X = V or L Z = Q or R | AGRNSWPSQISLQYRSGGSBYHTCGGTLIRQNWV JTAAHCVDYQKTFRVVAGDHNLSQNDGTEQYVSV QKIVVHPYWNSDNVAAGYDIALLRLAQSVTLNSYV QLGVLPQEGAILANNSPCYITGWGKTKTNGQLAQT LQQAYLPSVDYAICSSSSYWGSTVKNTMVCAGGD GVRSGCQGDSGGPLHCLVNGKYSXHGVTSFVSS RGCNVSRKPTVFTZVSAYISWINNVIASN |
| 108 | Mature human elastase I, minus N terminal "VVGGTEAGR" sequence (SEQ ID NO: 129) | Amino acid, single letter format, wherein: B = W or R J = M or V X = V or L Z = Q or R | NSWPSQISLQYRSGGSBYHTCGGTLIRQNWVJTA AHCVDYQKTFRVVAGDHNLSQNDGTEQYVSVQKI VVHPYWNSDNVAAGYDIALLRLAQSVTLNSYVQLG VLPQEGAILANNSPCYITGWGKTKTNGQLAQTLQQ AYLPSVDYAICSSSSYWGSTVKNTMVCAGGDGVR SGCQGDSGGPLHCLVNGKYSXHGVTSFVSSRGC NVSRKPTVFTZVSAYISWINNVIASN |
| 109 | FIG. 1A sequence | Nucleic Acid | GAATTCAGTACTCAGGACCTTCCGGAAACCAATG CCCGGGTAGTCGGAGGGACTGAGGCCGGGAGG AACTCCTGGCCCTCTCAGATTTCCCTCCAGTACC GGTCTGGAGGTTCCTGGTATCACACCTGTGGAG GGACCCTTATCAGACAGAACTGGGTGATGACAG CTGCACACTGCGTGGATTACCAGAAGACTTTCC GCGTGGTGGCTGGAGACCATAACCTGAGCCAGA ATGATGGCACTGAGCAGTACGTGAGTGTGCAGA AGATCGTGGTGCATCCATACTGGAACAGCGATA ACGTGGCTGCAGGCTATGACATCGCCCTGCTGC |

-continued

| SEQ ID NO. | Description | Type of sequence | Sequence |
|---|---|---|---|
| | | | GCCTGGCCCAGAGCGTTACCCTCAATAGCTATG TCCAGCTGGGTGTTCTGCCCCAGGAGGGAGCCA TCCTGGCTAACAACAGTCCCTGCTACATCACAGG CTGGGGCAAGACCAAGACCAATGGGCAGCTGG CCCAGACCTTGCAGCAGGCTTACCTGCCCTCTG TGGACTATGCCATCTGCTCCAGCTCCTCCTACTG GGGCTCCACTGTGAAGAACACTATGGTGTGTGC TGGTGGAGATGGAGTTCGCTCTGGATGTCAGGG TGACTCTGGGGGCCCCCTCCATTGCTTGGTGAA TGGCAAGTATTCTCTTCATGGAGTGACCAGCTTT GTGTCCAGCCGGGGCTGTAATGTCTCTAGAAAG CCTACAGTCTTCACACGGGTCTCTGCTTACATCT CCTGGATAAATAATGTCATCGCCTCCAACTGATA AGCTTGGATCCGTCGAC |
| 110 | FIG. 1A sequence | Amino Acid, single letter format | MKRILAIHQAMEGAPRVTLTSRANSISTSTHHSVLH SGAPVGGAGADGIVHRGQVSLLQGLGQLPIGLGLA PACDVAGTVVSQDGSLLGQNTQLDIAIEGNALGQA QQGDVIACSHVIAVPVWMHHDLLHTHVLLSAIILAQ VMVSSHHAESLLVIHAVCSCHHPVLSDKGPSTGVI PGTSRPVLEGNLRGPGVPPGLSPSDYPGIGFRKVL S |
| 111 | FIG. 1B sequence | Nucleic Acid | ACTATTGCCAGCATTGCTGCTAAAGAAGAAGGG GTATCTCTCGAGAAAAGAGAGGCTGAAGCTACT CAGGACCTTCCGGAAACCAATGCCCGGGTAGTC GGGGGG |
| 112 | FIG. 1B sequence | Amino Acid, three letter format | THR ILE ALA SER ILE ALA ALA LYS GLU GLU GLY VAL SER LEU GLU LYS ARG GLU ALA GLU ALA THR GLN ASP LEU PRO GLU THR ASN ALA ARG VAL VAL GLY GLY |
| 113 | FIG. 13 sequence | Nucleic Acid | CCGCGGACCCAGGACTTTCCAGAAACCAACGCC CGGGTAGTTGGAGGGACCGAGGCTCAGAGGAA TTCTTGGCCATCTCAGATTTCCCTCCAGTACCGG TCTGGAAGTTCGTGGGCTCACACCTGTGGAGGG ACCCTCATCAGGCAGAACTGGGTGATGACAGCC GCTCACTGCGTGGACAGAGAGTTGACCTTCCGT GTGGTGGTTGGAGAGCACAACCTGAACCAGAAC GATGGCACCGAGCAGTACGTGGGGGTGCAGAA GATCGTGGTGCATCCCTACTGGAACACCGACGA CGTGGCTGCAGGCTATGACATCGCCCTGCTGCG CCTGGCCCAGAGTGTAACCCTCAACAGCTACGT CCAGCTGGGTGTTCTGCCAAGGGCTGGGACCAT CCTGGCTAACAACAGTCCCTGCTACATCACAGG GTGGGGCCTGACCAGGACCAATGGGCAGCTGG CCCAGACCCTGCAGCAGGCTTACCTGCCCACCG TGGACTACGCCATCTGCTCCAGCTCCTCGTACT GGGGCTCCACCGTGAAGAACAGCATGGTGTGCG CCGGAGGGGACGGAGTTCGCTCTGGATGTCAG GGTGATTCTGGGGGCCCCCTTCATTGCTTGGTG AATGGTCAGTATGCTGTCCACGGTGTAACCAGCT TCGTGTCCCGCCTGGGCTGTAATGTCACCAGGA AGCCCACAGTCTTCACCAGGGTCTCTGCTTACAT CTCTTGGATAAATAACGTCATTGCCAGCAACTGA TAATCTAGA |
| 114 | FIG. 14 sequence | Amino Acid, single letter format | TQDFPETNARVVGGTEAQRNSWPSQISLQYRSGS SWAHTCGGTLIRQNWVMTAAHCVDRELTFRVVVG EHNLNQNDGTEQYVGVQKIVVHPYWNTDDVAAGY DIALLRLAQSVTLNSYVQLGVLPRAGTILANNSPCYI TGWGLTRTNGQLAQTLQQAYLPTVDYAICSSSSY WGSTVKNSMVCAGGDGVRSGCQGDSGGPLHCLV NGQYAVHGVTSFVSRLGCNVTRKPTVFTRVSAYIS WINNVIASN |
| 115 | Cleavage domain sequence of trypsin-activated pPROT101-24-V | Amino Acid, three letter format | Phe Pro Glu Thr Asn Ala Arg Val Val Gly |

| SEQ ID NO. | Description | Type of sequence | Sequence |
|---|---|---|---|
| 116 | Cleavage domain sequence of auto-activated pPROT101-42-V | Amino Acid, three letter format | Phe Pro Glu Thr Asn Ala Ala Val Val Gly |
| 117 | Cleavage domain sequence of auto-activated pPROT101-49-V | Amino Acid, three letter format | Leu Pro His Thr Asn Pro Ala Val Val Gly |
| 118 | Cleavage domain sequence of auto-activated pPROT101-55L-V | Amino Acid, three letter format | Phe Pro Glu Thr Asn His Ala Val Val Gly |
| 119 | Consensus elastase recognition sequence 5 (Positions $Xaa_1$ = P3, $Xaa_2$ = P2, $Xaa_3$ = P1) | Amino acid, three letter format | $Xaa_1$ $Xaa_2$ $Xaa_3$<br>$Xaa_1$ = any natural amino acid except pro or gly<br>$Xaa_2$ = pro, ala, leu, ile, gly, val, his or thr<br>$Xaa_3$ = ala, leu, val, ile, or ser |
| 120 | Consensus sequence 1 for the propeptide portion of the cleavage domain (Positions $Xaa_1$ = P5, $Xaa_2$ = P4, $Xaa_3$ = P3, $Xaa_4$ = P2, $Xaa_5$ = P1) | Amino acid, three letter format | $Xaa_1$ $Xaa_2$ $Xaa_3$ $Xaa_4$ $Xaa_5$<br>$Xaa_1$ = any natural amino acid<br>$Xaa_2$ = any natural amino acid except gly, lys, phe, tyr, trp, or arg<br>$Xaa_3$ = any natural amino acid except pro or gly<br>$Xaa_4$ = pro, ala, leu, ile, gly, val, his or thr<br>$Xaa_5$ = ala, leu, val, ile, or ser |
| 121 | Consensus sequence 2 for the activation peptide (Positions $Xaa_1$ = P10, $Xaa_2$ = P9, $Xaa_3$ = P8, $Xaa_4$ = P7, $Xaa_5$ = P6, $Xaa_6$ = P5, $Xaa_7$ = P4, $Xaa_8$ = P3, $Xaa_9$ = P2, $Xaa_{10}$ = P1) | Amino acid, three letter format | $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$<br>$Xaa_1$ = thr<br>$Xaa_2$ = gln or his<br>$Xaa_3$ = asp<br>$Xaa_4$ = leu<br>$Xaa_5$ = pro<br>$Xaa_6$ = any natural amino acid<br>$Xaa_7$ = any natural amino acid except gly, lys, phe, tyr, trp, or arg<br>$Xaa_8$ = any natural amino acid except pro or gly<br>$Xaa_9$ = pro, ala, leu, ile, gly, val, his or thr<br>$Xaa_{10}$ = ala, leu, val, ile, or ser |
| 122 | Proelastase consensus sequence 1 for residues P10 through P3' | Amino acid, three letter format | $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$<br>$Xaa_1$ = thr<br>$Xaa_2$ = gln or his<br>$Xaa_3$ = asp<br>$Xaa_4$ = leu<br>$Xaa_5$ = pro<br>$Xaa_6$ = any natural amino acid<br>$Xaa_7$ = any natural amino acid except gly, lys, phe, tyr, trp, or arg<br>$Xaa_8$ = any natural amino acid except pro or gly<br>$Xaa_9$ = pro, ala, leu, ile, gly, val, his or thr<br>$Xaa_{10}$ = ala, leu, val, ile, or ser<br>$Xaa_{11}$ = ala, leu, val, ile, or ser |

-continued

| SEQ ID NO. | Description | Type of sequence | Sequence |
|---|---|---|---|
| | | | Xaa$_{12}$ = gly, ala, or val |
| | | | Xaa$_{13}$ = gly, val, thr, phe, tyr, or trp |
| 123 | Proelastase cleavage domain consensus sequence 2 (Positions Xaa$_1$ = P5, Xaa$_2$ = P4, Xaa$_3$ = P3, Xaa$_4$ = P2, Xaa$_5$ = P1, Xaa$_6$ = P1', Xaa$_7$ = P2', Xaa$_8$ = P3') | Amino acid, three letter format | Xaa$_1$ Xaa$_2$ Xaa$_3$ Xaa$_4$ Xaa$_5$ Xaa$_6$ Xaa$_7$ Xaa$_8$<br>Xaa$_1$ = glu, his, pro, gly, asn, lys, or ala<br>Xaa$_2$ = thr, ala, pro or his<br>Xaa$_3$ = ala, leu, ile, met, lys, asn or val<br>Xaa$_4$ = pro, ala, leu, ile, gly, val, or thr<br>Xaa$_5$ = ala, leu, val, ile, or ser<br>Xaa$_6$ = ala, leu, val, ile, or ser<br>Xaa$_7$ = gly, ala, or val<br>Xaa$_8$ = gly, val, thr, phe, tyr, or trp |
| 124 | Consensus elastase recognition sequence 6 (Positions P3-P2-P1) | Amino acid, three letter format | Xaa$_1$ Xaa$_2$ Xaa$_3$<br>Xaa$_1$ = ala, leu, ile, met, lys, asn, his, or val<br>Xaa$_2$ = pro, ala, leu, ile, gly, val, or thr<br>Xaa$_3$ = ala, leu, val, ile, or ser |
| 125 | Proelastase cleavage domain consensus sequence 3 (Positions Xaa$_1$ = P5, Xaa$_2$ = P4, Xaa$_3$ = P3, Xaa$_4$ = P2, Xaa$_5$ = P1, Xaa$_6$ = P1', Xaa$_7$ = P2', Xaa$_8$ = P3') | Amino acid, three letter format | Xaa$_1$ Xaa$_2$ Xaa$_3$ Xaa$_4$ Xaa$_5$ Xaa$_6$ Xaa$_7$ Xaa$_8$<br>Xaa$_1$ = glu, his, pro, gly, asn, lys, or ala<br>Xaa$_2$ = thr, ala, pro or his<br>Xaa$_3$ = ala, leu, ile, met, lys, asn, thr, or val<br>Xaa$_4$ = pro, ala, leu, ile, gly, val, asn, or thr<br>Xaa$_5$ = ala, leu, val, ile, asn, or ser<br>Xaa$_6$ = ala, leu, val, ile, or ser<br>Xaa$_7$ = gly, ala, or val<br>Xaa$_8$ = gly, val, thr, phe, tyr, or trp |

SPECIFIC EMBODIMENTS, CITATION OF REFERENCES

The present invention is exemplified by the specific embodiments below.

In a 1$^{st}$ embodiment, the disclosure provides a protein comprising (i) an elastase activation sequence comprising an elastase recognition sequence operably linked to (ii) the amino acid sequence of a mature elastase.

In a 2$^{nd}$ embodiment, the disclosure provides a protein of the 1$^{st}$ embodiment, wherein the elastase recognition sequence comprises SEQ ID NO:11.

In a 3$^{rd}$ embodiment, the disclosure provides a protein of the 1$^{st}$ embodiment, wherein the elastase recognition sequence comprises SEQ ID NO:12.

In a 4$^{th}$ embodiment, the disclosure provides a protein of the 1$^{st}$ embodiment, wherein the elastase recognition sequence comprises SEQ ID NO:13.

In a 5$^{th}$ embodiment, the disclosure provides a protein of the 1$^{st}$ embodiment, wherein the elastase recognition sequence comprises SEQ ID NO:93.

In a 6$^{th}$ embodiment, the disclosure provides a protein of the 1$^{st}$ embodiment, 2$^{nd}$ embodiment or 4$^{th}$ embodiment, wherein the elastase recognition sequence comprises any one of SEQ ID NO:14, SEQ ID NO:15, SEQ ID NO:18, SEQ ID NO:20 or SEQ ID NO:21.

In a 7$^{th}$ embodiment, the disclosure provides a protein of the 1$^{st}$ embodiment, wherein the activation sequence comprises SEQ ID NO:80.

In an 8$^{th}$ embodiment, the disclosure provides a protein of the 1$^{st}$ embodiment or the 7$^{th}$ embodiment, wherein the activation sequence comprises SEQ ID NO:23, SEQ ID NO:72, or SEQ ID NO:73.

In a 9$^{th}$ embodiment, the disclosure provides a protein of the 1$^{st}$ embodiment, wherein the protein comprises a cleavage domain comprising SEQ ID NO:74.

In a 10$^{th}$ embodiment, the disclosure provides a protein of the 1$^{st}$ embodiment or 9$^{th}$ embodiment, wherein the cleavage domain comprises any one of SEQ ID NO:42, SEQ ID NO:43, SEQ ID NO:48, SEQ ID NO:49, SEQ ID NO:52, SEQ ID NO:53, SEQ ID NO:54 and SEQ ID NO:55.

In an 11$^{th}$ embodiment, the disclosure provides a protein of any one of the 1$^{st}$-5$^{th}$ or 7$^{th}$ embodiments which comprises SEQ ID NO:64.

In a 12$^{th}$ embodiment, the disclosure provides a protein of any one of the 1$^{st}$-5$^{th}$ or 7$^{th}$ embodiments which comprises SEQ ID NO:69.

In a 13$^{th}$ embodiment, the disclosure provides a type I proelastase protein comprising a cleavage domain sequence of SEQ ID NO:74.

In a 14$^{th}$ embodiment, the disclosure provides a type I proelastase protein of the 13$^{th}$ embodiment, wherein the cleavage domain comprises any one of SEQ ID NO:42, SEQ ID NO:43, SEQ ID NO:48, SEQ ID NO:49, SEQ ID NO:52, SEQ ID NO:53, SEQ ID NO:54 or SEQ ID NO:55.

In a 15$^{th}$ embodiment, the disclosure provides a type I proelastase protein of the 13$^{th}$ embodiment or 14$^{th}$ embodiment, wherein the mature elastase sequence comprises a sequence having at least 85% sequence identity to the amino acid sequence from position 6 (e.g., C-terminal to the P5' residue according to the elastase amino acid designations herein) to the end of SEQ ID NO:84 or SEQ ID NO:1.

In a 16th embodiment, the disclosure provides a type I proelastase protein of the 13th embodiment or 14th embodiment, which comprises a sequence having at least 95% sequence identity to the amino acid sequence from position 6 (e.g., C-terminal to the P5' residue according to the elastase amino acid designations herein) to the end of SEQ ID NO:84 or SEQ ID NO:1.

In a 17th embodiment, the disclosure provides a type I proelastase protein of the 13th embodiment or 14th embodiment, which comprises a sequence having at least 98% sequence identity to the amino acid sequence from position 6 to the end of SEQ ID NO:84 or SEQ ID NO:1.

In a 18th embodiment, the disclosure provides a type I proelastase protein of the 13th embodiment or 14th embodiment, wherein the mature elastase comprises a sequence having up to 10 conservative amino acid changes relative to the amino acid sequence from position 6 to the end of SEQ ID NO:84 or SEQ ID NO:1.

In a 19th embodiment, the disclosure provides a type I proelastase protein of the 13th embodiment or 14th embodiment, which comprises a sequence having up to 7 conservative amino acid changes relative to the amino acid sequence from position 6 to the end of SEQ ID NO:84 or SEQ ID NO:1.

In a 20th embodiment, the disclosure provides a type I proelastase protein of the 13th embodiment or 14th embodiment, which comprises a sequence having up to 5 conservative amino acid changes relative to the amino acid sequence from position 6 to the end of SEQ ID NO:84 or SEQ ID NO:1.

In a 21st embodiment, the disclosure provides a type I proelastase protein of any one of the 13th to the 20th embodiments, wherein the amino acid residue denoted by "$Xaa_1$" in SEQ ID NO:74 is glutamate or histidine.

In a 22nd embodiment, the disclosure provides a type I proelastase protein of any one of the 13th to the 21st embodiments, wherein the amino acid residue denoted by "$Xaa_4$" in SEQ ID NO:74 is proline.

In a 23rd embodiment, the disclosure provides a type I proelastase protein of any one of the 13th to the 22nd embodiments, wherein the amino acid residue denoted by "$Xaa_5$" in SEQ ID NO:74 is alanine.

In a 24th embodiment, the disclosure provides a type I proelastase protein of any one of the 13th to 23rd embodiments, wherein the amino acid residue denoted by "$Xaa_1$" in SEQ ID NO:74 is histidine, by "$Xaa_4$" in SEQ ID NO:74 is proline, and by "$Xaa_5$" in SEQ ID NO:74 is alanine.

In a 25th embodiment, the disclosure provides a type I proelastase protein of any one of the 13th to 24th embodiments which comprises the amino acid sequence of SEQ ID NO:103.

In a 26th embodiment, the disclosure provides a type I proelastase protein of the 25th embodiment which comprises the amino acid sequence of SEQ ID NO:64.

In a 27th embodiment, the disclosure provides a type I proelastase protein of the 25th embodiment which comprises the amino acid sequence of SEQ ID NO:69.

In a 28th embodiment, the disclosure provides a protein of any one of the 1st to 27th embodiments which is isolated.

In a 29th embodiment, the disclosure provides a protein of any one of the 1st to 27th embodiments which comprises a signal sequence.

In a 30th embodiment, the disclosure provides a protein comprising (i) a signal sequence; (ii) an elastase activation sequence comprising an elastase recognition sequence; and (iii) the amino acid sequence of a mature elastase.

In a 31st embodiment, the disclosure provides a protein of the 30th embodiment, wherein the signal sequence is operable in *Pichia pastoris*.

In a 32nd embodiment, the disclosure provides a protein of the 30th embodiment, wherein the signal sequence is a yeast α-factor signal peptide.

In a 33rd embodiment, the disclosure provides a protein of the 32rd embodiment, wherein the yeast α-factor signal peptide comprises the amino acid sequence of SEQ ID NO:34.

In a 34th embodiment, the disclosure provides a protein of the 30th embodiment, wherein the signal sequence is a mammalian secretion signal sequence.

In a 35th embodiment, the disclosure provides a protein of the 34th embodiment, wherein the mammalian secretion signal sequence is a porcine type I elastase signal sequence.

In a 36th embodiment, the disclosure provides a protein of the 34th embodiment, wherein the mammalian secretion signal sequence is a human type I elastase signal sequence.

In a 37th embodiment, the disclosure provides a protein of the 1st embodiment or the 30th embodiment wherein the elastase recognition sequence is a type I human elastase recognition sequence.

In a 38th embodiment, the disclosure provides a protein of the 1st embodiment or the 30th embodiment wherein the mature elastase is a human type I elastase.

In a 39th embodiment, the disclosure provides a protein of the 1st embodiment or the 39th embodiment wherein the mature elastase is a porcine type I elastase.

In a 40th embodiment, the disclosure provides a nucleic acid encoding a protein of any one of the 1st to 30th embodiments.

In a 41st embodiment, the disclosure provides a nucleic acid molecule comprising a nucleotide sequence that encodes a protein, said protein comprising (i) an activation sequence comprising an elastase recognition sequence operably linked to (ii) the amino acid sequence of an elastase.

In a 42nd embodiment, the disclosure provides a nucleic acid molecule of the 41st embodiment, wherein the protein further comprises a signal sequence operably linked to said activation sequence.

In a 43rd embodiment, the disclosure provides a nucleic acid molecule of the 41st embodiment or the 42nd embodiment, wherein the signal sequence is operable in *Pichia pastoris*.

In a 44th embodiment, the disclosure provides a nucleic acid of any one of the 41st to 43rd embodiments, wherein the elastase recognition sequence is a type I elastase recognition sequence.

In a 45th embodiment, the disclosure provides a nucleic acid of any one of the 41st to 44th embodiments, wherein the elastase recognition sequence is a type I human elastase recognition sequence.

In a 46th embodiment, the disclosure provides a nucleic acid molecule of any one of the 41st to 45th embodiments wherein the elastase recognition sequence comprises SEQ ID NO:11.

In a 47th embodiment, the disclosure provides a nucleic acid molecule of any one of the 41st to 45th embodiments wherein the elastase recognition sequence comprises SEQ ID NO:12.

In a 48th embodiment, the disclosure provides a nucleic acid molecule of any one of the 41st to 45th embodiments wherein the elastase recognition sequence comprises SEQ ID NO:13.

In a 49th embodiment, the disclosure provides a nucleic acid molecule of any one of the 41st to 45th embodiments wherein the elastase recognition sequence comprises SEQ ID NO:93.

In a 50th embodiment, the disclosure provides a nucleic acid of any one of the 41st to 46th and 48th embodiments, wherein the elastase recognition sequence comprises any one of SEQ ID NO:14, SEQ ID NO:15, SEQ ID NO:18, SEQ ID NO:20 or SEQ ID NO:21.

In a 51st embodiment, the disclosure provides a nucleic acid molecule of any one of the 41st to 50th embodiments, wherein the activation sequence comprises SEQ ID NO:80.

In a 52nd embodiment, the disclosure provides a nucleic acid molecule of any one of the 41st to 45th and 51st embodiments, wherein the activation sequence comprises SEQ ID NO:23, SEQ ID NO:72, or SEQ ID NO:73.

In a 53rd embodiment, the disclosure provides a nucleic acid molecule of any one of the 41st to 46th embodiments, wherein the protein comprises a cleavage domain comprising SEQ ID NO:74.

In a 54th embodiment, the disclosure provides a nucleic acid molecule of any one of the 41st to 46th and 53rd embodiments, wherein the cleavage domain comprises any one of SEQ ID NO:42, SEQ ID NO:43, SEQ ID NO:48, SEQ ID NO:49, SEQ ID NO:52, SEQ ID NO:53, SEQ ID NO:54 and SEQ ID NO:55.

In a 55th embodiment, the disclosure provides a nucleic acid of any one of the 41st to 54th embodiments, wherein the elastase is a mature human type I elastase.

In a 56th embodiment, the disclosure provides a nucleic acid of any one of the 41st to 54th embodiments, wherein the elastase is a mature porcine type I elastase.

In a 57th embodiment, the disclosure provides a nucleic acid of any one of the 41st to 54th embodiments, wherein the elastase comprises the amino acid sequence of any one of SEQ ID NO:5, SEQ ID NO:84, SEQ ID NO:87, and SEQ ID NO:39.

In a 58th embodiment, the disclosure provides a nucleic acid of the 57th embodiment wherein the elastase comprises the amino acid sequence of SEQ ID NO:1 or SEQ ID NO:4.

In a 59th embodiment, the disclosure provides a nucleic acid molecule of any one of the 42nd to 58th embodiments, wherein the signal sequence is a yeast α-factor signal peptide.

In a 60th embodiment, the disclosure provides a nucleic acid molecule of the 59th embodiment, wherein the protein comprises the amino acid sequence of any one of SEQ ID NO:34, SEQ ID NO:50, SEQ ID NO:51, SEQ ID NO:96 and SEQ ID NO:97.

In a 61st embodiment, the disclosure provides a nucleic acid molecule of any one of the 42nd and 44th to 58th embodiments, wherein the signal sequence is a mammalian secretion signal sequence.

In a 62nd embodiment, the disclosure provides a nucleic acid molecule of the 61st embodiment wherein the mammalian secretion signal sequence is a porcine type I elastase signal sequence.

In a 63rd embodiment, the disclosure provides a nucleic acid molecule of the 61st embodiment wherein the mammalian secretion signal sequence is a human type I elastase signal sequence.

In a 64th embodiment, the disclosure provides a nucleic acid molecule of any one of the 41st to 63rd embodiments, wherein the protein comprises the amino acid sequence of any one of SEQ ID NOS:88 to 91 and 98 to 103.

In a 65th embodiment, the disclosure provides a nucleic acid molecule of the 64th embodiment, wherein the protein comprises the amino acid sequence of any one of SEQ ID NOS.:6 to 9 and 64 to 69.

In a 66th embodiment, the disclosure provides a nucleic acid molecule of the 64th embodiment, wherein the protein comprises any of the combinations of elastase polymorphisms set forth in Table 2.

In a 67th embodiment, the disclosure provides a nucleic acid molecule of the 64th embodiment, wherein the protein comprises any of the combinations of elastase polymorphisms set forth in Table 3.

In a 68th embodiment, the disclosure provides a protein encoded by the nucleic acid molecule of any one of the 41' to 67th embodiments.

In a 69th embodiment, the disclosure provides a protein of the 68th embodiment which is isolated.

In a 70th embodiment, the disclosure provides a vector comprising the nucleic acid molecule of any one of the 41' to 67th embodiments.

In a 71st embodiment, the disclosure provides a vector of the 70th embodiment further comprising a nucleotide sequence that controls gene expression is operably linked to the nucleotide sequence which encodes said protein.

In a 72nd embodiment, the disclosure provides a vector of the 70th embodiment or the 71st embodiment in which the nucleotide sequence which encodes said protein is multimerized.

In a 73rd embodiment, the disclosure provides a host cell comprising the vector of any one of the 70th to 72nd embodiments.

In a 74th embodiment, the disclosure provides a host cell of the 73rd embodiment in which at least one copy of said vector is integrated into the host cell genome.

In a 75th embodiment, the disclosure provides a host cell of the 74th embodiment in which one copy of said vector is integrated into the host cell genome.

In a 76th embodiment, the disclosure provides a host cell of the 74th embodiment in which two to five copies of said vector are integrated into the host cell genome.

In a 77th embodiment, the disclosure provides a host cell of the 74th or 76th embodiment in which two copies of said vector are integrated into the host cell genome.

In a 78th embodiment, the disclosure provides a host cell of the 74th or 76th embodiment in which three copies of said vector are integrated into the host cell genome.

In a 79th embodiment, the disclosure provides a host cell comprising at least one copy of the nucleic acid molecule of any one of the 41st to 67th embodiments integrated into its genome.

In an 80th embodiment, the disclosure provides a host cell of the 79th embodiment in which one copy of said nucleic acid molecule is integrated into its genome.

In an 81st embodiment, the disclosure provides a host cell of the 79th embodiment in which two to five copies of said nucleic acid molecule is integrated into its genome.

In an 82nd embodiment, the disclosure provides a host cell of the 79th embodiment in which two copies of said nucleic acid molecule is integrated into its genome.

In an 83rd embodiment, the disclosure provides a host cell of the 79th embodiment in which three copies of said nucleic acid molecule is integrated into its genome.

In an 84th embodiment, the disclosure provides a cell genetically engineered to express the nucleic acid molecule of any one of the 41' to 67th embodiments.

In an 85th embodiment, the disclosure provides a cell of the 84th embodiment, wherein the nucleotide sequence is operably linked to a methanol-inducible promoter.

In an 86th embodiment, the disclosure provides a *Pichia pastoris* cell genetically engineered to express the nucleotide sequence of any one of the 41' to 67th embodiments.

In an 87th embodiment, the disclosure provides a *Pichia pastoris* cell of the 87th embodiment, in which the nucleotide sequence is operably linked to a methanol inducible promoter.

In an 88th embodiment, the disclosure provides a cell culture supernatant comprising the protein of any one of the 1st to 27th embodiments or the 68th embodiment.

In an 89th embodiment, the disclosure provides a method of producing an elastase protein, comprising culturing the host cell of the 84th embodiment under conditions in which the protein is produced.

In a 90th embodiment, the disclosure provides a method of producing an elastase protein, comprising culturing the host cell of the 85th embodiment under conditions in which the protein is produced.

In a 91st embodiment, the disclosure provides a method of producing an elastase protein, comprising culturing the host cell of the 86th embodiment under conditions in which the protein is produced.

In a 92nd embodiment, the disclosure provides a method of producing an elastase protein, comprising culturing the host cell of the 87th embodiment under conditions in which the protein is produced.

In a 93rd embodiment, the disclosure provides a method of the 91st embodiment or the 92nd embodiment, wherein said conditions include a period of growth or induction at a pH of 2 to 6.

In a 94th embodiment, the disclosure provides a method of the 91st embodiment or the 92nd embodiment, wherein said conditions comprise a period of growth or induction at a temperature of 22° C. to 28° C.

In a 95th embodiment, the disclosure provides a method of any one of the 89th to 92nd embodiments, wherein the host cell is cultured in complex medium.

In a 96th embodiment, the disclosure provides a method of the 95th embodiment, wherein the complex medium is buffered methanol-complex medium or buffered glycerol-complex medium.

In a 97th embodiment, the disclosure provides a method of any one of the 89th to 96th embodiments, wherein the host cell is cultured in the presence of a citrate, succinate or acetate compound.

In a 98th embodiment, the disclosure provides a method of the 97th embodiment, wherein the citrate, succinate or acetate compound is sodium citrate, sodium succinate or sodium acetate, respectively.

In a 99th embodiment, the disclosure provides a method of the 97th embodiment or the 98th embodiment, wherein one citrate, succinate or acetate compound is present in said culture at a concentration of 5-50 mM, 7.5-100 mM, 10-150 mM, 50-200 mM, 100-150 mM, 75-125 mM, or 90-110 mM.

In a 100th embodiment, the disclosure provides a method of the 97th embodiment or the 98th embodiment, wherein more than one citrate, succinate or acetate compound is present in said culture, and wherein the total concentration of citrate, succinate or acetate compounds in said solution is 5-50 mM, 7.5-100 mM, 10-150 mM, 50-200 mM, 100-150 mM, 75-125 mM, or 90-110 mM.

In a 101st embodiment, the disclosure provides a method of any one of the 89th to 100th embodiments further comprising recovering the protein.

In a 102nd embodiment, the disclosure provides a method of the 95th embodiment, wherein the protein is recovered by recovering the supernatant.

In a 103rd embodiment, the disclosure provides a method of the 95th embodiment, wherein the protein is recovered from the supernatant.

In a 104th embodiment, the disclosure provides a method of embodiment any one of the 95th to 104th embodiments, wherein the protein recovered lacks the signal sequence.

In a 105th embodiment, the disclosure provides a method of embodiment any one of the 95th to 104th embodiments, wherein the protein recovered lacks both the signal sequence and the activation sequence.

In a 106th embodiment, the disclosure provides a method of any one of the 89th to 92nd and 93rd to 105th embodiments, further comprising raising the pH of a solution containing the protein to a pH of 6 to 12.

In a 107th embodiment, the disclosure provides a method of any one of the 89th to 92nd and 93rd to 106th embodiments, which further comprises contacting the protein with a catalytic amount of an elastase.

In a 108th embodiment, the disclosure provides a method of any one of 89th to 92nd and 93rd to 106th embodiments, which further comprises subjecting the protein to autoactivating conditions, contacting the protein with a catalytic amount of an elastase, or both.

In a 109th embodiment, the disclosure provides a method of the 108th embodiment, wherein the protein is subjected to autoactivation conditions.

In a 110th embodiment, the disclosure provides a method of the 109th embodiment, wherein the protein is in the supernatant when subjected to autoactivation conditions.

In a 111th embodiment, the disclosure provides a method of producing an elastase protein, comprising:
(a) culturing a host cell capable of expressing a recombinant proelastase protein in the presence of a first citrate, succinate or acetate compound;
(b) recovering the recombinant proelastase protein from said host cell culture; and
(c) optionally, exposing the recombinant proelastase protein to activation conditions to produce a mature elastase protein.
thereby producing an elastase protein.

In a 112th embodiment, the disclosure provides a method of the 111th embodiment, wherein the method comprises the step of exposing the recombinant proelastase protein to activation conditions to produce a mature elastase protein.

In a 113th embodiment, the disclosure provides a method of the 112th embodiment, wherein the recombinant proelastase protein is purified prior to said exposure to activating conditions.

In a 114th embodiment, the disclosure provides a method of the 113th embodiment, wherein said recombinant proelastase protein is purified in the presence of a second citrate, succinate or acetate compound, such that a solution comprising said purified proelastase protein and second citrate, succinate or acetate compound is produced.

In a 115th embodiment, the disclosure provides a method of any one of the 111th to 114th embodiments, wherein said first citrate, succinate or acetate compound is sodium citrate, sodium succinate or sodium acetate, respectively.

In a 116th embodiment, the disclosure provides a method of the 114th embodiment or 115th embodiment, wherein said second citrate, succinate or acetate compound is sodium citrate, sodium succinate or sodium acetate, respectively.

In a 117th embodiment, the disclosure provides a method of any one of the 114th to 116th embodiments, wherein said first and second citrate, succinate or acetate compound are the same.

In a 118th embodiment, the disclosure provides a method of any one of the 114th to 116th embodiments, wherein said first and second citrate, succinate or acetate compound are different.

In a 119th embodiment, the disclosure provides a method of any one of the 114th to 118th embodiments, wherein one citrate, succinate or acetate compound is present in said culture at a concentration of 5-50 mM, 7.5-100 mM, 10-150 mM, 50-200 mM, 100-150 mM, 75-125 mM, or 90-110 mM.

In a 120th embodiment, the disclosure provides a method of any one of the 114th to 118th embodiments, wherein more than one citrate, succinate or acetate compound is present in said culture, and wherein the total concentration of citrate, succinate or acetate compounds in said culture is 5-50 mM, 7.5-100 mM, 10-150 mM, 50-200 mM, 100-150 mM, 75-125 mM, or 90-110 mM.

In a 121st embodiment, the disclosure provides a method of any one of the 111th to 120th embodiments, wherein one citrate, succinate or acetate compound is present in said solution at a concentration of 5-50 mM, 7.5-100 mM, 10-150 mM, 50-200 mM, 100-150 mM, 75-125 mM, or 90-110 mM.

In a 122nd embodiment, the disclosure provides a method of any one of the 111th to 120th embodiments, wherein more than one citrate, succinate or acetate compound is present in said solution, and wherein the total concentration of citrate, succinate or acetate compounds in said solution is 5-50 mM, 7.5-100 mM, 10-150 mM, 50-200 mM, 100-150 mM, 75-125 mM, or 90-110 mM.

In a 123rd embodiment, the disclosure provides a method of any one of the 111th to 122nd embodiments, wherein the host cell is cultured in complex medium.

In a 124th embodiment, the disclosure provides a method of the 123rd embodiment, wherein the complex medium is buffered methanol-complex medium or buffered glycerol-complex medium.

In a 125th embodiment, the disclosure provides a method of any one of the 111th to 124th embodiments wherein the proelastase protein is recovered from the supernatant of said host cell.

In a 126th embodiment, the disclosure provides a method of any one of the 111th to 125th embodiments, wherein said activation conditions comprise exposure to trypsin.

In a 127th embodiment, the disclosure provides a method of any one of the 111th to 125th embodiments, wherein said activation conditions are autoactivation conditions.

In a 128th embodiment, the disclosure provides a method of any one of the 111th to 127th embodiments which further comprises the step of isolating said mature elastase protein.

In a 129th embodiment, the disclosure provides a method of any one of the 111th to 128th embodiments, wherein the mature elastase protein is a mature type I elastase protein.

In a 130th embodiment, the disclosure provides a method of the 129th embodiment, wherein the mature type I elastase protein is a human type I mature elastase protein.

In a 131st embodiment, the disclosure provides a method of the 129th embodiment, wherein the mature type I elastase protein is a porcine type I mature elastase protein.

In a 132nd embodiment, the disclosure provides a method of producing a mature elastase protein, comprising:

(a) lyophilizing a proelastase protein;
(b) storing the lyophilized proelastase protein;
(c) reconstituting the lyophilized proelastase protein; and
(d) activating the reconstituted proelastase protein,
thereby producing a mature elastase protein.

In a 133rd embodiment, the disclosure provides a method of the 132nd embodiment, wherein the proelastase protein is recombinant.

In a 134th embodiment, the disclosure provides a method of the 133rd embodiment, wherein the proelastase protein is made by or obtainable by a process comprising (i) culturing a host cell that is capable of expressing the proelastase protein under conditions in which the proelastase protein is expressed; and (ii) recovering the proelastase protein.

In a 135th embodiment, the disclosure provides a method of the 134th embodiment, wherein the host cell is cultured in complex medium.

In a 136th embodiment, the disclosure provides a method of the 135th embodiment, wherein the complex medium is buffered methanol-complex medium or buffered glycerol-complex medium.

In a 137th embodiment, the disclosure provides a method of any one of the 132nd to 136th embodiments, wherein the host cell is cultured in the presence of a citrate, succinate or acetate compound.

In a 138th embodiment, the disclosure provides a method of the 137th embodiment, wherein the citrate, succinate or acetate compound is sodium citrate, sodium succinate or sodium acetate, respectively.

In a 139th embodiment, the disclosure provides a method of the 137th embodiment or 138th embodiment, wherein one citrate, succinate or acetate compound is present in said culture at a concentration of 5-50 mM, 7.5-100 mM, 10-150 mM, 50-200 mM, 100-150 mM, 75-125 mM, or 90-110 mM.

In a 140th embodiment, the disclosure provides a method of the 137th embodiment or 138th embodiment, wherein more than one citrate, succinate or acetate compound is present in said culture, and wherein the total concentration of citrate, succinate or acetate compounds in said solution is 5-50 mM, 7.5-100 mM, 10-150 mM, 50-200 mM, 100-150 mM, 75-125 mM, or 90-110 mM.

In a 141st embodiment, the disclosure provides a method of any one of the 132st to 140th embodiments wherein the proelastase protein is recovered from the supernatant of said host cell.

In a 142nd embodiment, the disclosure provides a method of any one of the 132nd to 141st embodiments, wherein the proelastase protein is purified prior to lyophilization.

In a 143rd embodiment, the disclosure provides a method of any one of the 132nd to 142nd embodiments, wherein the lyophilized proelastase protein is stored for a period of at least one day, at least one week, at least one month or at least three months.

In a 144th embodiment, the disclosure provides a method of any one of the 132nd to 143rd embodiments, wherein the proelastase protein is stored at a temperature of −80° C. to +4° C.

In a 145th embodiment, the disclosure provides a method of any one of the 132nd to 144th embodiments, wherein said activating step comprises trypsin activation.

In a 146th embodiment, the disclosure provides a method of any one of the 132nd to 144th embodiments, wherein said activating step comprises autoactivation.

In a 147th embodiment, the disclosure provides a method of any one of the 132nd to 146th embodiments which further comprises the step of isolating said mature elastase protein.

In a 148th embodiment, the disclosure provides a method of any one of the 132nd to 147th embodiments, wherein the mature elastase protein is a mature type I elastase protein.

In a 149th embodiment, the disclosure provides a method of the 148th embodiment, wherein the mature type I elastase protein is a human type I mature elastase protein.

In a 150th embodiment, the disclosure provides a method of the 148th embodiment, wherein the mature type I elastase protein is a porcine type I mature elastase protein.

In a 151st embodiment, the disclosure provides a method of producing a mature type I elastase protein comprising subjecting a recombinant autoactivated type I proelastase protein to autoactivation conditions, contacting a recombinant autoactivated type I proelastase protein with a catalytic amount of elastase, or both, thereby producing a mature type I elastase protein.

In a 152nd embodiment, the disclosure provides a method of the 151st embodiment, wherein said recombinant autoactivated type I proelastase protein is obtained by or obtainable by a process comprising:
(a) culturing the host cell of the 84th or 86th embodiment under conditions in which the protein is expressed; and
(b) recovering the expressed protein,
thereby producing a recombinant autoactivated type I proelastase protein.

In a 153rd embodiment, the disclosure provides a method of the 152nd embodiment, wherein the host cell is cultured in complex medium.

In a 154th embodiment, the disclosure provides a method of the 153rd embodiment, wherein the complex medium is buffered methanol-complex medium or buffered glycerol-complex medium.

In a 155th embodiment, the disclosure provides a method of any one of the 152nd to 154th embodiments, wherein the host cell is cultured in the presence of a citrate, succinate or acetate compound.

In a 156th embodiment, the disclosure provides a method of the 155th embodiment, wherein the citrate, succinate or acetate compound is sodium citrate, sodium succinate or sodium acetate, respectively.

In a 157th embodiment, the disclosure provides a method of the 155th embodiment or 156th embodiment, wherein one citrate, succinate or acetate compound is present in said culture at a concentration of 5-50 mM, 7.5-100 mM, 10-150 mM, 50-200 mM, 100-150 mM, 75-125 mM, or 90-110 mM.

In a 158th embodiment, the disclosure provides a method of the 155th embodiment or 156th embodiment, wherein more than one citrate, succinate or acetate compound is present in said culture, and wherein the total concentration of citrate, succinate or acetate compounds in said solution is 5-50 mM, 7.5-100 mM, 10-150 mM, 50-200 mM, 100-150 mM, 75-125 mM, or 90-110 mM.

In a 159th embodiment, the disclosure provides a method of any one of the 152nd to 158th embodiments, wherein recovering the expressed protein comprises recovering the supernatant.

In a 160th embodiment, the disclosure provides a method of the 159th embodiment, wherein said autoactivation step is performed in the supernatant.

In a 161st embodiment, the disclosure provides a method of any one of the 152nd to 154th embodiments, wherein the expressed protein is recovered from the supernatant.

In a 162nd embodiment, the disclosure provides a method of the 161st embodiment, wherein said autoactivation step is performed in the supernatant.

In a 163rd embodiment, the disclosure provides a method of the 161st embodiment, which further comprises the step of purifying the expressed protein.

In a 164th embodiment, the disclosure provides a method of any one of the 151st to 163rd embodiments, wherein subjecting the recombinant autoactivated type I proelastase protein to autoactivation conditions comprises raising the pH of a solution containing the recovered protein.

In a 165th embodiment, the disclosure provides a method of the 164th embodiment, wherein the pH of the solution is raised to a basic pH.

In a 166th embodiment, the disclosure provides a method of the 165th embodiment, wherein the basic pH is in a range from 7 to 9.

In a 167th embodiment, the disclosure provides a method of the 166th embodiment, wherein the basic pH is 8.

In a 168th embodiment, the disclosure provides a method of any one of the 164th to 167th embodiments, wherein the recovered protein is at a concentration of 10 mg/ml or less in said solution.

In a 169th embodiment, the disclosure provides a method of any one of the 164th to 167th embodiments, wherein the recovered protein is at a concentration of 5 mg/ml or less in said solution.

In a 170th embodiment, the disclosure provides a method of any one of the 164th to 167th embodiments, wherein the recovered protein is at a concentration of 2 mg/ml or less in said solution.

In a 171st embodiment, the disclosure provides a method of any one of the 164th to 167th embodiments, wherein the recovered protein is at a concentration of 1 mg/ml or less in said solution.

In a 172nd embodiment, the disclosure provides a method of any one of the 164th to 167th embodiments, wherein the recovered protein is at a concentration of 0.5 mg/ml or less in said solution.

In a 173rd embodiment, the disclosure provides a method of any one of the 164th to 167th embodiments, wherein the recovered protein is at a concentration of 0.25 mg/ml or less in said solution.

In a 174th embodiment, the disclosure provides a method of any one of the 165th to 173rd embodiments, wherein the recovered protein is at a concentration of at least 0.1 mg/ml in said solution.

In a 175th embodiment, the disclosure provides a method of any one of the 165th to 173rd embodiments, wherein the recovered protein is at a concentration of at least 0.2 mg/ml in said solution.

In a 176th embodiment, the disclosure provides a method of any one of the 165th to 175th embodiments wherein the recovered protein is exposed to the basic pH for a period of 0.5 to 8 hours.

In a 177th embodiment, the disclosure provides a method of the 174th embodiment, wherein the recovered protein is exposed to the basic pH for a period of 2 to 7 hours.

In a 178th embodiment, the disclosure provides a method of the 177th embodiment, wherein the recovered protein is exposed to the basic pH for a period of 6 hours.

In a 179th embodiment, the disclosure provides a method of any one of the 165th to 178th embodiments, wherein said exposure to a basic pH is performed at a temperature of 22° C. to 28° C.

In a 180th embodiment, the disclosure provides a method of the 179th embodiment, wherein said exposure to a basic pH is performed at a temperature of 26° C.

In a 181st embodiment, the disclosure provides a method of the 152nd to 180th embodiment, wherein the recovered protein is stored prior to autoactivation.

In a 182nd embodiment, the disclosure provides a method of the 181st embodiment, wherein the recovered protein is lyophilized prior to storage.

In a 183rd embodiment, the disclosure provides a method of the 182nd embodiment, wherein the recovered protein is purified prior to lyophilization.

In a 184th embodiment, the disclosure provides a method of any one of the 181st to 183rd embodiments, wherein the recovered protein is stored for a period of at least one day, at least one week, at least one month or at least three months.

In a 185th embodiment, the disclosure provides a method of the 184th embodiment, wherein the recovered protein is stored at a temperature from 80° C. to +4° C.

In a 186th embodiment, the disclosure provides a method of any one of the 150th to 185th embodiments inasfar as such embodiments do not depend on the 160th or 162nd embodiments, wherein the recombinant autoactivated type I proelastase is purified prior to subjecting it to autoactivation conditions.

In a 187th embodiment, the disclosure provides a method of any one of the 150th to 186th embodiments, which further comprises the step of isolating said mature type I elastase protein.

In a 188th embodiment, the disclosure provides a method of any one of the 150th to 187th embodiments, wherein the mature type I elastase protein is a human type I mature elastase protein.

In a 189th embodiment, the disclosure provides a method of any one of the 150th to 187th embodiments, wherein the mature type I elastase protein is a porcine type I mature elastase protein.

In a 190th embodiment, the disclosure provides a method of producing a mature type I elastase protein comprising:
  (a) culturing the host cell of the 84th or 86th embodiment under conditions in which the protein is expressed;
  (b) recovering the expressed protein;
  (c) purifying the recovered protein;
  (d) raising the pH of a solution containing the protein or contacting the recovered protein with a catalytic amount of elastase to produce a mature type I elastase protein,
thereby producing a mature type I elastase protein.

In a 191st embodiment, the disclosure provides a method of the 190th embodiment, wherein the host cell is cultured in complex medium.

In a 192nd embodiment, the disclosure provides a method of the 191st embodiment, wherein the complex medium is buffered methanol-complex medium or buffered glycerol-complex medium.

In a 193rd embodiment, the disclosure provides a method of any one of the 190th to 192nd embodiments, wherein the host cell is cultured in the presence of a citrate, succinate or acetate compound.

In a 194th embodiment, the disclosure provides a method of the 193rd embodiment, wherein the citrate, succinate or acetate compound is sodium citrate, sodium succinate or sodium acetate, respectively.

In a 195th embodiment, the disclosure provides a method of the 193rd embodiment or 194th embodiment, wherein one citrate, succinate or acetate compound is present in said culture at a concentration of 5-50 mM, 7.5-100 mM, 10-150 mM, 50-200 mM, 100-150 mM, 75-125 mM, or 90-110 mM.

In a 196th embodiment, the disclosure provides a method of the 193rd embodiment or 194th embodiment, wherein more than one citrate, succinate or acetate compound is present in said culture, and wherein the total concentration of citrate, succinate or acetate compounds in said solution is 5-50 mM, 7.5-100 mM, 10-150 mM, 50-200 mM, 100-150 mM, 75-125 mM, or 90-110 mM.

In a 197th embodiment, the disclosure provides a method of any one of the 190th to 196th embodiments, which further comprises the step of (e) purifying said mature type I elastase.

In a 198th embodiment, the disclosure provides a method of any one of the 190th to 197th embodiments, wherein the mature type I elastase protein is a human type I mature elastase protein.

In a 199th embodiment, the disclosure provides a method of any one of the 190th to 197th embodiments, wherein the mature type I elastase protein is a porcine type I mature elastase protein.

In a 200th embodiment, the disclosure provides a method of producing a mature type I elastase protein comprising:
  (a) culturing the host cell of the 84th or 86th embodiment under conditions in which the protein is expressed;
  (b) recovering the expressed protein; and
  (c) exposing the recovered protein to a basic pH until a mature protein is produced;
thereby producing a mature type I elastase protein.

In a 201st embodiment, the disclosure provides a method of the 200th embodiment, wherein the host cell is cultured in complex medium.

In a 202nd embodiment, the disclosure provides a method of the 201st embodiment, wherein the complex medium is buffered methanol-complex medium or buffered glycerol-complex medium.

In a 203rd embodiment, the disclosure provides a method of any one of the 200th to 202nd embodiments, wherein the host cell is cultured in the presence of a citrate, succinate or acetate compound.

In a 204th embodiment, the disclosure provides a method of the 203rd embodiment, wherein the citrate, succinate or acetate compound is sodium citrate, sodium succinate or sodium acetate, respectively.

In a 205th embodiment, the disclosure provides a method of the 203rd embodiment or 204th embodiment, wherein one citrate, succinate or acetate compound is present in said culture at a concentration of 5-50 mM, 7.5-100 mM, 10-150 mM, 50-200 mM, 100-150 mM, 75-125 mM, or 90-110 mM.

In a 206th embodiment, the disclosure provides a method of the 203rd embodiment or the 204th embodiment, wherein more than one citrate, succinate or acetate compound is present in said culture, and wherein the total concentration of citrate, succinate or acetate compounds in said solution is 5-50 mM, 7.5-100 mM, 10-150 mM, 50-200 mM, 100-150 mM, 75-125 mM, or 90-110 mM.

In a 207th embodiment, the disclosure provides a method of any one of the 200th to 206th embodiments, wherein the basic pH is 7 to 9.

In a 208th embodiment, the disclosure provides a method of the 207th embodiment, wherein the basic pH is 8.

In a 209th embodiment, the disclosure provides a method of any one of the 200th to 208th embodiments, wherein recovered protein is at a concentration of 10 mg/ml or less when exposed to the basic pH.

In a 210th embodiment, the disclosure provides a method of any one of the 200th to 208th embodiments, wherein recovered protein is at a concentration of 5 mg/ml or less when exposed to the basic pH.

In a 211st embodiment, the disclosure provides a method of any one of the 200$^{th}$ to 208$^{th}$ embodiments, wherein recovered protein is at a concentration of 2 mg/ml or less when exposed to the basic pH.

In a 212$^{th}$ embodiment, the disclosure provides a method of any one of the 200$^{th}$ to 208$^{th}$ embodiments, wherein recovered protein is at a concentration of 1 mg/ml or less when exposed to the basic pH.

In a 213$^{th}$ embodiment, the disclosure provides a method of any one of the 200$^{th}$ to 208$^{th}$ embodiments, wherein recovered protein is at a concentration of 0.5 mg/ml or less when exposed to the basic pH.

In a 214$^{th}$ embodiment, the disclosure provides a method of any one of the 200$^{th}$ to 208$^{th}$ embodiments, wherein recovered protein is at a concentration of 0.25 mg/ml or less when exposed to the basic pH.

In a 215$^{th}$ embodiment, the disclosure provides a method of any one of the 209$^{th}$ to 214$^{th}$ embodiments, wherein recovered protein is at a concentration of at least 0.1 mg/ml when exposed to the basic pH.

In a 216$^{th}$ embodiment, the disclosure provides a method of any one of the 209$^{th}$ to 214$^{th}$ embodiments, wherein recovered protein is at a concentration of at least 0.2 mg/ml when exposed to the basic pH.

In a 217$^{th}$ embodiment, the disclosure provides a method of any one of the 200$^{th}$ to 214$^{th}$ embodiments, wherein the recovered protein is exposed to the basic pH for a period of 0.5 to 8 hours.

In a 218$^{th}$ embodiment, the disclosure provides a method of the 217$^{th}$ embodiment, wherein the recovered protein is exposed to the basic pH for a period of 2 to 7 hours.

In a 219$^{th}$ embodiment, the disclosure provides a method of the 218$^{th}$ embodiment, wherein the recovered protein is exposed to the basic pH for a period of 6 hours.

In a 220$^{th}$ embodiment, the disclosure provides a method of any one of the 200$^{th}$ to 219$^{th}$ embodiments, wherein said exposure to a basic pH is performed at a temperature of 22° C. to 28° C.

In a 221$^{st}$ embodiment, the disclosure provides a method of the 220$^{th}$ embodiment, wherein said exposure to a basic pH is performed at a temperature of 26° C.

In a 222$^{nd}$ embodiment, the disclosure provides a method of any one of the 200$^{th}$ to 221$^{st}$ embodiments, which further comprises the step of (d) isolating said mature type I elastase protein.

In a 223$^{rd}$ embodiment, the disclosure provides a method of any one of the 150$^{th}$ to 222$^{nd}$ embodiments, wherein the mature type I elastase is a mature porcine type I elastase.

In a 224$^{th}$ embodiment, the disclosure provides a method of any one of the 150$^{th}$ to 222$^{nd}$ embodiments, wherein the mature type I elastase is a mature human type I elastase.

In a 225$^{th}$ embodiment, the disclosure provides a method of producing a formulation of mature elastase protein, comprising:
(a) subjecting an autoactivated proelastase protein to autoactivating conditions to produce mature elastase protein; and
(b) formulating the mature elastase protein, thereby producing a formulation of mature elastase protein.

In a 226$^{th}$ embodiment, the disclosure provides a method of the 225$^{th}$ embodiment, wherein the autoactivated proelastase protein is recombinant.

In a 227$^{th}$ embodiment, the disclosure provides a method of the 226$^{th}$ embodiment further comprising, prior to step (a) recovering the proelastase protein from a culture of a host cell capable of expressing said autoactivated proelastase protein grown under conditions in which the proelastase protein is expressed.

In a 228$^{th}$ embodiment, the disclosure provides a method of the 225$^{th}$ embodiment or the 226$^{th}$ embodiment, further comprising, prior to step (b), purifying said mature elastase protein.

In a 229$^{th}$ embodiment, the disclosure provides a method of any one of the 225$^{th}$ to 228$^{th}$ embodiments, wherein said formulating step comprises lyophilizing said mature elastase protein.

In a 230$^{th}$ embodiment, the disclosure provides a method of the 229$^{th}$ embodiment, wherein the mature elastase protein is not mixed with buffer or buffer ingredients prior to lyophilization.

In a 231$^{st}$ embodiment, the disclosure provides a method of the 230$^{th}$ embodiment, wherein the mature elastase protein is mixed with one or more buffer ingredients following lyophilization.

In a 232$^{nd}$ embodiment, the disclosure provides a method of the 229$^{th}$ embodiment, wherein the mature elastase protein is mixed with buffer or one or more buffer ingredients prior to lyophilization.

In a 233$^{rd}$ embodiment, the disclosure provides a method of the 231$^{st}$ or 232$^{nd}$ embodiment, wherein the buffer is a phosphate buffered saline ("PBS") buffer or the buffer ingredients are PBS buffer ingredients.

In a 234$^{th}$ embodiment, the disclosure provides a method of any one of the 231$^{st}$ to 233$^{rd}$ embodiments, wherein the buffer comprises dextran or wherein the buffer ingredients comprise dextran.

In a 235$^{th}$ embodiment, the disclosure provides a method of the 234$^{th}$ embodiment, wherein the dextran is dextran-18.

In a 236$^{th}$ embodiment, the disclosure provides a method of any one of the 230$^{th}$ to 235$^{th}$ embodiments, wherein the buffer comprises polysorbate 80.

In a 237$^{th}$ embodiment, the disclosure provides a method of any one of the 229$^{th}$ to 236$^{th}$ embodiments, wherein said formulating step further comprises reconstituting the lyophilized mature elastase protein with a liquid.

In a 238$^{th}$ embodiment, the disclosure provides a method of the 237$^{th}$ embodiment, wherein the liquid is water.

In a 239$^{th}$ embodiment, the disclosure provides a method of the 237$^{th}$ embodiment, wherein the liquid is a buffer.

In a 240$^{th}$ embodiment, the disclosure provides a method of the 239$^{th}$ embodiment, wherein the buffer is full strength buffer, greater than full strength buffer, or less than full strength buffer.

In a 241$^{st}$ embodiment, the disclosure provides a method of any one of the 237$^{th}$ to 240$^{th}$ embodiments, wherein upon reconstitution a solution of mature elastase protein in full strength buffer, greater than full strength buffer, or less than full strength buffer is produced.

In a 242$^{nd}$ embodiment, the disclosure provides a method of the 241$^{st}$ embodiment, wherein buffer ingredients are present in the lyophilisate, added upon reconstitution, or both.

In a 243$^{rd}$ embodiment, the disclosure provides a method of any one of the 240$^{th}$ to 242$^{nd}$ embodiments, wherein full strength buffer comprises 1×PBS.

In a 244$^{th}$ embodiment, the disclosure provides a method of the 240$^{th}$ or 241$^{st}$ embodiment, wherein the less than full strength buffer comprises 0.1×PBS to 0.5×PBS.

In a 245$^{th}$ embodiment, the disclosure provides a method of the 244$^{th}$ embodiment, wherein the less than full strength buffer comprises 0.1×PBS.

In a 246th embodiment, the disclosure provides a method of the 244th embodiment, wherein the less than full strength buffer comprises 0.5×PBS.

In a 247th embodiment, the disclosure provides a method of the 240th or 241st embodiment, wherein the greater than full strength buffer comprises 1.1×PBS to 3×PBS.

In a 248th embodiment, the disclosure provides a method of the 247th embodiment, wherein the greater than full strength buffer comprises 1.5×PBS to 2×PBS.

In a 249th embodiment, the disclosure provides a method of any one of the 241st to 248th embodiments, wherein the buffer comprises dextran.

In a 250th embodiment, the disclosure provides a method of the 249th embodiment, wherein the dextran is dextran 18.

In a 251st embodiment, the disclosure provides a method of any one of the 241st to 250th embodiments, wherein the buffer comprises polysorbate 80.

In a 252nd embodiment, the disclosure provides a method of any one of the 241st to 251st embodiments, wherein the buffer is at a pH of 7 to 8.

In a 253rd embodiment, the disclosure provides a method of the 252nd embodiment, wherein the buffer is at a pH of 7.4.

In a 254th embodiment, the disclosure provides a method of any one of the 237th to 253rd embodiments, wherein the mature elastase protein is reconstituted to a concentration of 0.001 mg/ml to 50 mg/ml.

In a 255th embodiment, the disclosure provides a method of the 254th embodiment, wherein the mature elastase protein is reconstituted to a concentration of 0.1 mg/ml to 40 mg/ml.

In a 256th embodiment, the disclosure provides a method of the 255th embodiment, wherein the mature elastase protein is reconstituted to a concentration of 5 mg/ml to 30 mg/ml.

In a 257th embodiment, the disclosure provides a method of the 256th embodiment, wherein the mature elastase protein is reconstituted to a concentration of 10 mg/ml to 20 mg/ml.

In a 258th embodiment, the disclosure provides a method of any one of the 225th to 257th embodiments, wherein said formulation is a pharmaceutical composition comprising said mature elastase protein.

In a 259th embodiment, the disclosure provides a method of any one of the 225th to 258th embodiments, wherein the mature type I elastase protein is a human type I mature elastase protein.

In a 260th embodiment, the disclosure provides a method of any one of the 225th to 258th embodiments, wherein the mature type I elastase protein is a porcine type I mature elastase protein.

In a 261st embodiment, the disclosure provides a method of producing a lyophilized mature type I elastase comprising:
  (a) producing a mature type I elastase according to the method of any one of the 151st to 181st embodiments;
  (b) isolating mature type I elastase; and
  (c) lyophilizing said isolated mature type I elastase, thereby producing a lyophilized mature type I elastase.

In a 262nd embodiment, the disclosure provides a method of the 261st embodiment, wherein the lyophilized mature type I elastase is 95% to 100% pure.

In a 263rd embodiment, the disclosure provides a method of the 261st embodiment or 262nd embodiment, wherein the lyophilized mature type I elastase is at least 95% pure.

In a 264th embodiment, the disclosure provides a method of the 261st embodiment or 262nd embodiment, wherein the lyophilized mature type I elastase is at least 98% pure.

In a 265th embodiment, the disclosure provides a method of any one of the 261st to 264th embodiments, wherein the lyophilized mature type I elastase is purified to homogeneity.

In a 266th embodiment, the disclosure provides a method of any one of the 261st to 265th embodiments, wherein the mature type I elastase protein is a human type I mature elastase protein.

In a 267th embodiment, the disclosure provides a method of any one of the 261st to 265th embodiments, wherein the mature type I elastase protein is a porcine type I mature elastase protein.

In a 268th embodiment, the disclosure provides a method of any one of the 130th, 149th, 188th, 198th, 223rd, 259th, and 267th embodiments, wherein the mature human type I elastase protein consists essentially of SEQ ID NO:5, SEQ ID NO:84, or SEQ ID NO:87.

In a 269th embodiment, the disclosure provides a method of the 268th embodiment, wherein the mature human type I elastase protein consists essentially of SEQ ID NO:1 or SEQ ID NO:4.

In a 270th embodiment, the disclosure provides a method of any one of the 131st, 150th, 189th, 199th, 224th, 260th, and 268th embodiments, wherein the mature porcine type I elastase protein consists essentially of SEQ ID NO:39.

In a 271st embodiment, the disclosure provides a method of any one of the 111st to 128th, 132nd to 148th, 151st to 197th and 225th to 257th embodiments, wherein the proelastase protein is a protein of any one of embodiments 13 to 27.

In a 272nd embodiment, the disclosure provides a method of any one of the 200th to 222nd embodiments, wherein the expressed protein is a protein of any one of embodiments 13 to 27.

In a 273rd embodiment, the disclosure provides a mature human type I elastase produced by or obtainable by the method of any one of the 149th, 188th, 198th and 223rd embodiments.

In a 274th embodiment, the disclosure provides a mature human type I elastase of the 273rd embodiment which has a specific activity of 1 to 40 U/mg protein.

In a 275th embodiment, the disclosure provides a mature porcine type I elastase produced by or obtainable by the method of any one of the 150th, 189th, 199th and 224th embodiments.

In a 276th embodiment, the disclosure provides a mature human type I elastase of the 275th embodiment which has a specific activity of 10 to 100 U/mg protein.

In a 277th embodiment, the disclosure provides a pharmaceutical composition comprising a therapeutically effective amount of (a) the mature human type I elastase of the 273rd embodiment or 274th embodiment or (b) a formulation of mature human type I elastase produced by or obtainable by the method of the 259th embodiment.

In a 278th embodiment, the disclosure provides a pharmaceutical composition of the 277th embodiment, wherein the mature human type I elastase protein consists essentially of SEQ ID NO:5, SEQ ID NO:84, or SEQ ID NO:87.

In a 279th embodiment, the disclosure provides a pharmaceutical composition of the 278th embodiment, wherein the mature human type I elastase protein consists essentially of SEQ ID NO:1 or SEQ ID NO:4.

In a 280th embodiment, the disclosure provides a pharmaceutical composition comprising a therapeutically effective amount of (a) the mature porcine type I elastase of the 275th embodiment or 276th embodiment or (b) a formulation of mature porcine type I elastase produced by or obtainable by the method of the 260th embodiment.

In a 281st embodiment, the disclosure provides a pharmaceutical composition of the 280th embodiment, wherein the mature porcine type I elastase protein consists essentially of SEQ ID NO:39.

In a 282nd embodiment, the disclosure provides a pharmaceutical composition comprising (i) a therapeutically effective amount of mature human type I elastase and (ii) a pharmaceutically acceptable carrier, which pharmaceutical composition is characterized by at least one of the following properties:

(a) the composition is free of trypsin;
(b) the composition is substantially free of trypsin;
(c) the composition is free of any protein consisting of SEQ ID NOS: 2, 3, 37, 38, 70 and/or 71;
(d) the composition is substantially free of any protein consisting of SEQ ID NOS: 2, 3, 37, 38, 70 and/or 71;
(e) the composition is free of bacterial proteins;
(f) the composition is substantially free of bacterial proteins;
(g) the composition is free of mammalian proteins other than said mature human type I elastase;
(h) the composition is substantially free of mammalian proteins other than said mature human type I elastase.

In a 283rd embodiment, the disclosure provides a pharmaceutical composition comprising (i) a therapeutically effective amount of mature human type I elastase and (ii) a pharmaceutically acceptable carrier, which pharmaceutical composition is characterized by at least one of the following properties:

(a) the composition is free of trypsin;
(b) the composition is substantially free of trypsin;
(c) the composition is free of any protein consisting of SEQ ID NOS:70 and 71;
(d) the composition is substantially free of any protein consisting of SEQ ID NOS:2 and 3;
(e) the composition is free of bacterial proteins;
the composition is substantially free of bacterial proteins;
(g) the composition is free of mammalian proteins other than said mature human type I elastase;
(h) the composition is substantially free of mammalian proteins other than said mature human type I elastase.

In a 284th embodiment, the disclosure provides a pharmaceutical composition of the 282nd embodiment or 283rd embodiment which is characterized by at least two of the properties (a) to (h).

In a 285th embodiment, the disclosure provides a pharmaceutical composition of the 284th embodiment, wherein said at least two properties include (a) and (c).

In a 286th embodiment, the disclosure provides a pharmaceutical composition of the 284th embodiment, wherein said at least two properties include (b) and (d).

In a 287th embodiment, the disclosure provides a pharmaceutical composition of the 282nd embodiment or 283rd embodiment which is characterized by at least three of the properties (a) to (h).

In a 288th embodiment, the disclosure provides a pharmaceutical composition of the 284th embodiment, wherein said at least three properties include (a), (c) and (e).

In a 289th embodiment, the disclosure provides a pharmaceutical composition of the 284th embodiment, wherein said at least three properties include (b), (d), and (f).

In a 290th embodiment, the disclosure provides a pharmaceutical composition of the 282nd embodiment or 283rd embodiment which is characterized by at least four of the properties (a) to (h).

In a 291st embodiment, the disclosure provides a pharmaceutical composition of the 284th embodiment, wherein said at least four properties include (a), (c), (e) and (g).

In a 292nd embodiment, the disclosure provides a pharmaceutical composition of the 284th embodiment, wherein said at least four properties include (b), (d), (f), and (h).

In a 293rd embodiment, the disclosure provides a pharmaceutical composition of the 282nd embodiment or 283rd embodiment which is characterized by at least five of the properties (a) to (h).

In a 294th embodiment, the disclosure provides a pharmaceutical composition of the 282nd embodiment or 283rd embodiment which is characterized by at least six of the properties (a) to (h).

In a 295th embodiment, the disclosure provides a pharmaceutical composition of the 282nd embodiment or 283rd embodiment which is characterized by at least seven of the properties (a) to (h).

In a 296th embodiment, the disclosure provides a pharmaceutical composition of the 282nd embodiment or 283rd embodiment which is characterized by all properties (a) to (h).

In a 297th embodiment, the disclosure provides a pharmaceutical composition of any one of the 282nd to 296th embodiments which is free or substantially free of one, two, three or all four proteins consisting of SEQ ID NO:85, 86, 94 and 95.

In a 298th embodiment, the disclosure provides a pharmaceutical composition of any one of the 282nd to 297th embodiments which is free or substantially free of proteins consisting of
SEQ ID NO:85 and SEQ ID NO:86.

In a 299th embodiment, the disclosure provides a pharmaceutical composition of any one of the 282nd to 297th embodiments which is free or substantially free of proteins consisting of SEQ ID NO:94 and SEQ ID NO:95.

In a 300th embodiment, the disclosure provides a pharmaceutical composition of any one of the 282nd to 297th embodiments which is free or substantially free of one, two, or all three proteins consisting of SEQ ID NO:106, 107 and 108.

In a 301st embodiment, the disclosure provides a pharmaceutical composition of any one of the 282nd to 300th embodiments which contains pharmaceutically acceptable levels of endotoxins.

In a 302nd embodiment, the disclosure provides a pharmaceutical composition of the 301st embodiment, wherein said pharmaceutical composition is a liquid composition and wherein said pharmaceutically acceptable levels of endotoxins are 8 EU/ml or less.

In a 303rd embodiment, the disclosure provides a pharmaceutical composition of the 302nd embodiment, wherein said pharmaceutically acceptable levels of endotoxins are 5 EU/ml or less.

In a 304th embodiment, the disclosure provides a pharmaceutical composition of the 301st embodiment, wherein said pharmaceutical composition is a solid composition and wherein said pharmaceutically acceptable levels of endotoxins are 10 EU or less per gram of mature human type I elastase.

In a 305th embodiment, the disclosure provides a pharmaceutical composition of the 304th embodiment wherein said pharmaceutically acceptable levels of endotoxins are 5 EU or less per gram of mature human type I elastase.

In a 306th embodiment, the disclosure provides a pharmaceutical composition of any one of the 282nd to 305th embodiments in which the mature human type I elastase is characterized by a specific activity of 1 to 40 U/mg of protein.

In a 307$^{th}$ embodiment, the disclosure provides a pharmaceutical composition of the 306$^{th}$ embodiment in which the mature human type I elastase is characterized by a specific activity of 25 to 35 U/mg of protein.

In a 308$^{th}$ embodiment, the disclosure provides a pharmaceutical composition of the 306$^{th}$ embodiment in which the mature human type I elastase is characterized by a specific activity of greater than 10 U/mg of protein.

In a 309$^{th}$ embodiment, the disclosure provides a pharmaceutical composition of the 306$^{th}$ embodiment in which the mature human type I elastase is characterized by a specific activity of greater than 20 U/mg of protein.

In a 310$^{th}$ embodiment, the disclosure provides a pharmaceutical composition of any one of the 282$^{nd}$ to 309$^{th}$ embodiments, wherein the mature human type I elastase consists essentially of SEQ ID NO: 5, 84, or 87.

In a 311$^{th}$ embodiment, the disclosure provides a pharmaceutical composition of the 310$^{th}$ embodiment, wherein the mature human type I elastase consists essentially of SEQ ID NO:1 or SEQ ID NO:4.

In a 312$^{th}$ embodiment, the disclosure provides a pharmaceutical composition of any one of the 282$^{nd}$ to 311$^{th}$ embodiments in which the trypsin activity corresponds to less than 4 ng per 1 mg of mature human type I elastase protein.

In a 313$^{th}$ embodiment, the disclosure provides a pharmaceutical composition of the 312$^{th}$ embodiment in which the trypsin activity corresponds to less than 2 ng per 1 mg of mature human type I elastase protein.

In a 314$^{th}$ embodiment, the disclosure provides a lyophilized formulation of a protein consisting essentially of SEQ ID NO: 5, 84, or 87 which upon reconstitution to a concentration of said protein of 1 mg/ml the trypsin activity corresponds to less than 2 ng/ml trypsin.

In a 315$^{th}$ embodiment, the disclosure provides a lyophilized formulation of the 314$^{th}$ embodiment, wherein the moisture content is less than 5%.

In a 316$^{th}$ embodiment, the disclosure provides a lyophilized formulation of the 315th embodiment which comprises sodium ions, potassium ions, phosphate ions, and chloride ions.

In a 317$^{th}$ embodiment, the disclosure provides a lyophilized formulation of the 315$^{th}$ embodiment which comprises polysorbate-80.

In a 318$^{th}$ embodiment, the disclosure provides a lyophilized formulation of the 315$^{th}$ embodiment which comprises dextran.

In a 319$^{th}$ embodiment, the disclosure provides a lyophilized formulation of the 318$^{th}$ embodiment, wherein the dextran is dextran-18.

In a 320$^{th}$ embodiment, the disclosure provides a lyophilized formulation of the 311$^{th}$ embodiment which comprises sodium ions, potassium ions, phosphate ions, chloride ions and polysorbate-80.

In a 321$^{st}$ embodiment, the disclosure provides a lyophilized formulation of the 314$^{th}$ embodiment which comprises sodium ions, potassium ions, phosphate ions, chloride ions and dextran.

In a 322$^{nd}$ embodiment, the disclosure provides a lyophilized formulation of the 321$^{st}$ embodiment, wherein the dextran is dextran-18.

In a 323$^{rd}$ embodiment, the disclosure provides a lyophilized formulation of the 314$^{th}$ embodiment which comprises sodium ions, potassium ions, phosphate ions, chloride ions, polysorbate-80, and dextran.

In a 324$^{th}$ embodiment, the disclosure provides a lyophilized formulation of the 323$^{rd}$ embodiment, wherein the dextran is dextran-18.

In a 325$^{th}$ embodiment, the disclosure provides a liquid formulation comprising a solution of a least 0.1 mg/ml of a protein consisting essentially of SEQ ID NO: 5, 84, or 87 in which the trypsin activity corresponds to less than 2 ng/ml trypsin.

In a 326$^{th}$ embodiment, the disclosure provides a liquid formulation of the 325$^{th}$ embodiment, wherein the solution is a buffered solution.

In a 327$^{th}$ embodiment, the disclosure provides a liquid formulation of the 326$^{th}$ embodiment, wherein the solution is buffered to a pH of 7 to 8.

In a 328$^{th}$ embodiment, the disclosure provides a liquid formulation of the 326$^{th}$ embodiment in which the solution is PBS.

In a 329$^{th}$ embodiment, the disclosure provides a liquid formulation of the 328$^{th}$ embodiment in which the solution comprises 137 mM sodium chloride, 2.7 mM potassium phosphate, and 10 mM sodium phosphate.

In a 330$^{th}$ embodiment, the disclosure provides a liquid formulation of any one of the 325$^{th}$ to 329$^{th}$ embodiments which further comprises one or more excipients.

In a 331$^{st}$ embodiment, the disclosure provides a liquid formulation of the 330$^{th}$ embodiment in which said one or more excipients comprises dextran-18.

In a 332$^{nd}$ embodiment, the disclosure provides a liquid formulation of the 331$^{st}$ embodiment in which the dextran-18 is in the amount of 8% weight/volume of said solution.

In a 333$^{rd}$ embodiment, the disclosure provides a liquid formulation of the 330$^{th}$ embodiment in which said one or more excipients comprises polysorbate-80.

In a 334$^{th}$ embodiment, the disclosure provides a liquid formulation of the 333$^{rd}$ embodiment in which the polysorbate-80 is in the amount of 0.01% weight/volume of said solution.

In a 335$^{th}$ embodiment, the disclosure provides a liquid formulation of any one of the 325$^{th}$ to 334$^{th}$ embodiments in which the concentration of said protein in said solution is in the range of 0.001 mg/ml to 40 mg/ml.

In a 336$^{th}$ embodiment, the disclosure provides a liquid formulation of the 335$^{th}$ embodiment in which the concentration of said protein in said solution is in the range of 0.1 mg/ml to 20 mg/ml.

In a 337$^{th}$ embodiment, the disclosure provides a liquid formulation of any one of the 325$^{th}$ to 336$^{th}$ embodiments with further comprises one or more of a preservative, a solubilizer and a coloring agent.

In a 338$^{th}$ embodiment, the disclosure provides a liquid formulation of any one of the 325$^{th}$ to 337$^{th}$ embodiments which is substantially free of mammalian proteins other than said protein of SEQ ID NO:5, 84 or 87.

In a 339$^{th}$ embodiment, the disclosure provides a liquid formulation of any one of the 325$^{th}$ to 338$^{th}$ embodiments which is substantially free of bacterial proteins.

In a 340$^{th}$ embodiment, the disclosure provides a formulation made by or obtainable by the method of any one of the 225$^{th}$ to 258$^{th}$ embodiments.

In a 341$^{st}$ embodiment, the disclosure provides a formulation of the 340$^{th}$ embodiment which is a liquid formulation.

In a 342$^{nd}$ embodiment, the disclosure provides a formulation of the 340$^{th}$ or 341$^{st}$ embodiment in which the mature type I elastase protein is a human type I mature elastase protein.

In a 343$^{rd}$ embodiment, the disclosure provides a formulation of the 342$^{nd}$ embodiment, wherein the mature human type I elastase protein consists essentially of SEQ ID NO:5, SEQ ID NO:84, or SEQ ID NO:87.

In a 344$^{th}$ embodiment, the disclosure provides a formulation of the 342$^{nd}$ embodiment, wherein the mature human type I elastase protein consists essentially of SEQ ID NO:1 or SEQ ID NO:4.

In a 345$^{th}$ embodiment, the disclosure provides a formulation of the 340$^{th}$ or 341$^{st}$ embodiment in which the mature type I elastase protein is a porcine type I mature elastase protein.

In a 346$^{th}$ embodiment, the disclosure provides a formulation of the 345$^{th}$ embodiment, wherein the mature porcine type I elastase protein consists essentially of SEQ ID NO:39.

In a 347$^{th}$ embodiment, the disclosure provides a method of removing one or more incorrectly processed mature elastase proteins from a mixture of correctly and incorrectly processed mature elastase proteins, said method comprising:

(a) subjecting a composition comprising a mixture of correctly and incorrectly processed mature elastase proteins to a pH at which the correctly processed mature enzyme is active;

(b) maintaining such pH until such time that one or more incorrectly processed mature elastase proteins are degraded, thereby removing said one or more incorrectly processed mature elastase proteins from a mixture of correctly and incorrectly processed mature elastase proteins.

In a 348$^{th}$ embodiment, the disclosure provides a method of the 347$^{th}$ embodiment, wherein said one or more incorrectly processed mature elastase proteins contain at least one additional or fewer amino acid at the N-terminus relative to correctly processed mature elastase proteins.

In a 349$^{th}$ embodiment, the disclosure provides a method of the 347$^{th}$ or 348$^{th}$ embodiment wherein said pH is between 5 and 12.

In a 350$^{th}$ embodiment, the disclosure provides a method of any one of the 347$^{th}$ to 349$^{th}$ embodiments, wherein said one or more incorrectly processed mature elastase proteins are degraded by 50% to 100%.

In a 351$^{st}$ embodiment, the disclosure provides a method of the 348$^{th}$ embodiment, wherein said one or more incorrectly processed mature elastase proteins are degraded by 50% to 99%.

In a 352$^{nd}$ embodiment, the disclosure provides a method of the 348$^{th}$ embodiment, wherein said one or more incorrectly processed mature elastase proteins are degraded by 50% to 98%.

In a 353$^{rd}$ embodiment, the disclosure provides a method of the 348$^{th}$ embodiment, wherein said one or more incorrectly processed mature elastase proteins are degraded by 50% to 95%.

In a 354$^{th}$ embodiment, the disclosure provides a method of the 348$^{th}$ embodiment, wherein said one or more incorrectly processed mature elastase proteins are degraded by 50% to 90%.

In a 355$^{th}$ embodiment, the disclosure provides a method of any one of the 350$^{th}$ to 354$^{th}$ embodiments, wherein more than one incorrectly processed mature elastase protein is degraded by at least 50%.

In a 356$^{th}$ embodiment, the disclosure provides a method of the 355$^{th}$ embodiment, wherein all incorrectly processed mature elastase proteins in the mixture are degraded by at least 50%.

In a 357$^{th}$ embodiment, the disclosure provides a method of any one of the 350$^{th}$ to 354$^{th}$ embodiments wherein at least one incorrectly processed mature elastase protein is degraded by at least 75%.

In a 358$^{th}$ embodiment, the disclosure provides a method of the 357$^{th}$ embodiment, wherein more than one incorrectly processed mature elastase protein is degraded by at least 75%.

In a 359$^{th}$ embodiment, the disclosure provides a method of the 357$^{th}$ embodiment, wherein all incorrectly processed mature elastase proteins in the mixture are degraded by at least 75%.

In a 360$^{th}$ embodiment, the disclosure provides a method of any one of the 350$^{th}$ to 354$^{th}$ embodiments wherein at least one incorrectly processed mature elastase protein is degraded by at least 90%.

In a 361$^{st}$ embodiment, the disclosure provides a method of the 360$^{th}$ embodiment, wherein more than one incorrectly processed mature elastase protein is degraded by at least 90%.

In a 362$^{nd}$ embodiment, the disclosure provides a method of the 360$^{th}$ embodiment, wherein all incorrectly processed mature elastase proteins in the mixture are degraded by at least 90%.

In a 363$^{rd}$ embodiment, the disclosure provides a method of any one of the 347$^{th}$ to 362$^{nd}$ embodiments, wherein the composition is a liquid composition in which the total elastase protein is at a concentration of 10 mg/ml or less.

In a 364$^{th}$ embodiment, the disclosure provides a method of any one of the 347$^{th}$ to 362$^{nd}$ embodiments, wherein the composition is a liquid composition in which the total elastase protein is at a concentration of 5 mg/ml or less.

In a 365$^{th}$ embodiment, the disclosure provides a method of any one of the 347$^{th}$ to 362$^{nd}$ embodiments, wherein the composition is a liquid composition in which the total elastase protein is at a concentration of 2 mg/ml or less.

In a 366$^{th}$ embodiment, the disclosure provides a method of any one of the 347$^{th}$ to 362$^{nd}$ embodiments, wherein the composition is a liquid composition in which the total elastase protein is at a concentration of 1 mg/ml or less.

In a 367$^{th}$ embodiment, the disclosure provides a method of any one of the 347$^{th}$ to 362$^{nd}$ embodiments, wherein the composition is a liquid composition in which the total elastase protein is at a concentration of 0.5 mg/ml or less.

In a 368$^{th}$ embodiment, the disclosure provides a method of any one of the 347$^{th}$ to 362$^{nd}$ embodiments, wherein the composition is a liquid composition in which the total elastase protein is at a concentration of 0.25 mg/ml or less.

In a 369$^{th}$ embodiment, the disclosure provides a method of any one of the 363$^{rd}$ to 368$^{th}$ embodiments, wherein the composition is a liquid composition in which the total elastase protein is at a concentration of at least 0.1 mg/ml.

In a 370$^{th}$ embodiment, the disclosure provides a method of any one of the 363$^{rd}$ to 368$^{th}$ embodiments, wherein the composition is a liquid composition in which the total elastase protein is at a concentration of at least 0.2 mg/ml.

In a 371$^{st}$ embodiment, the disclosure provides a method of any one of the 347$^{th}$ to 370$^{th}$ embodiments, wherein the trypsin activity in said composition is less than 4 ng/ml trypsin per mg of total elastase proteins.

In a 372$^{nd}$ embodiment, the disclosure provides a method of any one of the 347$^{th}$ to 370$^{th}$ embodiments, wherein the trypsin activity in said composition is less than 2 ng/ml trypsin per mg of total elastase proteins.

In a 373$^{rd}$ embodiment, the disclosure provides a method of any one of the 347$^{th}$ to 372$^{nd}$ embodiments, wherein the composition is free or substantially free of a protein consisting of SEQ ID NO:104 and/or is free or substantially free of a protein consisting of SEQ ID NO:105.

In a 374$^{th}$ embodiment, the disclosure provides a method of producing a pharmaceutical composition comprising a mature type I elastase, said method comprising (i) producing a lyophilized mature type I elastase by the method of any one of the 261$^{st}$ to 265$^{th}$ embodiments; and (ii) reconstituting the lyophilized mature type I elastase in water or a pharmaceutically acceptable carrier, thereby producing a pharmaceutical composition comprising a mature human type I elastase.

In a 375$^{th}$ embodiment, the disclosure provides a method of producing a pharmaceutical composition comprising a mature type I elastase, said method comprising reconstituting the lyophilized formulation of any one of the 314$^{th}$ to 324$^{th}$ embodiments in water or a pharmaceutically acceptable carrier, thereby producing a pharmaceutical composition comprising a mature type I elastase.

In a 376$^{th}$ embodiment, the disclosure provides a method of the 374$^{th}$ embodiment or the 375$^{th}$ embodiment where the pharmaceutical composition comprises phosphate.

In a 377$^{th}$ embodiment, the disclosure provides a method of any one of the 374$^{th}$ to 376$^{th}$ embodiments, wherein the mature type I elastase is mature human type I elastase.

In a 378$^{th}$ embodiment, the disclosure provides a method of the 377$^{th}$ embodiment characterized by a specific activity of 1 to 40 U/mg protein.

In a 379$^{th}$ embodiment, the disclosure provides a method of the 377$^{th}$ embodiment wherein the mature type I elastase is characterized by a specific activity of 25 to 35 U/mg protein.

In a 380$^{th}$ embodiment, the disclosure provides a method of any one of the 377$^{th}$ to 379$^{th}$ embodiments, wherein the mature human type I elastase in said pharmaceutical composition maintains 60% to 100% of its specific activity after at least a week of storage at 4° C., after at least a month of storage at 4° C., after at least two months of storage at 4° C., after at least three months of storage at 4° C., or after at least month six months of storage at 4° C.

In a 381$^{st}$ embodiment, the disclosure provides a method of any one of the 377$^{th}$ to 379$^{th}$ embodiments, wherein the mature human type I elastase in said pharmaceutical composition maintains 60% to 98% of its specific activity after at least a week of storage at 4° C., after at least a month of storage at 4° C., after at least two months of storage at 4° C., after at least three months of storage at 4° C., or after at least month six months of storage at 4° C.

In a 382$^{nd}$ embodiment, the disclosure provides a method of any one of the 377$^{th}$ to 379$^{th}$ embodiments, wherein the mature human type I elastase in said pharmaceutical composition maintains 60% to 95% of its specific activity after at least a week of storage at 4° C., after at least a month of storage at 4° C., after at least two months of storage at 4° C., after at least three months of storage at 4° C., or after at least month six months of storage at 4° C.

In a 383$^{rd}$ embodiment, the disclosure provides a method of any one of the 377$^{th}$ to 379$^{th}$ embodiments, wherein the mature human type I elastase in said pharmaceutical composition maintains 60% to 90% of its specific activity after at least a week of storage at 4° C., after at least a month of storage at 4° C., after at least two months of storage at 4° C., after at least three months of storage at 4° C., or after at least month six months of storage at 4° C.

In a 384$^{th}$ embodiment, the disclosure provides a method of any one of the 377$^{th}$ to 379$^{th}$ embodiments, wherein the mature human type I elastase in said pharmaceutical composition maintains 60% to 80% of its specific activity after at least a week of storage at 4° C., after at least a month of storage at 4° C., after at least two months of storage at 4° C., after at least three months of storage at 4° C., or after at least month six months of storage at 4° C.

In a 385$^{th}$ embodiment, the disclosure provides a method of any one of the 377$^{th}$ to 384$^{th}$ embodiments, wherein the mature human type I elastase in said pharmaceutical composition maintains at least 70% of its specific activity after a week of storage at 4° C.

In a 386$^{th}$ embodiment, the disclosure provides a pharmaceutical composition produced by or obtainable by the method of any one of the 374$^{th}$ to 385$^{th}$ embodiments.

In a 387$^{th}$ embodiment, the disclosure provides a method for therapeutically increasing the diameter of an artery or vein in a human subject in need thereof, the method comprising: locally administering to the wall of the artery or vein in the human subject (a) the pharmaceutical composition of any one of the 277$^{th}$ to 313$^{th}$ and 386$^{th}$ embodiments, (b) the liquid formulation of any one of the 325$^{th}$ to 339$^{th}$ embodiments, or (c) the formulation of the 341$^{st}$ embodiment in a dose sufficient to increase the diameter of the artery or vein.

In a 388$^{th}$ embodiment, the disclosure provides a method of the 387$^{th}$ embodiment, wherein the diameter of the vessel, the lumenal diameter of the vessel, or both, are increased.

In a 389$^{th}$ embodiment, the disclosure provides a method for preventing or treating vasospasm of an artery or vein in a human subject in need thereof, the method comprising:

locally administering to the wall of the artery or vein in the human subject (a) the pharmaceutical composition of any one of the 277$^{th}$ to 313$^{th}$ and 386$^{th}$ embodiments, (b) the liquid formulation of any one of the 325$^{th}$ to 339$^{th}$ embodiments, or (c) the formulation of the 341$^{st}$ embodiment in a dose sufficient to prevent or treat vasospasm of the artery or vein.

In a 390$^{th}$ embodiment, the disclosure provides a method for treating an obstructed artery or vein in a human subject in need of such treatment, the method comprising: locally administering to the wall of the artery or vein in the human subject (a) the pharmaceutical composition of any one of the 277$^{th}$ to 313$^{th}$ and 386$^{th}$ embodiments, (b) the liquid formulation of any one of the 325$^{th}$ to 339$^{th}$ embodiments, or (c) the formulation of the 341$^{st}$ embodiment, wherein said administration results in proteolysis of elastin in the wall of the artery or vein leading to enlargement of the diameter of the artery or vein.

In a 391$^{st}$ embodiment, the disclosure provides a method for treating an artery or vein connected to an arteriovenous hemodialysis graft or arteriovenous fistula in a human subject in need of such treatment, the method comprising: locally administering to the wall of the artery or vein in the human subject ((a) the pharmaceutical composition of any one of the 277$^{th}$ to 313$^{th}$ and 386$^{th}$ embodiments, (b) the liquid formulation of any one of the 325$^{th}$ to 339$^{th}$ embodiments, or (c) the formulation of the 341$^{st}$ embodiment, wherein said administration results in proteolysis of elastin in the wall of the artery or vein leading to enlargement of the diameter of the artery or vein.

In a 392$^{nd}$ embodiment, the disclosure provides a method for treating a vein in a human subject for use in hemodialysis, the method comprising: locally administering to the wall of the vein in the human subject (a) the pharmaceutical composition of any one of the 277th to 313th and 386th embodiments, (b) the liquid formulation of any one of the 325th to 339th embodiments, or (c) the formulation of the 341st embodiment, wherein said administration results in proteolysis of elastin in the wall of the vein leading to enlargement of the diameter of the vein.

In a 393rd embodiment, the disclosure provides a method of any one of the 387th to 392nd embodiments, which further comprises inserting a portion of a delivery apparatus into the wall of the artery or vein to deliver elastase to the wall of the artery or vein.

In a 394th embodiment, the disclosure provides a method of any one of the 387th to 393rd embodiments, wherein the pharmaceutical composition or liquid formulation is administered by a catheter.

In a 395th embodiment, the disclosure provides a method of any one of the 387th to 394th embodiments, wherein the wherein the pharmaceutical composition or liquid formulation is administered directly into the wall of the artery or vein.

In a 396th embodiment, the disclosure provides a method of any one of the 387th to 395th embodiments, wherein the artery or vein is obstructed.

In a 397th embodiment, the disclosure provides a method of the 396th embodiment, wherein the artery or vein is obstructed by stenosis.

In a 398th embodiment, the disclosure provides a method of the 397th embodiment, wherein the obstruction permits passage of an insufficient volume of blood prior to the treatment.

In a 399th embodiment, the disclosure provides a method of the 398th embodiment, wherein the obstruction is a stenosis.

In a 400th embodiment, the disclosure provides a method of the 399th embodiment, wherein the artery or vein is obstructed by intimal hyperplasia.

In a 401st embodiment, the disclosure provides a method of any one of the 387th to 400th embodiments, wherein the pharmaceutical composition or liquid formulation is administered to an obstructed coronary or peripheral artery.

In a 402nd embodiment, the disclosure provides a method of any one of the 387th to 395th embodiments, wherein the artery or vein is susceptible to obstruction by intimal hyperplasia.

In a 403rd embodiment, the disclosure provides a method of any one of the 387th to 400th and 402nd embodiments, wherein the composition is administered to the wall of a vein.

In a 404th embodiment, the disclosure provides a method of the 403rd embodiment, wherein the vein is connected to an arteriovenous hemodialysis graft or arteriovenous fistula.

In a 405th embodiment, the disclosure provides a method of the 404th embodiment, wherein the vein is for use in hemodialysis.

In a 406th embodiment, the disclosure provides a method of the 405th embodiment, further comprising directly connecting the vein to an artery or connecting the vein to an artery via a graft.

In a 407th embodiment, the disclosure provides a method of any one of the 387th to 394th embodiments, wherein the composition is administered to the adventitial surface of a surgically exposed artery or vein.

In a 408th embodiment, the disclosure provides a method of any one of the 387th to 407th embodiments, wherein the mature type I elastase protein in said pharmaceutical composition, liquid formulation or formulation, respectively, is a human type I mature elastase protein.

In a 409th embodiment, the disclosure provides a method of the 408th embodiment, wherein the mature human type I elastase protein consists essentially of SEQ ID NO:5, SEQ ID NO:84, or SEQ ID NO:87.

In a 410th embodiment, the disclosure provides a method of the 408th embodiment, wherein the mature human type I elastase protein consists essentially of SEQ ID NO:1 or SEQ ID NO:4.

In a 411th embodiment, the disclosure provides a method of any one of the 387th to 407th embodiments, wherein the mature type I elastase protein in said pharmaceutical composition, liquid formulation or formulation, respectively, is a porcine type I mature elastase protein.

In a 412th embodiment, the disclosure provides a method of the 411th embodiment, wherein the mature porcine type I elastase protein consists essentially of SEQ ID NO:39.

In a 413th embodiment, the disclosure provides a unit dosage comprising 0.0033 mg to 200 mg of (a) mature human type I elastase of the 273rd embodiment or the 274th embodiment or (b) a formulation of mature human type I elastase produced by or obtainable by the method of the 259th embodiment.

In a 414th embodiment, the disclosure provides a unit dosage of the 413th embodiment, wherein the mature human type I elastase protein consists essentially of SEQ ID NO:5, SEQ ID NO:84, or SEQ ID NO:87.

In a 415th embodiment, the disclosure provides a unit dosage comprising 0.0033 mg to 200 mg of (a) the mature porcine type I elastase of the 275th embodiment or the 276th embodiment or (b) a formulation of mature porcine type I elastase produced by or obtainable by the method of the 260th embodiment.

In a 416th embodiment, the disclosure provides a unit dosage of the 415th embodiment, wherein the mature porcine type I elastase protein consists essentially of SEQ ID NO:39.

In a 417th embodiment, the disclosure provides a unit dosage of any one of the 413th to 416th embodiments which comprises 0.5 mg to 50 mg of said mature type I elastase.

In a 418th embodiment, the disclosure provides a unit dosage of the 417th embodiment which comprises 1 mg to 20 mg of said mature type I elastase.

In a 419th embodiment, the disclosure provides a unit dosage of the 418th embodiment which comprises 5 mg to 10 mg of said mature type I elastase.

In a 420th embodiment, the disclosure provides a unit dosage of any one of the 413th to 419th embodiments which is in a container, pack, dispenser, or catheter.

In a 421st embodiment, the disclosure provides a kit comprising an elastase protein according to any one of the 1st to 39th and 68th to 69th embodiments or obtained or obtainable by the method of any one of the 89th to 224th, 261st to 276th, and 347th to 373rd embodiments, a nucleic acid according to any one of the 40th to 67th embodiments, a vector according to any one of the 70th to 72nd embodiments, a cell according to any one of the 73rd to 87th embodiments, a cell culture supernatant according to the 88th embodiment, an elastase formulation according to any one of the 314th to 346th embodiments or obtained or obtainable by the method of any one of the 261st to 276th embodiments, a pharmaceutical composition according to the method of any one of the 277th to 313th and 386th embodiments, or obtained or obtainable by the method of any one of the 374th to 385th embodiments, or a unit dosage according to any one of the 413th to 420th embodiments.

In a 422nd embodiment, the disclosure provides a kit of the 421st embodiment which is a therapeutic kit.

In a 423rd embodiment, the disclosure provides a kit of the 422nd embodiment which comprises a container, pack, dispenser, or catheter.

In a 424th embodiment, the disclosure provides a kit of the 423rd embodiment which is a manufacturing kit.

The invention is further exemplified by the following Specific Embodiments that pertain to proelastase proteins of SEQ ID NO:64 and SEQ ID NO:69:

In a 1st Specific Embodiment, the disclosure provides a protein comprising the amino acid sequence of SEQ ID NO:64 or SEQ ID NO:69.

In a 2nd Specific Embodiment, the disclosure provides a protein of the 1st Specific Embodiment which is isolated.

In a 3rd Specific Embodiment, the disclosure provides a nucleic acid molecule comprising a nucleotide sequence encoding a protein of the 1st Specific Embodiment.

In a 4th Specific Embodiment, the disclosure provides a nucleic acid molecule of the 3rd Specific Embodiment, wherein the protein comprises a signal sequence operably linked to said amino acid sequence of SEQ ID NO:64 or SEQ ID NO:69.

In a 5th Specific Embodiment, the disclosure provides a nucleic acid molecule of the 4th Specific Embodiment, wherein the signal sequence is operable in *Pichia pastoris*.

In a 6th Specific Embodiment, the disclosure provides a nucleic acid molecule of the 5th Specific Embodiment, wherein the signal sequence is a yeast α-factor signal peptide.

In a 7th Specific Embodiment, the disclosure provides a vector comprising the nucleic acid molecule of the 4th Specific Embodiment.

In an 8th Specific Embodiment, the disclosure provides a vector of the 7th Specific Embodiment in which the nucleotide sequence is multimerized.

In a 9th Specific Embodiment, the disclosure provides a host cell comprising the vector of the 7th Specific Embodiment.

In a 10th Specific Embodiment, the disclosure provides a host cell of the 9th Specific Embodiment in which at least one copy of said vector is integrated into the host cell genome.

In a 11th Specific Embodiment, the disclosure provides a host cell of the 10th Specific Embodiment in which two to five copies of said vector are integrated into the host cell genome.

In a 12th Specific Embodiment, the disclosure provides a host cell of the 9th Specific Embodiment in which the nucleotide sequence is multimerized.

In a 13th Specific Embodiment, the disclosure provides a host cell of the 12th Specific Embodiment in which the vector comprises two to five copies of said nucleotide sequence.

In a 14th Specific Embodiment, the disclosure provides a cell genetically engineered to express the nucleic acid molecule of the 3rd Specific Embodiment.

In a 15th Specific Embodiment, the disclosure provides a cell of the 14th Specific Embodiment, which is a *Pichia pastoris* cell.

In a 16th Specific Embodiment, the disclosure provides a cell of the 15th Specific Embodiment, wherein the nucleotide sequence is operably linked to a methanol-inducible promoter.

In a 17th Specific Embodiment, the disclosure provides a cell culture supernatant comprising the protein of the 1st Specific Embodiment.

In a 18th Specific Embodiment, the disclosure provides a method of producing an elastase protein, comprising culturing the cell of the 15th Specific Embodiment under conditions in which the protein of SEQ ID NO:64 or SEQ ID NO:69 is expressed.

In a 19th Specific Embodiment, the disclosure provides a method of the 18th Specific Embodiment, wherein said conditions include one, two, three or all four of: (i) a period of growth or induction at a pH of 2 to 6; (ii) a period of growth or induction at a temperature of 22° C. to 28° C.; (iii) culturing in complex medium; or (iv) culturing in the presence of a citrate, succinate or acetate compound.

In a 20th Specific Embodiment, the disclosure provides a method of the 18th Specific Embodiment which further comprises recovering the protein.

In a 21st Specific Embodiment, the disclosure provides a method of the 18th Specific Embodiment, which further comprises exposing said protein of SEQ ID NO:64 or SEQ ID NO:69 to activation conditions to produce a mature elastase protein.

In a 22nd Specific Embodiment, the disclosure provides a method of the 21st Specific Embodiment, wherein said protein is purified prior to said exposure to activating conditions.

In a 23rd Specific Embodiment, the disclosure provides a method of the 22nd Specific Embodiment, wherein said protein is purified in the presence of a citrate, succinate or acetate compound.

In a 24th Specific Embodiment, the disclosure provides a method of the 21st Specific Embodiment, further comprising purifying the mature elastase protein.

In a 25th Specific Embodiment, the disclosure provides a method of the 24th Specific Embodiment, further comprising lyophilizing the purified mature elastase protein.

In a 26th Specific Embodiment, the disclosure provides a method of making a mature elastase protein, comprising subjecting a cell culture supernatant according to the 17th Specific Embodiment to autoactivation conditions, thereby producing a mature elastase protein.

In a 27th Specific Embodiment, the disclosure provides a method of the 26th Specific Embodiment, further comprising purifying the mature elastase protein.

In a 28th Specific Embodiment, the disclosure provides a method of the 27th Specific Embodiment, further comprising lyophilizing the purified mature elastase protein.

In a 29th Specific Embodiment, the disclosure provides a method of making a pharmaceutical composition comprising a mature elastase protein, reconstituting a lyophilisate comprising the lyophilized proelastase protein produced by the method of the 25th Specific Embodiment- or the 28th Specific Embodiment.

In a 30th Specific Embodiment, the disclosure provides a method of the 29th Specific Embodiment, wherein the lyophilisate (a) comprises one or more buffer ingredients or (b) does not comprise buffer ingredients.

In a 31st Specific Embodiment, the disclosure provides a method of the 30th Specific Embodiment, wherein the lyophilisate is reconstituted with water or buffer.

In a 32nd Specific Embodiment, the disclosure provides a method of the 31st Specific Embodiment, wherein upon reconstitution a solution of mature elastase protein in full strength buffer, greater than full strength buffer, or less than full strength buffer is produced.

In a 33rd Specific Embodiment, the disclosure provides a method of the 32nd Specific Embodiment, wherein the buffer is phosphate buffered saline.

In a 34th Specific Embodiment, the disclosure provides a method of the 29th Specific Embodiment, wherein the mature elastase protein is reconstituted to a concentration of 0.001 mg/ml to 50 mg/ml.

In a 35th Specific Embodiment, the disclosure provides a method of the 29th Specific Embodiment, wherein the mature elastase protein has a specific activity of 1 to 40 U/mg protein.

In a 36th Specific Embodiment, the disclosure provides a pharmaceutical composition produced by the method of the 29th Specific Embodiment.

In a 37th Specific Embodiment, the disclosure provides a pharmaceutical composition of the 36th Specific Embodiment which is characterized by at least one, at least two, at least three, at least four, at least five, at least six or at least seven of the following properties:
 (a) the composition is free of trypsin;
 (b) the composition is substantially free of trypsin;
 (c) the composition is free of any protein consisting of SEQ ID NOS:70 and 71;
 (d) the composition is substantially free of any protein consisting of SEQ ID NOS:2 and 3;
 (e) the composition is free of bacterial proteins;
 (f) the composition is substantially free of bacterial proteins;
 (g) the composition is free of mammalian proteins other than said mature elastase protein;
 (h) the composition is substantially free of mammalian proteins other than said mature elastase protein;
 (i) the composition is free or substantially free of one, two, three or all four proteins consisting of SEQ ID NO:85, 86, 94 and 95;
 (j) the composition is free or substantially free of one, two, or all three proteins consisting of SEQ ID NO:106, 107 and 108;
 (k) the composition contains pharmaceutically acceptable levels of endotoxins;
 (l) the mature elastase protein in the composition is characterized by a specific activity of 1 to 40 U/mg of protein;
 (m) the trypsin activity in said composition corresponds to less than 4 ng per 1 mg of mature elastase protein;
 (n) the composition comprises polysorbate-80;
 (o) the composition comprises dextran;
 (p) the composition comprises sodium ions, potassium ions, phosphate ions, chloride ions and polysorbate-80;
 (q) the composition comprises sodium ions, potassium ions, phosphate ions, chloride ions and dextran;
 (r) the composition comprises sodium ions, potassium ions, phosphate ions, chloride ions, polysorbate-80, and dextran;
 (s) the mature elastase protein in said composition maintains 60% to 100% of its specific activity after at least a week of storage at 4° C., after at least a month of storage at 4° C., after at least two months of storage at 4° C., after at least three months of storage at 4° C., or after at least month six months of storage at 4° C.; and
 (t) the composition comprises a unit dosage of 0.0033 mg to 200 mg of said mature elastase protein.

In a 38th Specific Embodiment, the disclosure provides a pharmaceutical composition of the 37th Specific Embodiment, wherein the pharmaceutical composition is characterized by at least three characteristics, at least four characteristics or five characteristics independently selected from the following groups (i) through (v):
 (i) (a), (b) or (m)
 (ii) (e) or (f)
 (iii) (g) or (h)
 (iv) (k)
 (v) (l)

In a 39th Specific Embodiment, the disclosure provides a pharmaceutical composition of the 38th Specific Embodiment, wherein two of said at least three or at least said four characteristics are selected from groups (i) and (iv) or (v).

In a 40th Specific Embodiment, the disclosure provides a pharmaceutical composition of the 38th Specific Embodiment, wherein three of at least said four characteristics are selected from groups (i), (iv) and (v).

In a 41st Specific Embodiment, the disclosure provides a method of removing one or more incorrectly processed mature elastase proteins from a mixture of correctly and incorrectly processed mature elastase proteins, said method comprising:
 (a) subjecting a composition comprising a mixture of correctly and incorrectly processed mature elastase proteins to a pH at which the correctly processed mature enzyme is active;
 (b) maintaining such pH until such time that one or more incorrectly processed mature elastase proteins are degraded, thereby removing said one or more incorrectly processed mature elastase proteins from a mixture of correctly and incorrectly processed mature elastase proteins.

In a 42nd Specific Embodiment, the disclosure provides a method of the 41st Specific Embodiment, wherein said one or more incorrectly processed mature elastase proteins contain at least one additional or fewer amino acid at the N-terminus relative to correctly processed mature elastase proteins.

In a 43rd Specific Embodiment, the disclosure provides a method of the 41st Specific Embodiment wherein said pH is between 5 and 12.

In a 44th Specific Embodiment, the disclosure provides a method of any one of the 41st Specific Embodiments, wherein said one or more incorrectly processed mature elastase proteins are degraded by 50% to 100%.

In a 45th Specific Embodiment, the disclosure provides a method for therapeutically increasing the diameter of an artery or vein in a human subject in need thereof, the method comprising: locally administering to the wall of the artery or vein in the human subject the pharmaceutical composition of the 36th Specific Embodiment in a dose sufficient to increase the diameter of the artery or vein.

In a 46th Specific Embodiment, the disclosure provides a method of the 45th Specific Embodiment, wherein the diameter of the vessel, the lumenal diameter of the vessel, or both, are increased.

In a 47th Specific Embodiment, the disclosure provides a method for preventing or treating vasospasm of an artery or vein in a human subject in need thereof, the method comprising: locally administering to the wall of the artery or vein in the human subject the pharmaceutical composition of the 36th Specific Embodiment in a dose sufficient to prevent or treat vasospasm of the artery or vein.

In a 48th Specific Embodiment, the disclosure provides a method for treating an obstructed artery or vein in a human subject in need of such treatment, the method comprising: locally administering to the wall of the artery or vein in the human subject the pharmaceutical composition of the 36th Specific Embodiments, wherein said administration results in proteolysis of elastin in the wall of the artery or vein leading to enlargement of the diameter of the artery or vein.

In a 49th Specific Embodiment, the disclosure provides a method for treating an artery or vein connected to an arteriovenous hemodialysis graft or arteriovenous fistula in a human subject in need of such treatment, the method comprising: locally administering to the wall of the artery or vein in the human subject the pharmaceutical composition of the 36$^{th}$ Specific Embodiment, wherein said administration results in proteolysis of elastin in the wall of the artery or vein leading to enlargement of the diameter of the artery or vein.

In a 50$^{th}$ Specific Embodiment, the disclosure provides a method for treating a vein in a human subject for use in hemodialysis, the method comprising: locally administering to the wall of the vein in the human subject the pharmaceutical composition of the 36$^{th}$ Specific Embodiment, wherein said administration results in proteolysis of elastin in the wall of the vein leading to enlargement of the diameter of the vein.

In a 51$^{st}$ Specific Embodiment, the disclosure provides a kit comprising the pharmaceutical composition of the 36$^{th}$ Specific Embodiment.

In a 52$^{nd}$ Specific Embodiment, the disclosure provides a kit of the 51$^{st}$ Specific Embodiment wherein the pharmaceutical composition is in a container, pack, dispenser, or catheter.

The claims of U.S. provisional application No. 60/992,319, filed Dec. 4, 2007 are incorporated by reference herein in their entireties, and each embodiment set forth in such claims is incorporated by reference as a specific embodiment herein.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein; the disclosure of each such reference is hereby incorporated herein by reference in its entirety.

What is claimed is:

1. An autoactivating type I pancreatic proelastase protein comprising an amino acid sequence which is at least 90% identical to a reference amino acid sequence consisting of SEQ ID NO:73 linked at its C-terminus to the N-terminus of SEQ ID NO:1, wherein the first thirteen amino acids of the reference amino acid sequence are P10-P9-P8-P7-P6-P5-P4-P3-P2-P1-P1'-P2'-P3', and wherein:
   (a) the amino acid residues at the P10-P5 and P1'-P3' positions in the protein are each independently selected from any natural amino acid;
   (b) the amino acid residue at the P4 position in the protein is any natural amino acid except glycine, lysine, phenylalanine, tyrosine, tryptophan, or arginine;
   (c) the amino acid residue at the P3 position in the protein is any natural amino acid except proline or glycine;
   (d) the amino acid residue at the P2 position in the protein is proline, alanine, leucine, isoleucine, glycine, valine, histidine, or threonine; and
   (e) the amino acid residue at the P1 position in the protein is alanine, leucine, valine, isoleucine, or serine.

2. The autoactivating type I pancreatic proelastase protein of claim 1, wherein:
   (a) the amino acid residue at the P5 position in the protein is glutamate, histidine, proline, glycine, asparagine, lysine, or alanine;
   (b) the amino acid residue at the P4 position in the protein is threonine, alanine, proline, or histidine;
   (c) the amino acid residue at the P3 position in the protein is alanine, leucine, isoleucine, methionine, lysine, asparagine, or valine;
   (d) the amino acid residue at the P2 position in the protein is proline, alanine, leucine, isoleucine, glycine, valine, or threonine; and
   (e) the amino acid residue at the P1 position in the protein is alanine, leucine, valine, isoleucine, or serine.

3. The autoactivating type I pancreatic proelastase protein of claim 1, wherein the amino acid residue at the P5 position in the protein is histidine.

4. The autoactivating type I pancreatic proelastase protein of claim 1, wherein the amino acid residue at the P4 position in the protein is threonine.

5. The autoactivating type I pancreatic proelastase protein of claim 1, wherein the amino acid residue at the P3 position in the protein is asparagine.

6. The autoactivating type I pancreatic proelastase protein of claim 1, wherein the amino acid residue at the P2 position in the protein is proline.

7. The autoactivating type I pancreatic proelastase protein of claim 1, wherein the amino acid residue at the P1 position in the protein is alanine.

8. The autoactivating type I pancreatic proelastase protein of claim 1, wherein the amino acid residues at the P3-P1 positions in the protein have the amino acid sequence of SEQ ID NO:20.

9. The autoactivating type I pancreatic proelastase protein of claim 1, wherein the amino acid residues at the P10-P1 positions in the protein have the amino acid sequence of SEQ ID NO:73.

10. The autoactivating type I pancreatic proelastase protein of claim 1, wherein the amino acid residues at the P10-P3' positions in the protein have the amino acid sequence of SEQ ID NO:55.

11. The autoactivating type I pancreatic proelastase protein of claim 1, wherein the protein comprises an amino acid sequence which is at least 95% identical to the reference amino acid sequence.

12. The autoactivating type I pancreatic proelastase protein of claim 1, wherein the protein comprises an amino acid sequence which is at least 99% identical to the reference amino acid sequence.

13. The autoactivating type I pancreatic proelastase protein of claim 1, wherein the protein comprises an amino acid sequence which is identical to the reference amino acid sequence.

14. The autoactivating type I pancreatic proelastase protein of claim 1, which further comprises a signal sequence.

15. The autoactivating type I pancreatic proelastase protein of claim 1, which is isolated.

16. The autoactivating type I pancreatic proelastase protein of claim 1, wherein the autoactivating type I pancreatic proelastase protein produces a mature type I pancreatic elastase having elastase activity following autoactivation.

17. The autoactivating type I pancreatic proelastase protein of claim 1, wherein the autoactivating type I pancreatic proelastase protein comprises a cleavage site that is cleaved by a mature type I pancreatic elastase having elastase activity.

18. The autoactivating type I pancreatic proelastase protein of claim 1, wherein autoactivation of the type I pancreatic proelastase protein produces a mature type I pancreatic elastase having elastase activity.

* * * * *